US011485697B2

(12) United States Patent
Andahazy et al.

(10) Patent No.: US 11,485,697 B2
(45) Date of Patent: Nov. 1, 2022

(54) ANTIMALARIAL COMPOSITIONS AND USES THEREOF

(71) Applicant: THE SCRIPPS RESEARCH INSTITUTE, La Jolla, CA (US)

(72) Inventors: Wil Joseph Andahazy, Alexandria, VA (US); Arnab K. Chatterjee, San Diego, CA (US); Case W. Mcnamara, San Marcos, CA (US); Federico C. Beasley, San Diego, CA (US); Anders Mikal Eliasen, San Diego, CA (US); Hank Michael James Petrassi, San Diego, CA (US); Jason T. Roland, San Diego, CA (US); Timothy Wells, Chambesy (CH); Olga Vladimirovna Zatolochnaya, Danbury, CT (US); Fei Zhou, San Diego, CA (US); Peter G. Schultz, La Jolla, CA (US); Anil Kumar Gupta, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 17/177,314

(22) Filed: Feb. 17, 2021

(65) Prior Publication Data

US 2021/0179524 A1 Jun. 17, 2021

Related U.S. Application Data

(63) Continuation of application No. 16/311,869, filed as application No. PCT/US2017/038173 on Jun. 19, 2017, now Pat. No. 10,947,176.

(60) Provisional application No. 62/352,455, filed on Jun. 20, 2016.

(51) Int. Cl.
| | |
|---|---|
| *C07C 50/32* | (2006.01) |
| *A61K 9/10* | (2006.01) |
| *A61P 33/02* | (2006.01) |
| *A61K 47/44* | (2017.01) |
| *A61K 9/14* | (2006.01) |
| *A61K 45/06* | (2006.01) |
| *A61P 33/06* | (2006.01) |
| *A61K 31/232* | (2006.01) |
| *A61K 31/47* | (2006.01) |

(52) U.S. Cl.
CPC .............. *C07C 50/32* (2013.01); *A61K 9/10* (2013.01); *A61K 9/141* (2013.01); *A61K 31/232* (2013.01); *A61K 31/47* (2013.01); *A61K 45/06* (2013.01); *A61K 47/44* (2013.01); *A61P 33/02* (2018.01); *A61P 33/06* (2018.01); *C07C 2601/14* (2017.05)

(58) Field of Classification Search
CPC ................................. C07C 50/32; A61P 33/06
See application file for complete search history.

(56) References Cited

U.S. PATENT DOCUMENTS

| | | |
|---|---|---|
| 4,981,874 A | 1/1991 | Latter et al. |
| 5,021,426 A | 6/1991 | Baldwin et al. |
| 5,310,762 A | 5/1994 | Latter et al. |
| 7,842,840 B2 | 11/2010 | Nardi et al. |
| 10,947,176 B2 * | 3/2021 | Andahazy ............... C07C 50/32 |

FOREIGN PATENT DOCUMENTS

| | | |
|---|---|---|
| EP | 0 362 996 | 4/1990 |
| EP | 0 580 185 | 1/1994 |
| JP | H0291037 A | 3/1990 |
| WO | WO 93/20044 | 10/1993 |
| WO | WO 96/34855 | 11/1996 |

OTHER PUBLICATIONS

Kulshreshtha, A. K. et al. "Pharmaceutical Suspensions, From Formulation Development to Manufacturing", *AAPS Press*, 2010, pp. 1-337.
Qiu et al., Pharmacist's Manual, 2001, pp. 1-2.
Written Opinion in International Application No. PCT/US2017/038173, Sep. 6, 2017, pp. 1-10.
El Hage, S. et al. "Synthesis and antimalarial activity of new atovaquone derivatives" *European Journal of Medicinal Chemistry*, 2009, pp. 4778-4782, vol. 44.
Larsen, S.W. et al. "Critical Factors Influencing the In Vivo Performance of Long-acting Lipophilic Solutions—Impact on In Vitro Release Method Design" *The AAPS Journal*, 2009, pp. 762-770, vol. 11, No. 4.
Wang, J. et al. "The powerful applications of polyunsaturated fatty acids in improving the therapeutic efficacy of anticancer drugs" *Expert Opin. Drug Deliv.*, 2012, pp. 1-7, vol. 9, No. 1.
Zaro, J.L. "Lipid-Based Carriers for Prodrugs to Enhance Delivery" *The AAPS Journal*, 2014, pp. 1-10.
El Hage, S. et al. (2009): STN International HCAPLUS database (Columbus, Ohio), Accession No. 2009 : 1253778, pp. 1-2.
Latter, et al. (1990): STN International HCAPLUS database (Columbus, Ohio), Accession No. 1990 : 552064, p. 1.

* cited by examiner

*Primary Examiner* — Golam M Shameem
(74) *Attorney, Agent, or Firm* — Saliwanchik, Lloyd & Eisenschenk

(57) ABSTRACT

Provided herein are compounds, compositions and method of using thereof to treat or prevent malaria.

11 Claims, 42 Drawing Sheets

Top curve (squares): ELQ-300

Bottom curve (circles): Compound 2

100 mg/mL Synperonic Formulation 100 mg/mL 3% TPGS Formulation

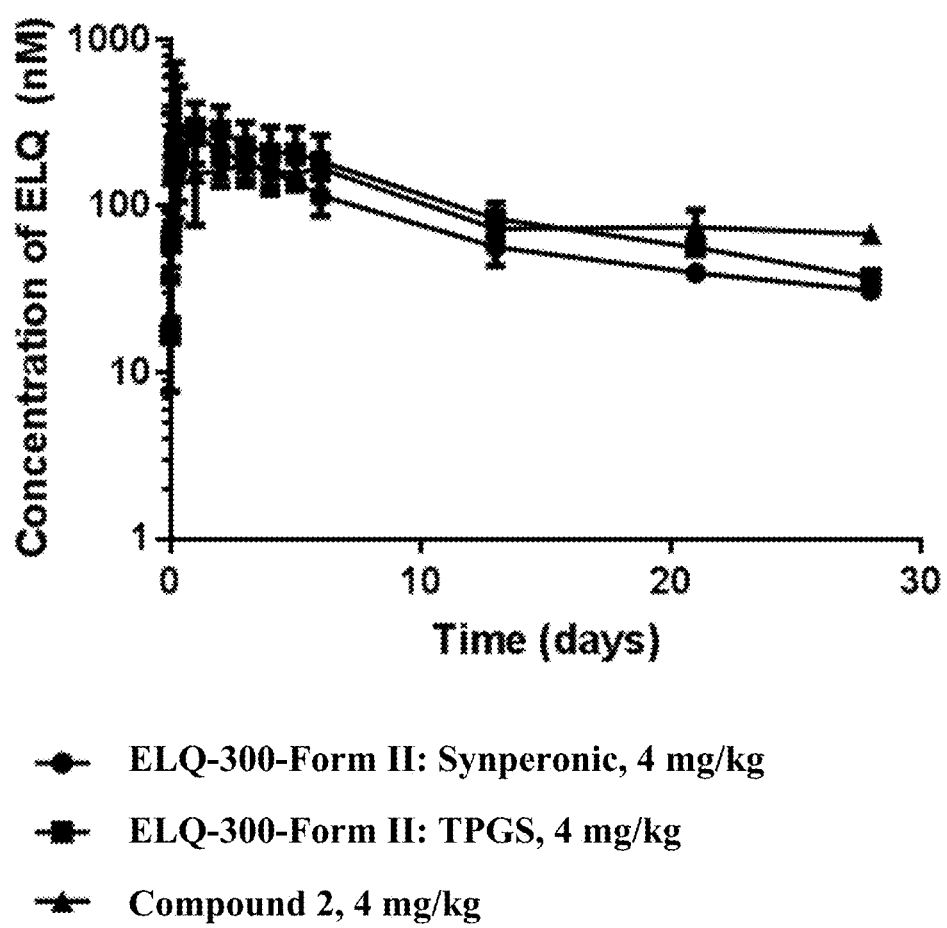

Top curve (squares): Compound 33 (60 mg/kg)

Bottom curve (circles): Compound 33 (20 mg/kg)

Top curve (squares): Compound 35 (30 mg/kg)

Bottom curve (circles): Compound 35 (10.5 mg/kg)

Top curve (squares): Compound 2 (24 mg/kg)

Bottom curve (circles): Compound 2 (8 mg/kg)

ANTIMALARIAL COMPOSITIONS AND USES THEREOF

CROSS-REFERENCE

This application is a continuation of U.S. application Ser. No. 16/311,869, filed Dec. 20, 2018, now allowed, which is the U.S. National Stage Application of International Patent Application No. PCT/US2017/038173, filed on Jun. 19, 2017, which claims the benefit of U.S. Application Ser. No. 62/352,455 filed Jun. 20, 2016, all of which is incorporated by reference in their entirety.

BACKGROUND

Malaria is an infectious disease widespread in tropical and sub-tropical regions of Africa, Asia, and the Americas. In 2010 the World Health Organization estimated that there were over 219 million documented cases of malaria and between 660,000 and 1.2 million deaths from the disease (Nayyar, Lancet Infectious Diseases, 12:488-496, 2012).

Malaria is a mosquito-borne infectious disease of humans and other animals caused by parasitic protozoans (a group of single-celled microorganisms) belonging to the *Plasmodium* type. Malaria initially manifests with mild to severe symptoms including: chills, fever, fatigue, headache, and nausea. Later symptoms include severe anemia, and blood clotting, which can lead to brain damage and other complications, and death. Although five species of *Plasmodium* (*P. falciparum, P. vivax, P. ovale, P. malariae*, and *P. knowlesi*) can infect humans, the majority of malarial deaths are caused by *P. falciparum* and *P. vivax*. Symptoms usually begin ten to fifteen days after being bitten. If not properly treated, people may have recurrences of the disease months later. In those who have recently survived an infection, reinfection usually causes milder symptoms. This partial resistance disappears over months to years if the person has no continuing exposure to malaria. Five species of the *plasmodium* parasite can infect humans; the most serious forms of the disease are caused by *Plasmodium falciparum*. Malaria caused by *Plasmodium vivax, Plasmodium ovale* and *Plasmodium malariae* causes milder disease in humans that is not generally fatal. A fifth species, *Plasmodium knowlesi*, is a zoonosis that causes malaria in macaques but can also infect humans. When a mosquito bites an infected person, a small amount of blood is taken, which contains malaria parasites. These develop within the mosquito, and about one week later, when the mosquito takes its next blood meal, the parasites are injected with the mosquito's saliva into the person being bitten. After a period of between two weeks and several months (occasionally years) spent in the liver, the malaria parasites start to multiply within red blood cells, causing symptoms that include fever, and headache. In severe cases the disease worsens leading to hallucinations, coma, and death.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travelers to malaria-endemic countries (prophylaxis). Resistance has developed to several antimalarial drugs, most notably chloroquine.

Malaria transmission can be reduced by preventing mosquito bites by distribution of inexpensive mosquito nets and insect repellents, or by mosquito-control measures such as spraying insecticides inside houses and draining standing water where mosquitoes lay their eggs.

BRIEF SUMMARY OF THE INVENTION

Described herein are compounds of Formula (IV) or a pharmaceutically acceptable salt, solvate, or stereoisomer thereof:

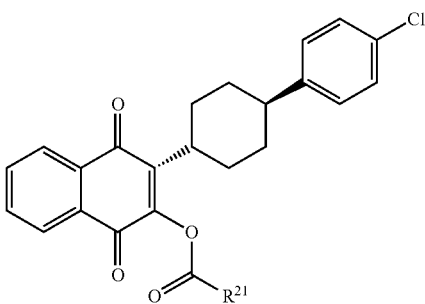

wherein $R^{21}$ is optionally substituted $C_3$-$C_{30}$alkenyl or optionally substituted $C_2$-$C_{30}$alkynyl.

In a compound of Formula (IV), $R^{21}$ may be $C_3$-$C_{30}$alkenyl. In a compound of Formula (IV), $R^{21}$ may be $C_6$-$C_{30}$alkenyl. In a compound of Formula (IV), $R^{21}$ may be $C_6$-$C_{25}$alkenyl. In a compound of Formula (IV), $R^{21}$ may be $C_{15}$-$C_{25}$alkenyl. In a compound of Formula (IV), $R^{21}$ may be

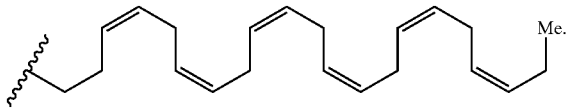 [SMILES: *CC/C=C\C/C=C\C/C=C\C/C=C\C/C=C\C/C=C\CC]

Also described herein is a pharmaceutical composition comprising:
(i) an oil; and
(ii) a compound of Formula (III) or a pharmaceutically acceptable salt, solvate, or stereoisomer thereof:

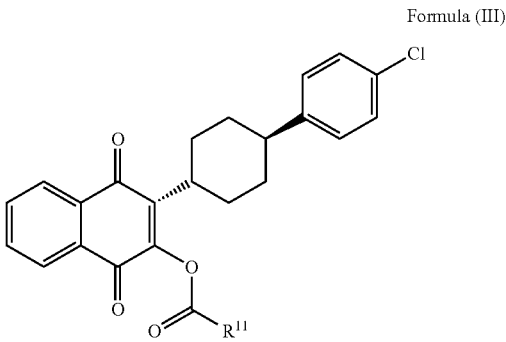

Formula (III)

wherein:
$R^{11}$ is a lipophilic moiety.

In the pharmaceutical composition comprising a compound of Formula (III), $R^{11}$ may be optionally substituted $C_1$-$C_{30}$alkyl, optionally substituted $C_2$-$C_{30}$alkenyl, or optionally substituted $C_2$-$C_{30}$alkynyl. In the pharmaceutical composition comprising a compound of Formula (III), $R^{11}$ may be optionally substituted $C_1$-$C_{20}$alkyl, optionally substituted $C_2$-$C_{20}$alkenyl, or optionally substituted $C_2$-$C_{20}$alkynyl. In the pharmaceutical composition comprising a compound of Formula (III), $R^{11}$ may be $C_1$-$C_6$alkyl. In the pharmaceutical composition comprising a compound of Formula (III), $R^{11}$ may be $C_7$-$C_{30}$alkyl. In the pharmaceutical composition comprising a compound of Formula (III), $R^{11}$ may be $R^{11}$ is

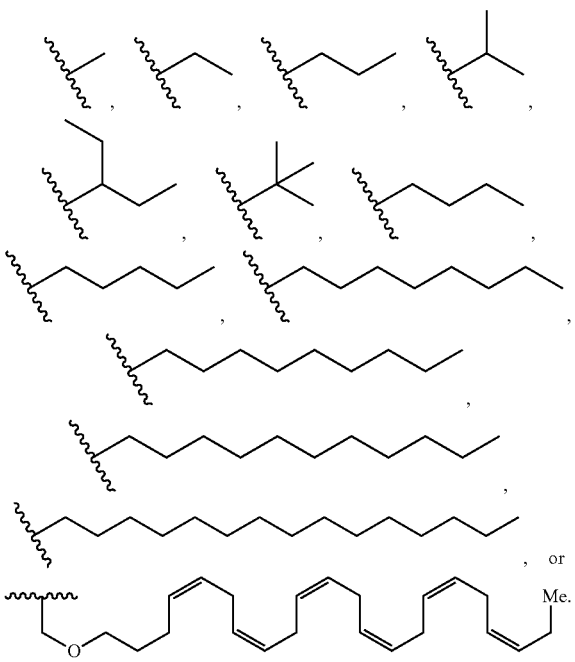

In the pharmaceutical composition comprising a compound of Formula (III), $R^{11}$ may be $C_2$-$C_{30}$alkenyl. In the pharmaceutical composition comprising a compound of Formula (III), $R^{11}$ may be $C_3$-$C_{30}$alkenyl. In the pharmaceutical composition comprising a compound of Formula (III), $R^{11}$ may be $C_6$-$C_{30}$alkenyl. In the pharmaceutical composition comprising a compound of Formula (III), $R^{11}$ may be $C_6$-$C_{25}$alkenyl. In the pharmaceutical composition comprising a compound of Formula (III), $R^{11}$ may be $C_{15}$-$C_{25}$alkenyl. In the pharmaceutical composition comprising a compound of Formula (III), $R^{11}$ may be $R^{11}$ is

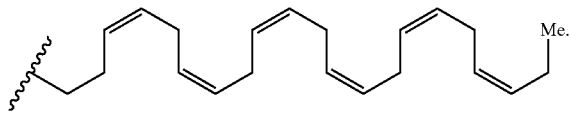 [SMILES: *CC/C=C\C/C=C\C/C=C\C/C=C\C/C=C\C/C=C\CC]

In the pharmaceutical composition comprising a compound of Formula (III), the oil may be a vegetable oil. In the pharmaceutical composition comprising a compound of Formula (III), the oil may be selected from corn oil, peanut oil, sesame oil, olive oil, palm oil, safflower oil, soybean oil, cottonseed oil, rapeseed oil, sunflower oil and mixtures thereof. In the pharmaceutical composition comprising a compound of Formula (III), the oil may be sesame oil.

In the pharmaceutical composition comprising a compound of Formula (III), the concentration of the compound of Formula (III) or a pharmaceutically acceptable salt, solvate, or stereoisomer thereof may be greater than about 50 mg/mL. In the pharmaceutical composition comprising a compound of Formula (III), the concentration of the compound of Formula (III) or a pharmaceutically acceptable salt, solvate, or stereoisomer thereof may be greater than about 100 mg/mL. In the pharmaceutical composition comprising a compound of Formula (III), the concentration of the compound of Formula (III) or a pharmaceutically acceptable salt, solvate, or stereoisomer thereof may be greater than about 200 mg/mL.

Described herein are methods for the treatment or prevention of malaria in a subject comprising administering to the subject a compound of Formula (IV) or a pharmaceutical composition comprising a compound of Formula (III). In the method for the treatment or prevention of malaria, the pharmaceutical composition may be administered by subcutaneous or intramuscular injection. In the method for the treatment or prevention of malaria, the pharmaceutical composition may be effective for sustained or controlled release. In the method for the treatment or prevention of malaria, the compound of Formula (II) or a pharmaceutically acceptable salt, solvate, or stereoisomer thereof, comprised in the pharmaceutical composition may be administered at a dose of about 5 to about 20 mg/day. In the method for the treatment or prevention of malaria, the compound of Formula (III) or a pharmaceutically acceptable salt, solvate, or stereoisomer thereof, comprised in the pharmaceutical composition may be released from the pharmaceutical composition over a period of a minimum of about 30 days after administration. In the method for the treatment or prevention of malaria, the compound of Formula (III) or a pharmaceutically acceptable salt, solvate, or stereoisomer thereof, comprised in the pharmaceutical composition is released from the pharmaceutical composition at a rate providing an average concentration of trans-2-[4-(4-chlorophenyl)cyclohexyl]-3-hydroxy-1,4-naphthalenedione in the blood plasma of said subject of at least about 1000 nM over about 13 weeks. In the method for the treatment or prevention of malaria, the method may further comprise administering an additional antimalarial agent. In the method for the treatment or prevention of malaria, the additional antimalarial agent is selected from artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300.

Described herein are methods of killing or inhibiting the growth of a *Plasmodium* species comprising contacting the species with an effective amount of a compound of Formula (IV). In the method of killing or inhibiting the growth of a *Plasmodium* species, the *Plasmodium* species is *Plasmodium falciparum*, *Plasmodium vivax*, *Plasmodium ovale*, *Plasmodium malariae*, or *Plasmodium knowlesi*.

BRIEF DESCRIPTION OF THE DRAWINGS

FIG. 20 depicts a comparison in exposure of ELQ-300 following IM administration of Compound 2 in sesame oil (4 mg/kg) versus two ELQ-300-Form II suspensions (4 mg/kg).

DETAILED DESCRIPTION OF THE INVENTION

Figure 1:
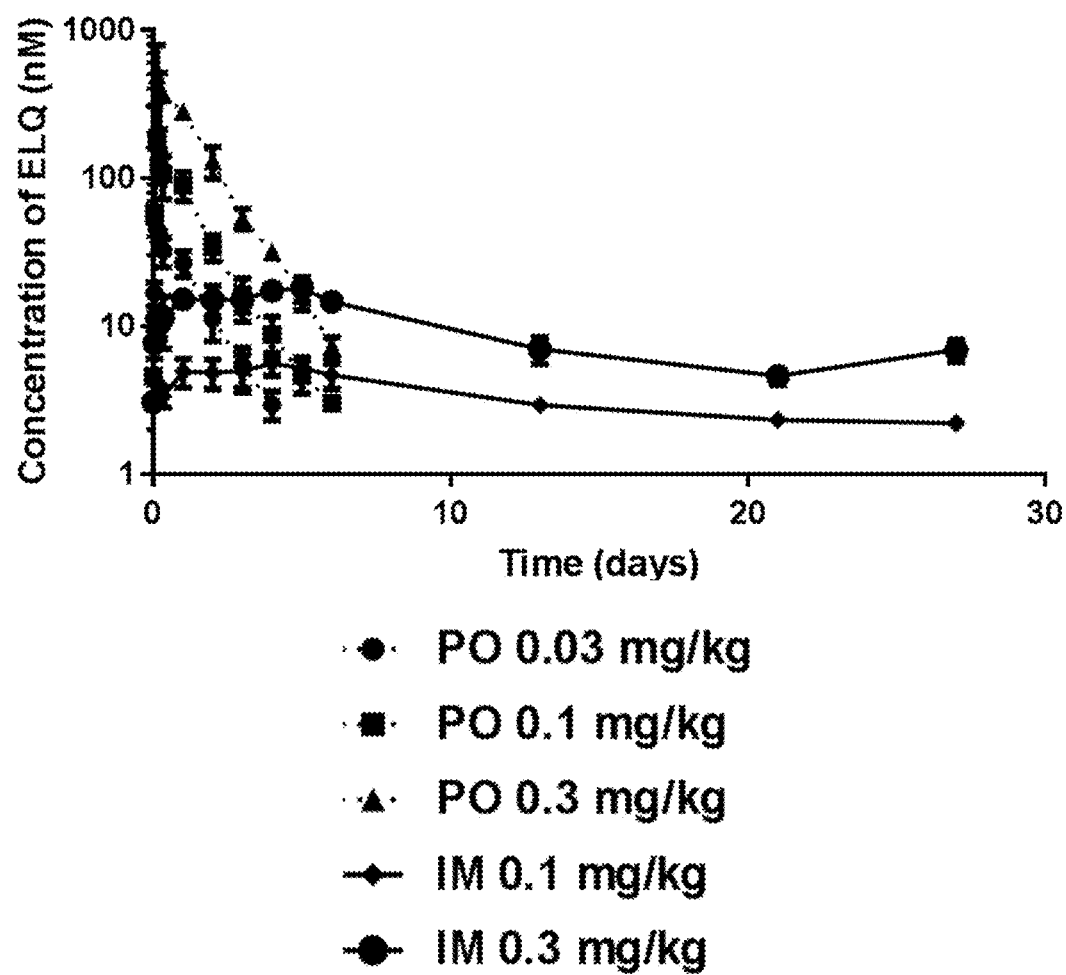
FIG. 1 depicts the exposure of ELQ-300 following PO or IM dosing with Compound 2.

Seasonal malaria chemoprevention (SMC) has been an effective strategy to reduce malaria mortality and morbidity rates by up to 75% in children aged 3-59 months. Provided as recurring monthly doses given throughout the season of highest malaria transmission (3-4 months), a single oral or injectable dose would be preferred to ensure continuous coverage throughout the entire season and simplify patient compliance to maximize chemoprevention with a target efficacy goal of >95%. Although many treatments are under development, the challenge of producing a widely available single-dose treatment that provides a high level of protection for a sustained period is still to be met.

Disclosed herein are new formulations comprising derivatives of atovaquone, an approved antimalarial compound or comprising derivatives of ELQ-300. New sustained release formulations, such as depot formulation, comprising these derivatives are investigated. Disclosed herein are new suspension formulations comprising nanoparticles or microparticles of new crystalline forms of ELQ-300, atovaquone, or pyronaridine. Also disclosed herein are new suspension formulations comprising nanoparticles or microparticles of crystalline derivatives of atovaquone or comprising crystalline derivatives of a ELQ-300. Disclosed herein are method of treating or preventing malaria comprising administering one of these new formulations to a subject in need thereof.

Definitions

As used in the specification and appended claims, unless specified to the contrary, the following terms have the meaning indicated below.

"Oxo" refers to the =O substituent.

"Thioxo" refers to the =S substituent.

"Alkyl" refers to a linear or branched hydrocarbon chain radical, which is fully saturated, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{12}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{12}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, $C_5$-$C_{12}$ alkyl, and $C_7$-$C_{20}$ alkyl. Representative alkyl groups include, but are not limited to, methyl, ethyl, propyl, butyl, butyl, butyl, pentyl, hexyl, heptyl, octyl, nonyl, decanyl, undecanyl, dodecane, tridecane, tetradecane, pentadecane, hexadecane, heptadecane, octadecane, nonadecane, icosane, and the like. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), and the like. Representative linear alkyl groups include, but are not limited to, methyl, ethyl, n-propyl, n-butyl, n-pentyl and the like. The alkyl may be

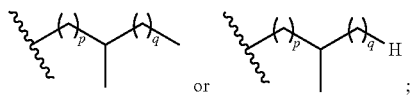

wherein each p and q is independently 0-18. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. An alkyl may be optionally substituted with one or more of oxo, halogen, —OR$^a$, —CN, and —N(R$^a$)$_2$. An alkyl may be optionally substituted with one or more of oxo, halogen, —OH, —CN, and —NH$_2$.

"Alkenyl" refers to a straight or branched hydrocarbon chain radical group consisting solely of carbon and hydrogen atoms, containing at least one carbon-carbon double bond, and having from two to twenty carbon atoms. An alkenyl comprising up to 30 carbon atoms is referred to as a $C_2$-$C_{30}$ alkenyl, likewise, for example, an alkenyl comprising up to 12 carbon atoms is a $C_2$-$C_{12}$ alkenyl. Alkenyls (and other moieties defined herein) comprising other numbers of carbon atoms are represented similarly. Alkenyl groups include, but are not limited to $C_2$-$C_{30}$ alkenyl, $C_2$-$C_{20}$ alkenyl, $C_2$-$C_{15}$ alkenyl, $C_2$-$C_{10}$ alkenyl, $C_2$-$C_8$ alkenyl, $C_2$-$C_6$ alkenyl, $C_2$-$C_4$ alkenyl, $C_2$-$C_3$ alkenyl, $C_2$-$C_8$ alkenyl, $C_3$-$C_8$ alkenyl, $C_4$-$C_8$ alkenyl, $C_5$-$C_{12}$ alkenyl, and $C_7$-$C_{20}$ alkenyl. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. The alkenyl may be

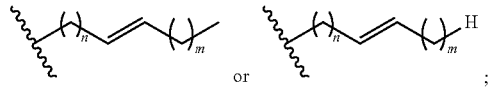

wherein each n and m is independently 0-18. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. An alkenyl may be optionally substituted with one or more of oxo, halogen, —OR$^a$, —CN, and —N(R$^a$)$_2$. An alkenyl may be optionally substituted with one or more of oxo, halogen, —OH, —CN, and —NH$_2$.

"Alkynyl" refers to a straight or branched hydrocarbon chain radical group consisting solely of carbon and hydrogen atoms, containing at least one carbon-carbon triple bond, having from two to twenty carbon atoms. An alkynyl comprising up to 30 carbon atoms is referred to as a $C_2$-$C_{30}$ alkynyl, likewise, for example, an alkynyl comprising up to 12 carbon atoms is a $C_2$-$C_{12}$ alkynyl. Alkynyls (and other moieties defined herein) comprising other numbers of carbon atoms are represented similarly. Alkynyl groups include, but are not limited to $C_2$-$C_{30}$ alkynyl, $C_2$-$C_{20}$ alkynyl, $C_2$-$C_{15}$ alkynyl, $C_2$-$C_{10}$ alkynyl, $C_2$-$C_8$ alkynyl, $C_2$-$C_6$ alkynyl, $C_2$-$C_4$ alkynyl, $C_2$-$C_3$ alkynyl, $C_2$-$C_8$ alkynyl, $C_3$-$C_8$ alkynyl, $C_4$-$C_8$ alkynyl, $C_5$-$C_{12}$ alkynyl, and $C_7$-$C_{20}$ alkynyl. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. An alkynyl may be optionally substituted with one or more of oxo, halogen, —OR$^a$, —CN, and —N(R$^a$)$_2$. An alkynyl may be optionally substituted with one or more of oxo, halogen, —OH, —CN, and —NH$_2$.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. An alkylene may comprise one to eight carbon atoms (e.g., $C_1$-$C_8$ alkylene). An alkylene may comprise one to five carbon atoms (e.g., $C_1$-$C_5$ alkylene). An alkylene may comprise one to four carbon atoms (e.g., $C_1$-$C_4$ alkylene). An alkylene may comprise one to three carbon atoms (e.g., $C_1$-$C_3$ alkylene). An alkylene may comprise one to two carbon atoms (e.g., $C_1$-$C_2$ alkylene). An alkylene may comprise one carbon atom (e.g., $C_1$ alkylene). An alkylene may comprise five to eight carbon atoms (e.g., $C_5$-$C_8$ alkylene An alkylene may comprise two to five carbon atoms (e.g., $C_2$-$C_5$ alkylene An alkylene may comprise three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N (R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each R$^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. An alkylene may be optionally substituted with one or more of oxo, halogen, —OR$^a$, —CN, and —N(R$^a$)$_2$. An alkylene may be optionally substituted with one or more of oxo, halogen, —OH, —CN, and —NH$_2$.

"Aminoalkyl" refers to a radical of the formula —R$^c$—N(R$^a$)$_2$ or —R$^c$—N(R$^a$)—R$^c$, where each R$^c$ is independently an alkylene chain as defined above, for example, methylene, ethylene, and the like; and each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkoxy" refers to a radical of the formula —OR$^a$ where R$^a$ is an alkyl radical as defined. Unless stated otherwise specifically in the specification, an alkoxy group may be optionally substituted as described above for alkyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted by one or more of the following substituents: alkyl, alkenyl, alkynyl, halo, fluoroalkyl, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^b$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl (optionally substituted with one or more alkyl groups), heterocycloalkylalkyl, heteroaryl or heteroarylalkyl, or two R$^a$ attached to the same nitrogen atom are combined to form a heterocycloalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated. An aryl may be optionally substituted with one or more of halogen, alkyl, —OR$^a$, —CN, and —N(R$^a$)$_2$. An aryl may be optionally substituted with one or more of halogen, methyl, —OH, —CN, and —NH$_2$.

"Aryloxy" refers to a radical bonded through an oxygen atom of the formula —O-aryl, where aryl is as defined above.

"Aralkyl" refers to a radical of the formula —R$^c$-aryl where is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Cycloalkyl" or "carbocycle" refers to a stable, non-aromatic, monocyclic or polycyclic carbocyclic ring, which may include fused (when fused with an aryl or a heteroaryl ring, the cycloalkyl is bonded through a non-aromatic ring atom) or bridged ring systems, which is saturated or unsaturated comprising 2 to 20 carbon atoms. Cycloalkyls include, but are not limited to $C_3$-$C_{20}$ cycloalkyl, $C_3$-$C_{15}$ cycloalkyl, $C_3$-$C_{10}$ cycloalkyl, $C_3$-$C_8$ cycloalkyl, $C_3$-$C_6$ cycloalkyl, $C_3$-$C_5$ cycloalkyl, and $C_3$-$C_4$ cycloalkyl, $C_2$-$C_8$ cycloalkyl, $C_3$-$C_8$ cycloalkyl, $C_4$-$C_8$ cycloalkyl, $C_5$-$C_{12}$ cycloalkyl, and $C_7$-$C_{20}$ cycloalkyl. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, the cycloalkyl is optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated. A cycloalkyl may be optionally substituted with one or more of oxo, halogen, alkyl, —$OR^a$, —CN, and —N($R^a$)$_2$. A cycloalkyl may be optionally substituted with one or more of oxo, halogen, methyl, —OH, —CN, and —NH$_2$.

"Cycloalkylalkyl" refers to a radical of the formula —$R^c$-cycloalkyl where $R^c$ is an alkylene chain as defined above. The alkylene chain and the cycloalkyl radical are optionally substituted as defined above.

"Fused" refers to any ring structure described herein which is fused to an existing ring structure. When the fused ring is a heterocycloalkyl ring or a heteroaryl ring, any carbon atom on the existing ring structure which becomes part of the fused heterocycloalkyl ring or the fused heteroaryl ring may be replaced with a nitrogen atom.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)$OR^a$, —C(O)N($R^a$)$_2$, —N($R^a$)C(O)$OR^f$, —OC(O)—$NR^aR^f$, —N($R^a$)C(O)$R^f$, —N($R^a$)S(O)$_t$$R^f$ (where t is 1 or 2), —S(O)$_t$$R^f$ (where t is 1 or 2), —S(O)$_t$$OR^f$ (where t is 1 or 2) and —S(O)$_t$N($R^a$)$_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl.

"Halo" or "halogen" refers to bromo, chloro, fluoro or iodo. Halogen may refer to chloro or fluoro. Halogen may refer to fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —$OR^a$ where $R^a$ is a haloalkyl radical as defined. Unless stated otherwise specifically in the specification, a haloalkoxy group may be optionally substituted as described below.

"Heterocycloalkyl" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Heterocycloalkyls include, but are not limited to $C_2$-$C_{20}$ heterocycloalkyl, $C_2$-$C_{15}$ heterocycloalkyl, $C_2$-$C_{10}$ heterocycloalkyl, $C_2$-$C_8$ heterocycloalkyl, $C_2$-$C_6$ heterocycloalkyl, $C_2$-$C_5$ heterocycloalkyl, and $C_2$-$C_4$ heterocycloalkyl, $C_2$-$C_8$ heterocycloalkyl, $C_3$-$C_8$ heterocycloalkyl, $C_4$-$C_8$ heterocycloalkyl, $C_5$-$C_{12}$ heterocycloalkyl, and $C_7$-$C_{20}$ heterocycloalkyl. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, 2-oxo-1,3-dioxol-4-yl, 1,1-dioxidotetrahydro-2H-thiopyranyl, tetrahydro-2H-thiopyranyl, and tetrahydro-2H-pyranyl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group is optionally substituted by one or more of the following substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^b$ is independently a direct bond or a straight or branched alkylene or alkenylene chain, and is a straight or branched alkylene or alkenylene chain, and where each of the above substituents is unsubstituted unless otherwise indicated. A heterocycloalkyl may be optionally substituted with one or more of oxo, halogen, alkyl, —OR$^a$, —CN, and —N(R$^a$)$_2$. A heterocycloalkyl may be optionally substituted with one or more of oxo, halogen, methyl, —OH, —CN, and —NH$_2$.

"Heterocycloalkyllalkyl" refers to a radical of the formula —R$^c$-heterocycloalkyl where is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkyllalkyl radical is optionally substituted as defined above for an alkylene chain. The heterocycloalkyl part of the heterocycloalkylalkyl radical is optionally substituted as defined above for a heterocycloalkyl group.

"Heterocycloalkylalkoxy" refers to a radical bonded through an oxygen atom of the formula —O—R$^c$-heterocycloalkyl where is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain. The heterocycloalkyl part of the heterocycloalkylalkoxy radical is optionally substituted as defined above for a heterocycloalkyl group.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl may be is a 5-membered heteroaryl. The heteroaryl may be a 6-membered heteroaryl. For purposes of this invention, the heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted by one or more of the following substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each R$^b$ is independently a direct bond or a straight or branched alkylene or alkenylene chain, and is a straight or branched alkylene or alkenylene chain, and where each of the above substituents is unsubstituted unless otherwise indicated. A heteroaryl may be optionally substituted with one or more of halogen, alkyl, —OR$^a$, —CN, and —N(R$^a$)$_2$. A heteroaryl may be optionally substituted with one or more of halogen, methyl, —OH, —CN, and —NH$_2$.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

A "tautomer" refers to a molecule wherein a proton shift from one atom of a molecule to another atom of the same molecule is possible. The compounds presented herein may exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

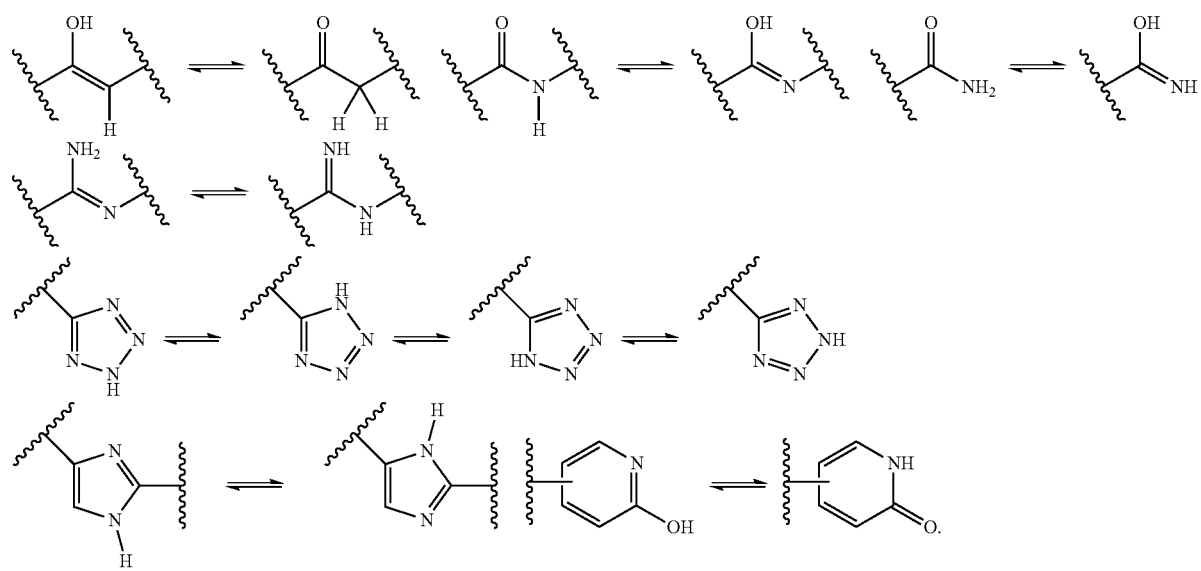

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. "Optionally substituted" and "substituted or unsubstituted" and "unsubstituted or substituted" are used interchangeably herein.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. The pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof.

When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range varies between 1% and 10% of the stated number or numerical range.

The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The term "nanoparticles" refers to particles in the nanometer range. The size of the particles should be below a maximum size above which administration by subcutaneous or intramuscular injection becomes impaired or even no longer is possible. Said maximum size depends for example on the limitations imposed by the needle diameter or by adverse reactions of the body to large particles, or both.

The term "microparticles" refers to particles in the micrometer range. The size of the particles should be below a maximum size above which administration by subcutaneous or intramuscular injection becomes impaired or even no longer is possible. Said maximum size depends for example on the limitations imposed by the needle diameter or by adverse reactions of the body to large particles, or both.

As used herein, "to treat" a condition or "treatment" of the condition (e.g., malaria) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver, preventing systemic disease, preventing the symptomatic stage of malaria, and/or preventing establishment of *Plasmodium* infection); delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "preventing" includes preventing the initiation of malaria and/or reducing the severity or intensity of malaria.

Compounds

Described herein are compounds of Formula (I') or a pharmaceutically acceptable salt, solvate, polymorphs, or stereoisomer thereof:

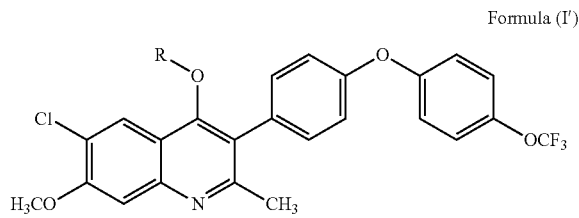

Formula (I')

wherein:
R is —CH$_2$OC(=O)R$^1$, —R$^2$, —C(=O)OR$^3$, or —C(=O)R$^4$;
R$^1$ is optionally substituted C$_1$-C$_{20}$alkyl, optionally substituted C$_2$-C$_{20}$alkenyl, optionally substituted C$_2$-C$_{20}$alkynyl, optionally substituted C$_3$-C$_8$cycloalkyl, or optionally substituted C$_2$-C$_8$heterocycloalkyl;
R$^2$ is optionally substituted (C$_1$-C$_6$alkylene)aryl, optionally substituted (C$_1$-C$_6$alkylene)heteroaryl, optionally substituted (C$_1$-C$_6$alkylene)C$_3$-C$_8$cycloalkyl, or optionally substituted (C$_1$-C$_6$alkylene)C$_2$-C$_8$heterocycloalkyl;
R$^3$ is optionally substituted C$_1$-C$_{20}$alkyl, optionally substituted C$_2$-C$_{20}$alkenyl, or optionally substituted C$_2$-C$_{20}$alkynyl; provided that R$^3$ is not ethyl; and
R$^4$ is optionally substituted C$_1$-C$_{20}$alkyl, optionally substituted C$_2$-C$_2$alkenyl, or optionally substituted C$_2$-C$_{20}$alkynyl.

Described herein are compounds of Formula (I) or a pharmaceutically acceptable salt, solvate, polymorphs, or stereoisomer thereof:

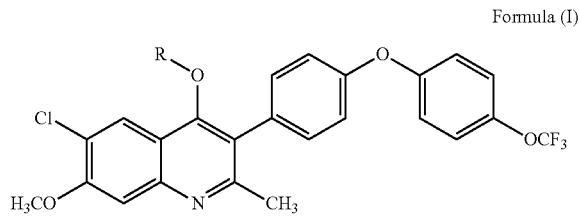

Formula (I)

wherein:
R is —C(R$^{1a}$)$_2$OC(=O)R$^1$, —R$^2$, —C(=O)OR$^3$, or —C(=O)R$^4$;
R$^1$ is optionally substituted C$_1$-C$_{30}$alkyl, optionally substituted C$_2$-C$_{30}$alkenyl, optionally substituted C$_2$-C$_{30}$alkynyl, optionally substituted C$_3$-C$_8$cycloalkyl, or optionally substituted C$_2$-C$_8$heterocycloalkyl;
each R$^{1a}$ is independently hydrogen, halogen, or optionally substituted C$_1$-C$_6$alkyl;
or two R$^{1a}$ are taken together with the carbon atom to which they are attached to form an optionally substituted C$_3$-C$_8$cycloalkyl;
R$^2$ is optionally substituted (C$_1$-C$_6$alkylene)aryl, optionally substituted (C$_1$-C$_6$alkylene)heteroaryl, optionally substituted (C$_1$-C$_6$alkylene)C$_3$-C$_8$cycloalkyl, or optionally substituted (C$_1$-C$_6$alkylene)C$_2$-C$_8$heterocycloalkyl;
R$^3$ is optionally substituted C$_5$-C$_{30}$alkyl, optionally substituted C$_4$-C$_{30}$alkenyl, or optionally substituted C$_2$-C$_{30}$alkynyl; and R⁴ is optionally substituted C₅-C₃₀alkyl, optionally substituted C₂-C₃₀alkenyl, or optionally substituted C₂-C₃₀alkynyl.

In a compound of Formula (I), R may be —C(R¹ᵃ)₂OC(=O)R¹, —C(=O)OR³, or —C(=O)R⁴. In a compound of Formula (I), R may be —C(R¹ᵃ)₂OC(=O)R¹ or —C(=O)OR³. In a compound of Formula (I), R may be —C(R¹ᵃ)₂OC(=O)R¹ or —C(=O)R⁴. In a compound of Formula (I), R may be —C(=O)OR³ or —C(=O)R⁴.

In a compound of Formula (I), R may be —C(R¹ᵃ)₂OC(=O)R¹. In a compound of Formula (I), R may be —C(R¹ᵃ)₂ OC(=O)R¹ and R¹ᵃ may each be hydrogen. In a compound of Formula (I), R may be —C(R¹ᵃ)₂OC(=O)R¹ and R¹ᵃ may each be C₁-C₆alkyl. In a compound of Formula (I), R may be —C(R¹ᵃ)₂OC(=O)R¹ and one R¹ᵃ may be C₁-C₆alkyl and one R¹ᵃ may be hydrogen. In a compound of Formula (I), R may be —C(R¹ᵃ)₂OC(=O)R¹ and one R¹ᵃ may be halogen and one R¹ᵃ may be hydrogen. In a compound of Formula (I), R may be —CH₂OC(=O)R¹. In a compound of Formula (I), R may be —CH₂OC(=O)R¹ and R¹ may be optionally substituted C₁-C₂₀alkyl, optionally substituted C₂-C₂₀alkenyl, or optionally substituted C₂-C₂₀alkynyl. In a compound of Formula (I), R may be —CH₂OC(=O)R¹ and R¹ may be optionally substituted C₁-C₂₀alkyl or optionally substituted C₂-C₂₀alkenyl. In a compound of Formula (I), R may be —CH₂OC(=O)R¹ and R¹ may be optionally substituted C₁-C₂₀alkyl or optionally substituted C₂-C₃₀alkenyl. In a compound of Formula (I), R may be —CH₂OC(=O)R¹ and R¹ may be C₁-C₂₀alkyl or C₂-C₂₀alkenyl. In a compound of Formula (I), R may be —CH₂OC(=O)R¹ and R¹ may be C₁-C₂₀alkyl or C₂-C₃₀alkenyl. In a compound of Formula (I), R may be —CH₂OC(=O)R¹ and R¹ may be C₁-C₃₀alkyl. In a compound of Formula (I), R may be —CH₂OC(=O)R¹ and R¹ may be C₁-C₂₅alkyl. In a compound of Formula (I), R may be —CH₂OC(=O)R¹ and R¹ may be C₁-C₂₀alkyl. In a compound of Formula (I), R may be —CH₂OC(=O)R¹ and R¹ may be C₁-C₁₅alkyl. In a compound of Formula (I), R may be —CH₂OC(=O)R¹ and R¹ may be C₁-C₆alkyl. In a compound of Formula (I), R may be —CH₂OC(=O)R¹ and R¹ may be C₁-C₇alkyl. In a compound of Formula (I), R may be —CH₂OC(=O)R¹ and R¹ may be C₇-C₂₀alkyl. In a compound of Formula (I), R may be —CH₂OC(=O)R¹ and R¹ may be substituted C₁-C₂₀alkyl or substituted C₂-C₂₀alkenyl. In a compound of Formula (I), R may be —CH₂OC(=O)R¹ and R¹ may be substituted C₁-C₂₀alkyl or substituted C₂-C₃₀alkenyl. In a compound of Formula (I), R may be —CH₂OC(=O)R¹ and R¹ may be substituted C₁-C₃₀alkyl. In a compound of Formula (I), R may be —CH₂OC(=O)R¹ and R¹ may be substituted C₁-C₂₅alkyl. In a compound of Formula (I), R may be —CH₂OC(=O)R¹ and R¹ may be substituted C₁-C₂₀alkyl. In a compound of Formula (I), R may be —CH₂OC(=O)R¹ and R¹ may be substituted C₁-C₁₅alkyl. In a compound of Formula (I), R may be —CH₂OC(=O)R¹ and R¹ may be substituted C₁-C₆alkyl. In a compound of Formula (I), R may be —CH₂OC(=O)R¹ and R¹ may be substituted C₁-C₇alkyl. In a compound of Formula (I), R may be —CH₂OC(=O)R¹ and R¹ may be substituted C₇-C₂₀alkyl. In a compound of Formula (I), R may be —CH₂OC(=O)R¹ and R¹ may be

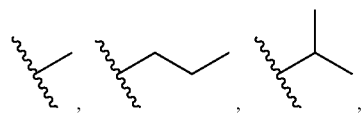

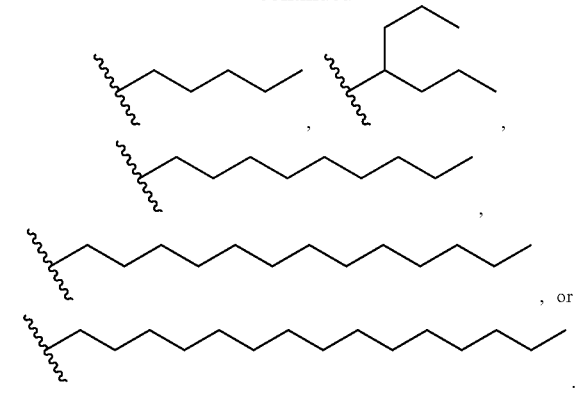

In a compound of Formula (I), R may be —CH₂OC(=O)R¹ and R¹ may be

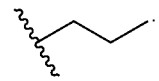 [SMILES: *CCC]

In a compound of Formula (I), R may be —CH₂OC(=O)R¹ and R¹ may be C₂-C₃₀alkenyl. In a compound of Formula (I), R may be —CH₂OC(=O)R¹ and R¹ may be C₂-C₆alkenyl. In a compound of Formula (I), R may be —CH₂OC(=O)R¹ and R¹ may be C₇-C₃₀alkenyl. In a compound of Formula (I), R may be —CH₂OC(=O)R¹ and R¹ may be C₁₅-C₂₀alkenyl. In a compound of Formula (I), R may be —CH₂OC(=O)R¹ and R¹ may be C₁₅-C₃₀alkenyl. In a compound of Formula (I), R may be —CH₂OC(=O)R¹ and R¹ may be C₂₀-C₃₀alkenyl. In a compound of Formula (I), R may be —CH₂OC(=O)R¹ and R¹ may be substituted C₂-C₃₀alkenyl. In a compound of Formula (I), R may be —CH₂OC(=O)R¹ and R¹ may be substituted C₂-C₆alkenyl. In a compound of Formula (I), R may be —CH₂OC(=O)R¹ and R¹ may be substituted C₇-C₃₀alkenyl. In a compound of Formula (I), R may be —CH₂OC(=O)R¹ and R¹ may be substituted C₁₅-C₂₀alkenyl. In a compound of Formula (I), R may be —CH₂OC(=O)R¹ and R¹ may be substituted C₁₅-C₃₀alkenyl. In a compound of Formula (I), R may be —CH₂OC(=O)R¹ and R¹ may be substituted C₂₀-C₃₀alkenyl. In a compound of Formula (I), R may be —CH₂OC(=O)R¹ and R¹ may be

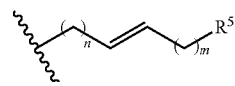

wherein R⁵ is H or methyl; n is 0-18; and m is 0-18; provided that n+m is less than 18 when R⁵ is H or n+m is less than 17 when R⁵ is methyl. In a compound of Formula (I), n may be 0. In a compound of Formula (I), n may be 1. In a compound of Formula (I), n may be 2. In a compound of Formula (I), n may be 3. In a compound of Formula (I), n may be 4. In a compound of Formula (I), n may be 5. In a compound of Formula (I), n may be 6. In a compound of Formula (I), n may be 7. In a compound of Formula (I), n may be 8. In a compound of Formula (I), n may be 9. In a compound of Formula (I), n may be 10. In a compound of Formula (I), n may be 11. In a compound of Formula (I), n may be 12. In a compound of Formula (I), n may be 13. In a compound of Formula (I), n may be 14. In a compound of Formula (I), n may be 15. In a compound of Formula (I), n may be 16. In a compound of Formula (I), n may be 17. In a compound of Formula (I), n may be 18. In a compound of Formula (I), m may be 0. In a compound of Formula (I), m may be 1. In a compound of Formula (I), m may be 2. In a compound of Formula (I), m may be 3. In a compound of Formula (I), m may be 4. In a compound of Formula (I), m may be 5. In a compound of Formula (I), m may be 6. In a compound of Formula (I), m may be 7. In a compound of Formula (I), m may be 8. In a compound of Formula (I), m may be 9. In a compound of Formula (I), m may be 10. In a compound of Formula (I), m may be 11. In a compound of Formula (I), m may be 12. In a compound of Formula (I), m may be 13. In a compound of Formula (I), m may be 14. In a compound of Formula (I), m may be 15. In a compound of Formula (I), m may be 16. In a compound of Formula (I), m may be 17. In a compound of Formula (I), m may be 18.

In a compound of Formula (I), R may be —$CH_2OC(=O)R^1$ and $R^1$ may be

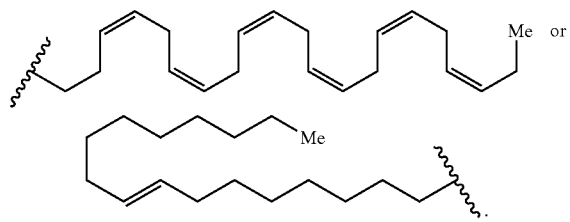

In a compound of Formula (I), R may be —$C(=O)OR^3$. In a compound of Formula (I), R may be —$C(=O)OR^3$ and $R^3$ may be optionally substituted $C_5$-$C_{20}$alkyl, optionally substituted $C_4$-$C_{20}$alkenyl, or optionally substituted $C_2$-$C_{20}$alkynyl. In a compound of Formula (I), R may be —$C(=O)OR^3$ and $R^3$ may be optionally substituted $C_5$-$C_{20}$alkyl or optionally substituted $C_4$-$C_{20}$alkenyl. In a compound of Formula (I), R may be —$C(=O)OR^3$ and $R^3$ may be $C_5$-$C_{30}$alkyl. In a compound of Formula (I), R may be —$C(=O)OR^3$ and $R^3$ may be $C_5$-$C_{20}$alkyl. In a compound of Formula (I), R may be —$C(=O)OR^3$ and $R^3$ may be $C_5$-$C_{10}$alkyl. In a compound of Formula (I), R may be —$C(=O)OR^3$ and $R^3$ may be $C_{11}$-$C_{30}$alkyl. In a compound of Formula (I), R may be —$C(=O)OR^3$ and $R^3$ may be $C_5$-$C_{15}$alkyl. In a compound of Formula (I), R may be —$C(=O)OR^3$ and $R^3$ may be $C_6$-$C_{16}$alkyl. In a compound of Formula (I), R may be —$C(=O)OR^3$ and $R^3$ may be substituted $C_5$-$C_{30}$alkyl. In a compound of Formula (I), R may be —$C(=O)OR^3$ and $R^3$ may be substituted $C_5$-$C_{20}$alkyl. In a compound of Formula (I), R may be —$C(=O)OR^3$ and $R^3$ may be substituted $C_5$-$C_{10}$alkyl. In a compound of Formula (I), R may be —$C(=O)OR^3$ and $R^3$ may be substituted $C_{11}$-$C_{30}$alkyl. In a compound of Formula (I), R may be —$C(=O)OR^3$ and $R^3$ may be substituted $C_5$-$C_{15}$alkyl. In a compound of Formula (I), R may be —$C(=O)OR^3$ and $R^3$ may be substituted $C_6$-$C_{16}$alkyl. In a compound of Formula (I), R may be —$C(=O)OR^3$ and $R^3$ may be

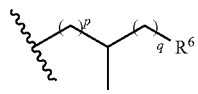

wherein $R^6$ is H or methyl; p is 0 to 18; and q is 0 to 18; provided that p+q is less than 18 when $R^6$ is H or p+q is less than 17 when $R^6$ is methyl; and provided that $R^3$ is not ethyl. In a compound of Formula (I), p may be 0. In a compound of Formula (I), p may be 1. In a compound of Formula (I), p may be 2. In a compound of Formula (I), p may be 3. In a compound of Formula (I), p may be 4. In a compound of Formula (I), p may be 5. In a compound of Formula (I), p may be 6. In a compound of Formula (I), p may be 7. In a compound of Formula (I), p may be 8. In a compound of Formula (I), p may be 9. In a compound of Formula (I), p may be 10. In a compound of Formula (I), p may be 11. In a compound of Formula (I), p may be 12. In a compound of Formula (I), p may be 13. In a compound of Formula (I), p may be 14. In a compound of Formula (I), p may be 15. In a compound of Formula (I), p may be 16. In a compound of Formula (I), p may be 17. In a compound of Formula (I), p may be 18. In a compound of Formula (I), q may be 0. In a compound of Formula (I), q may be 1. In a compound of Formula (I), q may be 2. In a compound of Formula (I), q may be 3. In a compound of Formula (I), q may be 4. In a compound of Formula (I), q may be 5. In a compound of Formula (I), q may be 6. In a compound of Formula (I), q may be 7. In a compound of Formula (I), q may be 8. In a compound of Formula (I), q may be 9. In a compound of Formula (I), q may be 10. In a compound of Formula (I), q may be 11. In a compound of Formula (I), q may be 12. In a compound of Formula (I), q may be 13. In a compound of Formula (I), q may be 14. In a compound of Formula (I), q may be 15. In a compound of Formula (I), q may be 16. In a compound of Formula (I), q may be 17. In a compound of Formula (I), q may be 18. In a compound of Formula (I), R may be —$C(=O)OR^3$ and $R^3$ may be

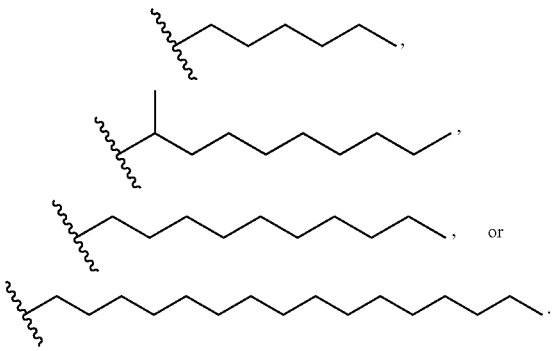

In a compound of Formula (I), R may be —$C(=O)R^4$.
In a compound of Formula (I), R may be —$C(=O)R^4$ and $R^4$ may be $C_5$-$C_{30}$alkyl. In a compound of Formula (I), R may be —$C(=O)R^4$ and $R^4$ may be optionally substituted $C_5$-$C_{20}$alkyl, optionally substituted $C_2$-$C_{20}$alkenyl, or optionally substituted $C_2$-$C_{20}$alkynyl. In a compound of Formula (I), R may be —$C(=O)R^4$ and $R^4$ may be optionally substituted $C_5$-$C_{20}$alkyl or optionally substituted $C_2$-$C_{20}$alkenyl. In a compound of Formula (I), R may be —$C(=O)R^4$ and $R^4$ may be $C_5$-$C_{30}$alkyl. In a compound of Formula (I), R may be —$C(=O)R^4$ and $R^4$ may be $C_5$-$C_{20}$alkyl. In a compound of Formula (I), R may be —$C(=O)R^4$ and $R^4$ may be $C_5$-$C_{10}$alkyl. In a compound of Formula (I), R may be —$C(=O)R^4$ and $R^4$ may be $C_{11}$-$C_{30}$alkyl. In a compound of Formula (I), R may be —$C(=O)R^4$ and $R^4$ may be $C_5$-$C_{15}$alkyl. In a compound of Formula (I), R may be —$C(=O)R^4$ and $R^4$ may be $C_{15}$-

$C_{30}$alkyl. In a compound of Formula (I), R may be —C(=O)$R^4$ and $R^4$ may be $C_{15}$-$C_{25}$alkyl. In a compound of Formula (I), R may be —C(=O)$R^4$ and $R^4$ may be substituted $C_5$-$C_{30}$alkyl. In a compound of Formula (I), R may be —C(=O)$R^4$ and $R^4$ may be substituted $C_5$-$C_{20}$alkyl. In a compound of Formula (I), R may be —C(=O)$R^4$ and $R^4$ may be substituted $C_5$-$C_{10}$alkyl. In a compound of Formula (I), R may be —C(=O)$R^4$ and $R^4$ may be substituted $C_{11}$-$C_{30}$alkyl. In a compound of Formula (I), R may be —C(=O)$R^4$ and $R^4$ may be substituted $C_5$-$C_{15}$alkyl. In a compound of Formula (I), R may be —C(=O)$R^4$ and $R^4$ may be substituted $C_{15}$-$C_{30}$alkyl. In a compound of Formula (I), R may be —C(=O)$R^4$ and $R^4$ may be substituted $C_{15}$-$C_{25}$alkyl.

Described herein are compounds of Formula (II') or a pharmaceutically acceptable salt, solvate, polymorphs, or stereoisomer thereof:

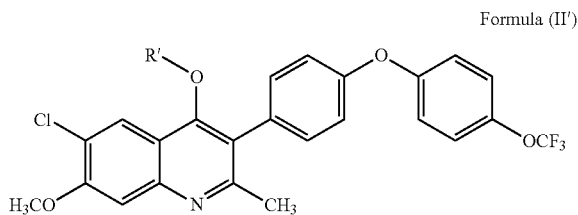

Formula (II')

wherein:
R' is —CH$_2$OC(=O)$R^7$, —$R^8$, —C(=O)O$R^9$, or —C(=O)$R^{10}$;
$R^7$ is optionally substituted $C_1$-$C_{20}$alkyl, optionally substituted $C_2$-$C_{20}$alkenyl, optionally substituted $C_2$-$C_{20}$alkynyl, optionally substituted $C_3$-$C_8$cycloalkyl, or optionally substituted $C_2$-$C_8$heterocycloalkyl;
$R^8$ is optionally substituted ($C_1$-$C_6$alkylene)aryl, optionally substituted ($C_1$-$C_6$alkylene)heteroaryl, optionally substituted ($C_1$-$C_6$alkylene)$C_3$-$C_8$cycloalkyl, or optionally substituted ($C_1$-$C_6$alkylene)$C_2$-$C_8$heterocycloalkyl;
$R^9$ is optionally substituted $C_1$-$C_{20}$alkyl, optionally substituted $C_2$-$C_{20}$alkenyl, or optionally substituted $C_2$-$C_{20}$alkynyl; and
$R^{10}$ is optionally substituted $C_1$-$C_{20}$alkyl, optionally substituted $C_2$-$C_{20}$alkenyl, or optionally substituted $C_2$-$C_{20}$alkynyl.

Described herein are compounds of Formula (II) or a pharmaceutically acceptable salt, solvate, polymorphs, or stereoisomer thereof:

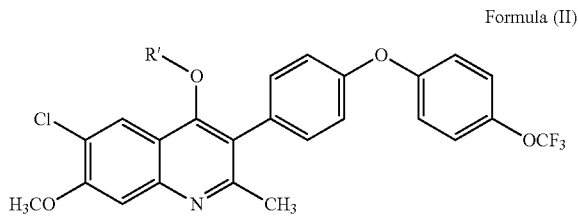

Formula (II)

wherein:
R' is —C($R^{7a}$)$_2$OC(=O)$R^7$, —$R^8$, —C(=O)O$R^9$, or —C(=O)$R^{10}$;
$R^7$ is optionally substituted $C_1$-$C_{30}$alkyl, optionally substituted $C_2$-$C_{30}$alkenyl, optionally substituted $C_2$-$C_{30}$alkynyl, optionally substituted $C_3$-$C_8$cycloalkyl, or optionally substituted $C_2$-$C_8$heterocycloalkyl;
each $R^{7a}$ is independently hydrogen, halogen, or optionally substituted $C_1$-$C_6$alkyl;
or two $R^{7a}$ are taken together with the carbon atom to which they are attached to form an optionally substituted $C_3$-$C_8$cycloalkyl;
$R^8$ is optionally substituted ($C_1$-$C_6$alkylene)aryl, optionally substituted ($C_1$-$C_6$alkylene)heteroaryl, optionally substituted ($C_1$-$C_6$alkylene)$C_3$-$C_8$cycloalkyl, or optionally substituted ($C_1$-$C_6$alkylene)$C_2$-$C_8$heterocycloalkyl;
$R^9$ is optionally substituted $C_1$-$C_{30}$alkyl, optionally substituted $C_2$-$C_{30}$alkenyl, or optionally substituted $C_2$-$C_{30}$alkynyl; and
$R^{10}$ is optionally substituted $C_1$-$C_{30}$alkyl, optionally substituted $C_2$-$C_{30}$alkenyl, or optionally substituted $C_2$-$C_{30}$alkynyl.

In a compound of Formula (II), R' may be —C($R^{7a}$)$_2$OC(=O)$R^7$, —C(=O)O$R^9$, or —C(=O)$R^{10}$. In a compound of Formula (I), R' may be —C($R^{7a}$)$_2$OC(=O)$R^7$ or —C(=O)O$R^9$. In a compound of Formula (II), R' may be —C($R^{7a}$)$_2$OC(=O)$R^7$ or —C(=O)$R^{10}$. In a compound of Formula (II), R' may be —C(=O)O$R^9$ or —C(=O)$R^{10}$.

In a compound of Formula (II), R' may be —C($R^{7a}$)$_2$OC(=O)$R^7$. In a compound of Formula (II), R' may be —C($R^{7a}$)$_2$OC(=O)$R^7$ and $R^{7a}$ may each be hydrogen. In a compound of Formula (II), R' may be —C($R^{7a}$)$_2$OC(=O)$R^7$ and $R^{7a}$ may each be $C_1$-$C_6$alkyl. In a compound of Formula (II), R' may be —C($R^{7a}$)$_2$OC(=O)$R^7$ and one $R^{7a}$ may be $C_1$-$C_6$alkyl and one $R^{7a}$ may be hydrogen. In a compound of Formula (II), R' may be —C($R^{7a}$)$_2$OC(=O)$R^7$ and one $R^{7a}$ may be halogen and one $R^{7a}$ may be hydrogen. In a compound of Formula (II), R' may be —CH$_2$OC(=O)$R^7$. In a compound of Formula (II), R' may be —CH$_2$OC(=O)$R^7$ and $R^7$ may be optionally substituted $C_1$-$C_{20}$alkyl, optionally substituted $C_2$-$C_{20}$alkenyl, or optionally substituted $C_2$-$C_{20}$alkynyl. In a compound of Formula (II), R' may be —CH$_2$OC(=O)$R^7$ and $R^7$ may be optionally substituted $C_1$-$C_{20}$alkyl or optionally substituted $C_2$-$C_{30}$alkenyl. In a compound of Formula (II), R' may be —CH$_2$OC(=O)$R^7$ and $R^7$ may be optionally substituted $C_1$-$C_{20}$alkyl or optionally substituted $C_2$-$C_{20}$alkenyl. In a compound of Formula (II), R' may be —CH$_2$OC(=O)$R^7$ and $R^7$ may be $C_1$-$C_{20}$alkyl or $C_2$-$C_{30}$alkenyl. In a compound of Formula (II), R' may be —CH$_2$OC(=O)$R^7$ and $R^7$ may be $C_1$-$C_{20}$alkyl or $C_2$-$C_{20}$alkenyl. In a compound of Formula (II), R' may be —CH$_2$OC(=O)$R^7$ and $R^7$ may be $C_1$-$C_{30}$alkyl. In a compound of Formula (II), R' may be —CH$_2$OC(=O)$R^7$ and $R^7$ may be $C_1$-$C_{25}$alkyl. In a compound of Formula (II), R' may be —CH$_2$OC(=O)$R^7$ and $R^7$ may be $C_1$-$C_{15}$alkyl. In a compound of Formula (II), R' may be —CH$_2$OC(=O)$R^7$ and $R^7$ may be $C_1$-$C_{20}$alkyl. In a compound of Formula (II), R' may be —CH$_2$OC(=O)$R^7$ and $R^7$ may be $C_1$-$C_6$alkyl. In a compound of Formula (II), R' may be —CH$_2$OC(=O)$R^7$ and $R^7$ may be $C_1$-$C_7$alkyl. In a compound of Formula (II), R' may be —CH$_2$OC(=O)$R^7$ and $R^7$ may be $C_7$-$C_{20}$alkyl. In a compound of Formula (II), R' may be —CH$_2$OC(=O)$R^7$ and $R^7$ may be substituted $C_1$-$C_{30}$alkyl. In a compound of Formula (II), R' may be —CH$_2$OC(=O)$R^7$ and $R^7$ may be substituted $C_1$-$C_{25}$alkyl. In a compound of Formula (II), R' may be —CH$_2$OC(=O)$R^7$ and $R^7$ may be substituted $C_1$-$C_{20}$alkyl. In a compound of Formula (II), R' may be —CH$_2$OC(=O)$R^7$ and $R^7$ may be substituted $C_1$-$C_{15}$alkyl. In a compound of Formula (II), R' may be —CH$_2$OC(=O)$R^7$ and $R^7$ may be substituted $C_1$-$C_6$alkyl. In a compound of Formula (II), R' may be —CH₂OC(=O)R⁷ and R⁷ may be substituted C₁-C₇alkyl. In a compound of Formula (II), R' may be —CH₂OC(=O)R⁷ and R⁷ may be substituted C₇-C₂₀alkyl. In a compound of Formula (II), R' may be —CH₂OC(=O)R⁷ and R⁷ may be

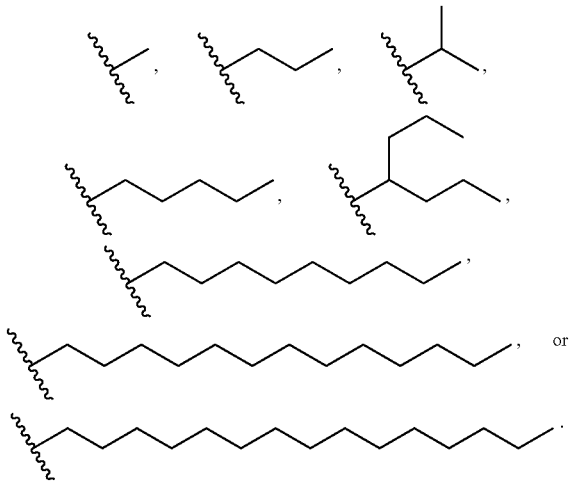

In a compound of Formula (II), R' may be —CH₂OC(=O)R⁷ and R⁷ may be

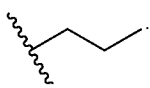

In a compound of Formula (II), R' may be —CH₂OC(=O)R⁷ and R⁷ may be C₂-C₃₀alkenyl. In a compound of Formula (II), R' may be —CH₂OC(=O)R⁷ and R⁷ may be C₂-C₆alkenyl. In a compound of Formula (II), R' may be —CH₂OC(=O)R⁷ and R⁷ may be C₇-C₃₀alkenyl. In a compound of Formula (II), R' may be —CH₂OC(=O)R⁷ and R⁷ may be C₁₅-C₂₀alkenyl. In a compound of Formula (II), R' may be —CH₂OC(=O)R⁷ and R⁷ may be C₁₅-C₃₀alkenyl. In a compound of Formula (II), R' may be —CH₂OC(=O)R⁷ and R⁷ may be C₂₀-C₃₀alkenyl. In a compound of Formula (II), R' may be —CH₂OC(=O)R⁷ and R⁷ may be substituted C₂-C₃₀alkenyl. In a compound of Formula (II), R' may be —CH₂OC(=O)R⁷ and R⁷ may be substituted C₂-C₆alkenyl. In a compound of Formula (II), R' may be —CH₂OC(=O)R⁷ and R⁷ may be substituted C₇-C₃₀alkenyl. In a compound of Formula (II), R' may be —CH₂OC(=O)R⁷ and R⁷ may be substituted C₁₅-C₂₀alkenyl. In a compound of Formula (II), R' may be —CH₂OC(=O)R⁷ and R⁷ may be substituted C₁₅-C₃₀alkenyl. In a compound of Formula (II), R' may be —CH₂OC(=O)R⁷ and R⁷ may be substituted C₂₀-C₃₀alkenyl. In a compound of Formula (II), R' may be —CH₂OC(=O)R⁷ and R⁷ may be

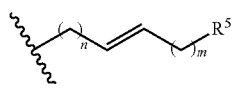

wherein R⁵ is H or methyl; n is 0-18; and m is 0-18; provided that n+m is less than 18 when R⁵ is H or n+m is less than 17 when R⁵ is methyl. In a compound of Formula (II), n may be 0. In a compound of Formula (II), n may be 1. In a compound of Formula (II), n may be 2. In a compound of Formula (II), n may be 3. In a compound of Formula (II), n may be 4. In a compound of Formula (II), n may be 5. In a compound of Formula (II), n may be 6. In a compound of Formula (II), n may be 7. In a compound of Formula (II), n may be 8. In a compound of Formula (II), n may be 9. In a compound of Formula (II), n may be 10. In a compound of Formula (II), n may be 11. In a compound of Formula (II), n may be 12. In a compound of Formula (II), n may be 13. In a compound of Formula (II), n may be 14. In a compound of Formula (II), n may be 15. In a compound of Formula (II), n may be 16. In a compound of Formula (II), n may be 17. In a compound of Formula (II), n may be 18. In a compound of Formula (II), m may be 0. In a compound of Formula (II), m may be 1. In a compound of Formula (II), m may be 2. In a compound of Formula (II), m may be 3. In a compound of Formula (II), m may be 4. In a compound of Formula (II), m may be 5. In a compound of Formula (II), m may be 6. In a compound of Formula (II), m may be 7. In a compound of Formula (II), m may be 8. In a compound of Formula (II), m may be 9. In a compound of Formula (II), m may be 10. In a compound of Formula (II), m may be 11. In a compound of Formula (II), m may be 12. In a compound of Formula (II), m may be 13. In a compound of Formula (II), m may be 14. In a compound of Formula (II), m may be 15. In a compound of Formula (II), m may be 16. In a compound of Formula (II), m may be 17. In a compound of Formula (II), m may be 18.

In a compound of Formula (II), R' may be —CH₂OC(=O)R⁷ and R⁷ may be

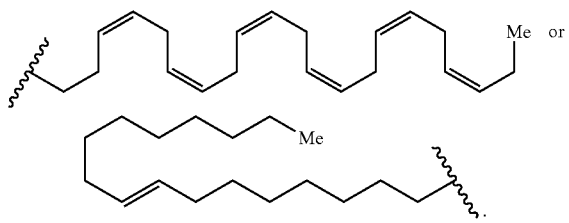

In a compound of Formula (II), R' may be —C(=O)OR⁹.
In a compound of Formula (II), R' may be —C(=O)OR⁹ and R⁹ may be optionally substituted C₁-C₂₀alkyl, optionally substituted C₂-C₂₀alkenyl, or optionally substituted C₂-C₂₀alkynyl. In a compound of Formula (II), R' may be —C(=O)OR⁹ and R⁹ may be optionally substituted C₁-C₂₀alkyl or optionally substituted C₂-C₂₀alkenyl. In a compound of Formula (II), R' may be —C(=O)OR⁹ and R⁹ may be C₅-C₃₀alkyl. In a compound of Formula (II), R' may be —C(=O)OR⁹ and R⁹ may be C₅-C₂₀alkyl. In a compound of Formula (II), R' may be —C(=O)OR⁹ and R⁹ may be C₅-C₁₀alkyl. In a compound of Formula (II), R' may be —C(=O)OR⁹ and R⁹ may be C₁₁-C₃₀alkyl. In a compound of Formula (II), R' may be —C(=O)OR⁹ and R⁹ may be C₅-C₁₅alkyl. In a compound of Formula (II), R' may be —C(=O)OR⁹ and R⁹ may be C₆-C₁₆alkyl. In a compound of Formula (II), R' may be —C(=O)OR⁹ and R⁹ may be substituted C₅-C₃₀alkyl. In a compound of Formula (II), R' may be —C(=O)OR⁹ and R⁹ may be substituted C₅-C₂₀alkyl. In a compound of Formula (II), R' may be —C(=O)OR⁹ and R⁹ may be substituted C₅-C₁₀alkyl. In a compound of Formula (II), R' may be —C(=O)OR⁹ and R⁹ may be substituted C₁₁-C₃₀alkyl. In a compound of Formula (II), R' may be —C(=O)OR⁹ and R⁹ may be substituted $C_5$-$C_{15}$alkyl. In a compound of Formula (II), R' may be —C(=O)OR$^9$ and R$^9$ may be substituted $C_6$-$C_{20}$alkyl. In a compound of Formula (II), R' may be —C(=O)OR$^9$ and R$^9$ may be

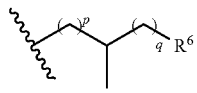

wherein R$^6$ is H or methyl; p is 0 to 18; and q is 0 to 18; provided that p+q is less than 18 when R$^6$ is H or p+q is less than 17 when R$^6$ is methyl. In a compound of Formula (II), p may be 0. In a compound of Formula (II), p may be 1. In a compound of Formula (II), p may be 2. In a compound of Formula (II), p may be 3. In a compound of Formula (II), p may be 4. In a compound of Formula (II), p may be 5. In a compound of Formula (II), p may be 6. In a compound of Formula (II), p may be 7. In a compound of Formula (II), p may be 8. In a compound of Formula (II), p may be 9. In a compound of Formula (II), p may be 10. In a compound of Formula (II), p may be 11. In a compound of Formula (II), p may be 12. In a compound of Formula (II), p may be 13. In a compound of Formula (II), p may be 14. In a compound of Formula (II), p may be 15. In a compound of Formula (II), p may be 16. In a compound of Formula (II), p may be 17. In a compound of Formula (II), p may be 18. In a compound of Formula (II), q may be 0. In a compound of Formula (II), q may be 1. In a compound of Formula (II), q may be 2. In a compound of Formula (II), q may be 3. In a compound of Formula (II), q may be 4. In a compound of Formula (II), q may be 5. In a compound of Formula (II), q may be 6. In a compound of Formula (II), q may be 7. In a compound of Formula (II), q may be 8. In a compound of Formula (II), q may be 9. In a compound of Formula (II), q may be 10. In a compound of Formula (II), q may be 11. In a compound of Formula (II), q may be 12. In a compound of Formula (II), q may be 13. In a compound of Formula (II), q may be 14. In a compound of Formula (II), q may be 15. In a compound of Formula (II), q may be 16. In a compound of Formula (II), q may be 17. In a compound of Formula (II), q may be 18. In a compound of Formula (II), R' may be —C(=O)OR$^9$ and R$^9$ may be

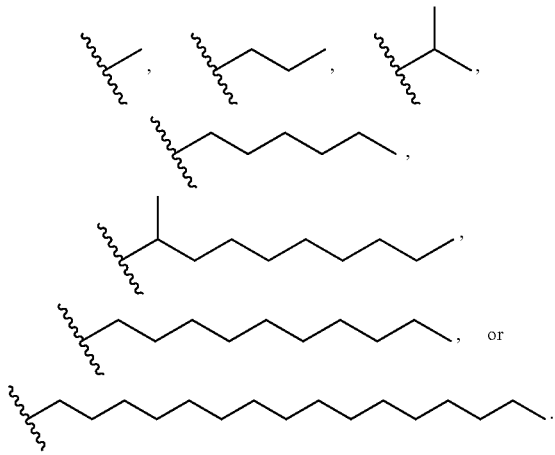

In a compound of Formula (II), R' may be —C(=O)R$^{10}$.
In a compound of Formula (II), R' may be —C(=O)R$^{10}$ and R$^{10}$ may be optionally substituted $C_1$-$C_{20}$alkyl, optionally substituted $C_2$-$C_{20}$alkenyl, or optionally substituted $C_2$-$C_{20}$alkynyl. In a compound of Formula (II), R' may be —C(=O)R$^{10}$ and R'$^{o}$ may be optionally substituted $C_1$-$C_{20}$alkyl or optionally substituted $C_2$-$C_{20}$alkenyl. In a compound of Formula (II), R' may be —C(=O)R$^{10}$ and R'$^{o}$ may be $C_5$-$C_{30}$alkyl. In a compound of Formula (II), R' may be —C(=O)R$^{10}$ and R'$^{o}$ may be $C_5$-$C_{20}$alkyl. In a compound of Formula (II), R' may be —C(=O)R$^{10}$ and R$^{10}$ may be $C_5$-$C_{10}$alkyl. In a compound of Formula (II), R' may be —C(=O)R$^{10}$ and R$^{10}$ may be $C_{11}$-$C_{30}$alkyl. In a compound of Formula (II), R' may be —C(=O)R$^{10}$ and R$^{10}$ may be $C_5$-$C_{15}$alkyl. In a compound of Formula (II), R' may be —C(=O)R$^{10}$ and R$^{10}$ may be $C_{15}$-$C_{30}$alkyl. In a compound of Formula (II), R' may be —C(=O)R$^{10}$ and R$^{10}$ may be $C_{15}$-$C_{25}$alkyl. In a compound of Formula (II), R' may be —C(=O)R$^{10}$ and R$^{10}$ may be substituted $C_5$-$C_{30}$alkyl. In a compound of Formula (II), R' may be —C(=O)R$^{10}$ and R$^{10}$ may be substituted $C_5$-$C_{20}$alkyl. In a compound of Formula (II), R' may be —C(=O)R$^{10}$ and R$^{10}$ may be substituted $C_5$-$C_{10}$alkyl. In a compound of Formula (II), R' may be —C(=O)R$^{10}$ and R$^{10}$ may be substituted $C_{11}$-$C_{30}$alkyl. In a compound of Formula (II), R' may be —C(=O)R$^{10}$ and R$^{10}$ may be substituted $C_5$-$C_{15}$alkyl. In a compound of Formula (II), R' may be —C(=O)R$^{10}$ and R$^{10}$ may be substituted $C_{15}$-$C_{30}$alkyl. In a compound of Formula (II), R' may be —C(=O)R$^{10}$ and R$^{10}$ may be substituted $C_{15}$-$C_{25}$alkyl.

Described herein are crystalline compounds of Formula (II) or a pharmaceutically acceptable salt, solvate, or stereoisomer thereof:

Formula (II)

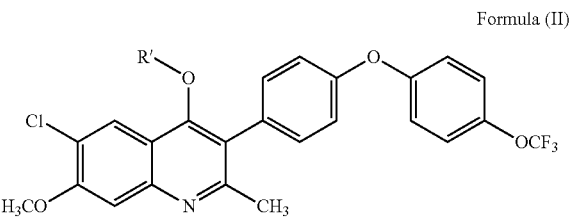

wherein:
R' is —C(R$^{7a}$)$_2$OC(=O)R$^7$, —R$^8$, —C(=O)OR$^9$, or —C(=O)R$^{10}$;
R$^7$ is optionally substituted $C_1$-$C_{30}$alkyl, optionally substituted $C_2$-$C_{30}$alkenyl, optionally substituted $C_2$-$C_{30}$alkynyl, optionally substituted $C_3$-$C_8$cycloalkyl, or optionally substituted $C_2$-$C_8$heterocycloalkyl;
each R$^{7a}$ is independently hydrogen, halogen, or optionally substituted $C_1$-$C_6$alkyl;
or two R$^{7a}$ are taken together with the carbon atom to which they are attached to form an optionally substituted $C_3$-$C_8$cycloalkyl;
R$^8$ is optionally substituted ($C_1$-$C_6$alkylene)aryl, optionally substituted ($C_1$-$C_6$alkylene)heteroaryl, optionally substituted ($C_1$-$C_6$alkylene)$C_3$-$C_8$cycloalkyl, or optionally substituted ($C_1$-$C_6$alkylene)$C_2$-$C_8$heterocycloalkyl;
R$^9$ is optionally substituted $C_1$-$C_{30}$alkyl, optionally substituted $C_2$-$C_{30}$alkenyl, or optionally substituted $C_2$-$C_{30}$alkynyl; and
R$^{10}$ is optionally substituted $C_1$-$C_{30}$alkyl, optionally substituted $C_2$-$C_{30}$alkenyl, or optionally substituted $C_2$-$C_{30}$alkynyl.

The crystalline compound of Formula (II) may be crystalline ((6-chloro-7-methoxy-2-methyl-3-(4-(4-(trifluoromethoxy)phenoxy)phenyl)quinolin-4-yl)oxy)methyl butyrate or a pharmaceutically acceptable salt, solvate, or stereoisomer thereof.

Figure 41:
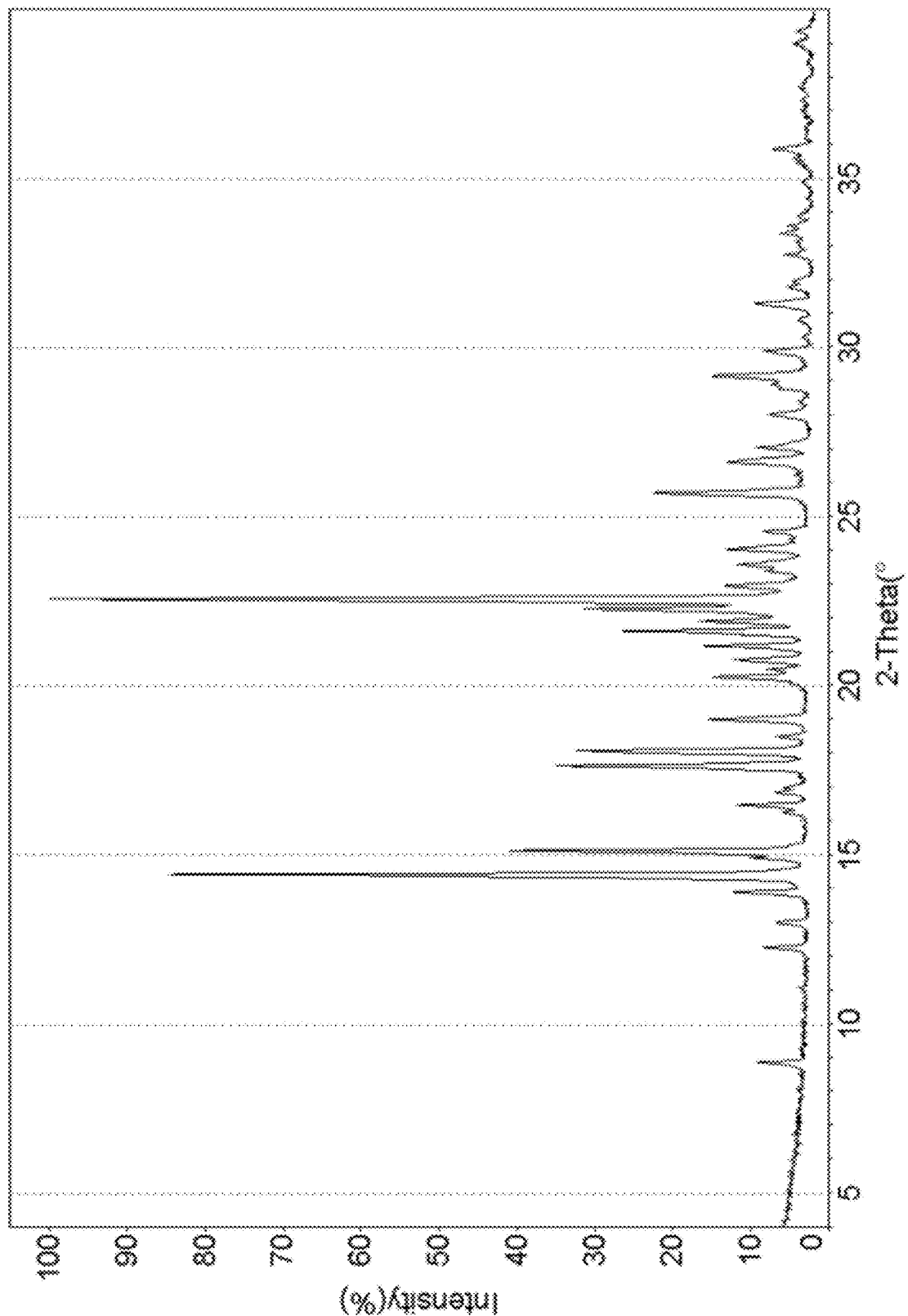
FIG. 41 depicts the characteristic X-ray diffraction pattern of crystalline Compound 2.
Figure 42A:
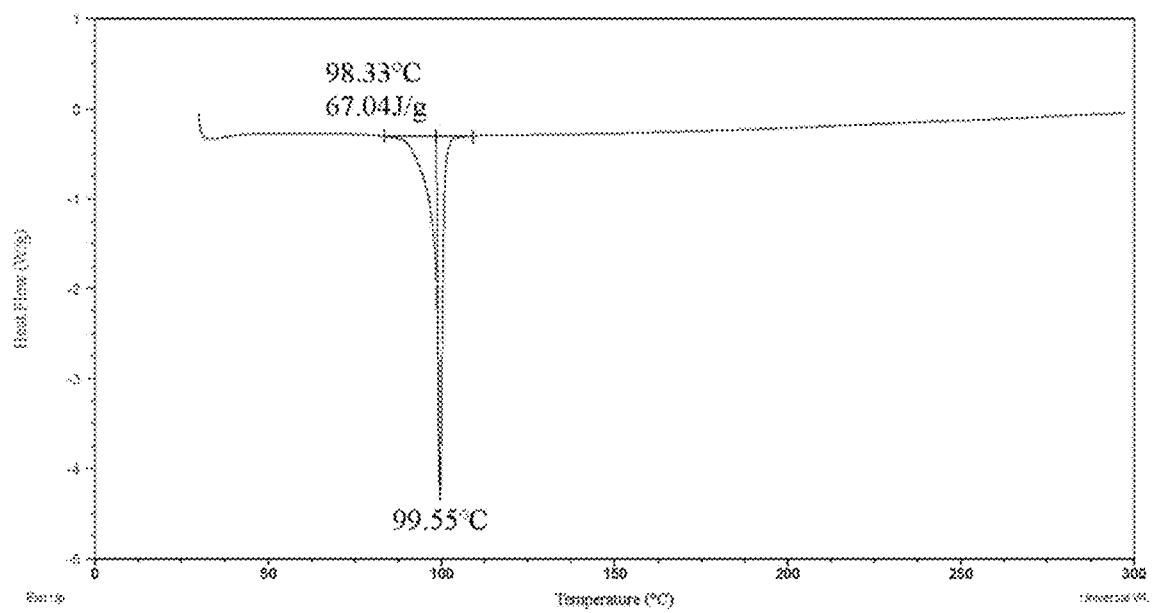
FIG. 42A depicts the DSC of crystalline Compound 2.

The crystalline form of ((6-chloro-7-methoxy-2-methyl-3-(4-(4-(trifluoromethoxy)phenoxy)phenyl)quinolin-4-yl)oxy)methyl butyrate may have at least one of the following properties:

(a) an X-Ray powder diffraction (XRPD) pattern substantially the same as shown in FIG. 41; or
(b) an X-ray powder diffraction (XRPD) pattern comprising characteristic peaks at about 14.4±0.1° 2θ, about 15.1±0.1° 2θ, about 17.7±0.1° 2θ, about 18.1±0.1° 2θ, about 22.3±0.1° 2θ, and about 22.6±0.1° 2θ; or
(c) a DSC thermogram substantially the same to the one set forth in FIG. 42A; or
(d) a DSC thermogram with an endotherm having a peak at about 99.5° C.

The crystalline form of (((6-chloro-7-methoxy-2-methyl-3-(4-(4-(trifluoromethoxy)phenoxy)phenyl)quinolin-4-yl)oxy)methyl butyrate may have an X-ray powder diffraction (XRPD) pattern further comprising characteristic peaks at about 19.0°±0.1° 2θ, about 20.3°±0.1° 2θ, about 21.2°±0.1° 2θ, about 26.7°±0.1° 2θ, and about 29.2°±0.1° 2θ.

Described herein are compounds of Formula (III) or a pharmaceutically acceptable salt, solvate, polymorphs, or stereoisomer thereof:

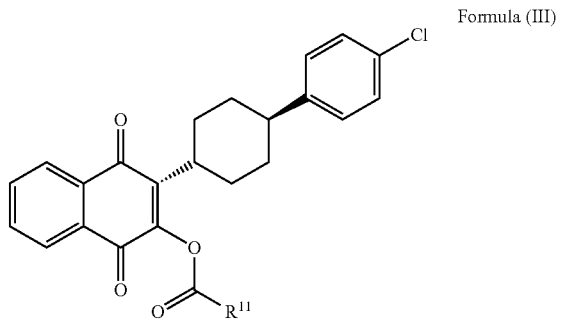

Formula (III)

wherein:
$R^{11}$ is a lipophilic moiety.

In a compound of Formula (III), $R^{11}$ may be optionally substituted $C_1$-$C_{30}$alkyl, optionally substituted $C_2$-$C_{30}$alkenyl, or optionally substituted $C_2$-$C_{30}$alkynyl. In a compound of Formula (III), $R^{11}$ may be optionally substituted $C_1$-$C_{20}$alkyl, optionally substituted $C_2$-$C_{20}$alkenyl, or optionally substituted $C_2$-$C_{20}$alkynyl.

In a compound of Formula (III), $R^{11}$ may be $C_1$-$C_{20}$alkyl. In a compound of Formula (III), $R^{11}$ may be $C_1$-$C_{30}$alkyl. In a compound of Formula (III), $R^{11}$ may be $C_1$-$C_6$alkyl. In a compound of Formula (III), $R^{11}$ may be $C_7$-$C_{30}$alkyl. In a compound of Formula (III), $R^{11}$ may be $C_7$-$C_{20}$alkyl. In a compound of Formula (III), $R^{11}$ may be substituted $C_1$-$C_{20}$alkyl. In a compound of Formula (III), $R^{11}$ may be substituted $C_1$-$C_{30}$alkyl. In a compound of Formula (III), $R^{11}$ may be substituted $C_1$-$C_6$alkyl. In a compound of Formula (III), $R^{11}$ may be substituted $C_7$-$C_{30}$alkyl. In a compound of Formula (III), $R^{11}$ may be substituted $C_7$-$C_{20}$alkyl. In a compound of Formula (III), $R^{11}$ may be

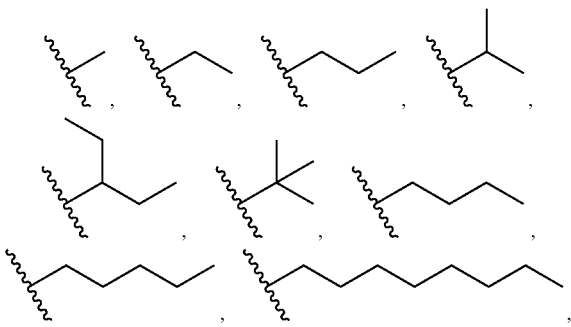

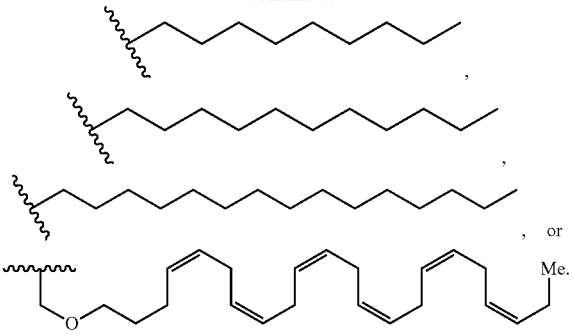

In a compound of Formula (III), $R^{11}$ may be $C_2$-$C_{30}$alkenyl. In a compound of Formula (III), $R^{11}$ may be $C_3$-$C_{30}$alkenyl. In a compound of Formula (III), $R^{11}$ may be $C_6$-$C_{30}$alkenyl. In a compound of Formula (III), $R^{11}$ may be $C_6$-$C_{25}$alkenyl. In a compound of Formula (III), $R^{11}$ may be $C_{15}$-$C_{25}$alkenyl. In a compound of Formula (III), $R^{11}$ may be $C_2$-$C_{25}$alkenyl. In a compound of Formula (III), $R^{11}$ may be $C_2$-$C_{20}$alkenyl. In a compound of Formula (III), $R^{11}$ may be $C_2$-$C_{15}$alkenyl. In a compound of Formula (III), $R^{11}$ may be $C_2$-$C_{10}$alkenyl. In a compound of Formula (III), $R^{11}$ may be $C_2$-$C_6$alkenyl. In a compound of Formula (III), $R^{11}$ may be $C_6$-$C_{30}$alkenyl. In a compound of Formula (III), $R^{11}$ may be $C_6$-$C_{25}$alkenyl. In a compound of Formula (III), $R^{11}$ may be substituted $C_2$-$C_{30}$alkenyl. In a compound of Formula (III), $R^{11}$ may be substituted $C_3$-$C_{30}$alkenyl. In a compound of Formula (III), $R^{11}$ may be substituted $C_6$-$C_{30}$alkenyl. In a compound of Formula (III), $R^{11}$ may be substituted $C_6$-$C_{25}$alkenyl. In a compound of Formula (III), $R^{11}$ may be substituted $C_{15}$-$C_{25}$alkenyl. In a compound of Formula (III), $R^{11}$ may be substituted $C_2$-$C_{25}$alkenyl. In a compound of Formula (III), $R^{11}$ may be substituted $C_2$-$C_{20}$alkenyl. In a compound of Formula (III), $R^{11}$ may be substituted $C_2$-$C_{15}$alkenyl. In a compound of Formula (III), $R^{11}$ may be substituted $C_2$-$C_{10}$alkenyl. In a compound of Formula (III), $R^{11}$ may be substituted $C_2$-$C_6$alkenyl. In a compound of Formula (III), $R^{11}$ may be substituted $C_6$-$C_{30}$alkenyl. In a compound of Formula (III), $R^{11}$ may be substituted $C_6$-$C_{25}$alkenyl. In a compound of Formula (III), $R^{11}$ may be

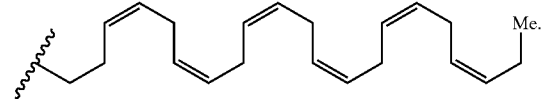 [SMILES: *CC/C=C\C/C=C\C/C=C\C/C=C\C/C=C\C/C=C\CC]

In a compound of Formula (III), $R^{21}$ may comprise between 1 and 10 double bonds. In a compound of Formula (III), $R^{21}$ may comprise between 1 and 6 double bonds. In a compound of Formula (III), $R^{21}$ may comprise between 4 and 8 double bonds. In a compound of Formula (III), $R^{21}$ may comprise between 4 and 6 double bonds. In a compound of Formula (III), $R^{21}$ may comprise between 2 and 8 double bonds. In a compound of Formula (III), $R^{21}$ may comprise between 2 and 6 double bonds. In a compound of Formula (III), $R^{21}$ may comprise more than 1 double bond. In a compound of Formula (III), $R^{21}$ may comprise more than 2 double bonds. In a compound of Formula (III), $R^{21}$ may comprise more than 3 double bonds. In a compound of Formula (III), $R^{21}$ may comprise more than 4 double bonds. In a compound of Formula (III), $R^{21}$ may comprise more than 5 double bonds. In a compound of Formula (III), $R^{21}$ may comprise 1 double bond. In a compound of Formula (III), $R^{21}$ may comprise 2 double bonds. In a compound of Formula (III), $R^{21}$ may comprise 3 double bonds. In a compound of Formula (III), $R^{21}$ may comprise 4 double bonds. In a compound of Formula (III), $R^{21}$ may comprise 5 double bonds. In a compound of Formula (III), $R^{21}$ may comprise 6 double bonds.

Described herein are compounds of Formula (IV) or a pharmaceutically acceptable salt, solvate, polymorphs, or stereoisomer thereof:

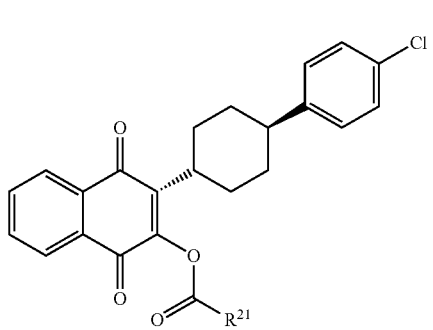

Formula (IV)

wherein $R^{21}$ is optionally substituted $C_3$-$C_{30}$alkenyl or optionally substituted $C_2$-$C_{30}$alkynyl.

In a compound of Formula (IV), $R^{21}$ may be $C_3$-$C_{30}$alkenyl or $C_2$-$C_{30}$alkynyl. In a compound of Formula (IV), $R^{21}$ may be $C_3$-$C_{30}$alkenyl. In a compound of Formula (IV), $R^{21}$ may be $C_6$-$C_{30}$alkenyl. In a compound of Formula (IV), $R^{21}$ may be $C_6$-$C_{25}$alkenyl. In a compound of Formula (IV), $R^{21}$ may be $C_{15}$-$C_{25}$alkenyl. In a compound of Formula (IV), $R^{21}$ may be substituted $C_3$-$C_{30}$alkenyl. In a compound of Formula (IV), $R^{21}$ may be substituted $C_6$-$C_{30}$alkenyl. In a compound of Formula (IV), $R^{21}$ may be substituted $C_6$-$C_{25}$alkenyl. In a compound of Formula (IV), $R^{21}$ may be substituted $C_{15}$-$C_{25}$alkenyl. In a compound of Formula (IV), $R^{21}$ may be

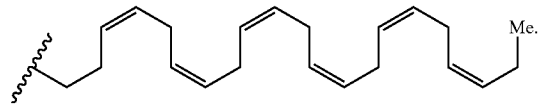 [SMILES: *CC/C=C\C/C=C\C/C=C\C/C=C\C/C=C\C/C=C\CC]

In a compound of Formula (IV), $R^{21}$ may comprise between 1 and 10 double bonds. In a compound of Formula (IV), $R^{21}$ may comprise between 1 and 6 double bonds. In a compound of Formula (IV), $R^{21}$ may comprise between 4 and 8 double bonds. In a compound of Formula (IV), $R^{21}$ may comprise between 4 and 6 double bonds. In a compound of Formula (IV), $R^{21}$ may comprise between 2 and 8 double bonds. In a compound of Formula (IV), $R^{21}$ may comprise between 2 and 6 double bonds. In a compound of Formula (IV), $R^{21}$ may comprise more than 1 double bond. In a compound of Formula (IV), $R^{21}$ may comprise more than 2 double bonds. In a compound of Formula (IV), $R^{21}$ may comprise more than 3 double bonds. In a compound of Formula (IV), $R^{21}$ may comprise more than 4 double bonds. In a compound of Formula (IV), $R^{21}$ may comprise more than 5 double bonds. In a compound of Formula (IV), $R^{21}$ may comprise 1 double bond. In a compound of Formula (IV), $R^{21}$ may comprise 2 double bonds. In a compound of Formula (IV), $R^{21}$ may comprise 3 double bonds. In a compound of Formula (IV), $R^{21}$ may comprise 4 double bonds. In a compound of Formula (IV), $R^{21}$ may comprise 5 double bonds. In a compound of Formula (IV), $R^{21}$ may comprise 6 double bonds.

Described herein are crystalline compounds of Formula (III) or a pharmaceutically acceptable salt, solvate, or stereoisomer thereof:

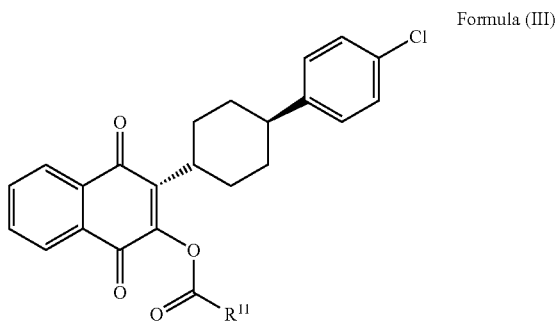

Formula (III)

wherein:
$R^{11}$ is a lipophilic moiety.

Described herein are crystalline forms of ELQ-300 or a pharmaceutically acceptable salt, solvate, or stereoisomer thereof:

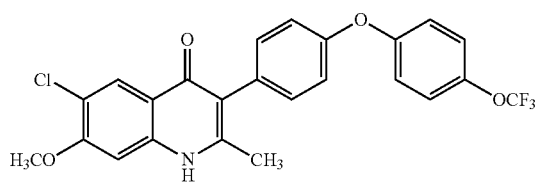 [SMILES: COc1cc2[nH]c(C)c(-c3ccc(Oc4ccc(OC(F)(F)F)cc4)cc3)c(=O)c2cc1Cl]

ELQ-300 (6-chloro-7-methoxy-2-methyl-3-(4-(4-(trifluoromethoxy)phenoxy)phenyl)quinolin-4(1H)-one). The crystalline form of ELQ-300, or a pharmaceutically acceptable salt, solvate, or stereoisomer thereof may be ELQ-300-Form IA. The crystalline form of ELQ-300, or a pharmaceutically acceptable salt, solvate, or stereoisomer thereof may be ELQ-300-Form IB. The crystalline form of ELQ-300, or a pharmaceutically acceptable salt, solvate, or stereoisomer thereof may be ELQ-300-Form II. The crystalline form of ELQ-300, or a pharmaceutically acceptable salt, solvate, or stereoisomer thereof may be ELQ-300-Form III. The crystalline form of ELQ-300, or a pharmaceutically acceptable salt, solvate, or stereoisomer thereof may be ELQ-300-Form IV. The crystalline form of ELQ-300, or a pharmaceutically acceptable salt, solvate, or stereoisomer thereof may be ELQ-300-Form V.

Described herein are crystalline forms of atovaquone or a pharmaceutically acceptable salt, solvate, or stereoisomer thereof:

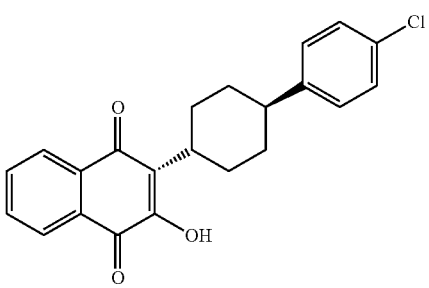

atovaquone (trans-2-[4-(4-chlorophenyl)cyclohexyl]-3-hydroxy-1,4-naphthalenedione).

The crystalline form of atovaquone, or a pharmaceutically acceptable salt, solvate, or stereoisomer thereof may be atovaquone—Form I. The crystalline form of atovaquone, or a pharmaceutically acceptable salt, solvate, or stereoisomer thereof may be atovaquone—Form II.

Described herein are crystalline forms of pyronaridine or a pharmaceutically acceptable salt, solvate, or stereoisomer thereof:

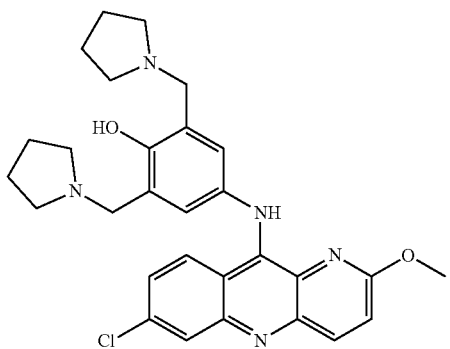 [SMILES: COc1ccc2nc3cc(Cl)ccc3c(Nc3cc(CN4CCCC4)c(O)c(CN4CCCC4)c3)c2n1]

pyronaridine (4-[(7-chloro-2-methoxy-pyrido[3,2-b]quinolin-10-yl)amino]-2,6-bis(pyrrolidin-1-ylmethyl)phenol).

The crystalline form of pyronaridine may be obtained from a pyronaridine salt. The pyronaridine salt may be pyronaridine pamoate, pyronaridine benzenesulfonate, pyronaridine palmitate, pyronaridine naphthalate, pyronaridine benzoate, pyronaridine edetate, pyronaridine edisylate, pyronaridine estolate, pyronaridine napsylate, pyronaridine mesylate, pyronaridine stearate, or pyronaridine valerate. The pyronaridine salt may be pyronaridine pamoate.

The crystalline form of pyronaridine, or a pharmaceutically acceptable salt, solvate, or stereoisomer thereof may be pyronaridine-Form I. The crystalline form of pyronaridine, or a pharmaceutically acceptable salt, solvate, or stereoisomer thereof may be pyronaridine-Form II. The crystalline form of pyronaridine, or a pharmaceutically acceptable salt, solvate, or stereoisomer thereof may be pyronaridine-Form III. The crystalline form of pyronaridine, or a pharmaceutically acceptable salt, solvate, or stereoisomer thereof may be pyronaridine-Form V. The crystalline form of pyronaridine, or a pharmaceutically acceptable salt, solvate, or stereoisomer thereof may be pyronaridine-Form V.

In some embodiments, the compound disclosed herein has the structure provided in Table 1.

TABLE 1

| Comp. | Name | Structure |
|---|---|---|
| 1 | (6-chloro-7-methoxy-2-methyl-3-(4-(4-(trifluoromethoxy)phenoxy)phenyl)quinolin-4-yloxy)methyl acetate | 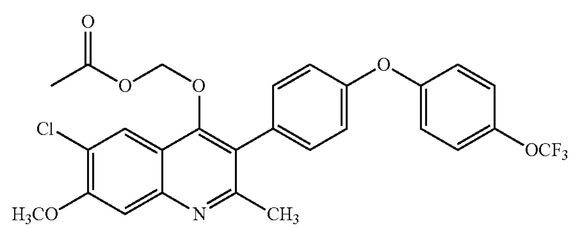 [SMILES: COc1cc2nc(C)c(-c3ccc(Oc4ccc(OC(F)(F)F)cc4)cc3)c(OCOC(C)=O)c2cc1Cl] |
| 2 | (6-chloro-7-methoxy-2-methyl-3-(4-(4-(trifluoromethoxy)phenoxy)phenyl)quinolin-4-yloxy)methyl butyrate | 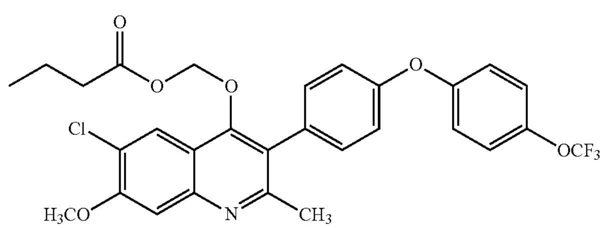 [SMILES: CCCC(=O)OCOc1c(-c2ccc(Oc3ccc(OC(F)(F)F)cc3)cc2)c(C)nc2cc(OC)c(Cl)cc12] |
| 3 | (6-chloro-7-methoxy-2-methyl-3-(4-(4-(trifluoromethoxy)phenoxy)phenyl)quinolin-4-yloxy)methyl isobutyrate | 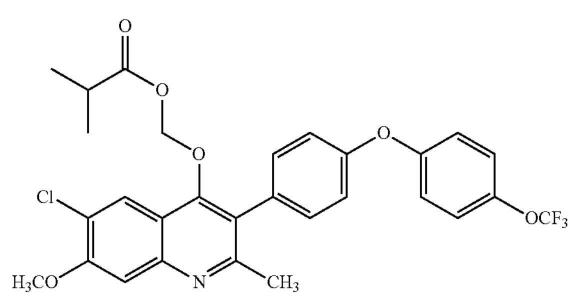 [SMILES: COc1cc2nc(C)c(-c3ccc(Oc4ccc(OC(F)(F)F)cc4)cc3)c(OCOC(=O)C(C)C)c2cc1Cl] |

TABLE 1-continued

| Comp. | Name | Structure |
|---|---|---|
| 4 | (6-chloro-7-methoxy-2-methyl-3-(4-(4-(trifluoromethoxy)phenoxy)phenyl)quinolin-4-yloxy)methyl hexanoate | 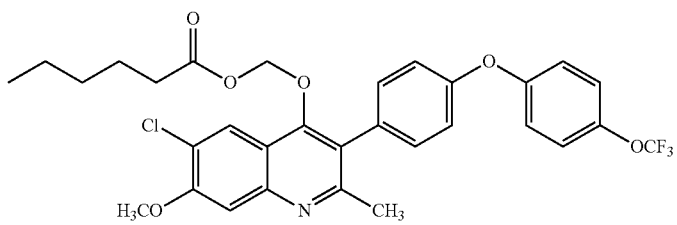 [SMILES: CCCCCC(=O)OCOc1c(-c2ccc(Oc3ccc(OC(F)(F)F)cc3)cc2)c(C)nc2cc(OC)c(Cl)cc12] |
| 5 | (6-chloro-7-methoxy-2-methyl-3-(4-(4-(trifluoromethoxy)phenoxy)phenyl)quinolin-4-yloxy)methyl cyclohexanecarboxylate | 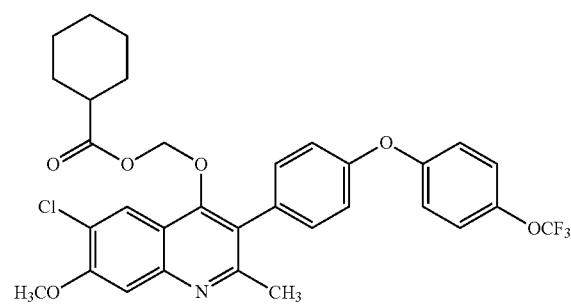 [SMILES: COc1cc2nc(C)c(-c3ccc(Oc4ccc(OC(F)(F)F)cc4)cc3)c(OCOC(=O)C3CCCCC3)c2cc1Cl] |
| 6 | 4-((6-chloro-7-methoxy-2-methyl-3-(4-(4-(trifluoromethoxy)phenoxy)phenyl)quinolin-4-yloxy)methyl)phenyl acetate | 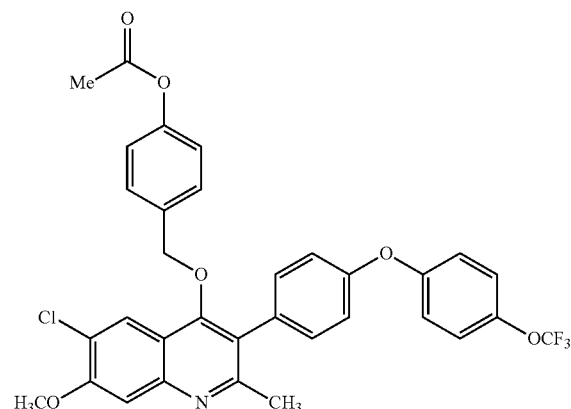 |
| 7 | (6-chloro-7-methoxy-2-methyl-3-(4-(4-(trifluoromethoxy)phenoxy)phenyl)quinolin-4-yloxy)methyl 2-propylpentanoate | 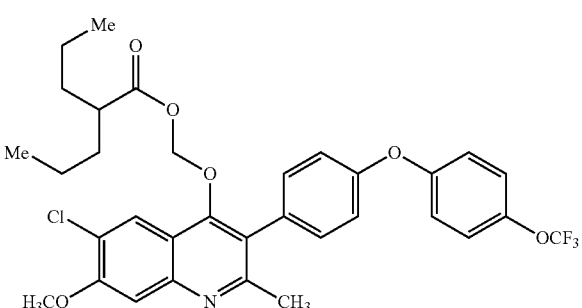 |
| 8 | (6-chloro-7-methoxy-2-methyl-3-(4-(4-(trifluoromethoxy)phenoxy)phenyl)quinolin-4-yloxy)methyl decanoate | 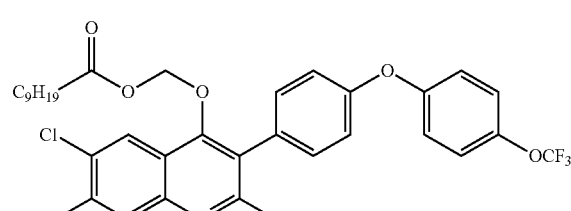 |

TABLE 1-continued

| Comp. | Name | Structure |
|---|---|---|
| 9 | (6-chloro-7-methoxy-2-methyl-3-(4-(4-(trifluoromethoxy)phenoxy)phenyl)quinolin-4-yloxy)methyl tetradecanoate | 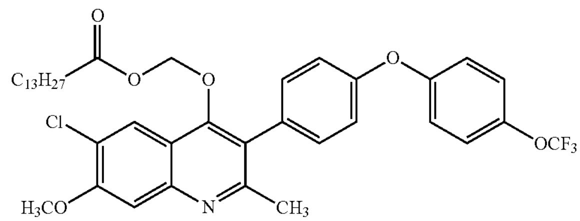 |
| 10 | (6-chloro-7-methoxy-2-methyl-3-(4-(4-(trifluoromethoxy)phenoxy)phenyl)quinolin-4-yloxy)methyl palmitate | 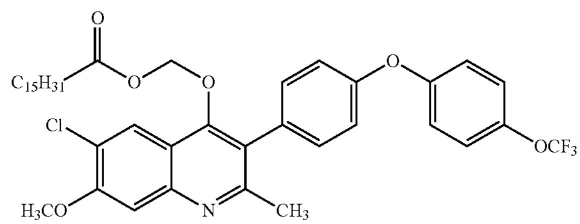 |
| 11 | (E)-(6-chloro-7-methoxy-2-methyl-3-(4-(4-(trifluoromethoxy)phenoxy)phenyl)quinolin-4-yloxy)methyl octadec-9-enoate | 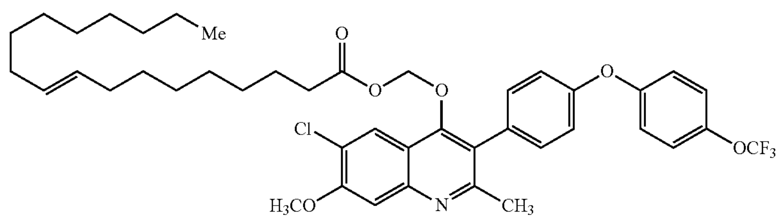 [SMILES: CCCCCCCC/C=C/CCCCCCCC(=O)OCOc1c(-c2ccc(Oc3ccc(OC(F)(F)F)cc3)cc2)c(C)nc2cc(OC)c(Cl)cc12] |
| 12 | 6-chloro-7-methoxy-2-methyl-3-(4-(4-(trifluoromethoxy)phenoxy)phenyl)quinolin-4-yl methyl carbonate | 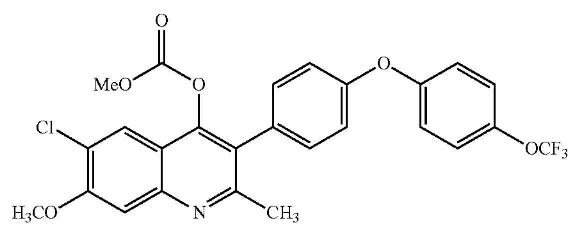 [SMILES: COC(=O)Oc1c(-c2ccc(Oc3ccc(OC(F)(F)F)cc3)cc2)c(C)nc2cc(OC)c(Cl)cc12] |
| 13 | 6-chloro-7-methoxy-2-methyl-3-(4-(4-(trifluoromethoxy)phenoxy)phenyl)quinolin-4-yl ethyl carbonate | 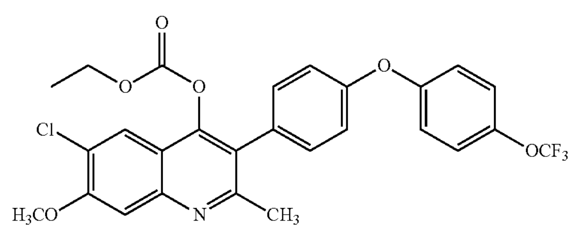 [SMILES: CCOC(=O)Oc1c(-c2ccc(Oc3ccc(OC(F)(F)F)cc3)cc2)c(C)nc2cc(OC)c(Cl)cc12] |
| 14 | 6-chloro-7-methoxy-2-methyl-3-(4-(4-(trifluoromethoxy)phenoxy)phenyl)quinolin-4-yl propyl carbonate | 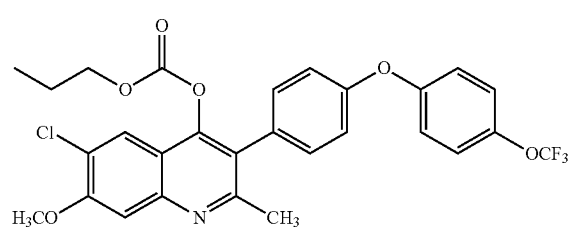 [SMILES: CCCOC(=O)Oc1c(-c2ccc(Oc3ccc(OC(F)(F)F)cc3)cc2)c(C)nc2cc(OC)c(Cl)cc12] |
| 15 | 6-chloro-7-methoxy-2-methyl-3-(4-(4-(trifluoromethoxy)phenoxy)phenyl)quinolin-4-yl isopropyl carbonate | 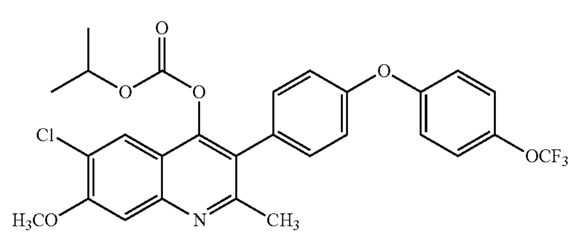 [SMILES: COc1cc2nc(C)c(-c3ccc(Oc4ccc(OC(F)(F)F)cc4)cc3)c(OC(=O)OC(C)C)c2cc1Cl] |

TABLE 1-continued

| Comp. | Name | Structure |
|---|---|---|
| 16 | 6-chloro-7-methoxy-2-methyl-3-(4-(4-(trifluoromethoxy)phenoxy)phenyl)quinolin-4-yl hexyl carbonate | 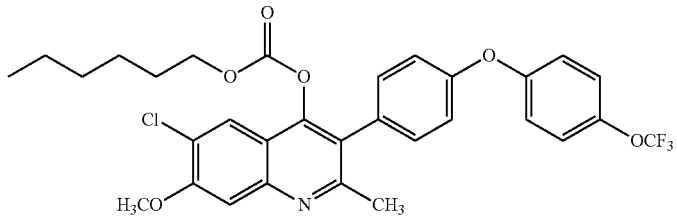 [SMILES: CCCCCCOC(=O)Oc1c(-c2ccc(Oc3ccc(OC(F)(F)F)cc3)cc2)c(C)nc2cc(OC)c(Cl)cc12] |
| 17 | 6-chloro-7-methoxy-2-methyl-3-(4-(4-(trifluoromethoxy)phenoxy)phenyl)quinolin-4-yl decyl carbonate | 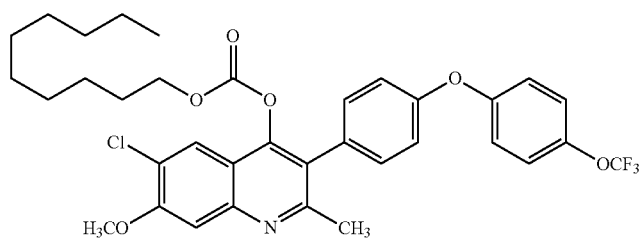 [SMILES: CCCCCCCCCCOC(=O)Oc1c(-c2ccc(Oc3ccc(OC(F)(F)F)cc3)cc2)c(C)nc2cc(OC)c(Cl)cc12] |
| 18 | 6-chloro-7-methoxy-2-methyl-3-(4-(4-(trifluoromethoxy)phenoxy)phenyl)quinolin-4-yl hexadecyl carbonate | 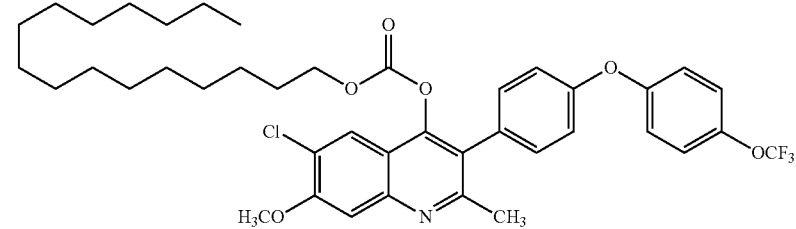 [SMILES: CCCCCCCCCCCCCCCCOC(=O)Oc1c(-c2ccc(Oc3ccc(OC(F)(F)F)cc3)cc2)c(C)nc2cc(OC)c(Cl)cc12] |
| 19 | 6-chloro-7-methoxy-2-methyl-3-(4-(4-(trifluoromethoxy)phenoxy)phenyl)quinolin-4-yl decan-2-yl carbonate | 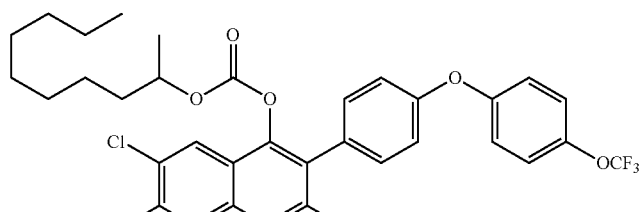 |
| 35 | ((6-chloro-7-methoxy-2-methyl-3-(4-(4-(trifluoromethoxy)phenoxy)phenyl)quinolin-4-yl)oxy)methyl (4Z,7Z,10Z,13Z,16Z,19Z)-docosa-4,7,10,13,16,19-hexaenoate | 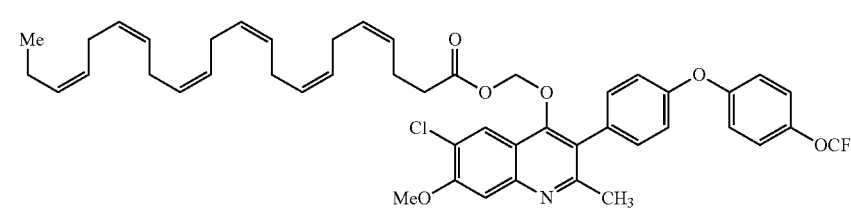 [SMILES: CC/C=C\C/C=C\C/C=C\C/C=C\C/C=C\C/C=C\CCC(=O)OCOc1c(-c2ccc(Oc3ccc(OC(F)(F)F)cc3)cc2)c(C)nc2cc(OC)c(Cl)cc12] |

In some embodiments, the compound disclosed herein has the structure provided in Table 2.

TABLE 2

| Comp. | Name | Structure |
|---|---|---|
| 20 | 3-((1r,4r)-4-(4-chlorophenyl)cyclohexyl)-1,4-dioxo-1,4-dihydronaphthalen-2-yl acetate | 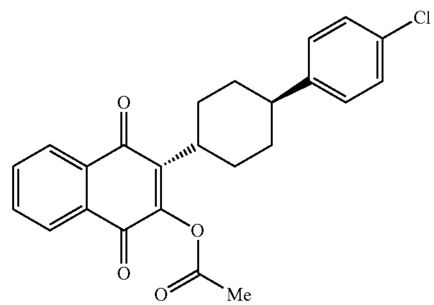 |
| 21 | 3-((1r,4r)-4-(4-chlorophenyl)cyclohexyl)-1,4-dioxo-1,4-dihydronaphthalen-1-2-yl propionate | 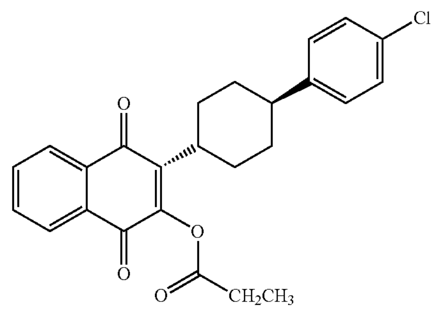 |
| 22 | 3-((1r,4r)-4-(4-chlorophenyl)cyclohexyl)-1,4-dioxo-1,4-dihydronaphthalen-2-yl butyrate | 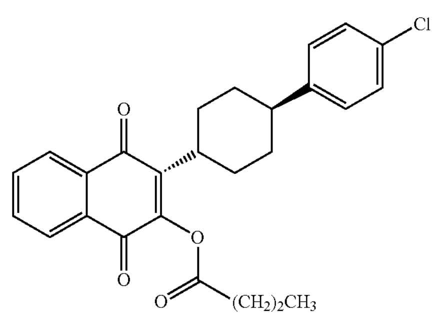 |
| 23 | 3-((1r,4r)-4-(4-chlorophenyl)cyclohexyl)-1,4-dioxo-1,4-dihydronapthalen-2-yl pivalate | 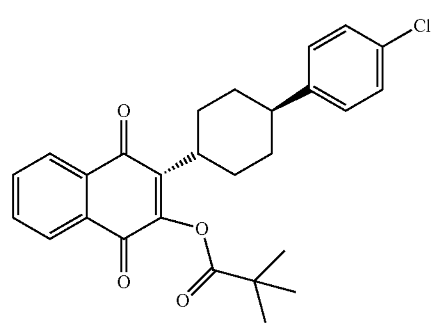 |

TABLE 2-continued

| Comp. | Name | Structure |
|---|---|---|
| 24 | 3-((1r,4r)-4-(4-chlorophenyl)cyclohexyl)-1,4-dioxo-1,4-dihydronaphthalen-2-yl isobutyrate | 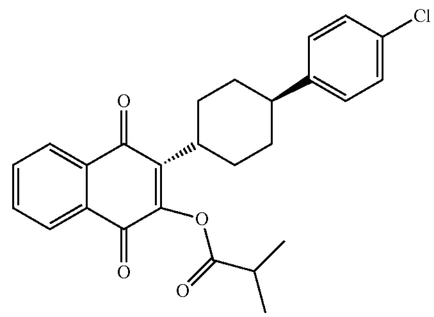 |
| 25 | 3-((1r,4r)-4-(4-chlorophenyl)cyclohexyl)-1,4-dioxo-1,4-dihydronaphthalen-2-yl hexanoate | 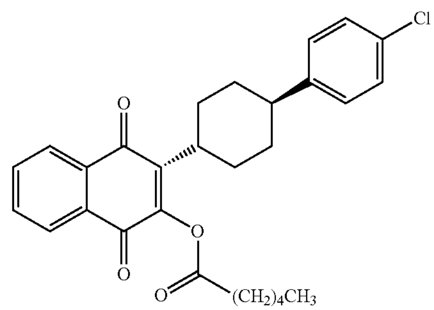 |
| 26 | 3-((1r,4r)-4-(4-chlorophenyl)cyclohexyl)-1,4-dioxo-1,4-dihydronaphthalen-2-yl pentanoate | 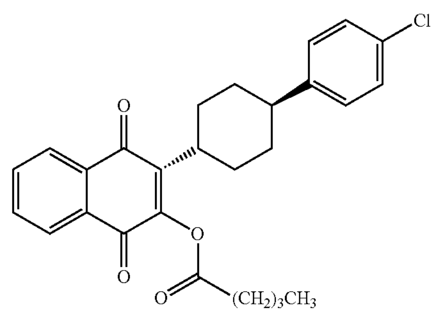 |
| 27 | 3-((1r,4r)-4-(4-chlorophenyl)cyclohexyl)-1,4-dioxo-1,4-dihydronaphthalen-2-yl decanoate | 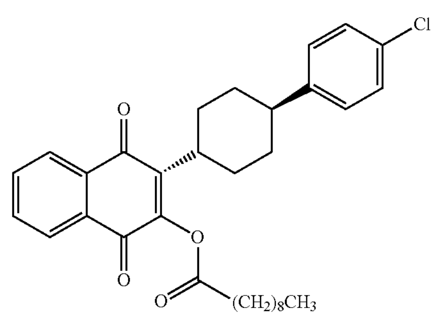 |
| 28 | 3-((1r,4r)-4-(4-chlorophenyl)cyclohexyl)-1,4-dioxo-1,4-dihydronaphthalen-2-yl dodecanoate | 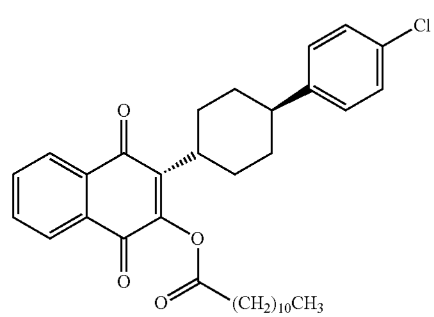 |

TABLE 2-continued

| Comp. | Name | Structure |
|---|---|---|
| 29 | 3-((1r,4r)-4-(4-chlorophenyl)cyclohexyl)-1,4-dioxo-1,4-dihydronaphthalen-2-yl palmitate | 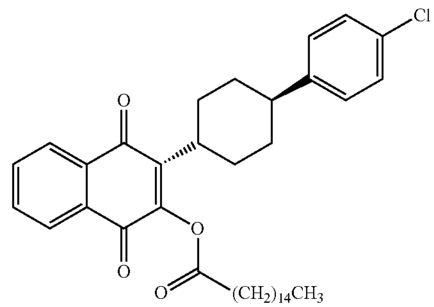 |
| 30 | 3-((1r,4r)-4-(4-chlorophenyl)cyclohexyl)-1,4-dioxo-1,4-dihydronaphthalen-2-yl 2-propylpentanoate | 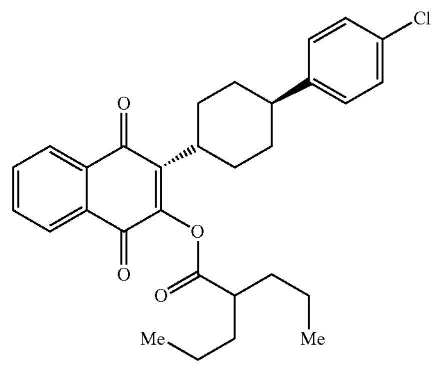 |
| 31 | 3-((1r,4r)-4-(4-chlorophenyl)cyclohexyl)-1,4-dioxo-1,4-dihydronaphthalen-2-yl butyrate | 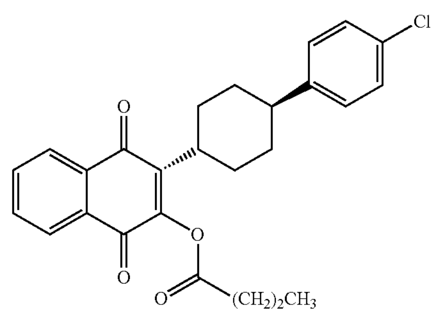 |
| 32 | 3-((1r,4r)-4-(4-chlorophenyl)cyclohexyl)-1,4-dioxo-1,4-dihydronaphthalen-2-yl nonanoate | 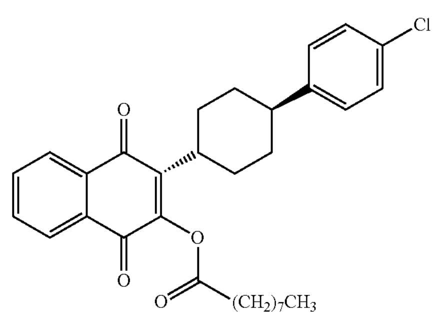 |
| 33 | 3-((1r,4r)-4-(4-chlorophenyl)cyclohexyl)-1,4-dioxo-1,4-dihydronaphthalen-2-yl (4Z,7Z,10Z,13Z,16Z,19Z)-docosa-4,7,10,13,16,19-hexaenoate | 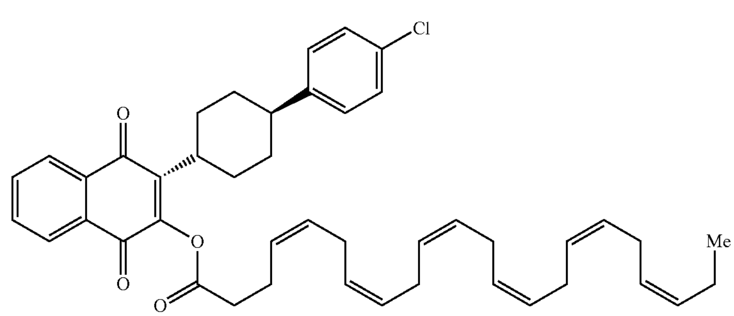 |

TABLE 2-continued

| Comp. | Name | Structure |
|---|---|---|
| 34 | 2-((1r,4r)-4-(4-chlorophenyl)cyclohexyl)-3-((((4Z,7Z,10Z,13Z,16Z,19Z)-docosa-4,7,10,13,16,19-hexaen-1-yl)oxy)methoxy)naphthalene-1,4-dione | 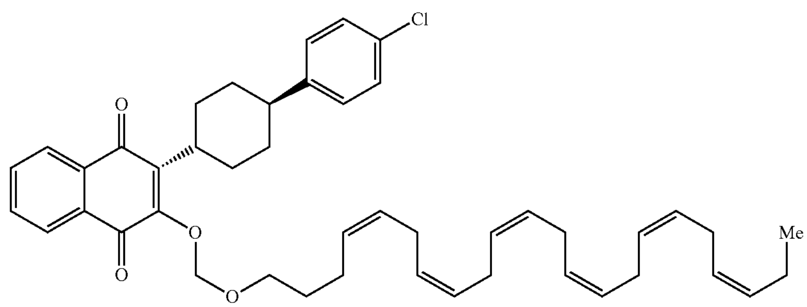 |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, the compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein.

In some situations, the compounds described herein possess one or more chiral centers and each center exists in the R configuration, or S configuration. The compounds described herein may possess three chiral centers and each center exists in the R configuration, or S configuration. The compounds described herein may possess four chiral centers and each center exists in the R configuration, or S configuration. The compounds described herein may include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. The compounds described herein may be prepared as their individual stereoisomers by reacting a racemic mixture of the compound with an optically active resolving agent to form a pair of diastereoisomeric compounds, separating the diastereomers and recovering the optically pure enantiomers. Dissociable complexes may be preferred (e.g., crystalline diastereomeric salts). The diastereomers may have distinct physical properties (e.g., melting points, boiling points, solubilities, reactivity, etc.) and are separated by taking advantage of these dissimilarities. The diastereomers may be separated by chiral chromatography, or preferably, by separation/resolution techniques based upon differences in solubility. The optically pure enantiomer may then be recovered, along with the resolving agent, by any practical means that would not result in racemization.

Labeled Compounds

The compounds described herein may exist in their isotopically-labeled forms. The methods disclosed herein may include methods of treating diseases by administering such isotopically-labeled compounds. The methods disclosed herein may include methods of treating diseases by administering such isotopically-labeled compounds as pharmaceutical compositions. Thus, the compounds disclosed herein may include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. The isotopically labeled compounds, pharmaceutically acceptable salt, ester, solvate, hydrate or derivative thereof may be prepared by any suitable method.

The compounds described herein may be labeled by other means, including, but not limited to, the use of chromophores or fluorescent moieties, bioluminescent labels, or chemiluminescent labels.

Pharmaceutically Acceptable Salts

The compounds described herein may exist as their pharmaceutically acceptable salts. The methods disclosed herein may include methods of treating diseases by administering such pharmaceutically acceptable salts. The methods disclosed herein may include methods of treating diseases by administering such pharmaceutically acceptable salts as pharmaceutical compositions.

The compounds described herein may possess acidic or basic groups and therefore react with any of a number of inorganic or organic bases, and inorganic and organic acids, to form a pharmaceutically acceptable salt. These salts may be prepared in situ during the final isolation and purification of the compounds of the invention, or by separately reacting a purified compound in its free form with a suitable acid or base, and isolating the salt thus formed.

Solvates

The compounds described herein may exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, may be formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Polymorphs

The compounds described herein, may be in crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The crystalline form may be ELQ-300-Form IA. The crystalline form may be ELQ-300-Form IB. The crystalline form may be ELQ-300-Form II. The crystalline form may be ELQ-300-Form III. The crystalline form may be ELQ-300-Form IV. The crystalline form may be ELQ-300-Form V.

The crystalline form may be a crystalline compound of Formula (II). The crystalline form may be crystalline 6-chloro-7-methoxy-2-methyl-3-(4-(4-(trifluoromethoxy)phenoxy)phenyl)quinolin-4-yl propionate. The crystalline form may be crystalline 6-chloro-7-methoxy-2-methyl-3-(4-(4-(trifluoromethoxy)phenoxy)phenyl)quinolin-4-yl ethyl carbonate. The crystalline form may be crystalline (6-chloro-7-methoxy-2-methyl-3-(4-(4-(trifluoromethoxy)phenoxy)phenyl)quinolin-4-yloxy)methyl butyrate.

The crystalline form may be atovaquone-Form I. The crystalline form may be atovaquone-Form II.

The crystalline form may be a crystalline compound of Formula (III). The crystalline form may be crystalline crystalline 3-((1r,4r)-4-(4-chlorophenyl)cyclohexyl)-1,4-dioxo-1,4-dihydronaphthalen-2-yl decanoate.

The crystalline form may be pyronaridine-Form I. The crystalline form may be pyronaridine-Form II. The crystalline form may be pyronaridine-Form III. The crystalline form may be pyronaridine-Form IV. The crystalline form may be pyronaridine-Form V.

Pharmaceutical Compositions

The compounds described herein may be formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, twentyfirst Ed (Lippincott Williams & Wilkins 2012); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

The compounds described herein may be administered in combination with pharmaceutically acceptable carriers, excipients or diluents, in a pharmaceutical composition. Administration of the compounds and compositions described herein can be effected by any method that enables delivery of the compounds to the site of action. The compounds disclosed herein, such as compounds of Formula (II) or Formula (III) may be formulated as a depot formulation for administration via intramuscular or subcutaneous injection. The compounds disclosed herein, such as crystalline ELQ-300 (ELQ-300-Form IA, ELQ-300-Form IB, ELQ-300-Form II, ELQ-300-Form III, ELQ-300-Form IV, or ELQ-300-Form V), crystalline compounds of Formula (II), crystalline atovaquone (atovaquone-Form I or atovaquone-Form II), crystalline compounds of Formula (III), or crystalline pyronaridine (pyronaridine-Form I, pyronaridine-Form II, pyronaridine-Form III, pyronaridine-Form IV, or pyronaridine-Form V) may be formulated as suspension for administration via intramuscular or subcutaneous injection.

Depot Formulation

Depot formulations are efficient, well-tolerated, sustained or delayed release compositions of the active ingredient that are therapeutically effective for a number of weeks, such as at least about one week, at least about two weeks, at least about three weeks, at least about four weeks, at least about five weeks, at least about six weeks, at least about seven weeks, at least about eight weeks, at least about nine weeks, at least ten about weeks, at least about eleven weeks, at least about twelve weeks or more. Depot formulations are efficient, well-tolerated, sustained or delayed release compositions of the active ingredient that are therapeutically effective for a number of days, such as at least about 5 days, at least about 10 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 105 days, at least about 110 days, at least about 115 days, at least about 120 days or more.

In addition to the active agent describe herein, additional ingredients may be used in the depot formulations of the present invention including surfactants, solubilizers, emulsifiers, preservatives, isotonicity agents, dispersing agents, wetting agents, fillers, solvents, buffers, stabilizers, lubricants, thickening agents, suspending agents, and combination thereof.

The depot formulation may comprise a compound disclosed herein and a suitable hydrophobic materials. The suitable hydrophobic material may be a monoglyceride, diglyceride, or a triglyceride. The suitable hydrophobic material may be an oil. The oil may be a biocompatible oil. The oil may be mineral oil. The oil may be castor oil. The oil may be vegetable oil. The vegetable oil may be selected from corn oil, peanut oil, sesame oil, olive oil, palm oil, safflower oil, soybean oil, cottonseed oil, rapeseed oil, sunflower oil and mixtures thereof. The oil may be sesame oil. The oil may be a semi-synthetic vegetable oil obtained by total esterification and/or hydrolysis and/or fractionation of a natural vegetable oil, for instance fatty acid triglycerides derived from vegetable oils, such as triglycerides of caprylic, capric, linoleic or succinic acids (sold under the trade names Miglyol™ 810, 812, 818, 820, 829), esters of propylene glycol and of a fatty acid, derived from vegetable oil, such as esters of propylene glycol and of caprylic and capric acids (sold under the trade name Miglyol™ 840), and also mixtures thereof.

The depot formulation may comprise a compound of Formula (II), or pharmaceutically acceptable salt, solvate, or stereoisomer thereof and an oil. The concentration of the compound of Formula (II), or pharmaceutically acceptable salt, solvate, or stereoisomer thereof in the oil may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL. The concentration may be more than about 20 mg/mL, more than about 30 mg/mL, more than about 40 mg/mL, more than about 50 mg/mL, more than about 60 mg/mL, more than about 70 mg/mL, more than about 80 mg/mL, more than about 90 mg/mL, more than about 100 mg/mL, more than about 150 mg/mL, or more than about 200 mg/mL.

The compound of Formula (II) may be released from the depot formulation at a rate providing an average plasma concentration of 6-chloro-7-methoxy-2-methyl-3-(4-(4-(trifluoromethoxy)phenoxy)phenyl)quinolin-4(1H)-one (ELQ-300) of at least about 1 µM over a period of about 12 weeks. The average plasma concentration of 6-chloro-7-methoxy-2-methyl-3-(4-(4-(trifluoromethoxy)phenoxy)phenyl)quinolin-4(1H)-one may be at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week. The average plasma concentration of 6-chloro-7-methoxy-2-methyl-3-(4-(4-(trifluoromethoxy) phenoxy)phenyl)quinolin-4(1H)-one may be at least about 100 nM over a period of about 4 weeks upon administration of a compound of Formula (II).

The depot formulation may comprise a compound of Formula (III), or pharmaceutically acceptable salt, solvate, or stereoisomer thereof and an oil. The concentration of the compound of Formula (III), or pharmaceutically acceptable salt, solvate, or stereoisomer thereof in the oil may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL. The concentration may be more than about 20 mg/mL, more than about 30 mg/mL, more than about 40 mg/mL, more than about 50 mg/mL, more than about 60 mg/mL, more than about 70 mg/mL, more than about 80 mg/mL, more than about 90 mg/mL, more than about 100 mg/mL, more than about 150 mg/mL, or more than about 200 mg/mL.

The compound of Formula (III) may be released from the depot formulation at a rate providing an average plasma concentration of trans-2-[4-(4-chlorophenyl)cyclohexyl]-3-hydroxy-1,4-naphthalenedione (atovaquone) of at least about 5 µM over a period of about 13 weeks. The average plasma concentration of trans-2-[4-(4-chlorophenyl)cyclohexyl]-3-hydroxy-1,4-naphthalenedione may be at least about 5 µM, at least about 4.5 µM, at least about 4 µM, at least about 3.5 µM, at least about 3 µM, at least about 2.5 µM, at least about 2 µM, at least about 1.5 µM, at least about 1 µM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 13 weeks, over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week. The average plasma concentration of trans-2-[4-(4-chlorophenyl)cyclohexyl]-3-hydroxy-1,4-naphthalenedione may be at least about 100 nM over a period of about 4 weeks upon administration of a compound of Formula (III).

The compound of Formula (III) may be 3-((1r,4r)-4-(4-chlorophenyl)cyclohexyl)-1,4-dioxo-1,4-dihydronaphthalen-2-yl (4Z,7Z,10Z,13Z,16Z,19Z)-docosa-4,7,10,13,16,19-hexaenoate and may be released from the depot formulation at a rate providing an average plasma concentration of trans-2-[4-(4-chlorophenyl)cyclohexyl]-3-hydroxy-1,4-naphthalenedione (atovaquone) of at least about 2 µM over a period of about 13 weeks. The average plasma concentration of trans-2-[4-(4-chlorophenyl)cyclohexyl]-3-hydroxy-1,4-naphthalenedione may be at least about 2 µM, about 1.9 µM, about 1.8 µM, about 1.7 µM, about 1.6 µM, about 1.5 µM, about 1.4 µM, about 1.3 µM, about 1.2 µM, about 1.1 µM, about 1 µM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 13 weeks, about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week. The average plasma concentration of trans-2-[4-(4-chlorophenyl)cyclohexyl]-3-hydroxy-1,4-naphthalenedione may be at least about 1000 nM over a period of about 13 weeks upon administration of 3-((1r,4r)-4-(4-chlorophenyl)cyclohexyl)-1,4-dioxo-1,4-dihydronaphthalen-2-yl (4Z,7Z,10Z,13Z,16Z,19Z)-docosa-4,7,10,13,16, 19-hexaenoate.

Nanoparticles or Microparticle Suspension

The compounds disclosed herein may be formulated as nanoparticle or microparticle suspensions. The pharmaceutical suspensions described herein comprise nanoparticles or microparticles of a crystalline compound disclosed herein and suitable excipients.

Nanoparticles are submicroscopic solid particles with size ranging from about 10 nm to about 1000 nm or from about 50 nm to about 1000 nm. The average particle size of the nanoparticles describe herein may be below about 1000 nm, or below about 900 nm, or below about 800 nm, or below about 700 nm, or below about 600 nm, or below about 500 nm, or below about 400 nm, or below about 300 nm, or below about 200 nm, or below about 100 nm. The lower limit of the average particle size may be as low as about 100 nm or as low as about 50 nm. The average particle size may be in the range of about 50 nm to about 1000 nm, or about 50 nm to about 500 nm, or about 50 nm to about 400 nm, or about 50 nm to about 300 nm, or about 50 nm to about 250 nm, or about 100 nm to about 250 nm, or about 150 nm to about 220 nm, or 100 to 200 nm, or about 150 nm to about 200 nm, e.g. about 100 nm, about 130 nm, or about 150 nm.

Microparticles are solid particles with size ranging from about 1 µm to about 1000 µm. The average particle size of the micro particles describe herein may be below about 1000 µm, or below about 900 µm, or below about 800 µm, or below about 700 µm, or below about 600 µm, or below about 500 µm, or below about 400 µm, or below about 300 µm, or below about 200 µm, or below about 100 µm, or below about 90 µm, or below about 80 µm, or below about 70 µm, or below about 60 µm, or below about 50 µm, or below about 40 µm, or below about 30 µm, or below about 20 µm, or below about 10 µm, or below about 5 µm, or below about 2 µm. The lower limit of the average particle size may be as low as about 10 µm or as low as about 5 µm. The average particle size may be in the range of about 1 µm to about 100 µm, or about 1 µm to about 50 µm, or about 1 µm to about 40 µm, or about 1 µm to about 30 µm, or about 1 µm to about 20 µm, or about 1 µm to about 10 µm or about 1 µm to about 5 µm, e.g. about 1 µm, about 2 µm, about 3 µm, about 4 µm, or about 5 µm. The nanoparticle or microparticle suspensions may be sustained or delayed release compositions of the active ingredient that are therapeutically effective for a number of weeks, such as at least about one week, at least about two weeks, at least about three weeks, at least about four weeks, at least about five weeks, at least about six weeks, at least about seven weeks, at least about eight weeks, at least about nine weeks, at least about ten weeks, at least about eleven weeks, at least about twelve weeks or more. The nanoparticle or microparticle suspensions are efficient, well-tolerated, sustained or delayed release compositions of the active ingredient that are therapeutically effective for a number of days, such as at least about 5 days, at least about 10 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 105 days, at least about 110 days, at least about 115 days, at least about 120 days or more.

In addition to the active agent, additional ingredients may be used in the nanoparticle or microparticle suspensions of the present invention including surfactants, solubilizers, emulsifiers, preservatives, isotonicity agents, dispersing agents, wetting agents, fillers, solvents, buffers, stabilizers, lubricants, thickening agents, suspending agents, and combination thereof. The suspension may comprise a suspending agent and a surfactant. Most commonly, surfactants are classified according to polar head group. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic. Anionic surfactants contain anionic functional groups at their head, such as sulfate, sulfonate, phosphate, and carboxylates. Prominent alkyl sulfates include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate. Others include: docusate (dioctyl sodium sulfosuccinate), perfluorooctanesulfonate (PFOS), perfluorobutanesulfonate, alkyl-aryl ether phosphates, alkyl ether phosphates. Cationic surfactant include pH-dependent primary, secondary, or tertiary amines such as octenidine dihydrochloride; and permanently charged quaternary ammonium salts such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Zwitterionic (amphoteric) surfactants have both cationic and anionic centers attached to the same molecule. The cationic part is based on primary, secondary, or tertiary amines or quaternary ammonium cations. The anionic part can be more variable and include sulfonates, as in the sultaines CHAPS (3-[(3-cholamidopropyl)dimethylammonio]-1-propanesulfonate) and cocamidopropyl hydroxysultaine. Betaines such as cocamidopropyl betaine have a carboxylate with the ammonium. The most common biological zwitterionic surfactants have a phosphate anion with an amine or ammonium, such as the phospholipids phosphatidylserine, phosphatidylethanolamine, phosphatidylcholine, and sphingomyelins. Nonionic surfactants include fatty alcohols, cetyl alcohol, stearyl alcohol, and cetostearyl alcohol, and oleyl alcohol. Also used as nonionic surfactants are polyethylene glycol alkyl ethers (such as octaethylene glycol monododecyl ether, pentaethylene glycol monodecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate, i.e., polysorbate 20 and polysorbate 80), sorbitan alkyl esters (such as Spans), cocamide MEA, cocamide DEA, dodecyldimethylamine oxide, triblock copolymer comprising blocks of polyethylene glycol and blocks of polypropylene glycol such as poly(ethylene glycol)-block-poly(propylene glycol)-Hock-poly(ethylene glycol) (such as poloxamers), and polyethoxylated tallow amine (POEA). The suspension may comprise between about 0.1 wt % and about 10 wt % of a surfactant. The suspension may comprise between about 0.5 wt % and about 5 wt % of a surfactant. The suspension may comprise between about 1 wt % and about 4 wt % of a surfactant. The suspension may comprise between about 2 wt % and about 4 wt % of a surfactant. The suspension may comprise between about 3 wt % of a surfactant. The suspension may comprise a nonionic surfactant. The nonionic surfactant may comprise polyethylene glycol. The nonionic surfactant may be a triblock copolymer comprising blocks of polyethylene glycol and blocks of polypropylene glycol such as poly(ethylene glycol)-Hock-poly(propylene glycol)-Hock-poly(ethylene glycol). The non-ionic surfactant may be Synperonic® F108. The nonionic surfactant may be Pluronic®. The nonionic surfactant may be a vitamin derivative, such as vitamin E derivative. The nonionic surfactant may be an esterification product of vitamin E succinate with polyethylene glycol. The nonionic surfactant may be an esterification product of vitamin E succinate with polyethylene glycol 1000. The non-ionic surfactant may be D-α-tocopheryl polyethylene glycol succinate. The non-ionic surfactant may be D-α-tocopheryl polyethylene glycol 1000 succinate (TPGS). The suspension may comprise an anionic surfactant. The anionic surfactant may be dodecyl sodium sulfate (SLS). The suspension may comprise a suspending agent. The suspension may comprise between about 0.1 wt % and about 10 wt % of a suspending agent. The suspension may comprise between about 0.5 wt % and about 5 wt % of a suspending agent. The suspension may comprise between about 0.5 wt % and about 2 wt % of a suspending agent. The suspension may comprise between about 0.5 wt % and about 1.5 wt % of a suspending agent. The suspension may comprise about 1 wt % of a suspending agent. The suspending agent may be selected from acacia, agar, alginic acid, bentonite, calcium stearate, carbomers, cellulose or cellulose derivatives (such as carboxymethylcellulose calcium, carboxymethylcellulose sodium, hydroxyethyl cellulose, hydroxyethylmethyl cellulose, hydroxypropyl cellulose, hydroxypropyl methylcellulose (HPMC), methylcellulose), carrageenan, ceratonia, colloidal silicon dioxide, dextrin, gelatin, guar gum, kaolin, magnesium aluminum silicate, maltitol, medium-chain triglycerides, microcrystalline cellulose, microcrystalline cellulose and carboxymethylcellulose sodium, polycarbophil, polyethylene glycol, potassium alginate, povidone, propylene glycol alginate, sesame oil, sodium alginate, sodium starch glycolate, sorbitan esters, sucrose, tragacanth, and xanthan gum. The suspending agent may be a cellulose derivative. The suspension may comprise hydroxypropyl methylcellulose (HPMC). The suspension may comprise one or more of Synperonic® F108, dodecyl sodium sulfate (SLS), or D-α-tocopheryl polyethylene glycol 1000 succinate (TPGS). The suspension may comprise one or more of Synperonic® F108, dodecyl sodium sulfate (SLS), D-α-tocopheryl polyethylene glycol 1000 succinate (TPGS), or hydroxypropyl methylcellulose (HPMC). The suspension may comprise D-α-tocopheryl polyethylene glycol 1000 succinate (TPGS) and hydroxypropyl methylcellulose (HPMC).

The nanoparticles or microparticle described herein may be prepared by means of micronization/particle size reduction/nanonization by mechanical means. The nanoparticles or microparticle may be prepared by dry milling. The nanoparticles or microparticle may be prepared by wet milling.

The pharmaceutical suspension may comprise crystalline 6-chloro-7-methoxy-2-methyl-3-(4-(4-(trifluoromethoxy)phenoxy)phenyl)quinolin-4(1H)-one or pharmaceutically acceptable salt, solvate, or stereoisomer thereof (such as ELQ-300-Form IA, ELQ-300-Form IB, ELQ-300-Form II, ELQ-300-Form III, ELQ-300-Form IV, or ELQ-300-Form V). The pharmaceutical suspension may comprise ELQ-300-Form II. The concentration of crystalline 6-chloro-7-methoxy-2-methyl-3-(4-(4-(trifluoromethoxy)phenoxy)phenyl)quinolin-4(1H)-one, or pharmaceutically acceptable salt, solvate, or stereoisomer thereof in the suspension may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL.

In some aspects, 6-chloro-7-methoxy-2-methyl-3-(4-(4-(trifluoromethoxy)phenoxy)phenyl)quinolin-4(1H)-one is released from the suspension at a rate providing an average plasma concentration of 6-chloro-7-methoxy-2-methyl-3-(4-(4-(trifluoromethoxy)phenoxy)phenyl)quinolin-4(1H)-one (ELQ-300) of at least about 3 μM over a period of about 12 weeks. The average plasma concentration of 6-chloro-7-methoxy-2-methyl-3-(4-(4-(trifluoromethoxy)phenoxy)phenyl)quinolin-4(1H)-one may be at least about 3 μM, at least about 2.5 μM, at least about 2 μM, at least about 1.5 μM, at least about 1 μM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week. The average plasma concentration of 6-chloro-7-methoxy-2-methyl-3-(4-(4-(trifluoromethoxy)phenoxy)phenyl)quinolin-4(1H)-one may be at least about 500 nM over a period of about 4 weeks.

The pharmaceutical suspension may comprise crystalline trans-2-[4-(4-chlorophenyl)cyclohexyl]-3-hydroxy-1,4-naphthalenedione, or pharmaceutically acceptable salt, solvate, or stereoisomer thereof (such as atovaquone-Form I or atovaquone-Form II). The pharmaceutical suspension may comprise atovaquone-Form II. The concentration of crystalline trans-2-[4-(4-chlorophenyl)cyclohexyl]-3-hydroxy-1,4-naphthalenedione, or pharmaceutically acceptable salt, solvate, or stereoisomer thereof in the suspension may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL.

In some aspects, trans-2-[4-(4-chlorophenyl)cyclohexyl]-3-hydroxy-1,4-naphthalenedione is released from the suspension at a rate providing an average plasma concentration of trans-2-[4-(4-chlorophenyl)cyclohexyl]-3-hydroxy-1,4-naphthalenedione (atovaquone) of at least about 5 μM over a period of about 12 weeks. The average plasma concentration of trans-2-[4-(4-chlorophenyl)cyclohexyl]-3-hydroxy-1,4-naphthalenedione may be at least about 5 μM, at least about 4.5 μM, at least about 4 μM, at least about 3.5 μM, at least about 3 μM, at least about 2.5 μM, at least about 2 μM, at least about 1.5 μM, at least about 1 μM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week. The average plasma concentration of trans-2-[4-(4-chlorophenyl)cyclohexyl]-3-hydroxy-1,4-naphthalenedione may be at least about 3 μM over a period of about 4 weeks.

The pharmaceutical suspension may comprise crystalline (6-chloro-7-methoxy-2-methyl-3-(4-(4-(trifluoromethoxy)phenoxy)phenyl)quinolin-4-yloxy)methyl butyrate (compound 2), or pharmaceutically acceptable salt, solvate, or stereoisomer thereof. The concentration of crystalline (6-chloro-7-methoxy-2-methyl-3-(4-(4-(trifluoromethoxy)phenoxy)phenyl)quinolin-4-yloxy)methyl butyrate, or pharmaceutically acceptable salt, solvate, or stereoisomer thereof in the suspension may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL.

In some aspects, (6-chloro-7-methoxy-2-methyl-3-(4-(4-(trifluoromethoxy)phenoxy)phenyl)quinolin-4-yloxy) methyl butyrate is released from the suspension at a rate providing an average plasma concentration of 6-chloro-7-methoxy-2-methyl-3-(4-(4-(trifluoromethoxy)phenoxy)phenyl)quinolin-4(1H)-one (ELQ-300) of at least about 3 µM over a period of about 12 weeks. The average plasma concentration of 6-chloro-7-methoxy-2-methyl-3-(4-(4-(trifluoromethoxy)phenoxy)phenyl)quinolin-4(1H)-one may be at least about 3 µM, at least about 2.5 µM, at least about 2 µM, at least about 1.5 µM, at least about 1 µM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week.

The pharmaceutical suspension may comprise crystalline compounds of Formula (II), or pharmaceutically acceptable salt, solvate, or stereoisomer thereof. The concentration of crystalline compounds of Formula (II), or pharmaceutically acceptable salt, solvate, or stereoisomer thereof in the suspension may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL.

In some aspects, the crystalline compound of Formula (II), or pharmaceutically acceptable salt, solvate, or stereoisomer thereof is released from the suspension at a rate providing an average plasma concentration of 6-chloro-7-methoxy-2-methyl-3-(4-(4-(trifluoromethoxy)phenoxy)phenyl)quinolin-4(1H)-one (ELQ-300) of at least about 3 µM over a period of about 12 weeks. The average plasma concentration of 6-chloro-7-methoxy-2-methyl-3-(4-(4-(trifluoromethoxy)phenoxy)phenyl)quinolin-4(1H)-one may be at least about 3 µM, at least about 2.5 µM, at least about 2 µM, at least about 1.5 µM, at least about 1 µM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week.

The pharmaceutical suspension may comprise crystalline compounds of Formula (III), or pharmaceutically acceptable salt, solvate, or stereoisomer thereof. The concentration of crystalline compounds of Formula (III), or pharmaceutically acceptable salt, solvate, or stereoisomer thereof in the suspension may be between about 20 mg/mL and about 500 mg/mL, between about 20 mg/mL and about 400 mg/mL, between about 20 mg/mL and about 300 mg/mL, between about 20 mg/mL and about 200 mg/mL, between about 20 mg/mL and about 100 mg/mL, or between about 50 mg/mL and about 100 mg/mL. The concentration may be at least about 20 mg/mL, at least about 30 mg/mL, at least about 40 mg/mL, at least about 50 mg/mL, at least about 60 mg/mL, at least about 70 mg/mL, at least about 80 mg/mL, at least about 90 mg/mL, or at least about 100 mg/mL. The concentration may be less than about 20 mg/mL, less than about 30 mg/mL, less than about 40 mg/mL, less than about 50 mg/mL, less than about 60 mg/mL, less than about 70 mg/mL, less than about 80 mg/mL, less than about 90 mg/mL, or less than about 100 mg/mL.

In some aspects, the crystalline compound of Formula (III), or pharmaceutically acceptable salt, solvate, or stereoisomer thereof is released from the suspension at a rate providing an average plasma concentration of trans-2-[4-(4-chlorophenyl)cyclohexyl]-3-hydroxy-1,4-naphthalenedione (atovaquone) of at least about 5 µM over a period of about 12 weeks. The average plasma concentration of trans-2-[4-(4-chlorophenyl)cyclohexyl]-3-hydroxy-1,4-naphthalenedione may be at least about 5 µM, at least about 4.5 µM, at least about 4 µM, at least about 3.5 µM, at least about 3 µM, at least about 2.5 µM, at least about 2 µM, at least about 1.5 µM, at least about 1 µM, at least about 900 nM, at least about 800 nM, at least about 700 nM, at least about 600 nM, at least about 500 nM, at least about 400 nM, at least about 300 nM, at least about 200 nM, at least about 100 nM, at least about 95 nM, at least about 90 nM, at least about 85 nM, at least about 80 nM, at least about 75 nM, at least about 70 nM, at least about 65 nM, at least about 60 nM, at least about 55 nM, at least about 50 nM, at least about 45 nM, at least about 40 nM, at least about 35 nM, at least about 30 nM, at least about 25 nM, or at least about 20 nM over a period of about 12 weeks, about 11 weeks, about 10 weeks, about 9 weeks, about 8 weeks, about 7 weeks, about 6 weeks, about 5 weeks, about 4 weeks, about 3 weeks, about 2 weeks, or about 1 week.

Methods of Treatment and Treatment Regiments

Described herein are methods for the treatment or prevention of malaria.

Described herein are methods for the treatment or prevention of malaria, comprising administering a therapeutically effective amount of a compound of Formula (I), or a pharmaceutically acceptable salt, solvate, or stereoisomer thereof to a subject in need thereof.

Described herein are methods for the treatment or prevention of malaria, comprising administering a pharmaceutical composition comprising an oil and a compound of Formula (II), or a pharmaceutically acceptable salt, solvate, or stereoisomer thereof to a subject in need thereof. The compound of Formula (II) may be ((6-chloro-7-methoxy-2-methyl-3-(4-(4-(trifluoromethoxy)phenoxy)phenyl)quinolin-4-yl)oxy)methyl butyrate.

Described herein are methods for the treatment or prevention of malaria, comprising administering a pharmaceutical composition comprising an oil and a compound of Formula (III), or a pharmaceutically acceptable salt, solvate, or stereoisomer thereof to a subject in need thereof. The compound of Formula (III) may be 3-((1r,4r)-4-(4-chlorophenyl)cyclohexyl)-1,4-dioxo-1,4-dihydronaphthalen-2-yl (4Z,7Z,10Z,13Z,16Z,19Z)-docosa-4,7,10,13,16,19-hexaenoate.

Described herein are methods for the treatment or prevention of malaria, comprising administering a pharmaceutical suspension comprising nanoparticles or microparticles of a crystalline form of 6-chloro-7-methoxy-2-methyl-3-(4-(4-(trifluoromethoxy)phenoxy)phenyl)quinolin-4(1H)-one, or a pharmaceutically acceptable salt, solvate, or stereoisomer thereof to a subject in need thereof. The crystalline form of 6-chloro-7-methoxy-2-methyl-3-(4-(4-(trifluoromethoxy)phenoxy)phenyl)quinolin-4(1H)-one may be ELQ-300-Form IA. The crystalline form of 6-chloro-7-methoxy-2-methyl-3-(4-(4-(trifluoromethoxy)phenoxy)phenyl)quinolin-4(1H)-one may be ELQ-300-Form IB. The crystalline form of 6-chloro-7-methoxy-2-methyl-3-(4-(4-(trifluoromethoxy)phenoxy)phenyl)quinolin-4(1H)-one may be ELQ-300-Form II. The crystalline form of 6-chloro-7-methoxy-2-methyl-3-(4-(4-(trifluoromethoxy)phenoxy)phenyl)quinolin-4(1H)-one may be ELQ-300-Form III. The crystalline form of 6-chloro-7-methoxy-2-methyl-3-(4-(4-(trifluoromethoxy)phenoxy)phenyl)quinolin-4(1H)-one may be ELQ-300-Form IV. The crystalline form of 6-chloro-7-methoxy-2-methyl-3-(4-(4-(trifluoromethoxy)phenoxy)phenyl)quinolin-4(1H)-one may be ELQ-300-Form V.

Described herein are methods for the treatment or prevention of malaria, comprising administering a pharmaceutical suspension comprising nanoparticles or microparticles of a crystalline compound of Formula (II), or a pharmaceutically acceptable salt, solvate, or stereoisomer thereof to a subject in need thereof. The crystalline compound of Formula (II) may be crystalline 6-chloro-7-methoxy-2-methyl-3-(4-(4-(trifluoromethoxy)phenoxy)phenyl)quinolin-4-yl propionate. The crystalline compound of Formula (II) may be 6-chloro-7-methoxy-2-methyl-3-(4-(4-(trifluoromethoxy)phenoxy)phenyl)quinolin-4-yl ethyl carbonate. The crystalline compound of Formula (II) may be (6-chloro-7-methoxy-2-methyl-3-(4-(4-(trifluoromethoxy)phenoxy)phenyl)quinolin-4-yloxy)methyl butyrate.

Described herein are methods for the treatment or prevention of malaria, comprising administering a pharmaceutical suspension comprising nanoparticles or microparticles of a crystalline form of trans-2-[4-(4-chlorophenyl)cyclohexyl]-3-hydroxy-1,4-naphthalenedione, or a pharmaceutically acceptable salt, solvate, or stereoisomer thereof to a subject in need thereof. The crystalline form of trans-2-[4-(4-chlorophenyl)cyclohexyl]-3-hydroxy-1,4-naphthalenedione may be atovaquone-Form I. The crystalline form of trans-2-[4-(4-chlorophenyl)cyclohexyl]-3-hydroxy-1,4-naphthalenedione may be atovaquone-Form II.

Described herein are methods for the treatment or prevention of malaria, comprising administering a pharmaceutical suspension comprising nanoparticles or microparticles of a crystalline compound of Formula (III), or a pharmaceutically acceptable salt, solvate, or stereoisomer thereof to a subject in need thereof. The crystalline compound of Formula (III) may be crystalline 3-((1r,4r)-4-(4-chlorophenyl)cyclohexyl)-1,4-dioxo-1,4-dihydronaphthalen-2-yl decanoate.

Described herein are methods for the treatment or prevention of malaria, comprising administering a pharmaceutical suspension comprising nanoparticles or microparticles of a crystalline form of 4-(7-chloro-2-methoxybenzo[b][1,5]naphthyridin-10-ylamino)-2,6-bis(pyrrolidin-1-ylmethyl)phenol, or a pharmaceutically acceptable salt, solvate, or stereoisomer thereof to a subject in need thereof. The crystalline form of 4-(7-chloro-2-methoxybenzo[b][1,5]naphthyridin-10-ylamino)-2,6-bis(pyrrolidin-1-ylmethyl)phenol may be pyronaridine-Form I. The crystalline form of 4-(7-chloro-2-methoxybenzo[b][1,5]naphthyridin-10-ylamino)-2,6-bis(pyrrolidin-1-ylmethyl)phenol may be pyronaridine-Form II. The crystalline form of 4-(7-chloro-2-methoxybenzo[b][1,5]naphthyridin-10-ylamino)-2,6-bis(pyrrolidin-1-ylmethyl)phenol may be pyronaridine-Form III. The crystalline form of 4-(7-chloro-2-methoxybenzo[b][1,5]naphthyridin-10-ylamino)-2,6-bis(pyrrolidin-1-ylmethyl)phenol may be pyronaridine-Form IV. The crystalline form of 4-(7-chloro-2-methoxybenzo[b][1,5]naphthyridin-10-ylamino)-2,6-bis(pyrrolidin-1-ylmethyl)phenol may be pyronaridine-Form V.

In some embodiments of any of the foregoing methods, the malaria is drug resistant (e.g., the malaria is resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof). The malaria may be liver stage.

The compounds described herein may be useful in any of the foregoing methods and, while not bound by theory, are believed to exert their desirable effects through their ability to inhibit the growth of or kill the parasitic protozoan which causes malaria (e.g., *P. falciparum, P. vivax, P. ovale, P. malariae, P. knowlesi*). The treatment of malaria may include causative prophylaxis, such as preventing the spread of *plasmodium* infection beyond the liver, preventing systemic disease, preventing the symptomatic stage of malaria, and/or preventing the establishment of the infection. The treatment of malaria may refers to treatment intended to achieve cure (e.g., of *P. vivax* or *P. malariae*), e.g., treatment for radical cure (i.e., clearing hypnozoites from the liver). The methods may include preventing spread of infection of a malaria-causing parasite as described herein from the liver.

The pharmaceutical compositions and the pharmaceutical suspension containing the compound(s) described herein may be administered for prophylactic and/or therapeutic treatments. In certain therapeutic applications, the pharmaceutical compositions and pharmaceutical suspensions are administered to a patient already suffering from malaria, in an amount sufficient to cure or at least partially arrest at least one of the symptoms of malaria. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, pharmaceutical compositions and pharmaceutical suspensions containing the compounds described herein are administered to a patient susceptible to or otherwise at risk of developing malaria. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.1 mg-100 mg per day. In one aspect, doses employed for adult human treatment are from about 0.5 mg to about 10 mg per day. The pharmaceutical composition or pharmaceutical suspension may be formulated to deliver from about 0.5 mg to about 10 mg per day for about 90 days. The pharmaceutical composition or pharmaceutical suspension may be formulated to deliver about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 3.1 mg, about 3.2 mg, about 3.3 mg, about 3.4 mg, about 3.5 mg, about 3.6 mg, about 3.7 mg, about 3.8 mg, about 3.9 mg, about 4 mg, about 4.1 mg, about 4.2 mg, about 4.3 mg, about 4.4 mg, about 4.5 mg, about 4.6 mg, about 4.7 mg, about 4.8 mg, about 4.9 mg, about 5 mg, about 5.1 mg, about 5.2 mg, about 5.3 mg, about 5.4 mg, about 5.5 mg, about 5.6 mg, about 5.7 mg, about 5.8 mg, about 5.9 mg, about 6 mg, about 6.1 mg, about 6.2 mg, about 6.3 mg, about 6.4 mg, about 6.5 mg, about 6.6 mg, about 6.7 mg, about 6.8 mg, about 6.9 mg, about 7 mg, about 7.1 mg, about 7.2 mg, about 7.3 mg, about 7.4 mg, about 7.5 mg, about 7.6 mg, about 7.7 mg, about 7.8 mg, about 7.9 mg, about 8 mg, about 8.1 mg, about 8.2 mg, about 8.3 mg, about 8.4 mg, about 8.5 mg, about 8.6 mg, about 8.7 mg, about 8.8 mg, about 8.9 mg, about 9 mg, about 9.1 mg, about 9.2 mg, about 9.3 mg, about 9.4 mg, about 9.5 mg, about 9.6 mg, about 9.7 mg, about 9.8 mg, about 9.9 mg, or about 10 mg per day for about 90 days, about 80 days, about 70 days, about 60 days, about 50 days, about 40 days, about 30 days, about 20 days, or about 10 days. The pharmaceutical composition or pharmaceutical suspension may be formulated to deliver from about 0.5 mg to about 10 mg per day for about 120 days. The pharmaceutical composition or pharmaceutical suspension may be formulated to deliver from about 0.5 mg to about 10 mg per day for about 120 days, about 115 days, about 110 days, about 105 days, about 100 days, about 95 days, about 90 days, about 85 days, about 80 days, about 75 days, about 70 days, about 65 days, about 60 days, about 55 days, about 50 days, about 45 days, about 40 days, about 35 days, about 30 days, about 25 days, about 20 days, about 15 days, or about 10 days.

In one embodiment, the dosages appropriate for the compound described herein, or a pharmaceutically acceptable salt thereof, are from about 0.01 to about 100 mg/kg per body weight. In one aspect, the dosage is from about 5 to about 50 mg/kg, or about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The daily dosage or the amount of active in the dosage form may be lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. The daily dosage amount of the compounds described herein may lie within a range of circulating concentrations that include the $ED_{50}$ with minimal toxicity. In certain embodiments, the daily dosage range and/or the unit dosage amount varies within this range depending upon the dosage form employed and the route of administration utilized.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, the benefit experienced by a patient may be increased by administering one of the compounds described herein with another agent (which also includes a therapeutic regimen) that also has therapeutic benefit. The other agent may be an additional antimalarial agent. The additional antimalarial agent may be artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300.

In any case, regardless of the disease, disorder or condition being treated, the overall benefit experienced by the patient may be additive of the two therapeutic agents or the patient may experience a synergistic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. The length required for treatment may vary, and the treatment length is adjusted to suit the specific needs of each subject. For example, in specific embodiments, a compound described herein or a formulation containing the compound is administered for at least 2 weeks, about 1 month to about 5 years.

EXAMPLES

The following examples are provided for illustrative purposes only and not to limit the scope of the claims provided herein.

Example 1: General Procedure for the Preparation of Compounds 1-5, 7-11, and 35

6-Chloro-7-methoxy-2-methyl-3-(4-(4-(trifluoromethoxy)phenoxy)phenyl)quinolin-4(1H)-one (1 equiv), $Cs_2CO_3$ (3 equiv), and anhydrous DMF (0.1 M) were added to a vial followed by the appropriate chloromethylester (3 equiv). The mixture was allowed to stir at 80° C. overnight. After that, the reaction was quenched with saturated aqueous $NH_4Cl$ solution, extracted with EtOAc, and washed with brine. The organic layers were combined, dried under $Na_2SO_4$, filtered, and concentrated under reduced pressure. The crude material was submitted to silica gel column chromatography to afford the desired products (eluent hexanes→hexanes:EtOAc=4:1) as white solids.

Example 2: General Procedure for the Preparation of Compounds 12-19

A suspension of 6-chloro-7-methoxy-2-methyl-3-(4-(4-(trifluoromethoxy)phenoxy)phenyl)quinolin-4(1H)-one (1 equiv) and NaH (2 equiv) in anhydrous THF (0.1 M) was stirred at 80° C. for 1 h. After cooling the reaction mixture to ambient temperature the appropriate chloroformate were added (2 equiv). The reaction mixture was then stirred at 80° C. for 2 h. After that, the reaction was quenched with saturated aqueous $NH_4Cl$ solution, extracted with EtOAc, and washed with brine. The organic layers were combined, dried under $Na_2SO_4$, filtered, and concentrated under reduced pressure. The crude material was submitted to silica gel column chromatography to afford the desired products (eluent hexanes→hexanes:EtOAc=4:1) as white solids.

Example 3: General Procedure for the Preparation of Compounds 20-33

To a suspension of trans-2-[4-(4-chlorophenyl)cyclohexyl]-3-hydroxy-1,4-naphthalenedione (1 equiv) and $K_2CO_3$ (2 equiv) in anhydrous $CH_3CN$ (0.1 M) was added the appropriate acid chloride (3.5 equiv). The reaction mixture stirred for 10 hours at 80° C. Upon completion, the reaction was cooled to ambient temperature and quenched with water, extracted with EtOAc, and washed with brine. The organic layers were combined, dried under $Na_2SO_4$, filtered, and concentrated under reduced pressure. The crude material was submitted to silica gel column chromatography to afford the desired products (eluent hexanes→hexanes: EtOAc=19:1) as yellow solids.

Analytical data are presented in table 3.

TABLE 3

| Cmpd. | Characterization Data (NMR and LCMS) |
|---|---|
| 2 | $^1$H NMR (400 MHz, CDCl$_3$) δ 8.06 (s, 1H), 7.47 (s, 1H), 7.41-7.36 (m, 2H), 7.26 (d, mz, 2H), 7.17-7.10 (m, 4H), 5.31 (s, 2H), 4.06 (s, 3H), 2.54 (s, 3H), 2.17 (t, J = 7.4 Hz, 2H), 1.54 (sex, J = 7.4 Hz, 2H), 0.85 (t, J = 7.4 Hz, 3H). $^{19}$F NMR (376 MHz, CDCl$_3$) δ-58.24 (s, 3F). MS-ESI: m/z 576.14 observed (M + H)$^+$ |
| 3 | $^1$H NMR (400 MHz, CDCl$_3$) δ 8.07 (s, 1H), 7.52 (s, 1H), 7.42-7.36 (m, 2H), 7.27 (m, 2H), 7.18-7.09 (m, 4H), 5.30 (s, 2H), 4.07 (s, 3H), 2.56 (s, 3H), 2.43 (sept, J = 7.0 Hz, 1H), 1.06 (d, J = 7.0 Hz, 6H). $^{19}$F NMR (376 MHz, CDCl$_3$) δ-58.23. MS-ESI: m/z 576.15 observed (M + H)$^+$ |
| 4 | $^1$H NMR (400 MHz, CDCl$_3$) δ 8.06 (s, 1H), 7.49 (s, 1H), 7.40-7.36 (m, 2H), 7.28-7.24 (m, 2H), 7.18-7.10 (m, 4H), 5.31 (s, 2H), 4.06 (s, 3H), 2.54 (s, 3H), 2.17 (t, J = 7.6 Hz, 2H), 1.48 (p, J = 7.5 Hz, 2H), 1.28-1.1 (m, 4H), 0.84 (t, J = 7.2 Hz, 3H). $^{19}$F NMR (376 MHz, CDCl$_3$) δ-58.24 (s, 3F). MS-ESI: m/z 604.16 observed (M + H)$^+$ |
| 8 | $^1$H NMR (400 MHz, CDCl$_3$) δ 8.06 (s, 1H), 7.48 (s, 1H), 7.41-7.35 (m, 2H), 7.30-7.23 (m, 2H), 7.18-7.07 (m, 4H), 5.31 (s, 2H), 4.07 (s, 3H), 2.55 (s, 3H), 2.18 (t, J = 7.6 Hz, 2H), 1.54-1.43 (m, 2H), 1.33-1.12 (m, 12H), 0.89 (t, J = 7.0 Hz, 3H). $^{19}$F NMR (376 MHz, CDCl$_3$) δ-58.24 (s, 3F). MS-ESI: m/z 659.83 observed (M + H)$^+$ |

TABLE 3-continued

| Cmpd. | Characterization Data (NMR and LCMS) |
|---|---|
| 9 | $^1$H NMR (400 MHz, CDCl$_3$) δ 8.06 (s, 1H), 7.48 (s, 1H), 7.41-7.26 (m, 2H), 7.31-7.23 (m, 2H), 7.19-7.09 (m, 4H), 5.31 (s, 2H), 4.07 (s, 3H), 2.55 (s, 3H), 2.18 (t, J = 7.5 Hz, 2H), 1.53-1.40 (m, 2H), 1.36-1.12 (m, 20H), 0.89 (t, J = 6.7 Hz, 3H). MS-ESI: m/z 716.29 observed (M + H)$^+$ |
| 10 | $^1$H NMR (400 MHz, CDCl$_3$) δ 8.06 (s, 1H), 7.47 (s, 1H), 7.41-7.35 (m, 2H), 7.30-7.23 (m, 2H), 7.17-7.10 (m, 4H), 5.31 (s, 2H), 4.06 (s, 3H), 2.55 (s, 3H), 2.18 (t, J = 7.5 Hz, 2H), 1.54-1.44 (m, 2H), 1.34-1.13 (m, 24H), 0.89 (t, J = 6.8 Hz, 3H). $^{19}$F NMR (376 MHz, CDCl$_3$) δ-58.24 (s, 3F). MS-ESI: m/z 745.30 observed (M + H)$^+$ |
| 12 | $^1$H NMR (400 MHz, CDCl$_3$) δ 7.89 (s, 1H), 7.53 (s, 1H), 7.32-7.22 (m, 4H), 7.15-7.06 (m, 4H), 4.07 (s, 3H), 3.77 (s, 3H), 2.55 (s, 3H). MS-ESI: m/z 534.04 observed (M + H)$^+$ |
| 13 | $^1$H NMR (400 MHz, CDCl$_3$) δ 7.91 (s, 1H), 7.55 (s, 1H), 7.35-7.18 (m, 4H), 7.15-7.07 (m, 4H), 4.18 (q, J = 7.1 Hz, 2H), 4.08 (s, 3H), 2.57 (s, 3H), 1.24 (t, J = 7.1 Hz, 3H). $^{19}$F NMR (376 MHz, CDCl$_3$) δ-58.25 (s, 3F). MS-ESI: m/z 548.10 observed (M + H)$^+$ |
| 14 | $^1$H NMR (400 MHz, CDCl$_3$) δ 7.91 (s, 1H), 7.55 (s, 1H), 7.34-7.22 (m, 4H), 7.15-7.05 (m, 4H), 4.12-4.05 (m, 5H), 2.57 (s, 3H), 1.62 (sex, J = 7.2, 2H), 0.90 (t, J = 7.4 Hz, 4H). $^{19}$F NMR (376 MHz, CDCl$_3$) δ-58.25 (s, 3F). MS-ESI: m/z 562.11 observed (M + H)$^+$ |
| 15 | $^1$H NMR (400 MHz, CDCl$_3$) δ 7.91 (s, 1H), 7.51 (s, 1H), 7.34-7.29 (m, 2H), 7.26-7.20 (m, 2H), 7.13-7.05 (m, 4H), 4.80 (sept, J = 6.3 Hz, 1H), 4.07 (s, 3H), 2.55 (s, 3H), 1.22 (d, J = 6.2 Hz, 6H). $^{19}$F NMR (376 MHz, CDCl$_3$) δ-58.25 (s, 3F). MS-ESI: m/z 562.11 observed (M + H)$^+$ |
| 16 | $^1$H NMR (400 MHz, CDCl$_3$) δ 7.90 (s, 1H), 7.52 (s, 1H), 7.36-7.21 (m, 4H), 7.18-7.04 (m, 4H), 4.12 (t, J = 6.7 Hz, 2H), 4.08 (s, 3H), 1.58 (p, J = 6.7 Hz, 3H), 1.38-1.22 (m, 6H), 0.91 (t, J = 6.9 Hz, 3H). MS-ESI: m/z 604.16 observed (M + H)$^+$ |
| 17 | $^1$H NMR (400 MHz, CDCl$_3$) δ 7.89 (s, 1H), 7.50 (s, 1H), 7.34-7.27 (m, 2H), 7.26-7.22 (m, 2H), 7.14-7.05 (m, 4H), 4.10 (t, J = 6.7 Hz, 2H), 4.06 (s, 3H), 2.55 (s, 3H), 1.62-1.51 (m, 2H), 1.34-1.22 (m, 14H), 0.92-0.89 (t, J = 7.0 Hz, 3H). $^{19}$F NMR (376 MHz, CDCl$_3$) δ-58.27 (s, 3F). MS-ESI: m/z 659.89 observed (M + H)$^+$ |
| 18 | $^1$H NMR (400 MHz, CDCl$_3$) δ 7.88 (s, 1H), 7.49 (s, 1H), 7.34-7.17 (m, 4H), 7.15-7.04 (m, 4H), 4.10 (t, J = 6.7 Hz, 2H), 4.06 (s, 3H), 2.55 (s, 3H), 1.57 (s, 2H), 1.34-1.22 (m, 26H), 0.88 (t, J = 7.0 Hz, 3H). $^{19}$F NMR (376 MHz, CDCl$_3$) δ-58.26 (s, 3F). MS-ESI: m/z 743.98 observed (M + H)$^+$ |
| 20 | $^1$H NMR (400 MHz, CDCl$_3$) δ 8.16-8.10 (m, 1H), 8.10-8.06 (m, 1H), 7.79-7.69 (m, 2H), 7.31-7.26 (m, 2H), 7.21-7.14 (m, 2H), 3.08 (tt, J = 12.3, 3.5 Hz, 1H), 2.60 (tt, J = 12.3, 3.3 Hz, 1H), 2.46 (s, 3H), 2.07-1.93 (m, 4H), 1.88-1.78 (m, 2H), 1.61-1.48 (m, 2H). |
| 21 | $^1$H NMR (400 MHz, Chloroform-d) δ 8.19-8.13 (m, 1H), 8.10 (dd, J = 7.2, 1.8 Hz, 1H), 7.83-7.71 (m, 2H) 7.30 (d, J = 8.8 Hz, 3H), 7.24-7.17 (m, 2H), 3.27-3.01 (m, 1H), 2.80 (q, J = 7.5 Hz, 2H), 2.62 (t, J = 12.1 Hz, 1H), 2.04 (dd, J = 15.4, 11.7 Hz, 5H), 1.91-1.78 (m, 2H), 1.39 (t, J = 7.5 Hz, 3H). |
| 22 | $^1$H NMR (400 MHz, CDCl$_3$) δ 8.14-8.10 (m, 1H), 8.10-8.06 (m, 1H), 7.78-7.69 (m, 2H), 7.27 (d, J = 8.5 Hz, 2H), 7.20-7.13 (m, 2H), 3.13-3.03 (m, 1H), 2.71 (t, J = 7.4 Hz, 2H), 2.59 (t, J = 12.3 Hz, 1H), 2.08-1.94 (m, 5H), 1.92-1.77 (m, 4H), 1.53 (d, J = 3.5 Hz, 1H), 1.13 (t, J = 7.4 Hz, 3H). |
| 23 | $^1$H NMR (400 MHz, Chloroform-d) δ 8.23-8.12 (m, 1H), 8.12-8.04 (m, 1H), 7.83-7.70 (m, 2H) 7.30 (d, J = 6.4 Hz, 2H), 7.24-7.15 (m, 2H), 3.12 (d, J = 12.3 Hz, 1H), 2.59 (t, J = 12.2 Hz, 1H), 2.02 (d, J = 13.3 Hz, 3H), 1.85 (d, J = 12.1 Hz, 2H), 1.64-1.52 (m, 2H), 1.50 (s, 9H). |
| 24 | $^1$H NMR (400 MHz, Chloroform-d) δ 8.18-8.12 (m, 1H), 8.12-8.06 (m, 1H), 7.81-7.71 (m, 2H) 7.30 (d, J = 8.4 Hz, 2H), 7.23-7.15 (m, 2H), 3.13 (d, J = 12.2 Hz, 1H), 2.60 (t, J = 12.3 Hz, 1H), 2.02 (d, J = 12.3 Hz, 5H), 1.85 (d, J = 11.4 Hz, 2H), 1.57 (m, 2H), 1.46 (d, J = 7.0 Hz, 6H). |
| 25 | $^1$H NMR (400 MHz, Chloroform-d) δ 8.18-8.13 (m, 1H), 8.10 (dd, J = 7.3, 1.7 Hz, 1H), 7.82-7.72 (m, 2H) 7.30 (d, J = 9.5 Hz, 2H), 7.19 (d, J = 8.4 Hz, 2H), 3.10 (s, 1H), 2.75 (t, J = 7.5 Hz, 2H), 2.62 (s, 1H), 2.02 (s, 4H), 1.87 (q, J = 7.9 Hz, 4H), 1.56-1.52 (m, 6H), 0.99 (t, J = 7.1 Hz, 3H). |
| 26 | $^1$H NMR (400 MHz, Chloroform-d) δ 8.20-8.12 (m, 1H), 8.10 (dd, J = 7.3, 1.7 Hz, 1H), 7.83-7.70 (m, 2H) 7.30 (d, J = 8.6 Hz, 2H), 7.20 (td, J = 6.3, 5.9, 2.3 Hz, 2H), 3.14-3.04 (m, 1H), 2.75 (t, J = 7.5 Hz, 2H), 2.68-2.56 (m, 1H), 2.02 (dd, J = 13.3, 7.7 Hz, 4H), 1.92-1.79 (m, 4H), 1.69-1.47 (m, 4H), 1.05 (t, J = 7.3 Hz, 3H). |
| 27 | $^1$H NMR (400 MHz, CDCl$_3$) δ 8.17-8.08 (m, 2H), 7.81-7.70 (m, 2H), 7.32-7.27 (m, 2H), 7.22-7.17 (m, 2H), 3.18-3.03 (m, 1H), 2.78-2.72 (m, 2H), 2.67-2.57 (m, 1H), 2.11-1.96 (m, 4H), 1.93-1.80 (m, 4H), 1.66-1.22 (m, 15H), 0.96-0.86 (m, 3H). |
| 28 | $^1$H NMR (400 MHz, CDCl$_3$) δ 8.20-8.05 (m, 2H), 7.85-7.68 (m, 2H), 7.36-7.23 (m, 2H), 7.23-7.09 (m, 2H), 3.18-3.00 (m, 1H), 2.75 (t, J = 7.4 Hz, 2H), 2.68-2.52 (m, 1H), 2.12-1.92 (m, 4H), 1.92-1.75 (m, 4H), 1.64-1.45 (m, 5H), 1.45-1.18 (m, 13H), 0.90 (t, J = 6.7 Hz, 3H). |
| 29 | $^1$H NMR (400 MHz, Chloroform-d) δ 8.17-8.12 (m, 1H), 8.12-8.07 (m, 1H), 7.81-7.67 (m 2H) 7.31 (m, 2H), 7.23-7.16 (m, 2H), 3.09 (d, J = 12.0 Hz, 1H), 2.74 (t, J = 7.5 Hz, 2H), 2.62 (t, J = 12.4 Hz, 1H), 2.01 (d, J = 12.3 Hz, 4H), 1.86 (q, J = 7.4 Hz, 4H), 1.67 (q, J = 7.2 Hz, 1H), 1.62-1.46 (m, 6H), 1.28 (d, 19H), 0.96-0.82 (m, 3H). |
| 30 | $^1$H NMR (400 MHz, Chloroform-d) δ 8.16-8.12 (m, 1H), 8.12-8.09 (m, 1H), 7.80-7.72 (m, 2H), 7.29 (m, 2H), 7.20-7.14 (m, 2H), 3.20-2.95 (m, 1H), 2.86-2.71 (m, 1H), 2.72-2.55 (m, 1H), 2.22-2.06 (m, 2H), 2.01 (d, J = 11.5 Hz, 4H), 1.97-1.76 (m, 4H), 1.74-1.43 (m, 9H), 1.06 (t, J = 7.1 Hz, 6H). |
| 31 | $^1$H NMR (400 MHz, Chloroform-d) δ 8.18-8.12 (m, 1H), 8.12-8.07 (m, 1H), 7.81-7.71 (m, 2H) 7.30 (d, J = 8.5 Hz, 2H), 7.23-7.16 (m, 2H), 3.22-2.97 (m, 1H), 2.73 (t, J = 7.4 Hz, 2H), 2.62 (t, J = 12.3 Hz, 1H), 2.06-1.96 (m, 5H), 1.96-1.80 (m, 4H), 1.15 (t, J = 7.4 Hz, 3H). |

TABLE 3-continued

| Cmpd. | Characterization Data (NMR and LCMS) |
|---|---|
| 32 | $^1$H NMR (400 MHz, Chloroform-d) δ 8.18-8.12 (m, 1H), 8.12-8.07 (m, 1H), 7.81-7.71 (m, 2H) 7.28 (m, 2H), 7.22-7.16 (m, 2H), 3.10 (m, 1H), 2.75 (t, J = 7.4 Hz, 2H), 2.66-2.54 (m, 1H), 2.02 (s, 4H), 1.86 (q, J = 7.2, 6.7 Hz, 4H), 1.38 (d, J = 46.6 Hz, 12H), 0.97-0.83 (m, 3H). |
| 33 | $^1$H NMR (400 MHz, CDCl$_3$) δ 8.14-8.12 (m, 1H), 8.10-8.08 (m, 1H), 7.78-7.71 (m, 2H), 7.27 (d, J = 8.5 Hz, 2H), 7.20-7.13 (m, 2H), 5.60-5.51 (m, 2H), 5.47-5.31 (m, 10H), 3.16-3.08 (m, 1H), 2.96-2.82 (m, 12H), 2.67-2.59 (m, 3H), 2.13-1.99 (m, 6H) 1.88-1.84 (m, 2H), 1.63-1.52 (m, 2H), 0.99 (t, J = 8.0 Hz, 3H). |
| 34 | $^1$H NMR (400 MHz, CDCl$_3$) δ 8.11-8.08 (m, 1H), 8.07-8.04 (m, 1H), 7.76-7.69 (m, 2H), 7.27 (d, J = 8.5 Hz, 2H), 7.20-7.13 (m, 2H), 5.52 (s, 2H), 5.45-5.29 (m, 12H), 3.82 (t, J = 8.0 Hz, 2H), 3.31-3.23 (m, 1H), 2.87-2.79 (m, 10H), 2.72-2.64 (m, 1H), 2.29 (qd, J = 12.0, 4.0 Hz, 2H), 2.22-2.16 (m, 2H), 2.13-2.05 (m, 2H), 2.04-1.99 (m, 2H), 1.80-1.70 (m, 4H),1.61-1.50 (m, 2H), 0.99 (t, J = 8.0 Hz, 3H). |
| 35 | $^1$H NMR (400 MHz, CDCl$_3$) δ 8.04 (s, 1H), 7.45 (s, 1H), 7.37-7.35 (m, 2H), 7.26-7.23 (m, 2H), 7.14-7.09 (m, 4H), 5.41-5.30 (m, 11H), 5.29 (s, 2H), 5.23-5.18 (m, 1H), 4.04 (s, 3H), 2.84-2.73 (m, 10H), 2.52 (s, 3H), 2.27-2.21 (m, 4H), 2.10-2.02 (m, 2H), 0.95 (t, J = 7.2 Hz, 3H); $^{19}$F NMR (376 MHz, CDCl$_3$) δ-58.24 (s, 3F). MS-ESI: m/z 816.10 observed (M + H)$^+$ |

Example 5: Sesame Oil Formulation

Sesame oil (10 μL) was dispensed into compound (10 mg). The mixture was vortexed, sonicated and warmed (using heat gun) to aid dissolution. The solubility of the compound was judged after the sesame oil mixture cooled to room temperature. If the compound was not completely dissolved, additional sesame oil was added in low-volume increments.

Example 6: General Methods and Materials for Solid State Characterization

Polarized Light Microscope (PLM)

Nikon LV100 PLM (Nikon Instruments Inc., USA) was used to examine the presence of big crystals (typically size larger than 5 μm) in the milled crystalline compounds suspensions. One drop of the test suspension was smeared on a microscope slide and covered by a cover slip for examination under crossed polarizers.

X-Ray Powder Diffraction (XRPD)

The X-ray powder diffraction patterns of all crystalline forms of the compounds were obtained on Bruker D8 advance X-ray powder diffractometer. Test materials were placed on monocrystalline silicon XRPD pan for analysis. The instrument specification and settings are as follows:
Tube: Cu: K-Alpha (λ=1.54179 Å).
Generator: Voltage: 40 kV; Current: 40 mA.
Scan Scope: 4 to 40 deg.
Sample rotation speed: 15 rpm.
Scanning rate: 10 deg./min.

Differential Scanning Calorimetry (DSC)

DSC data were acquired using a TA Q2000 DSC. A sample weighted between 0.5 and 1 mg was sealed into an aluminum pan with a pinhole. This pan was placed in the sample position in the calorimeter cell. An empty pan was placed in the reference position. The heating program was set to heat the sample from 30° C. to 300° C. at a rate of 10° C./min. When the run is completed, the data were analyzed using TA Universal Analysis.

Thermal Gravimetric Analysis (TGA)

TGA data were acquired using a TA Q5000 TGA. A sample weighted between 2 and 5 mg was placed in an open platinum pan and heated from 25° C. to 300° C. at a rate of 10° C./min. When the run is completed, the data were analyzed using TA Universal Analysis.

Size Distribution Measurement

Size distribution of milled crystalline compound suspensions was measured by Nicomp Zeta Potential & Particle Sizer 380 (Particle Sizing Systems Inc., USA). One drop of a test suspension was diluted with deionized water to a desired light scattering intensity (typically 300-700 kHz) and added into the sample cell to ⅓-⅔ of the cell volume. The sample cell was left in the cell pedestal for 5 min to allow temperature equilibration. The settings of instrument parameters are as follows:
Intensity setpoint: 300 kHz.
Fixed angle: 90°.
Temperature: 23° C.
Liquid viscosity: 0.933CP.
Liquid index of refraction: 1.333.

HPLC Method

Concentrations of the crystalline compound in suspensions were determined using Agilent HPLC 1200 and 1260 and the HPLC condition is as follows:

| | |
|---|---|
| Column | Ascentis Express C18, 100 × 4.6 mm, 2.7 μm |
| Mobile Phase | A = 0.1% H$_3$PO$_4$/H$_2$O |
| | B = ACN |
| Gradient | A:B Initial: 90:10 |
| | 6 min: 5:95 |
| | 8 min: 5:95 |
| Flow rate | 1.8 mL/min |
| Gradient Time | 8 min |
| | (+2 min re-equilibration) |
| Temperature | 40° C. |
| Injection volume | 10 μL |
| Wavelength | 210 nm |

Example 7: Synthesis of ELQ-300 Crystalline Forms

Figure 5:
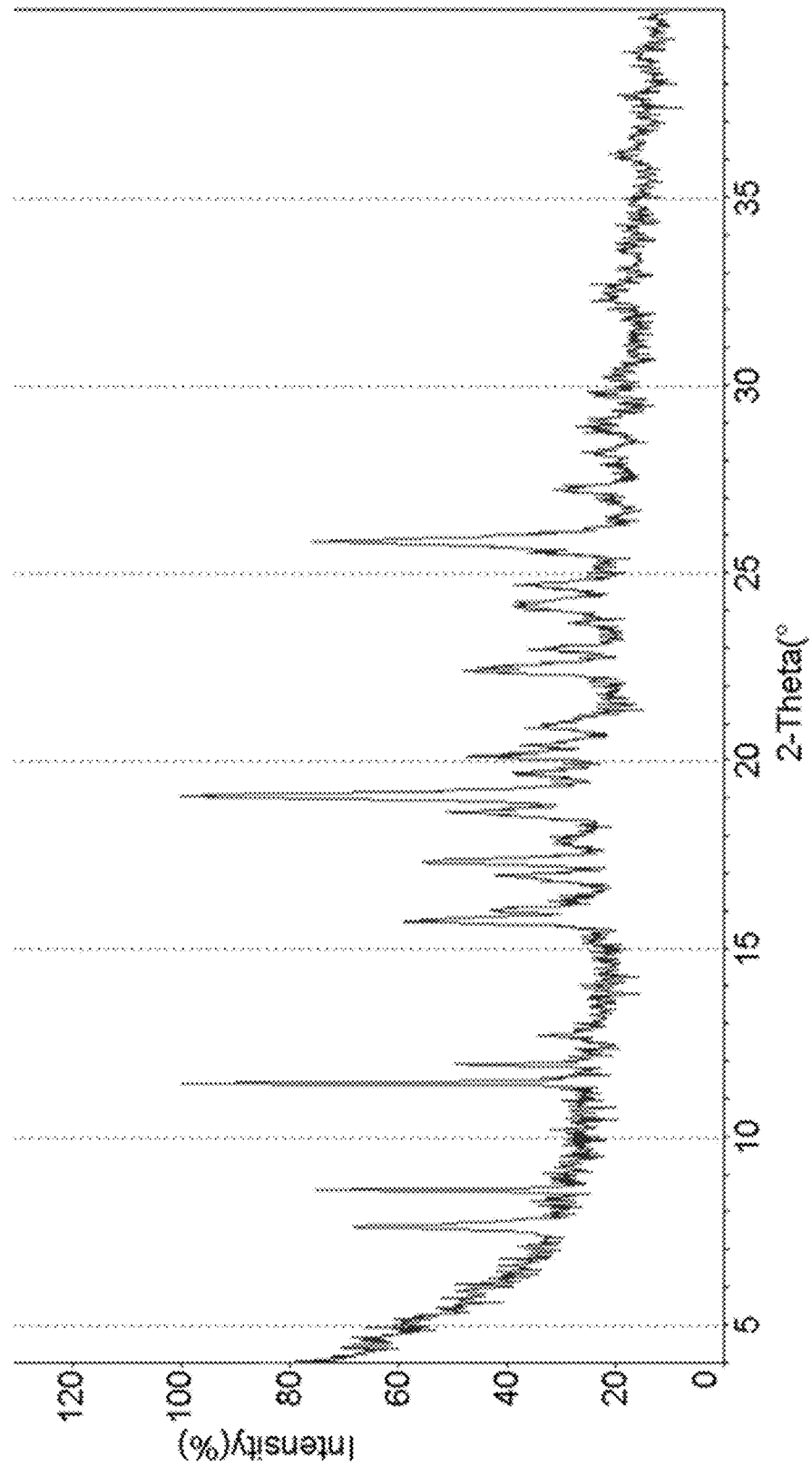
FIG. 5 depicts the characteristic X-ray diffraction pattern of the crystalline ELQ-300-Form IA.
Figure 6:
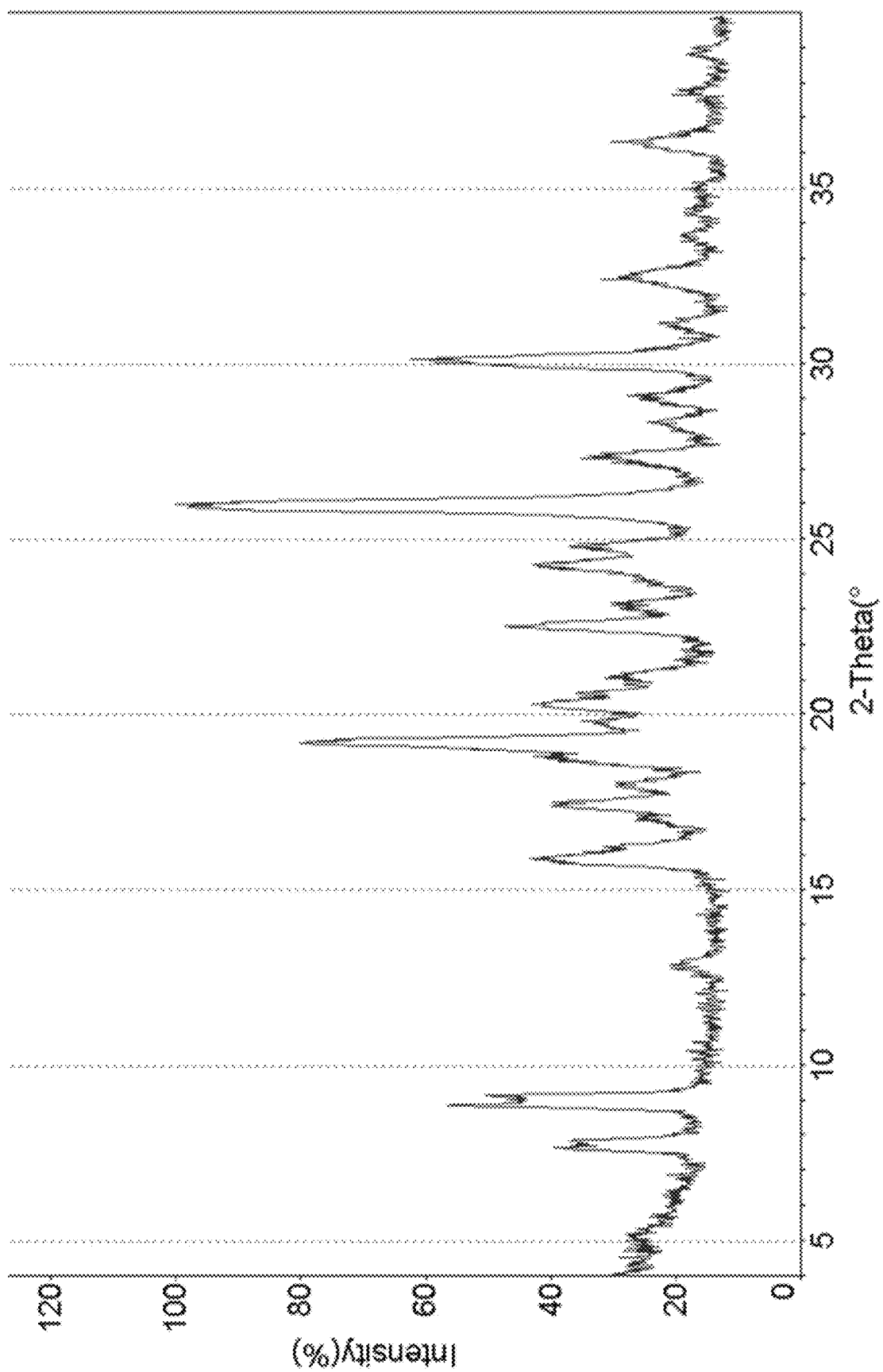
FIG. 6 depicts the characteristic X-ray diffraction pattern of the crystalline ELQ-300-Form IB.

ELQ-300 crystalline forms were prepared and characterized via DSC, XRPD and TGA. Two distinct crystalline forms of the raw material were identified, designated as form IA and form IB. Four new crystalline forms of ELQ-300 were identified and designated as Form II, Form III, Form IV and Form V. FIG. 5 shows the characteristic X-ray diffraction pattern of the crystalline ELQ-300-Form IA. FIG. 6 shows the characteristic X-ray diffraction pattern of the crystalline ELQ-300-Form IB.

Table 4 shows the characteristic reflections and the corresponding d-spacings for crystalline ELQ-300-Form IA.

TABLE 4

| No. | 2-Theta (°) | d-spacing (Å) |
|---|---|---|
| 1 | 7.65 | 11.55 |
| 2 | 8.63 | 10.24 |
| 3 | 11.46 | 7.71 |
| 4 | 11.96 | 7.39 |
| 5 | 12.74 | 6.94 |
| 6 | 15.79 | 5.61 |
| 7 | 16.07 | 5.51 |
| 8 | 16.45 | 5.38 |
| 9 | 16.96 | 5.22 |
| 10 | 17.34 | 5.11 |
| 11 | 18.67 | 4.75 |
| 12 | 19.09 | 4.65 |
| 13 | 19.72 | 4.50 |
| 14 | 20.16 | 4.40 |
| 15 | 20.45 | 4.34 |
| 16 | 20.93 | 4.24 |
| 17 | 22.44 | 3.96 |
| 18 | 23.02 | 3.86 |
| 19 | 24.18 | 3.68 |
| 20 | 24.73 | 3.60 |
| 21 | 25.89 | 3.44 |
| 22 | 27.27 | 3.27 |
| 23 | 28.26 | 3.16 |
| 24 | 28.95 | 3.08 |
| 25 | 29.15 | 3.06 |
| 26 | 29.86 | 2.99 |
| 27 | 30.27 | 2.95 |
| 28 | 32.31 | 2.77 |
| 29 | 32.74 | 2.73 |
| 30 | 36.21 | 2.48 |
| 31 | 37.77 | 2.38 |

Table 5 shows the characteristic reflections and the corresponding d-spacings for crystalline ELQ-300-Form IB.

TABLE 5

| No. | 2-Theta (°) | d-spacing (Å) |
|---|---|---|
| 1 | 5.23 | 16.87 |
| 2 | 7.77 | 11.36 |
| 3 | 8.90 | 9.93 |
| 4 | 12.90 | 6.86 |
| 5 | 15.95 | 5.55 |
| 6 | 16.26 | 5.45 |
| 7 | 17.00 | 5.21 |
| 8 | 17.43 | 5.08 |
| 9 | 18.09 | 4.90 |
| 10 | 18.77 | 4.72 |
| 11 | 19.23 | 4.61 |
| 12 | 19.84 | 4.47 |
| 13 | 20.33 | 4.36 |
| 14 | 20.63 | 4.30 |
| 15 | 22.56 | 3.94 |
| 16 | 23.16 | 3.84 |
| 17 | 24.32 | 3.66 |
| 18 | 24.83 | 3.58 |
| 19 | 26.04 | 3.42 |
| 20 | 27.40 | 3.25 |
| 21 | 28.37 | 3.14 |
| 22 | 29.14 | 3.06 |
| 23 | 30.17 | 2.96 |
| 24 | 31.20 | 2.86 |
| 25 | 32.52 | 2.75 |
| 26 | 33.68 | 2.66 |
| 27 | 34.35 | 2.61 |
| 28 | 36.37 | 2.47 |
| 29 | 37.85 | 2.38 |
| 30 | 38.91 | 2.31 |

First Preparation of Crystalline ELQ-300-Form II and Characterization

Figure 7:
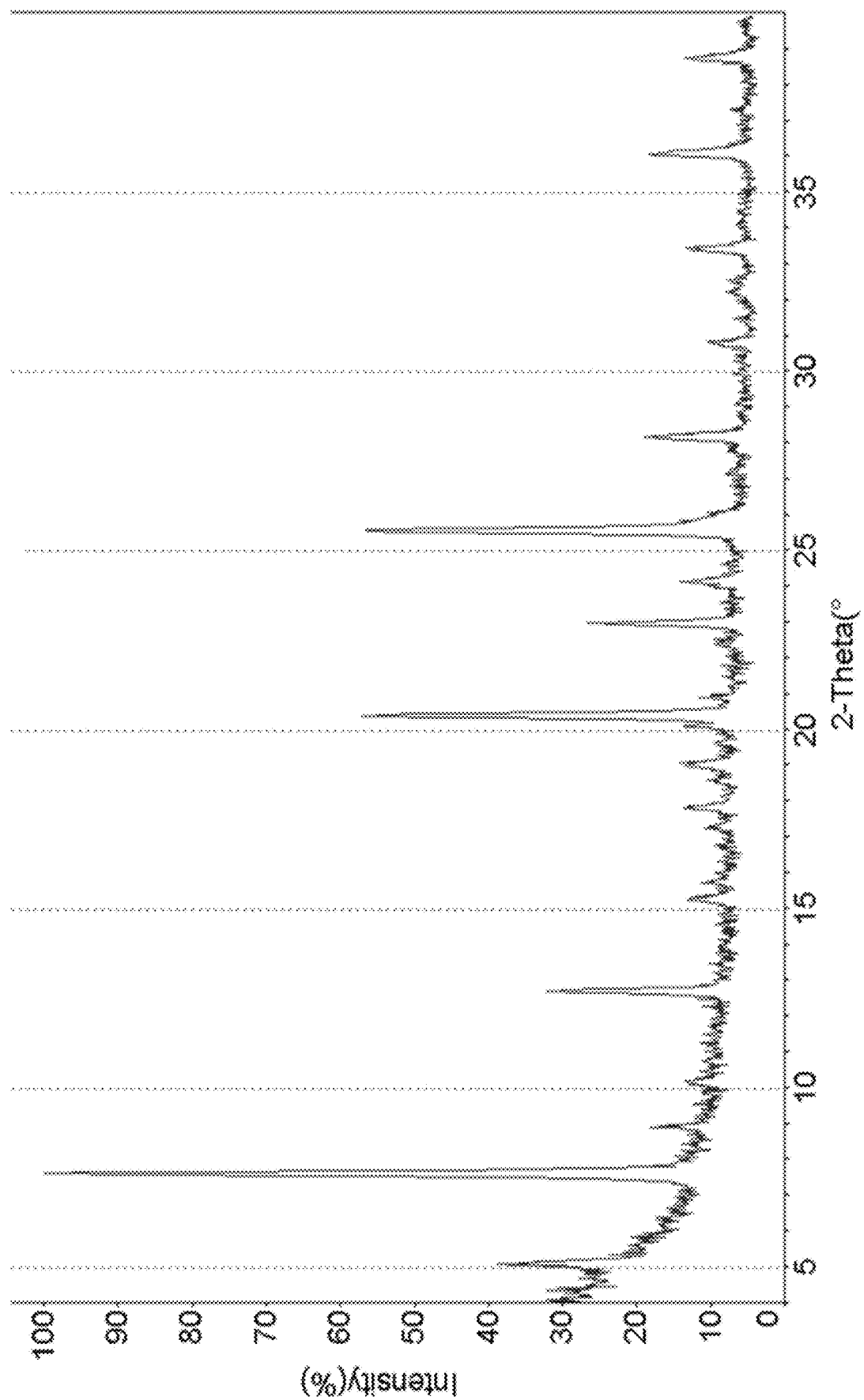
FIG. 7 depicts the characteristic X-ray diffraction pattern of the crystalline ELQ-300-Form II (first preparation).
Figure 8:
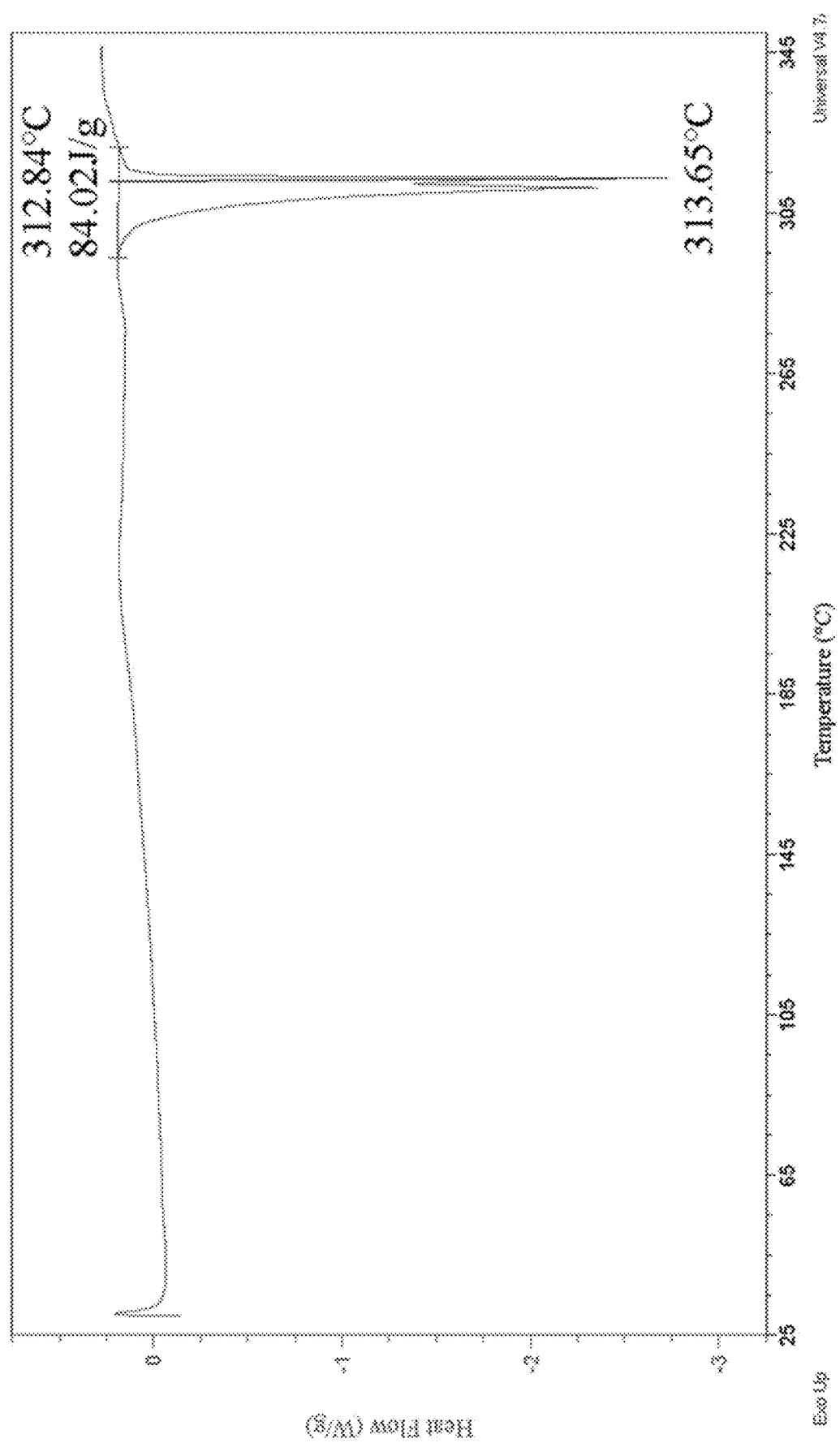
FIG. 8 depicts the DSC of the crystalline ELQ-300-Form II (first preparation).

All operations were carried out at room temperature, at 18-23° C. unless specifically stated. 37 mg of ELQ-300-Form IA was completely dissolved in 5 mL of DCM-MeOH mixture (1:1). The solution was stirred at 200 rpm and 15 mL of hexane was added to the solution over about 0.5 min. Precipitates were observed after addition of hexane and the suspension was kept stirring at 200 rpm for 3 hours. The sample was centrifuged at 14,000 rpm for 10 min and the precipitates were dried overnight in a vacuum oven at 40° C. Obtained product was characterized by XRPD and DSC and shown to be a new crystalline form, which was designated ELQ-300-Form II. FIG. 7 shows the characteristic X-ray diffraction pattern of the crystalline ELQ-300-Form II. Characteristic reflections and the corresponding d-spacings for crystalline Form II are shown in Table 6. FIG. 8 shows the DSC of the crystalline ELQ-300-Form II.

TABLE 6

| No. | 2-Theta (°) | d-spacing (Å) |
|---|---|---|
| 1 | 4.37 | 20.19 |
| 2 | 5.12 | 17.24 |
| 3 | 7.67 | 11.52 |
| 4 | 8.94 | 9.89 |
| 5 | 10.23 | 8.64 |
| 6 | 12.74 | 6.94 |
| 7 | 15.29 | 5.79 |
| 8 | 15.76 | 5.62 |
| 9 | 17.30 | 5.12 |
| 10 | 17.85 | 4.97 |
| 11 | 18.63 | 4.76 |
| 12 | 19.11 | 4.64 |
| 13 | 20.14 | 4.41 |
| 14 | 20.43 | 4.34 |
| 15 | 20.94 | 4.24 |
| 16 | 22.43 | 3.96 |
| 17 | 23.01 | 3.86 |
| 18 | 24.18 | 3.68 |
| 19 | 25.62 | 3.47 |
| 20 | 28.20 | 3.16 |
| 21 | 30.88 | 2.89 |
| 22 | 31.54 | 2.83 |
| 23 | 32.28 | 2.77 |
| 24 | 32.62 | 2.74 |
| 25 | 33.50 | 2.67 |
| 26 | 36.11 | 2.49 |
| 27 | 38.79 | 2.32 |

1st Scale Up of Crystalline ELQ-300-Form II and Characterization

Figure 9:
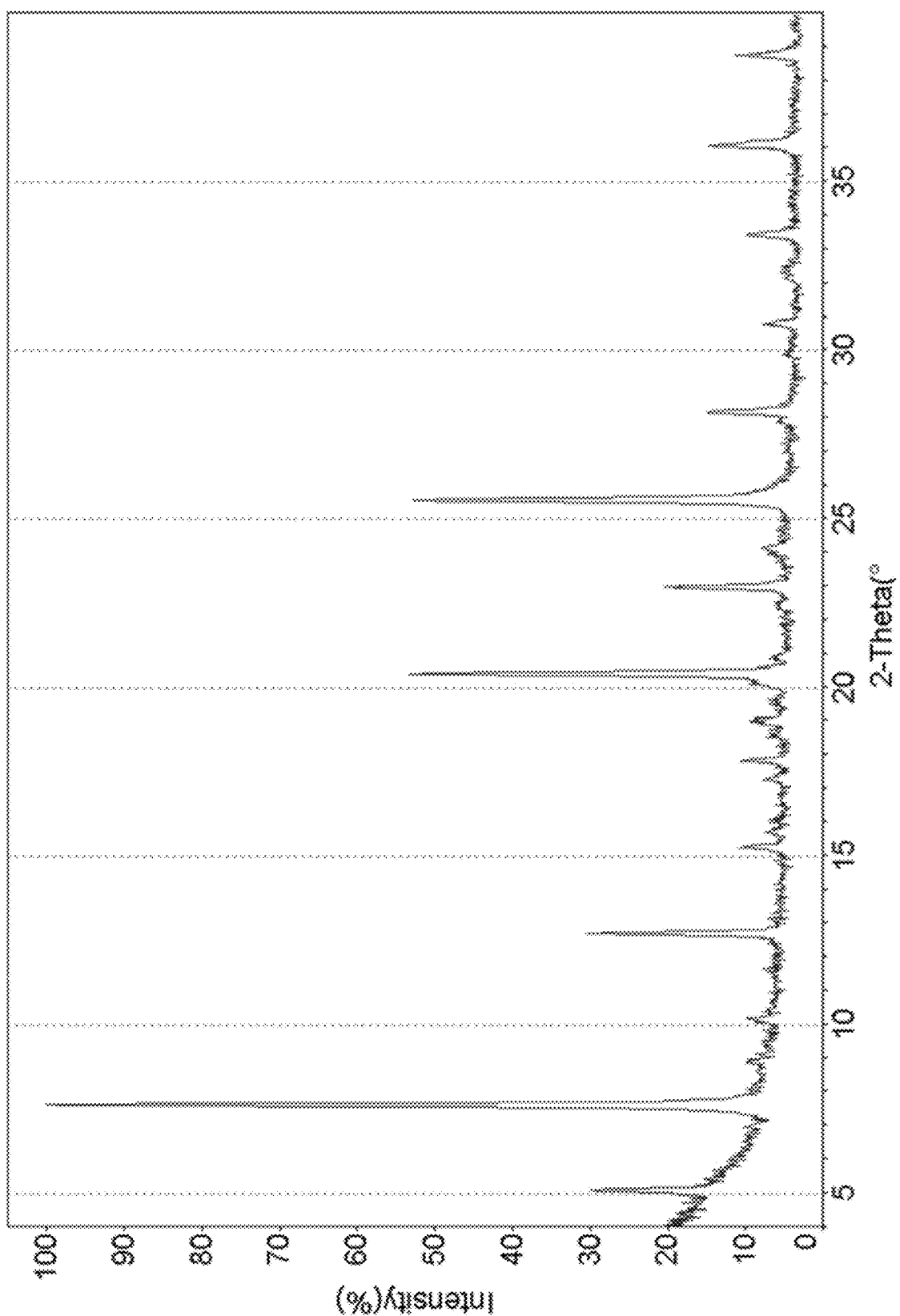
FIG. 9 depicts the characteristic X-ray diffraction pattern of the scaled up crystalline ELQ-300-Form II ($1^{st}$ scale up batch).

All operations were carried out at room temperature, at 18-23° C. unless specifically stated. 188.64 mg of ELQ-300-Form IA was completely dissolved in 15 mL of DCM-MeOH mixture (1:1). The solution was stirred at 200 rpm and 45 mL of hexane was added to the solution over about 1 min. Precipitates were observed after addition of hexane and the suspension was kept stirring at 200 rpm for 3 hours. The sample was centrifuged at 14,000 rpm for 10 min and the precipitates were dried overnight in a vacuum oven at 40° C. Obtained product was characterized by XRPD to confirm the formation of crystalline Form II and named as 1st scale up batch of crystalline ELQ-300-Form II. FIG. 9 shows the characteristic X-ray diffraction pattern of the scaled up crystalline ELQ-300-Form II (1st scale up batch). Characteristic reflections and the corresponding d-spacings for the scaled up crystalline ELQ-300-Form II (1st scale up batch) are shown in Table 7.

TABLE 7

| No. | 2-Theta (°) | d-spacing (Å) |
|---|---|---|
| 1 | 5.11 | 17.29 |
| 2 | 7.65 | 11.55 |

TABLE 7-continued

| No. | 2-Theta (°) | d-spacing (Å) |
|---|---|---|
| 3 | 8.95 | 9.87 |
| 4 | 10.21 | 8.66 |
| 5 | 12.74 | 6.94 |
| 6 | 15.28 | 5.79 |
| 7 | 15.70 | 5.64 |
| 8 | 17.30 | 5.12 |
| 9 | 17.85 | 4.97 |
| 10 | 18.56 | 4.78 |
| 11 | 19.05 | 4.66 |
| 12 | 19.68 | 4.51 |
| 13 | 19.68 | 4.51 |
| 14 | 20.12 | 4.41 |
| 15 | 20.43 | 4.34 |
| 16 | 22.48 | 3.95 |
| 17 | 23.03 | 3.86 |
| 18 | 24.19 | 3.68 |
| 19 | 25.60 | 3.48 |
| 20 | 27.93 | 3.19 |
| 21 | 28.22 | 3.16 |
| 22 | 29.92 | 2.98 |
| 23 | 30.82 | 2.90 |
| 24 | 32.18 | 2.78 |
| 25 | 32.36 | 2.76 |
| 26 | 32.54 | 2.75 |
| 27 | 33.47 | 2.68 |
| 28 | 36.11 | 2.49 |
| 29 | 38.81 | 2.32 |

$2^{nd}$ Scale Up of Crystalline ELQ-300-Form II and Characterization

Figure 10:
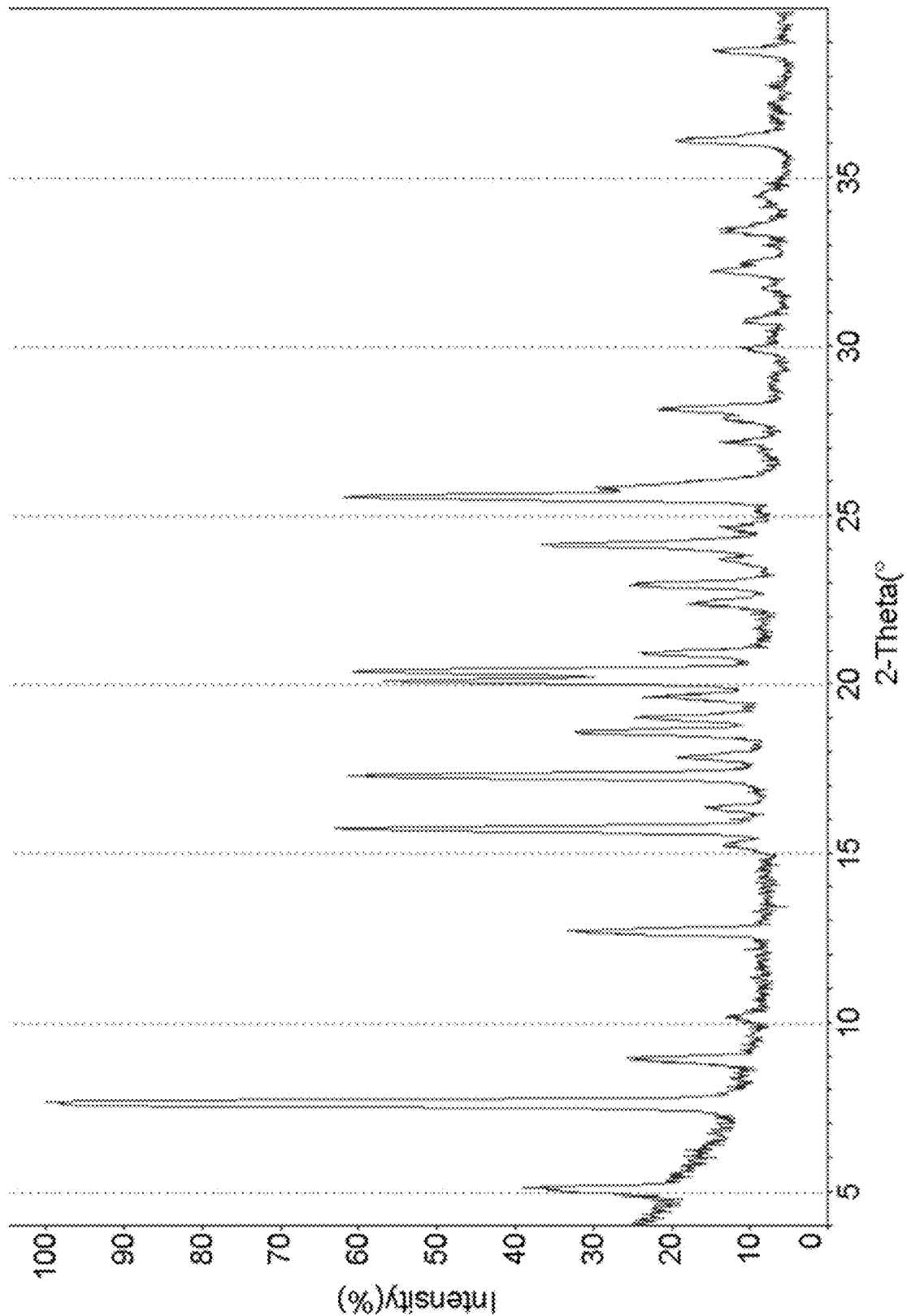
FIG. 10 depicts the characteristic X-ray diffraction pattern of the $2^{nd}$ scale up batch of crystalline ELQ-300-Form II ($2^{nd}$ scale up batch).
Figure 11:
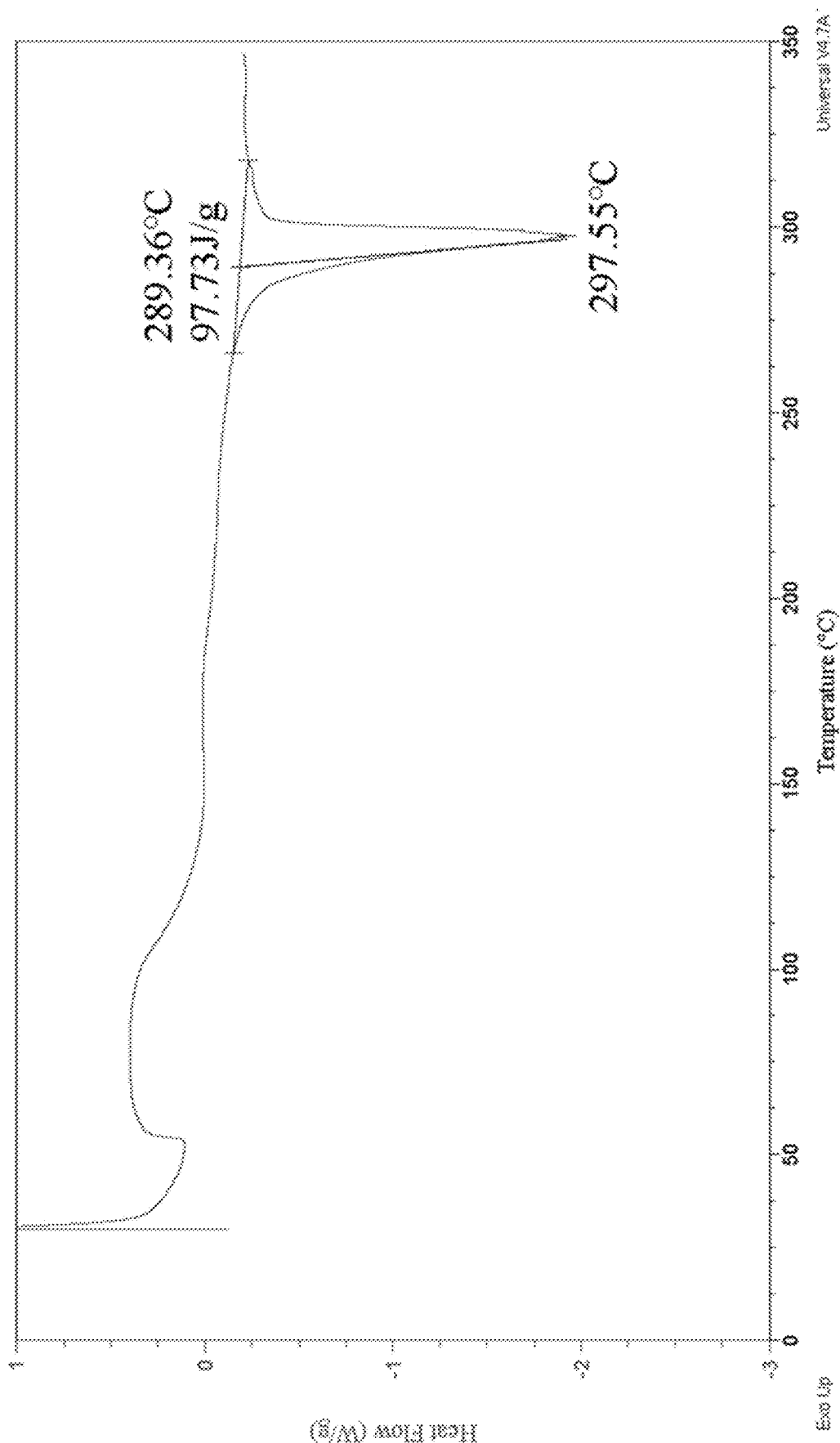
FIG. 11 depicts the DSC of crystalline ELQ-300-Form II ($2^{nd}$ scale up batch).

All operations were carried out at room temperature, at 18-23° C. unless specifically stated. 1.2 grams of ELQ-300-Form IB was completely dissolved in 100 mL of DCM-MeOH mixture (1:1). The solution was stirred at 200 rpm and 290 mL of hexane was added to the solution over about 3 min. Precipitates were observed after addition of hexane and the suspension was kept stirring at 200 rpm for 2 days. The sample was centrifuged at 14,000 rpm for 10 min and the precipitates were dried overnight in a vacuum oven at 40° C. Obtained product was characterized by XRPD and DSC to confirm the formation of crystalline Form II and named as $2^{nd}$ scale up batch of crystalline ELQ-300-Form II. FIG. 10 shows the characteristic X-ray diffraction pattern of the $2^{nd}$ scale up batch of crystalline ELQ-300-Form II. Characteristic reflections and the corresponding d-spacings for the $2^{nd}$ scale up batch of crystalline Form II are shown in Table 8. FIG. 11 shows the DSC of the $2^{nd}$ scale up batch of crystalline ELQ-300-Form II ($2^{nd}$ scale up batch).

TABLE 8

| No. | 2-Theta (°) | d-spacing (Å) |
|---|---|---|
| 1 | 5.16 | 17.10 |
| 2 | 7.69 | 11.48 |
| 3 | 8.99 | 9.83 |
| 4 | 10.21 | 8.66 |
| 5 | 12.22 | 7.24 |
| 6 | 12.75 | 6.94 |
| 7 | 15.28 | 5.79 |
| 8 | 15.77 | 5.62 |
| 9 | 16.40 | 5.40 |
| 10 | 17.33 | 5.11 |
| 11 | 17.90 | 4.95 |
| 12 | 18.65 | 4.75 |
| 13 | 19.07 | 4.65 |
| 14 | 19.66 | 4.51 |
| 15 | 20.14 | 4.41 |
| 16 | 20.41 | 4.35 |
| 17 | 20.98 | 4.23 |
| 18 | 22.43 | 3.96 |
| 19 | 22.98 | 3.87 |
| 20 | 23.76 | 3.74 |
| 21 | 24.22 | 3.67 |
| 22 | 24.71 | 3.60 |
| 23 | 25.61 | 3.48 |
| 24 | 25.88 | 3.44 |
| 25 | 27.22 | 3.27 |
| 26 | 27.96 | 3.19 |
| 27 | 28.21 | 3.16 |
| 28 | 30.01 | 2.98 |
| 29 | 30.74 | 2.91 |
| 30 | 32.28 | 2.77 |
| 31 | 32.52 | 2.75 |
| 32 | 33.43 | 2.68 |
| 33 | 34.19 | 2.62 |
| 34 | 34.49 | 2.60 |
| 35 | 36.13 | 2.48 |
| 36 | 37.86 | 2.37 |
| 37 | 38.83 | 2.32 |

Crystalline ELQ-300-Form III and ELQ-300-Form IV

Crystalline ELQ-300-Form III was prepared by slurry method using THF as the solvent and it was shown to be a solvate by DSC. After heating at 100° C. for 5 min, the crystalline ELQ-300-Form III transferred to a new crystalline form, which was designated crystalline ELQ-300-Form IV.

Preparation and Characterization of Crystalline ELQ-300-Form III

Figure 12:
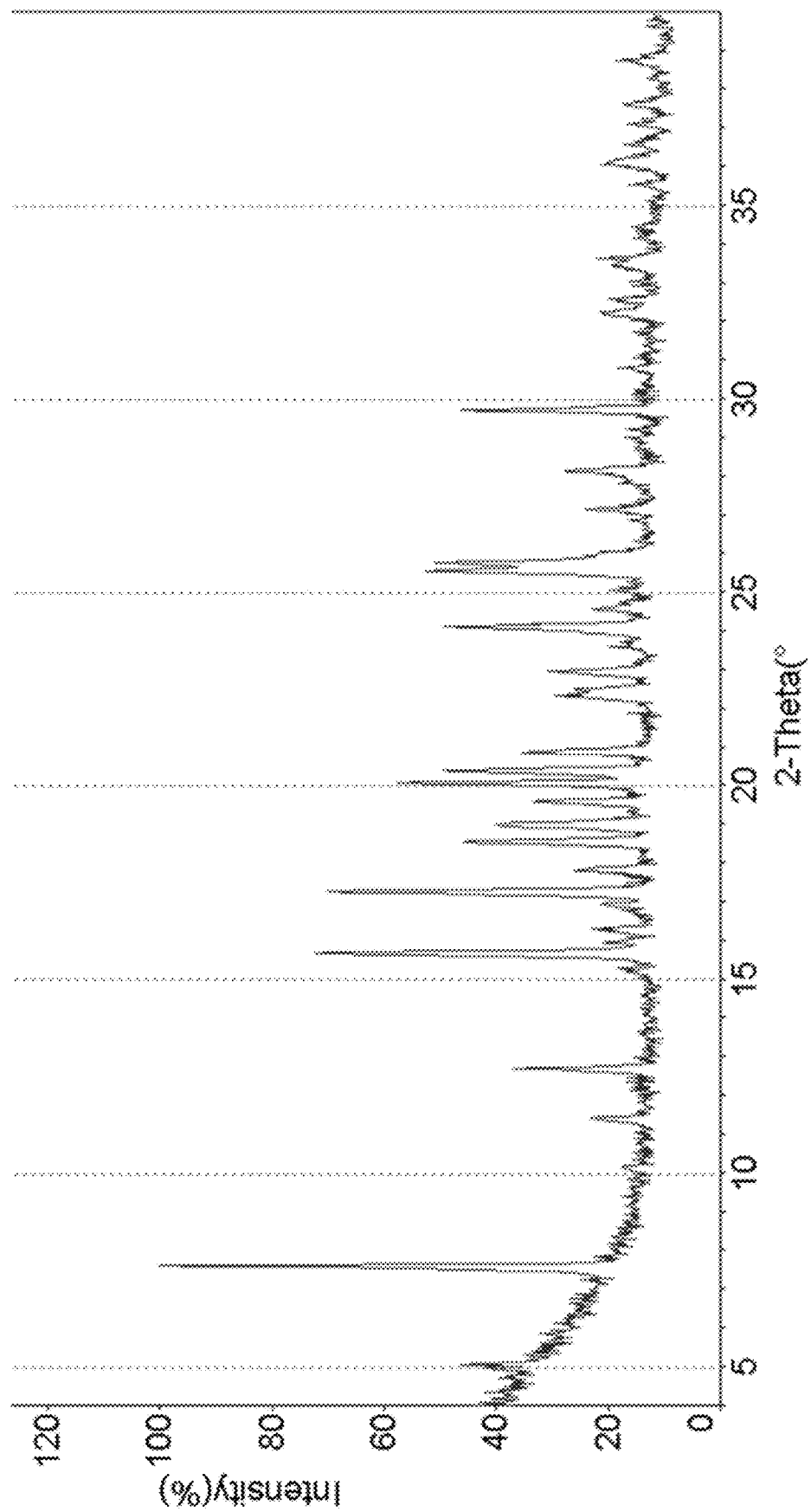
FIG. 12 depicts the characteristic X-ray diffraction pattern of the crystalline ELQ-300-Form III.
Figure 13A:
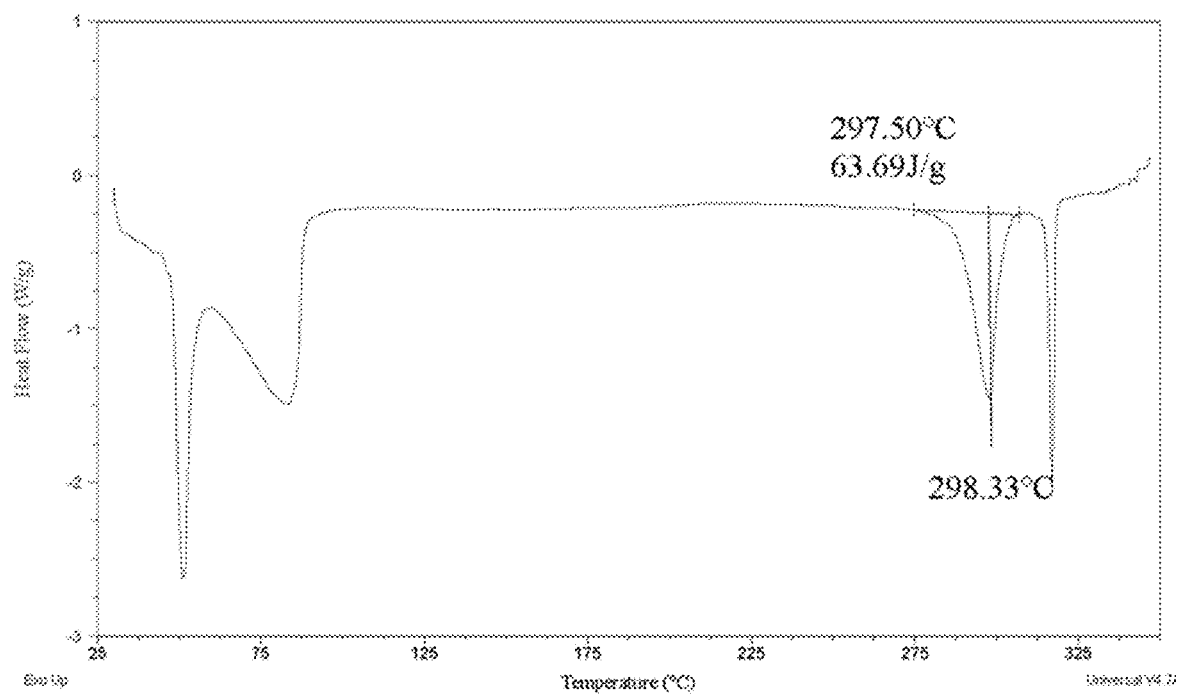
FIG. 13A depicts the DSC of crystalline ELQ-300-Form III.
Figure 13B:
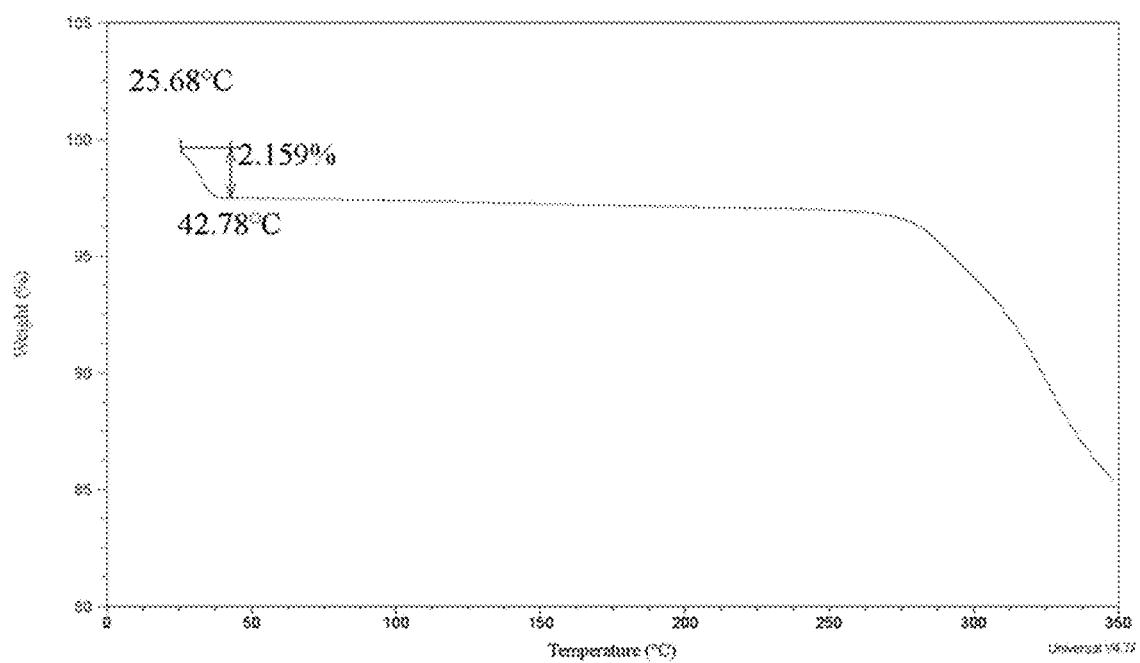
FIG. 13B depicts the TGA of crystalline ELQ-300-Form III.

About 30 mg of crystalline ELQ-300-Form IA was suspended in 0.3 mL of THF in an 1.5 mL sealed glass vial. The vial was placed in an Eppendorf Thermomixer and shaked at 50° C., 700 rpm for 72 h. The vial was centrifuged to collect solids. XRPD showed that the isolated solids have a new XRPD pattern. Thus, the wet solids were dried overnight in a vacuum oven at 40° C. and the resulting dried product was characterized by XRPD and DSC to confirm the formation of a new crystalline Form, which was designated as ELQ-300-Form III. FIG. 12 shows the characteristic X-ray diffraction pattern of the crystalline ELQ-300-Form III. Characteristic reflections and the corresponding d-spacings for crystalline ELQ-300-Form III are shown in Table 9. DSC and TGA of crystalline ELQ-300-Form III are shown in FIG. 13A and FIG. 13B respectively.

TABLE 9

| No. | 2-Theta (°) | d-spacing (Å) |
|---|---|---|
| 1 | 5.09 | 17.34 |
| 2 | 7.65 | 11.55 |
| 3 | 11.45 | 7.72 |
| 4 | 12.74 | 6.94 |
| 5 | 15.31 | 5.78 |
| 6 | 15.72 | 5.63 |
| 7 | 15.98 | 5.54 |
| 8 | 16.33 | 5.42 |
| 9 | 16.97 | 5.22 |
| 10 | 17.30 | 5.12 |
| 11 | 17.85 | 4.96 |
| 12 | 18.58 | 4.77 |
| 13 | 19.03 | 4.66 |
| 14 | 19.62 | 4.52 |
| 15 | 20.10 | 4.41 |
| 16 | 20.43 | 4.34 |
| 17 | 20.91 | 4.25 |
| 18 | 22.38 | 3.97 |
| 19 | 23.00 | 3.86 |
| 20 | 23.65 | 3.76 |
| 21 | 24.16 | 3.68 |

TABLE 9-continued

| No. | 2-Theta (°) | d-spacing (Å) |
|---|---|---|
| 22 | 24.62 | 3.61 |
| 23 | 25.10 | 3.55 |
| 24 | 25.60 | 3.48 |
| 25 | 25.81 | 3.45 |
| 26 | 27.18 | 3.28 |
| 27 | 27.86 | 3.20 |
| 28 | 28.20 | 3.16 |
| 29 | 29.05 | 3.07 |
| 30 | 29.25 | 3.05 |
| 31 | 29.76 | 3.00 |
| 32 | 32.28 | 2.77 |
| 33 | 32.62 | 2.74 |
| 34 | 33.09 | 2.71 |
| 35 | 33.49 | 2.67 |
| 36 | 33.68 | 2.66 |
| 37 | 34.20 | 2.62 |
| 38 | 34.51 | 2.60 |
| 39 | 35.58 | 2.52 |
| 40 | 36.12 | 2.49 |
| 41 | 36.62 | 2.45 |
| 42 | 37.14 | 2.42 |
| 43 | 37.66 | 2.39 |
| 44 | 38.79 | 2.32 |

Preparation and Characterization of Crystalline ELQ-300-Form IV

Figure 14:
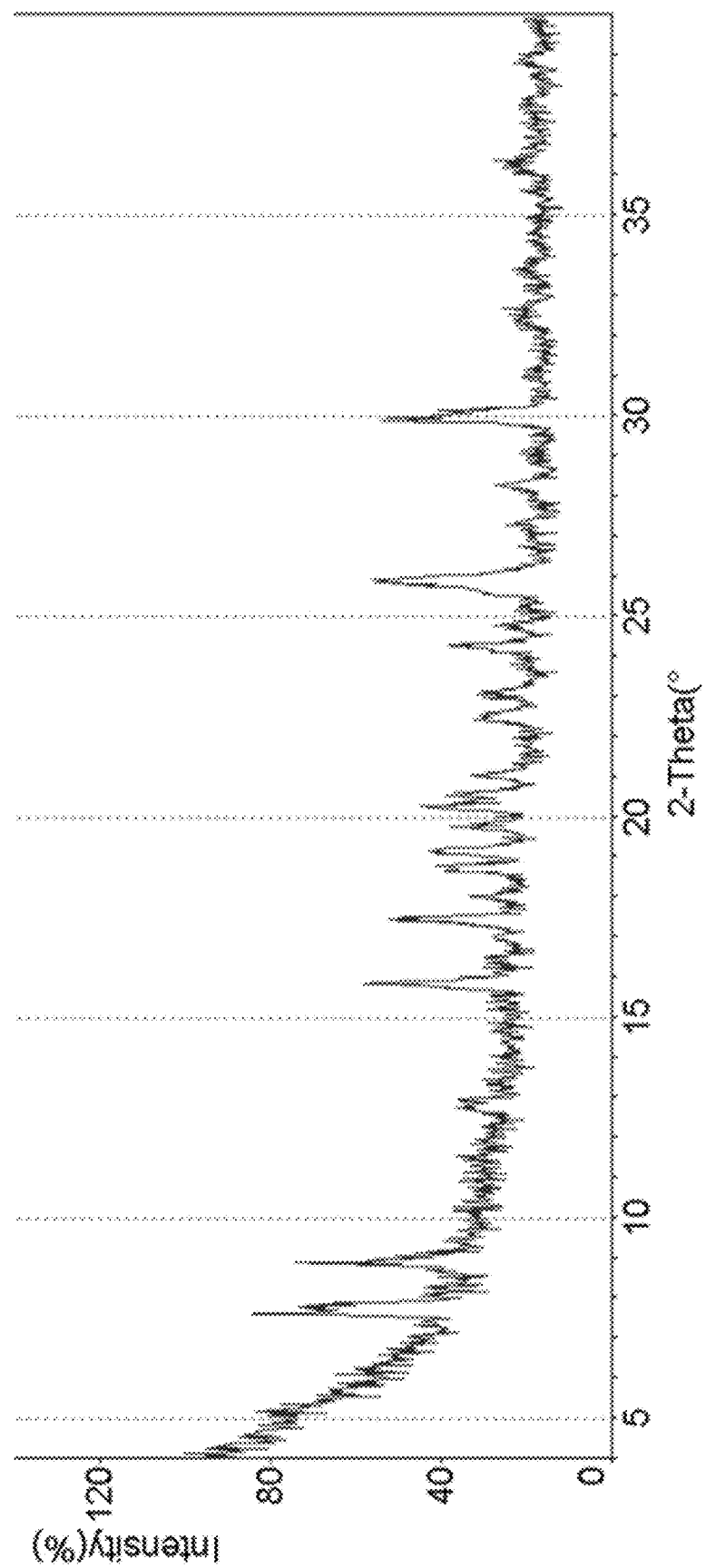
FIG. 14 depicts the characteristic X-ray diffraction pattern of the crystalline ELQ-300-Form IV.
Figure 15A:
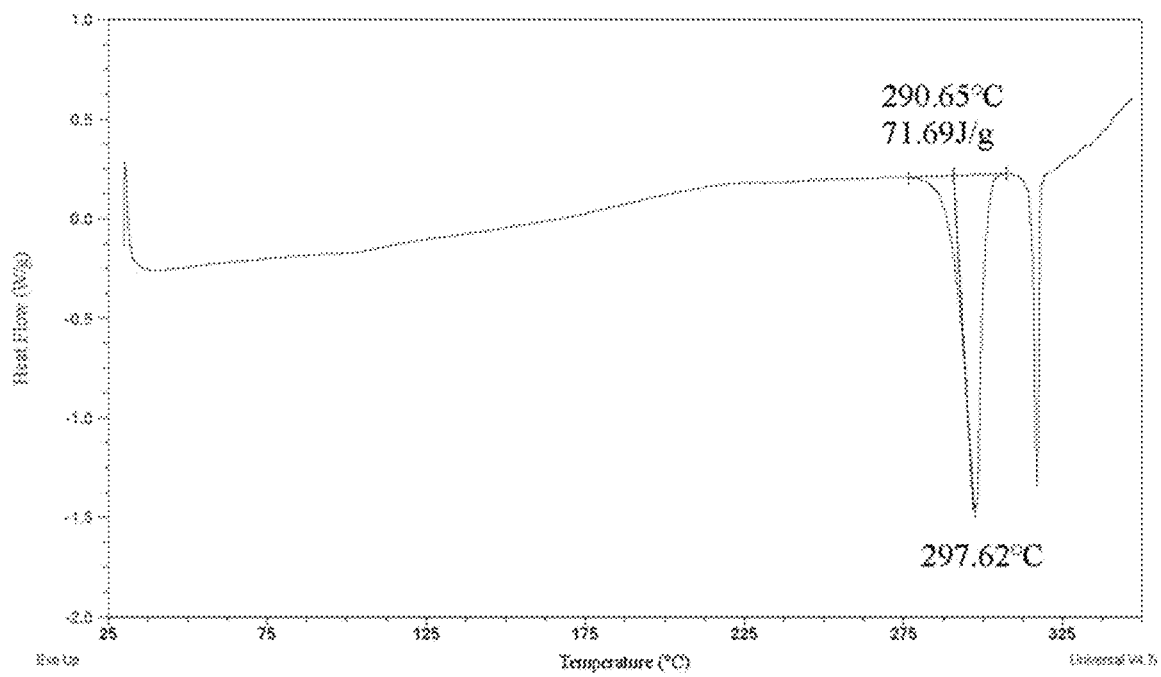
FIG. 15A depicts the DSC of crystalline ELQ-300-Form IV.
Figure 15B:
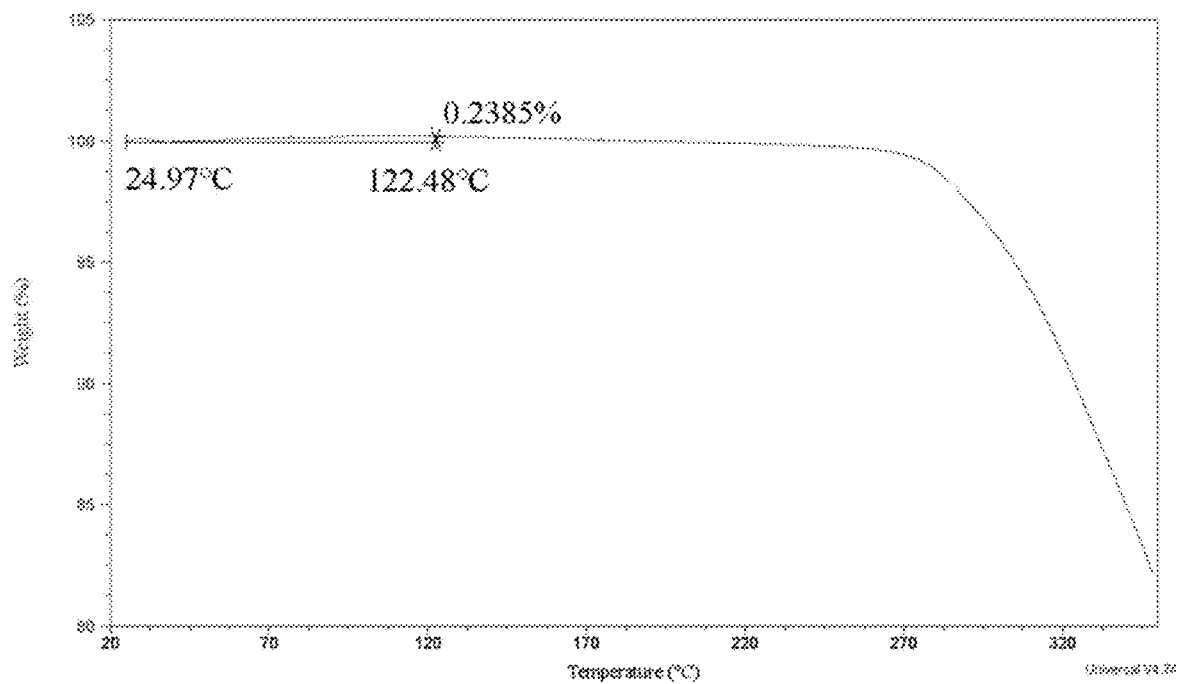
FIG. 15B depicts the TGA of crystalline ELQ-300-Form IV.

The crystalline ELQ-300-Form III obtained from slurry in THF was heated to 100° C. and maintained the temperature for 5 min, the obtained product was characterized by XRPD, DSC and TGA and shown to be a new crystalline Form, which was designated crystalline ELQ-300-Form IV. FIG. 14 shows the characteristic X-ray diffraction pattern of the crystalline ELQ-300-Form IV. Characteristic reflections and the corresponding d-spacings for crystalline ELQ-300-Form IV are shown in Table 10. DSC and TGA of crystalline ELQ-300-Form IV are shown in FIG. 15A and FIG. 15B respectively.

TABLE 10

| No. | 2-Theta (°) | d-spacing (Å) |
|---|---|---|
| 1 | 7.65 | 11.55 |
| 2 | 8.91 | 9.92 |
| 3 | 12.97 | 6.82 |
| 4 | 15.88 | 5.58 |
| 5 | 17.45 | 5.08 |
| 6 | 18.04 | 4.91 |
| 7 | 18.81 | 4.71 |
| 8 | 19.19 | 4.62 |
| 9 | 19.77 | 4.49 |
| 10 | 20.29 | 4.37 |
| 11 | 20.64 | 4.30 |
| 12 | 21.08 | 4.21 |
| 13 | 22.48 | 3.95 |
| 14 | 23.17 | 3.84 |
| 15 | 24.33 | 3.66 |
| 16 | 24.83 | 3.58 |
| 17 | 25.95 | 3.43 |
| 18 | 27.32 | 3.26 |
| 19 | 28.32 | 3.15 |
| 20 | 29.92 | 2.98 |
| 21 | 30.07 | 2.97 |
| 22 | 32.46 | 2.76 |
| 23 | 32.72 | 2.74 |
| 24 | 33.70 | 2.66 |
| 25 | 36.23 | 2.48 |
| 26 | 36.41 | 2.47 |

Preparation and Characterization of Crystalline ELQ-300-Form V

Crystalline Form V was prepared by slurry method using NMP as the solvent. About 48 mg of crystalline ELQ-300-Form IA was suspended in 0.2 mL of NMP in an 1.5 mL sealed glass vial. The vial was placed in an Eppendorf Thermomixer and shaked at 37° C., 700 rpm for 24 h. The vial was centrifuged to collect the solids. XRPD showed that the isolated solids have a new XRPD pattern. Thus, 0.5 mL of ethanol was added to the wet solids for removing NMP. The sample was centrifuged at 14,000 rpm for 10 min and the supernatant was removed. The precipitated solids were dried overnight in a vacuum oven at 30° C. and analyzed by XRPD, DSC and TGA. The obtained product was shown to be a new crystalline Form, which was designated ELQ-300-Form V.

Figure 16:
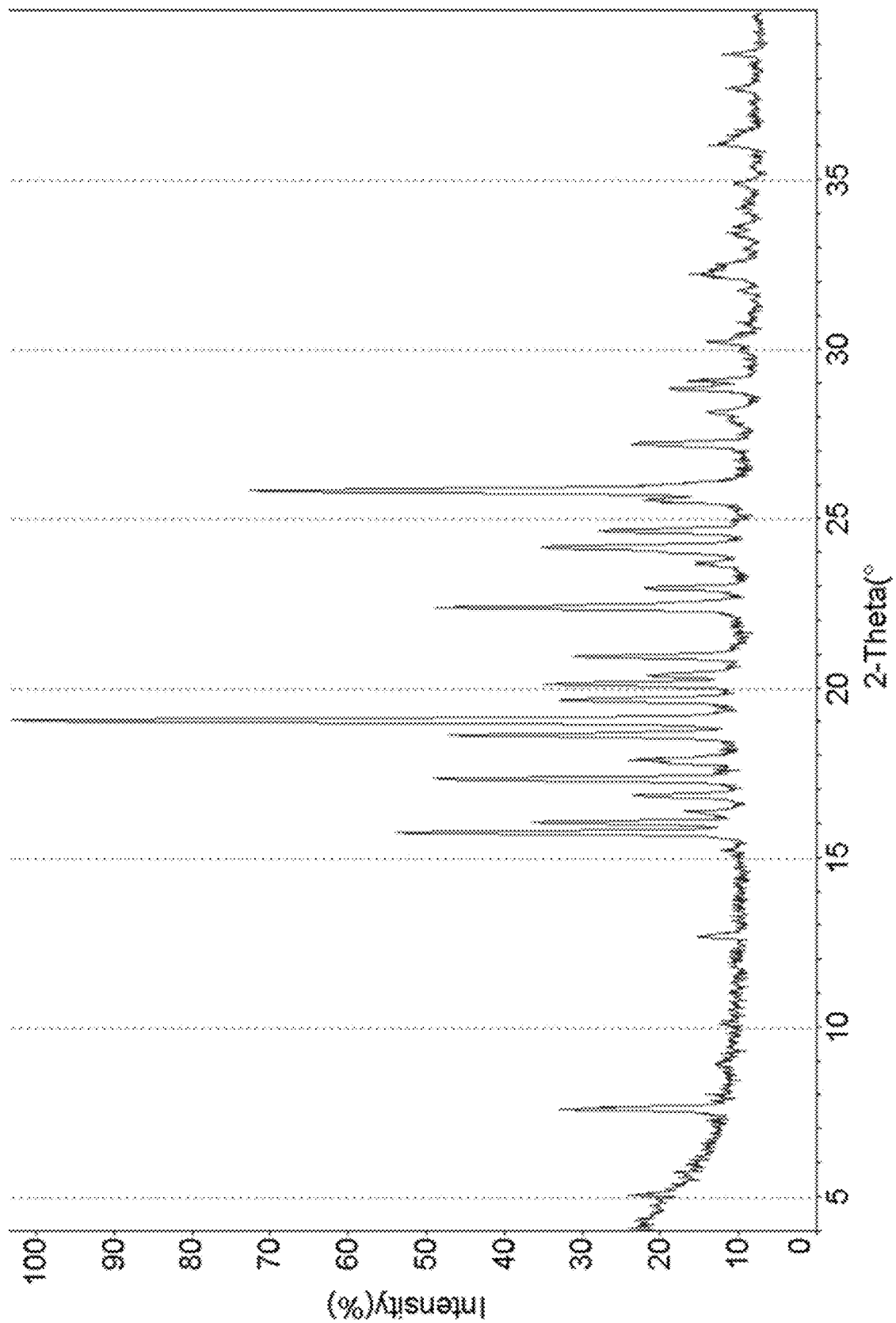
FIG. 16 depicts the characteristic X-ray diffraction pattern of the crystalline ELQ-300-Form V.
Figure 17A:
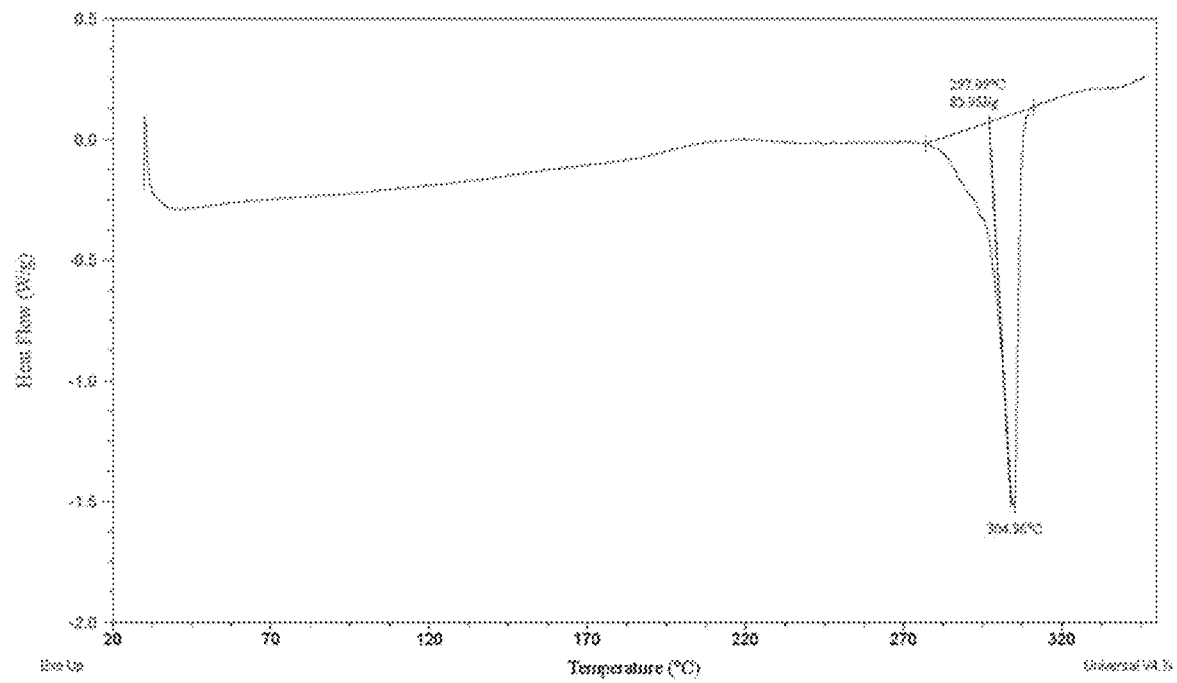
FIG. 17A depicts the DSC of crystalline ELQ-300-Form V.
Figure 17B:
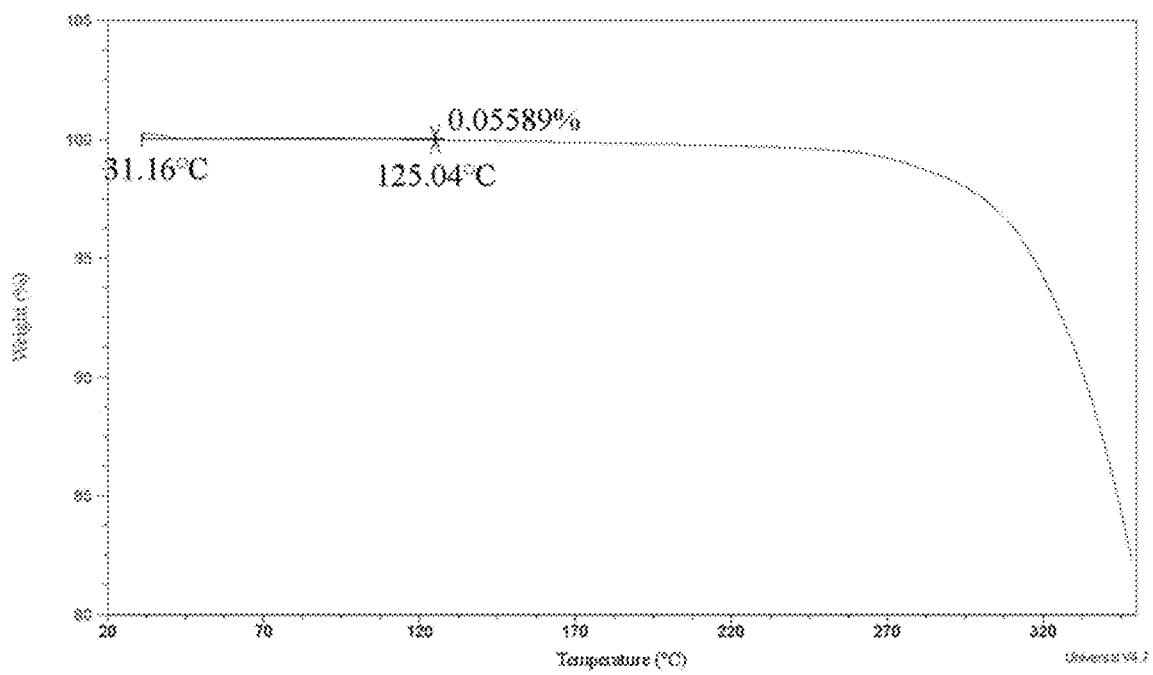
FIG. 17B depicts the TGA of crystalline ELQ-300-Form V.

FIG. 16 shows the characteristic X-ray diffraction pattern of the crystalline ELQ-300-Form V. Characteristic reflections and the corresponding d-spacings for crystalline Form V are shown in Table 11. DSC and TGA of crystalline ELQ-300-Form V are shown in FIG. 17A and FIG. 17B respectively.

TABLE 11

| No. | 2-Theta (°) | d-spacing (Å) |
|---|---|---|
| 1 | 7.61 | 11.60 |
| 2 | 12.72 | 6.96 |
| 3 | 15.28 | 5.79 |
| 4 | 15.79 | 5.61 |
| 5 | 16.09 | 5.51 |
| 6 | 16.40 | 5.40 |
| 7 | 16.88 | 5.25 |
| 8 | 17.37 | 5.10 |
| 9 | 17.92 | 4.94 |
| 10 | 18.66 | 4.75 |
| 11 | 19.09 | 4.65 |
| 12 | 19.68 | 4.51 |
| 13 | 20.14 | 4.41 |
| 14 | 20.41 | 4.35 |
| 15 | 20.98 | 4.23 |
| 16 | 22.44 | 3.96 |
| 17 | 23.01 | 3.86 |
| 18 | 23.71 | 3.75 |
| 19 | 24.22 | 3.67 |
| 20 | 24.69 | 3.60 |
| 21 | 25.60 | 3.48 |
| 22 | 25.89 | 3.44 |
| 23 | 27.26 | 3.27 |
| 24 | 27.95 | 3.19 |
| 25 | 28.20 | 3.16 |
| 26 | 28.87 | 3.09 |
| 27 | 29.11 | 3.07 |
| 28 | 30.01 | 2.98 |
| 29 | 30.29 | 2.95 |
| 30 | 30.84 | 2.90 |
| 31 | 31.79 | 2.81 |
| 32 | 32.26 | 2.77 |
| 33 | 32.56 | 2.75 |
| 34 | 33.48 | 2.67 |
| 35 | 33.68 | 2.66 |
| 36 | 34.22 | 2.62 |
| 37 | 34.44 | 2.60 |
| 38 | 34.93 | 2.57 |
| 39 | 36.09 | 2.49 |
| 40 | 37.77 | 2.38 |
| 41 | 38.77 | 2.32 |

Example 8: Preparation and Characterization of ELQ-300 Crystalline Form Suspension Wet-milling method was used to prepare the suspensions. Crystalline ELQ-300-Form II was selected as the raw material for milling and suspensions in two formulations were prepared:

(a) 1% (w/v) Synperonic® F108 (Flake)—0.2% (w/v) dodecyl sodium sulfate (SLS, Richjoint Chemicals); and (b) 3% (w/v) D-α-tocopheryl polyethylene glycol 1000 succinate (TPGS, Sigma Aldrich).

ELQ-300-Form II suspensions were prepared at two concentrations, 15 mg/mL and 100 mg/mL, respectively.

Preparation of 15 mg/mL ELQ-300-Form II Suspension

The 1$^{st}$ scale up batch of crystalline ELQ-300-Form II was used to prepare 15 mg/mL ELQ-300-Form II suspensions. About 30 mg of the obtained crystalline ELQ-300-Form II was weighted in a 30 mL high-density polyethylene bottle. 1.2 mL of suspension vehicle, i.e., 1% (w/v) Synperonic® F108—0.2% (w/v) SLS or 3% (w/v) TPGS, was added. 2.4 mL of zirconium beads with a diameter of 0.8 mm (YTZ® Grinding Media, Nikkato Co., Japan) were added using a measuring cylinder. The bottles were placed on a US Stoneware Roller Mixer and the rolling speed was set at 220 rpm. The milling duration was 2 days and one drop of milled suspension was diluted with deionized water to for size distribution measurement by Nicomp Zeta Potential & Particle Sizer 380. The suspensions were also examined under PLM to see if the obtained products contained particles bigger than 5 μm. If a majority of the particles were smaller than 5 μm, the suspensions were collected using a 1 mL pipette. Concentrations of ELQ-300-Form II in the suspensions were determination by HPLC. The suspensions were further diluted with their corresponding formulation vehicles to a final concentration of 15 mg/mL and stored in sealed glass vials at room temperature before PK study. Visual inspection of the suspensions showed that the products were homogeneous, syringeable and easily resuspendable following short-time vortex or water-bath sonication, suitable for preclinical PK study via intramuscular injection. The suspensions were characterized on dosing day by particle sizer and HPLC to ensure that the samples remained stable after storage at room temperature in terms of particle size and API concentration.

Preparation of 100 mg/mL ELQ-300-Form II Suspension

The 2$^{nd}$ scaled up batch of crystalline ELQ-300-Form II was used for preparing aqueous ELQ-300-Form II suspension at 100 mg/mL. Initially, the targeted concentration of ELQ-300-Form II suspensions was set at 200 mg/mL. About 250 mg of the crystalline ELQ-300-Form II was weighted in a 30 mL high-density polyethylene bottle. 1 mL of suspension vehicle, i.e., 1% (w/v) Synperonic® F108—0.2% (w/v) SLS or 3% (w/v) TPGS, was added. 2 mL of zirconium beads with a diameter of 0.8 mm (YTZ® Grinding Media, Nikkato Co., Japan) were added using a measuring cylinder. The bottles were placed on a US Stoneware Roller Mixer and the rolling speed was set at 220 rpm. After 2 days of milling, the crystals suspended in both milling vehicles formed a solid paste. Thus, extra milling medium (approximately 1 mL) was added to each sample for getting a liquid form for continued milling. The samples were milled for 72 h and the products were characterized by Nicomp Zeta Potential & Particle Sizer 380, PLM and HPLC as described above. The suspensions were further diluted with their corresponding formulation vehicles to a final concentration of 100 mg/mL for PK study. Visual inspection of the suspensions showed that the products were homogeneous, syringeable and easily resuspendable following short-time vortex or water-bath sonication, suitable for preclinical PK study via intramuscular injection. The suspensions were characterized on dosing day by particle sizer and HPLC to ensure that the samples remained stable after storage at room temperature in terms of particle size and API concentration.

Example 9: Synthesis of Atovaquone Crystalline Forms

Polymorph screening of atovaquone identified two stable forms. The raw form is characterized by large crystals of varying shape with lengths as large as 5 mm (atovaquone-form I). A second polymorph was identified by evaporation of the raw API from acetone:1,4-dioxane (1:1). This crystalline form, named atovaquone-form II, was characterized by PLM and found to be small needles.

Characterization of the Crystalline Atovaquone-Form I

Figure 23:
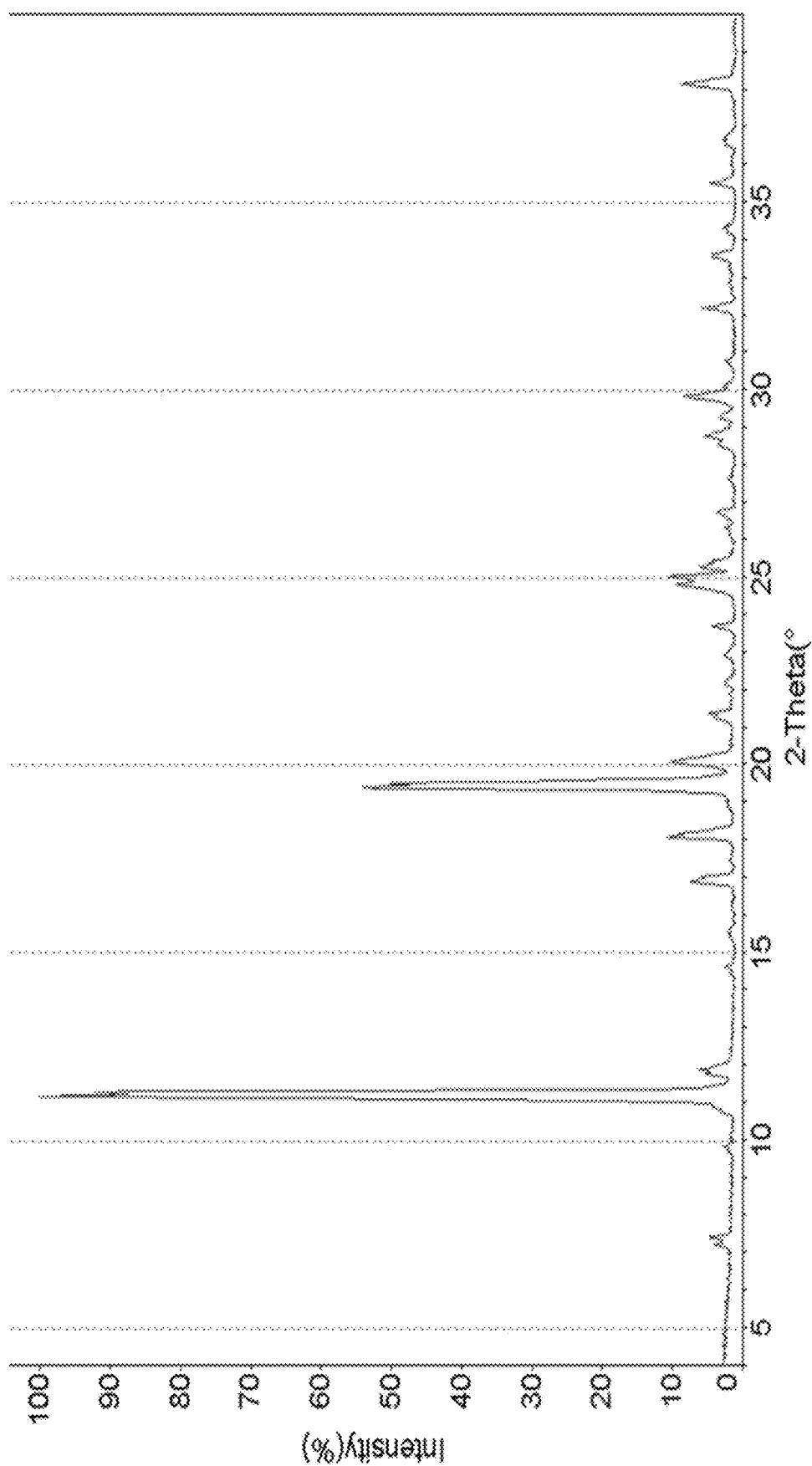
FIG. 23 depicts the characteristic X-ray diffraction pattern of the crystalline atovaquone-Form I.
Figure 24A:
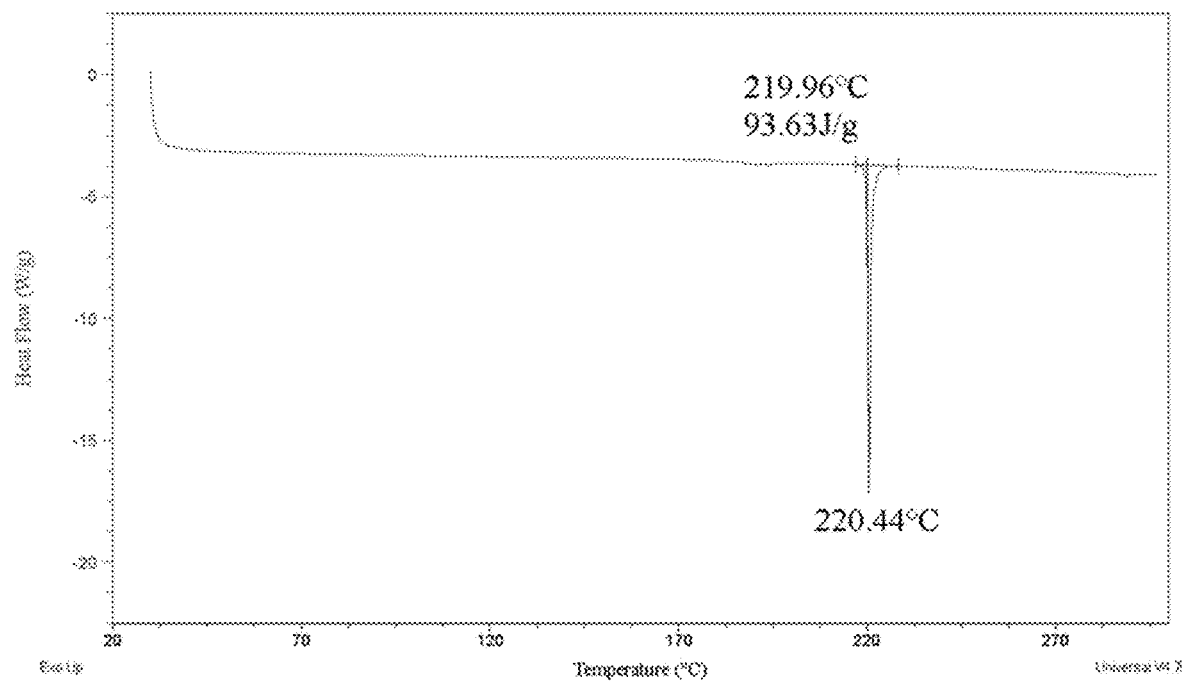
FIG. 24A depicts the DSC of crystalline atovaquone-Form I.
Figure 24B:
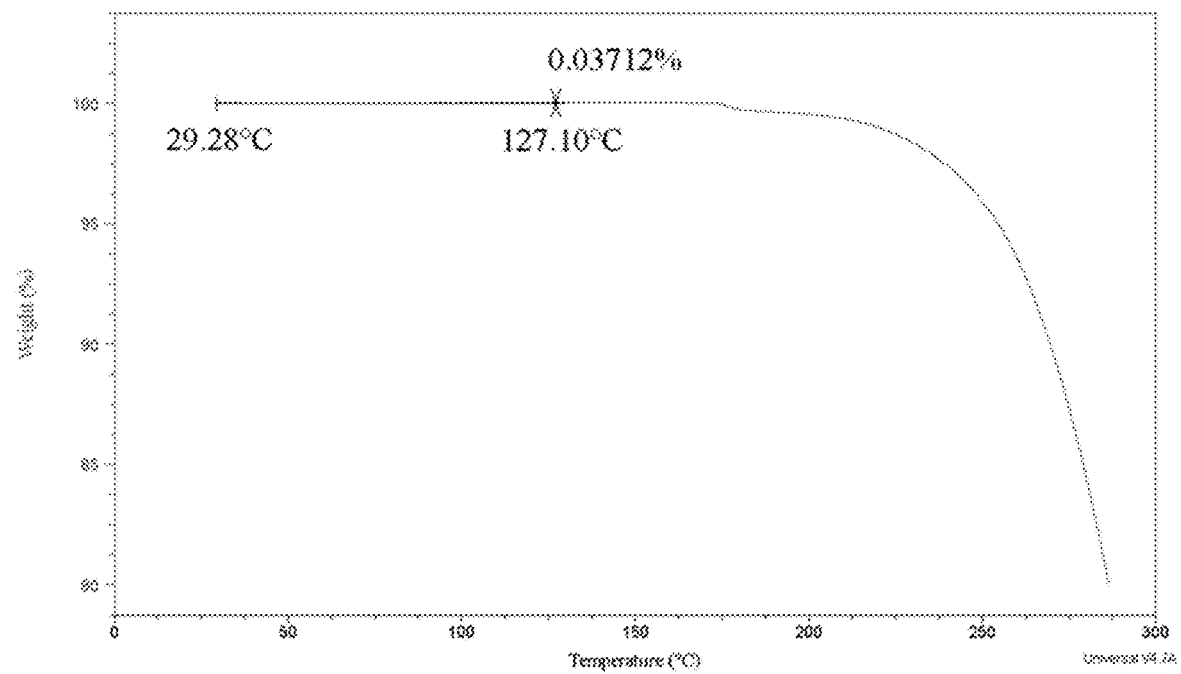
FIG. 24B depicts the TGA of crystalline atovaquone-Form I.

The crystalline atovaquone-Form I was characterized by XRPD and DSC. FIG. 23 shows the characteristic X-ray diffraction pattern of the crystalline atovaquone-Form I. Characteristic reflections and the corresponding d-spacings for crystalline atovaquone-Form I are shown in Table 12. FIG. 24A shows DSC of the crystalline atovaquone-Form I. FIG. 24B shows TGA of the crystalline atovaquone-Form I.

TABLE 12

| No. | 2-Theta (°) | d-spacing (Å) |
| --- | --- | --- |
| 1 | 7.26 | 12.17 |
| 2 | 7.44 | 11.87 |
| 3 | 9.88 | 8.95 |
| 4 | 10.90 | 8.11 |
| 5 | 11.21 | 7.89 |
| 6 | 11.92 | 7.42 |
| 7 | 14.66 | 6.04 |
| 8 | 15.61 | 5.67 |
| 9 | 16.29 | 5.44 |
| 10 | 16.94 | 5.23 |
| 11 | 17.54 | 5.05 |
| 12 | 18.11 | 4.90 |
| 13 | 19.43 | 4.57 |
| 14 | 20.12 | 4.41 |
| 15 | 21.42 | 4.14 |
| 16 | 22.25 | 3.99 |
| 17 | 22.98 | 3.87 |
| 18 | 23.73 | 3.75 |
| 19 | 24.86 | 3.58 |
| 20 | 25.07 | 3.55 |
| 21 | 25.31 | 3.52 |
| 22 | 26.36 | 3.38 |
| 23 | 26.79 | 3.33 |
| 24 | 27.66 | 3.22 |
| 25 | 28.59 | 3.12 |
| 26 | 28.81 | 3.10 |
| 27 | 29.30 | 3.05 |
| 28 | 29.87 | 2.99 |
| 29 | 30.14 | 2.96 |
| 30 | 30.84 | 2.90 |
| 31 | 32.23 | 2.78 |
| 32 | 32.91 | 2.72 |
| 33 | 33.63 | 2.66 |
| 34 | 34.36 | 2.61 |
| 35 | 35.56 | 2.52 |
| 36 | 36.02 | 2.49 |
| 37 | 36.69 | 2.45 |
| 38 | 38.21 | 2.35 |
| 39 | 39.63 | 2.27 |

Preparation and Characterization of the Crystalline Atovaquone-Form II

Figure 25:
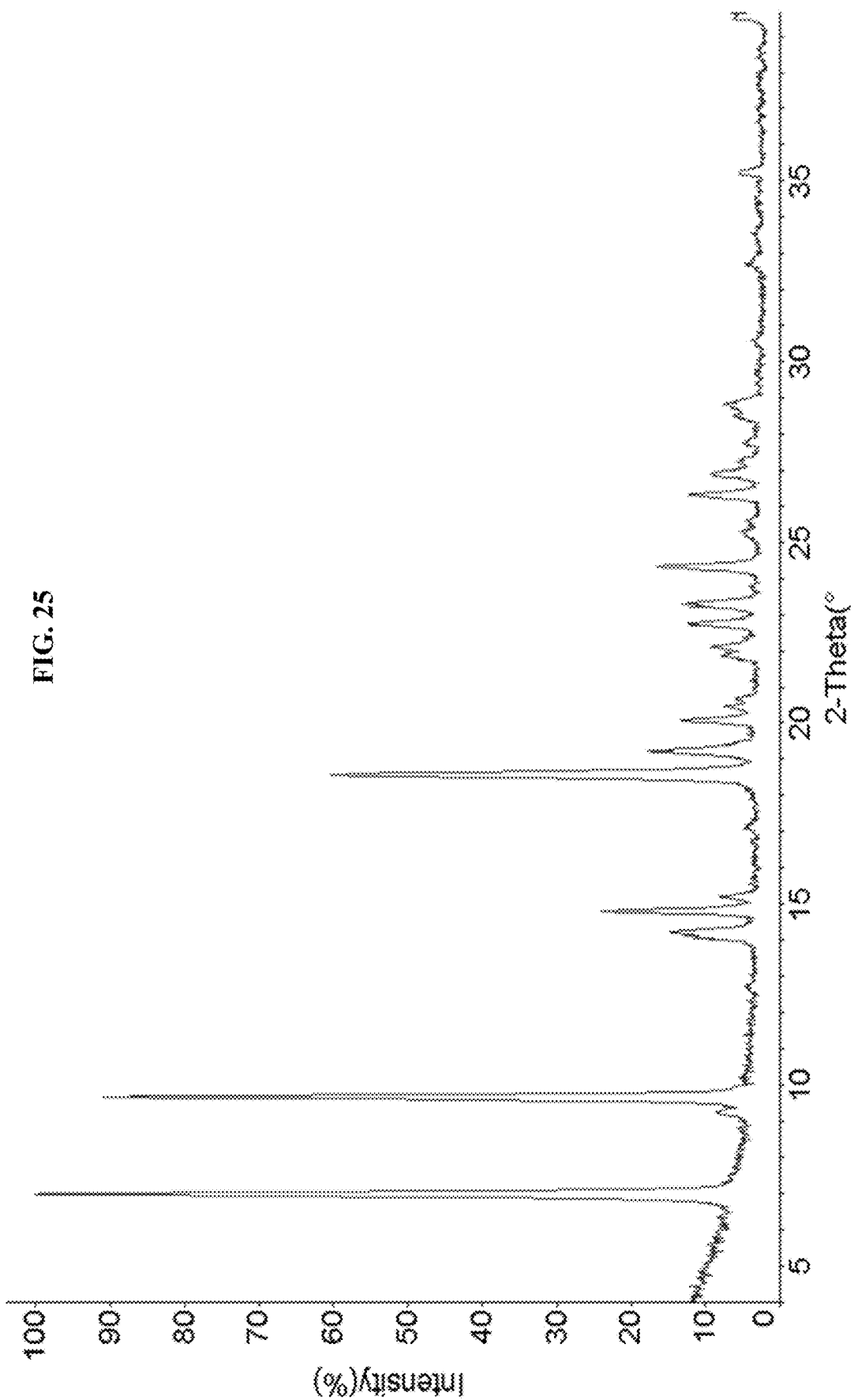
FIG. 25 depicts the characteristic X-ray diffraction pattern of the crystalline atovaquone-Form II.
Figure 26A:
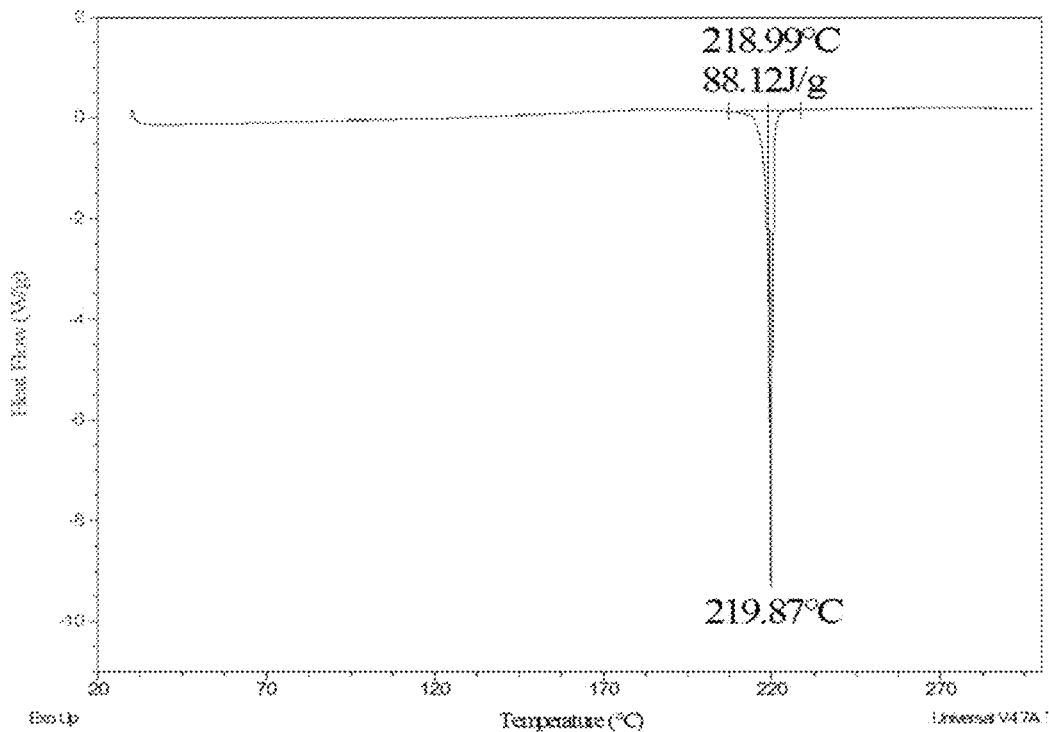
FIG. 26A depicts the DSC of crystalline atovaquone-Form II.
Figure 26B:
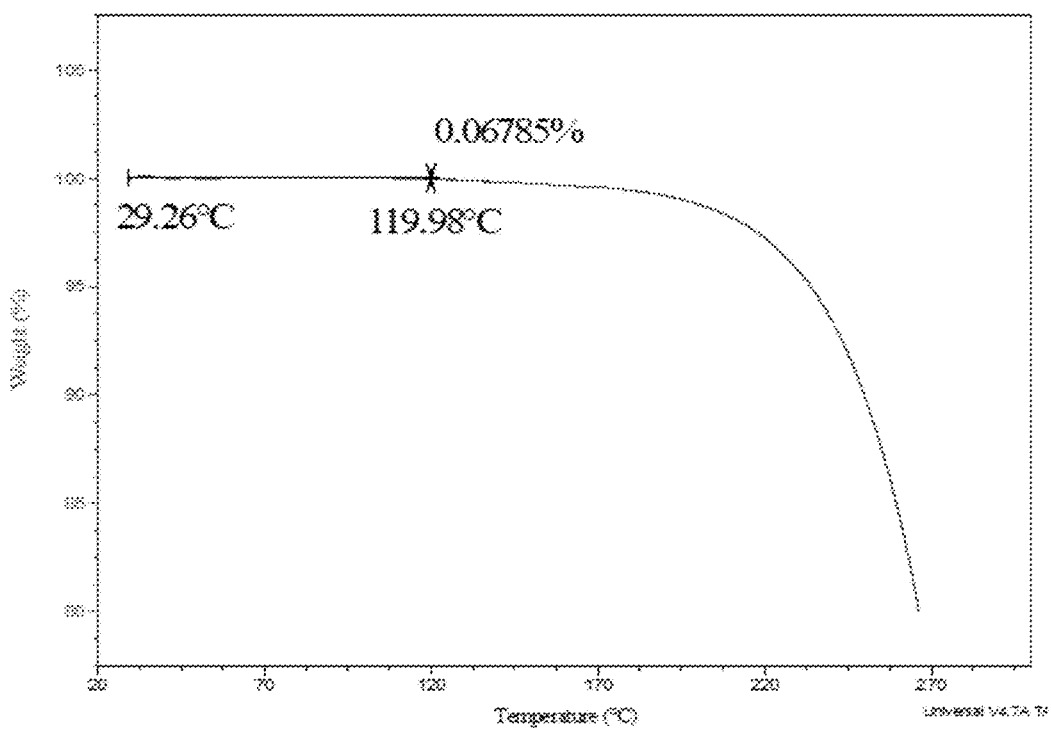
FIG. 26B depicts the TGA of crystalline atovaquone-Form II.
Figure 27:
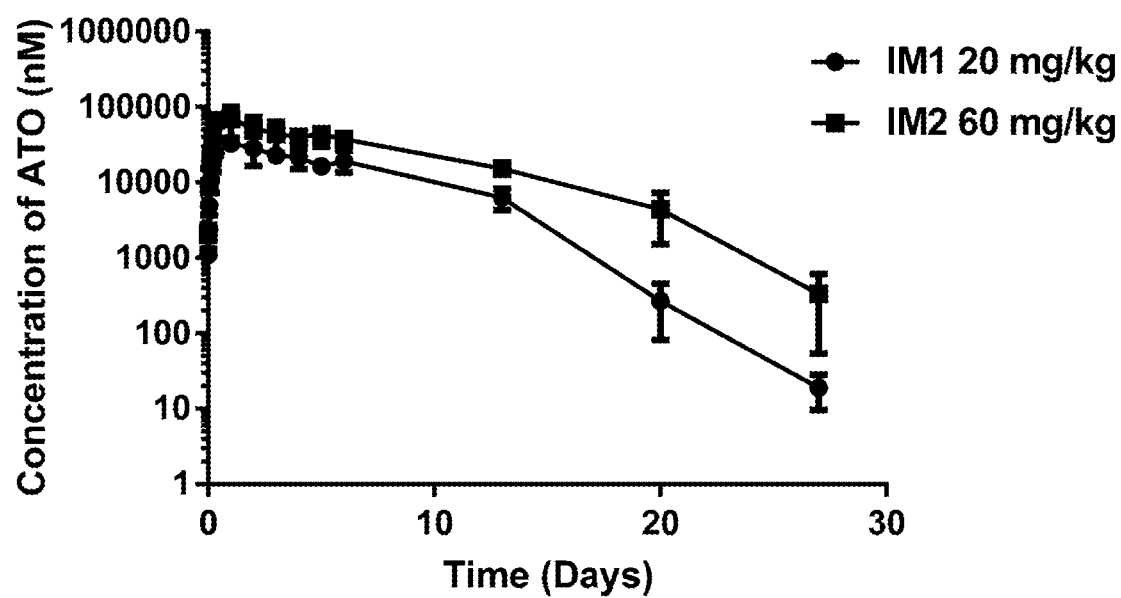
FIG. 27 depicts the exposure of atovaquone following IM injection of two atovaquone-Form II suspensions (200 mg/mL Synperonic).

Crystalline atovaquone-Form II was prepared by solvent evaporation method. All operations were carried out at room temperature, at 18-23° C. unless specifically stated. 300 mg of atovaquone-Form I was weighted in a 40 mL glass vial and 9 mL of a mixture of acetone and 1,4-dioxane (volume ratio: 1:1) was added. Short time of vortex or sonication (around 5 to 10 s) was also used and atovaquone-Form I completely dissolved easily. The vial was covered with a piece of aluminium foil with pinholes for overnight solvent evaporation in a fume cupboard at room temperature. The obtained solids were further dried overnight in a vacuum oven at 30° C. and then characterized by XRPD, DSC and TGA. The product was shown to be a new crystalline Form, which was designated crystalline atovaquone-Form II. FIG. 25 shows the characteristic X-ray diffraction pattern of the crystalline atovaquone-Form II. Characteristic reflections and the corresponding d-spacings for crystalline atovaquone-Form II are shown in Table 13. FIG. 26A shows the DSC of the crystalline atovaquone-Form II. FIG. 26B shows the DSC of the crystalline atovaquone-Form II.

TABLE 13

| No. | 2-Theta (°) | d-spacing (Å) |
|---|---|---|
| 1 | 7.02 | 12.57 |
| 2 | 9.29 | 9.51 |
| 3 | 9.71 | 9.10 |
| 4 | 12.77 | 6.93 |
| 5 | 14.29 | 6.19 |
| 6 | 14.86 | 5.96 |
| 7 | 15.25 | 5.80 |
| 8 | 17.14 | 5.17 |
| 9 | 18.62 | 4.76 |
| 10 | 19.29 | 4.60 |
| 11 | 20.13 | 4.41 |
| 12 | 20.53 | 4.32 |
| 13 | 20.73 | 4.28 |
| 14 | 21.92 | 4.05 |
| 15 | 22.17 | 4.01 |
| 16 | 22.78 | 3.90 |
| 17 | 23.36 | 3.81 |
| 18 | 24.38 | 3.65 |
| 19 | 25.35 | 3.51 |
| 20 | 25.66 | 3.47 |
| 21 | 26.38 | 3.38 |
| 22 | 26.97 | 3.30 |
| 23 | 27.29 | 3.27 |
| 24 | 27.78 | 3.21 |
| 25 | 28.59 | 3.12 |
| 26 | 28.88 | 3.09 |
| 27 | 30.66 | 2.91 |
| 28 | 32.77 | 2.73 |
| 29 | 33.60 | 2.67 |
| 30 | 35.27 | 2.54 |
| 31 | 37.72 | 2.38 |
| 32 | 38.04 | 2.36 |
| 33 | 38.46 | 2.34 |
| 34 | 38.72 | 2.32 |
| 35 | 39.66 | 2.27 |

Example 10: Preparation and Characterization of Atovaquone Crystalline Form Suspension Wet-milling method was used to prepare crystalline atovaquone suspensions. Both crystalline atovaquone-Form I and atovaquone-Form II were used as the raw material for milling and suspensions using 1% (w/v) Synperonic® F108 (Flake)—0.2% (w/v) dodecyl sodium sulfate (SLS, Richjoint Chemicals), targeted concentration of 200 mg/mL. However, crystalline atovaquone-Form I was not suitable for the suspension preparation, as big rod-shaped crystals around 5 mm in length were observed in collected suspension, which may be explained by the Ostwald ripening theory. In contrast, a nanosuspension of crystalline atovaquone Form II at 200 mg/mL was successfully prepared and used in the PK studies.

Preparation of 200 mg/mL Nanosuspensions Using Crystalline Atovaquone-Form II

Crystalline atovaquone-Form II was used to prepare 200 mg/mL nanosuspension. About 200 mg of the obtained crystalline atovaquone-Form II was weighted in a 30 mL high-density polyethylene bottle. 0.8 mL of suspension vehicle, i.e., 1% (w/v) Synperonic® F108—0.2% (w/v) SLS, was added. 1.6 mL of zirconium beads with a diameter of 0.8 mm (YTZ® Grinding Media, Nikkato Co., Japan) were added using a measuring cylinder. The bottles were placed on a US Stoneware Roller Mixer and the rolling speed was set at 220 rpm. The milling duration was 3 days and one drop of milled suspension was diluted with deionized water for size distribution measurement by Nicomp Zeta Potential & Particle Sizer 380. The suspension was also examined under PLM to see if the obtained product contained particles bigger than 5 µm. If a majority of the particles were smaller than 5 µm, the suspension was collected using an 1 mL pipette. Concentration of atovaquone-Form II in the suspension was determined by HPLC. The suspension was further diluted with 1% (w/v) Synperonic® F108—0.2% (w/v) SLS to a final concentration of 200 mg/mL. The final product was stored in an 1.5 mL sealed glass vial at room temperature and protected from light before PK study. Visual inspection of the suspensions showed that the products were homogeneous, syringeable and easily resuspendable following short-time vortex or water-bath sonication, suitable for preclinical PK study via intramuscular injection. The suspensions were characterized on dosing day by particle sizer and HPLC to ensure that the samples remained stable after storage at room temperature in terms of particle size and API concentration.

Example 11: Synthesis of Pyronaridine Crystalline Forms

Four new crystalline forms of pyronaridine are summarized in Table 14 and designated as Form II, Form III, Form IV and Form V.

TABLE 14

| Crystalline Form No. | Preparation method | Solvent used and conditions | |
|---|---|---|---|
| Form II | Slurry method | EtOH | 40° C., 48 hr |
| Form III | Slurry method | IPA | 40° C., 48 hr |
| | | acetone | |
| | | THF | |
| | | 1,4-Dioxane | |
| Form IV | Slurry method | MeOH:H2O (v:v, 3:1) | 40° C., 48 hr |
| | | EtOH:H2O (v:v, 3:1) | |
| | | Acetone:H2O (v:v, 1:2) | |
| | | IPA:H2O (v:v, 1:1) | |
| Form V | Heating method | No solvents used, heated to 120° C., for 5 min | |

Characterization of the Crystalline Pyronaridine-Form I

Figure 28:
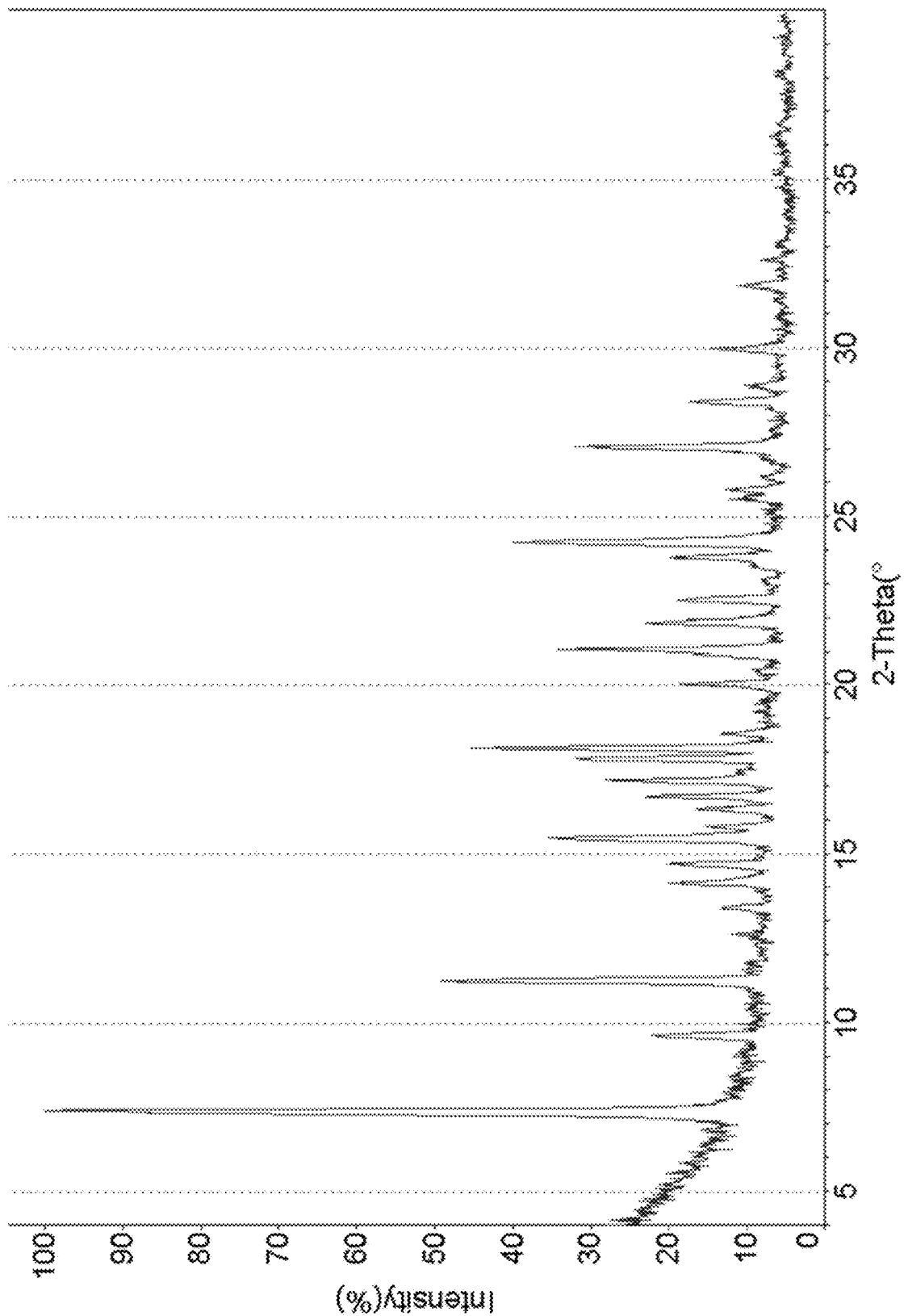
FIG. 28 depicts the characteristic X-ray diffraction pattern of the crystalline pyronaridine-Form I.
Figure 29A:
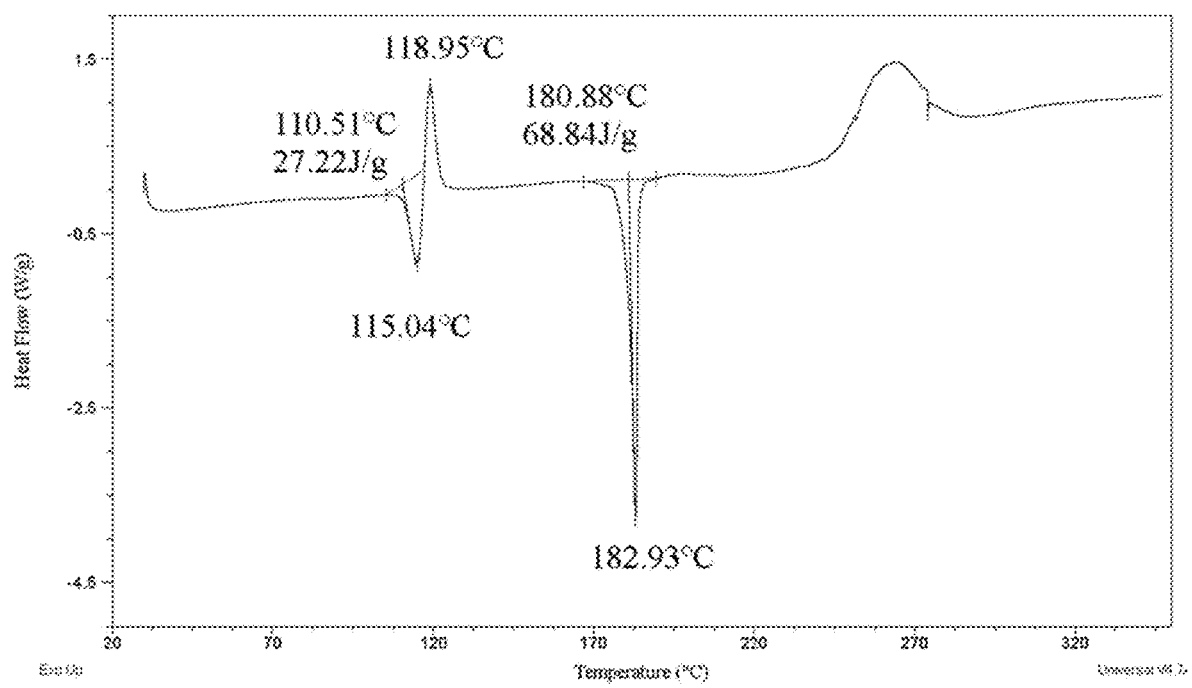
FIG. 29A depicts the DSC of crystalline pyronaridine-Form I.
Figure 29B:
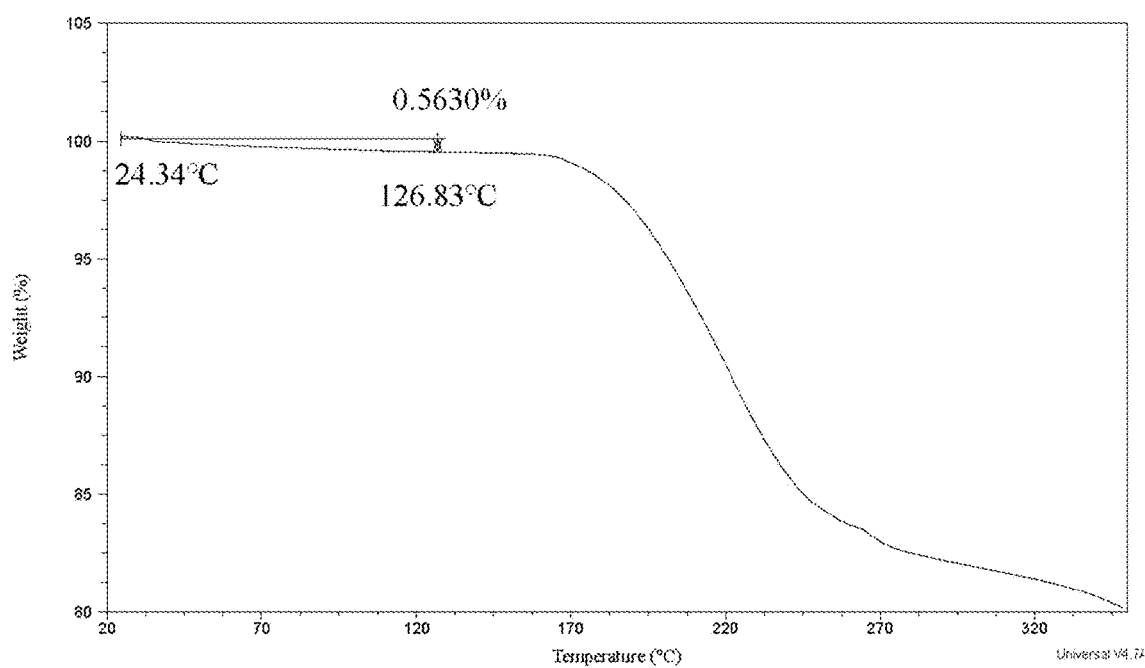
FIG. 29B depicts the TGA of crystalline pyronaridine-Form I.

Crystalline pyronaridine-Form I was characterized by XRPD, DSC and TGA. FIG. 28 shows the characteristic X-ray diffraction pattern of the crystalline pyronaridine-Form I. Characteristic reflections and the corresponding d-spacings for crystalline pyronaridine-Form I are shown in Table 15. FIG. 29A shows DSC of the crystalline pyronaridine-Form I. FIG. 29B shows TGA of the crystalline pyronaridine-Form I.

TABLE 15

| No. | 2-Theta (°) | d-spacing (Å) |
|---|---|---|
| 1 | 7.44 | 11.88 |
| 2 | 9.65 | 9.16 |
| 3 | 11.29 | 7.83 |
| 4 | 12.65 | 6.99 |
| 5 | 13.41 | 6.60 |
| 6 | 14.19 | 6.24 |
| 7 | 14.74 | 6.00 |
| 8 | 15.51 | 5.71 |
| 9 | 15.85 | 5.59 |
| 10 | 16.38 | 5.41 |
| 11 | 16.72 | 5.30 |
| 12 | 17.23 | 5.14 |

TABLE 15-continued

| No. | 2-Theta (°) | d-spacing (Å) |
|---|---|---|
| 13 | 17.88 | 4.96 |
| 14 | 18.18 | 4.88 |
| 15 | 18.60 | 4.77 |
| 16 | 20.06 | 4.42 |
| 17 | 20.51 | 4.33 |
| 18 | 21.12 | 4.20 |
| 19 | 21.89 | 4.06 |
| 20 | 22.58 | 3.93 |
| 21 | 23.56 | 3.77 |
| 22 | 23.83 | 3.73 |
| 23 | 24.30 | 3.66 |
| 24 | 25.57 | 3.48 |
| 25 | 25.86 | 3.44 |
| 26 | 26.22 | 3.40 |
| 27 | 26.75 | 3.33 |
| 28 | 27.13 | 3.28 |
| 29 | 28.47 | 3.13 |
| 30 | 28.96 | 3.08 |
| 31 | 30.03 | 2.97 |
| 32 | 31.89 | 2.80 |
| 33 | 32.65 | 2.74 |
| 34 | 36.31 | 2.47 |

Preparation of Crystalline Pyronaridine-Form II, Pyronaridine-Form III and Pyronaridine-Form IV and Characterization Results Crystalline Form II, Form III and Form IV of pyronaridine were prepared by slurry method using different solvents (details summarized in Table 14). About 30 mg of crystalline pyronaridine-Form I was suspended in 0.2 mL of each solvent in a 1.5 mL sealed glass vial. The vial was placed in an Eppendorf Thermomixer and shaken at 40° C., 700 rpm for 48 h. The API solids were collected by centrifugation and shown to be new crystalline forms. Thus, the wet solids were dried overnight in a vacuum oven at 30° C. and the resulting dried products were characterized by XRPD, DSC and TGA.

Figure 30:
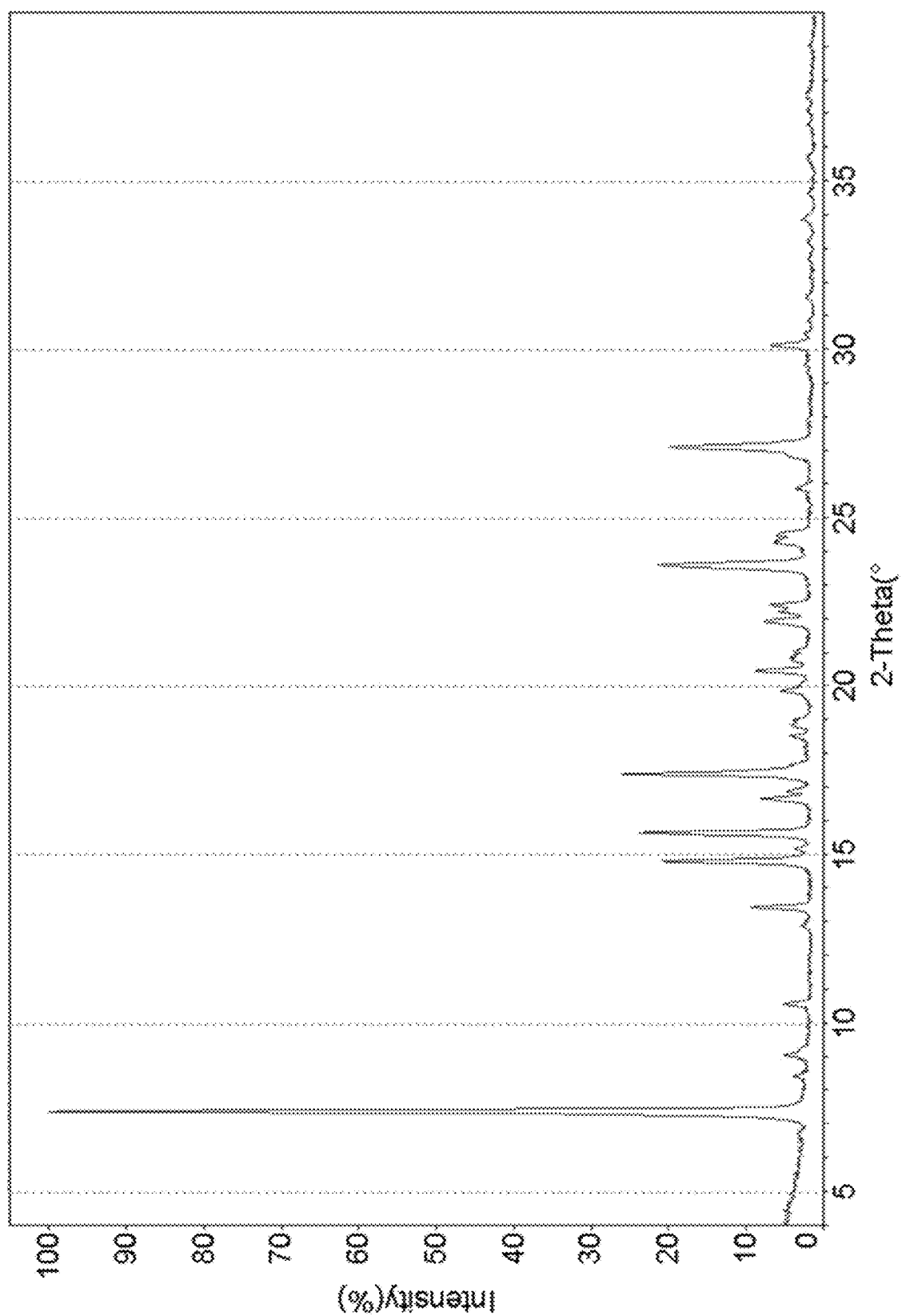
FIG. 30 depicts the characteristic X-ray diffraction pattern of the crystalline pyronaridine-Form II.
Figure 31A:
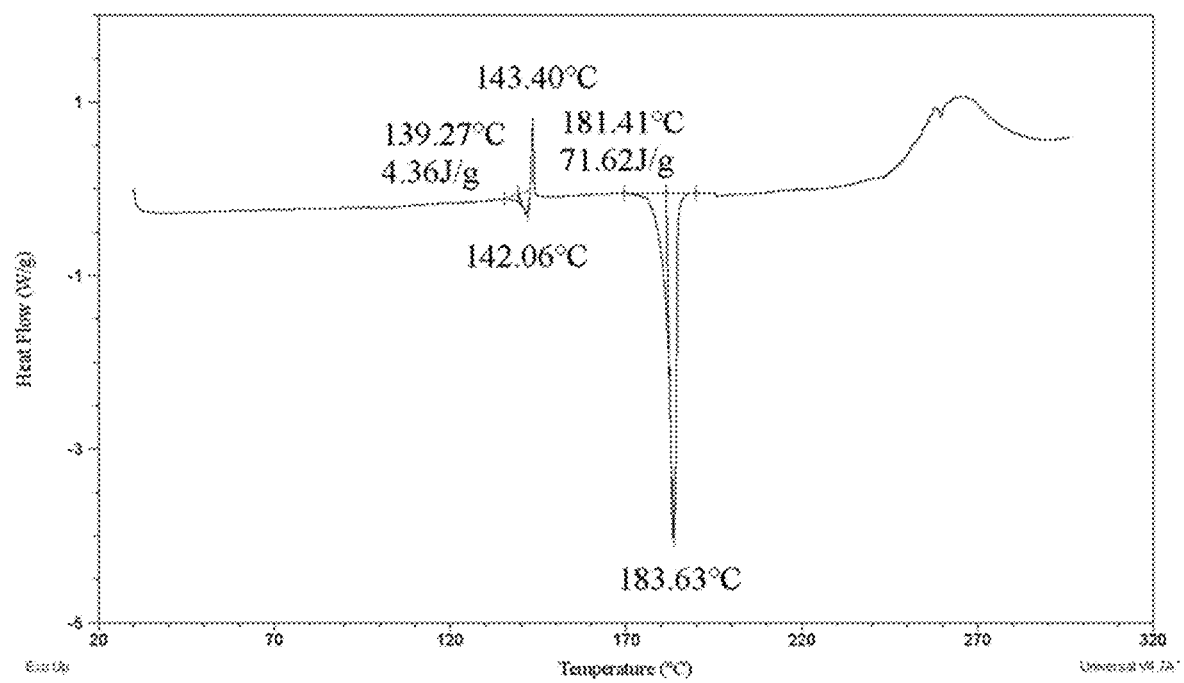
FIG. 31A depicts the DSC of crystalline pyronaridine-Form II.
Figure 31B:
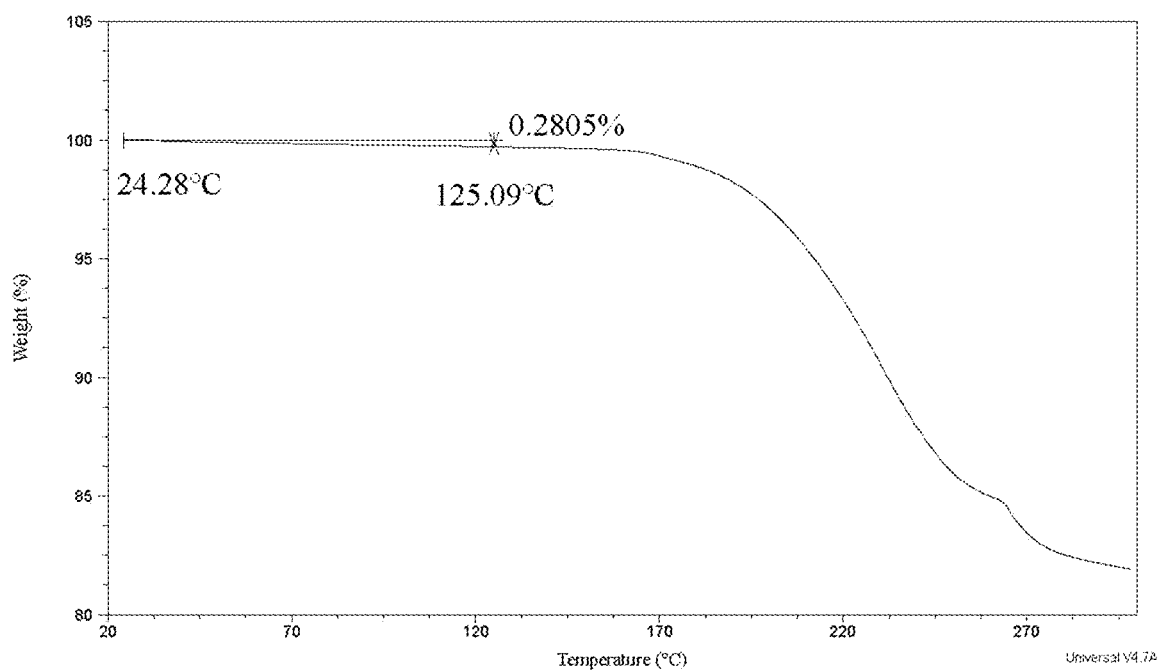
FIG. 31B depicts the TGA of crystalline pyronaridine-Form II.

The new crystalline form obtained from slurry in ethanol was designated pyronaridine-Form II. FIG. 30 shows the characteristic X-ray diffraction pattern of the crystalline pyronaridine-Form II. Characteristic reflections and the corresponding d-spacings for crystalline pyronaridine-Form II are shown in Table 16. FIG. 31A shows the DSC of the crystalline pyronaridine-Form II. FIG. 31B shows the TGA of the crystalline pyronaridine-Form II.

TABLE 16

| No. | 2-Theta (°) | d-spacing (Å) |
|---|---|---|
| 1 | 6.76 | 13.06 |
| 2 | 7.40 | 11.94 |
| 3 | 8.45 | 10.46 |
| 4 | 9.08 | 9.73 |
| 5 | 10.62 | 8.33 |
| 6 | 12.93 | 6.84 |
| 7 | 13.48 | 6.56 |
| 8 | 14.84 | 5.96 |
| 9 | 15.23 | 5.81 |
| 10 | 15.67 | 5.65 |
| 11 | 16.68 | 5.31 |
| 12 | 16.92 | 5.24 |
| 13 | 17.43 | 5.08 |
| 14 | 18.20 | 4.87 |
| 15 | 18.57 | 4.77 |
| 16 | 18.91 | 4.69 |
| 17 | 19.90 | 4.46 |
| 18 | 20.49 | 4.33 |
| 19 | 20.93 | 4.24 |
| 20 | 21.08 | 4.21 |
| 21 | 21.97 | 4.04 |
| 22 | 22.27 | 3.99 |

TABLE 16-continued

| No. | 2-Theta (°) | d-spacing (Å) |
|---|---|---|
| 23 | 22.46 | 3.95 |
| 24 | 23.65 | 3.76 |
| 25 | 24.32 | 3.66 |
| 26 | 24.56 | 3.62 |
| 27 | 25.94 | 3.43 |
| 28 | 27.17 | 3.28 |
| 29 | 29.61 | 3.01 |
| 30 | 30.19 | 2.96 |
| 31 | 30.52 | 2.93 |
| 32 | 31.59 | 2.83 |
| 33 | 32.20 | 2.78 |
| 34 | 32.76 | 2.73 |
| 35 | 33.31 | 2.69 |
| 36 | 33.92 | 2.64 |
| 37 | 34.69 | 2.58 |
| 38 | 35.70 | 2.51 |
| 39 | 36.71 | 2.45 |
| 40 | 37.18 | 2.42 |
| 41 | 37.60 | 2.39 |
| 42 | 39.08 | 2.30 |

Figure 32:
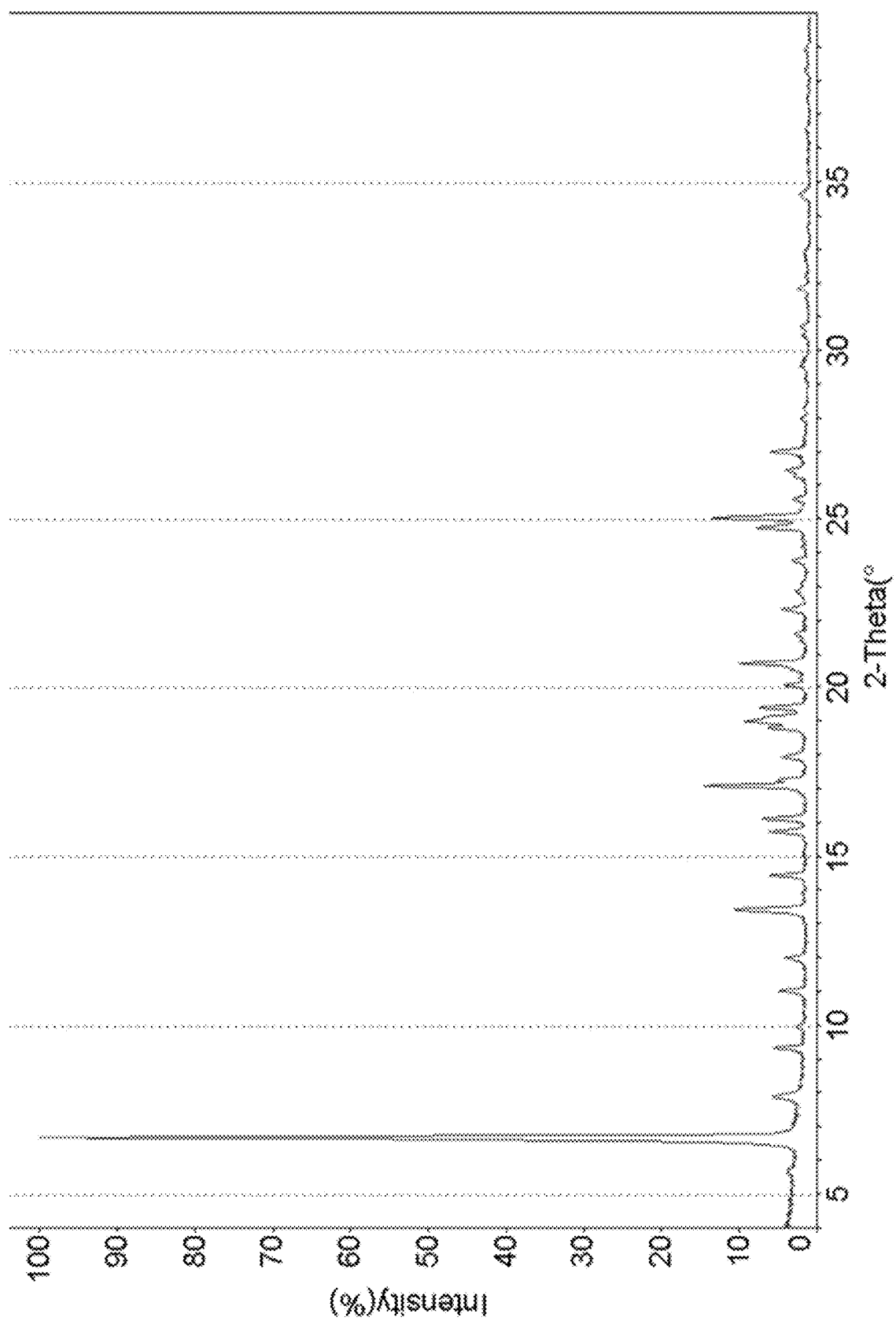
FIG. 32 depicts the characteristic X-ray diffraction pattern of the crystalline pyronaridine-Form III.
Figure 33A:
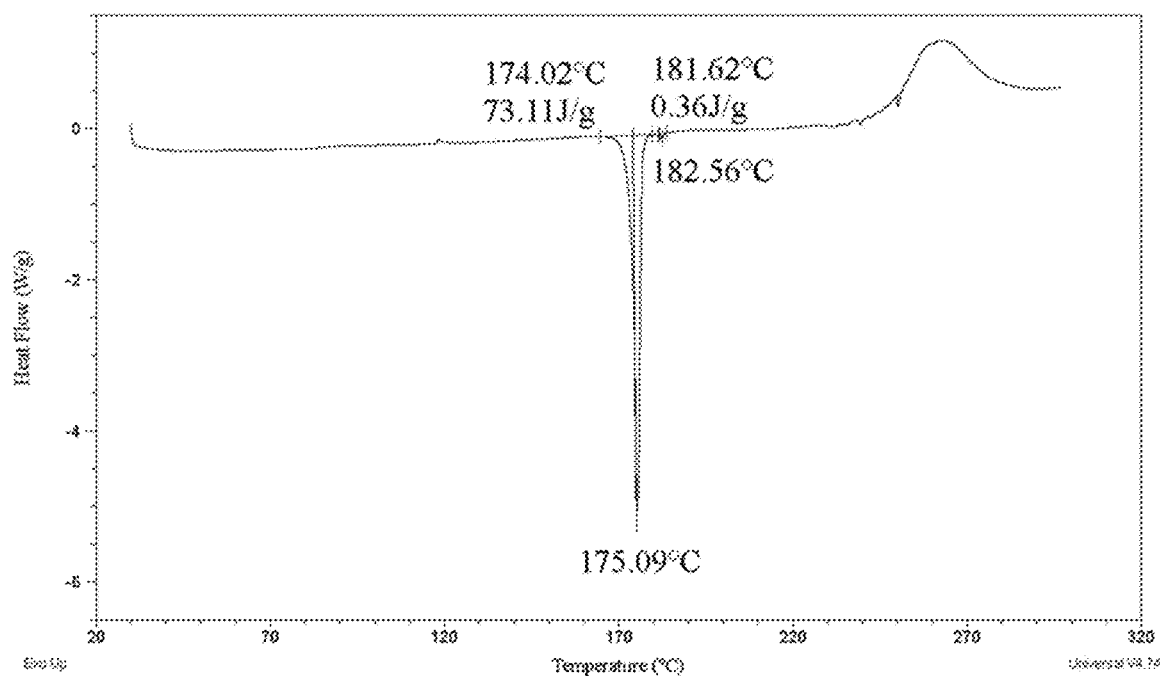
FIG. 33A depicts the DSC of crystalline pyronaridine-Form III.
Figure 33B:
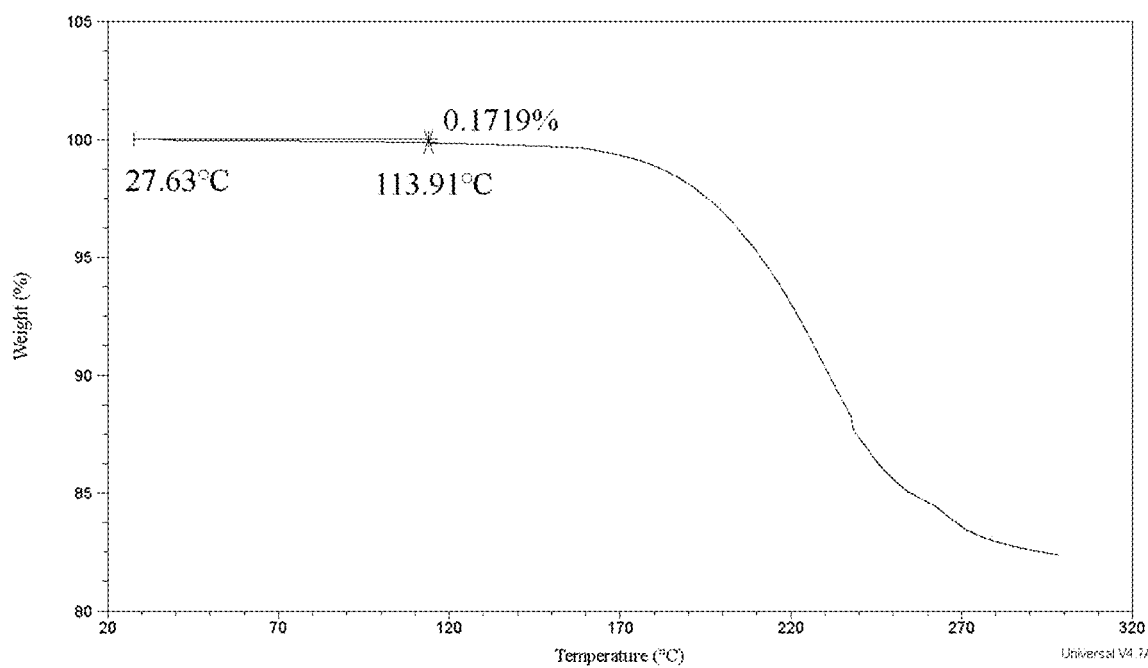
FIG. 33B depicts the TGA of crystalline pyronaridine-Form III.

After slurry in IPA, acetone, THF and 1,4-Dioxane, the crystalline pyronaridine-Form I transferred to another new crystalline form, which was designated pyronaridine-Form III. FIG. 32 shows the characteristic X-ray diffraction pattern of the crystalline pyronaridine-Form III. Characteristic reflections and the corresponding d-spacings for crystalline Form III are shown in Table 17. FIG. 33A shows the DSC of the crystalline pyronaridine-Form III. FIG. 33B shows the TGA of the crystalline pyronaridine-Form III.

TABLE 17

| No. | 2-Theta (°) | d-spacing (Å) |
|---|---|---|
| 1 | 5.68 | 15.55 |
| 2 | 6.71 | 13.17 |
| 3 | 7.91 | 11.16 |
| 4 | 9.37 | 9.43 |
| 5 | 9.98 | 8.86 |
| 6 | 11.05 | 8.00 |
| 7 | 12.04 | 7.35 |
| 8 | 13.46 | 6.57 |
| 9 | 14.49 | 6.11 |
| 10 | 15.77 | 5.61 |
| 11 | 16.17 | 5.48 |
| 12 | 17.13 | 5.17 |
| 13 | 17.98 | 4.93 |
| 14 | 18.84 | 4.71 |
| 15 | 19.03 | 4.66 |
| 16 | 19.44 | 4.56 |
| 17 | 20.10 | 4.41 |
| 18 | 20.77 | 4.27 |
| 19 | 21.46 | 4.14 |
| 20 | 21.65 | 4.10 |
| 21 | 22.38 | 3.97 |
| 22 | 22.94 | 3.87 |
| 23 | 23.17 | 3.84 |
| 24 | 23.83 | 3.73 |
| 25 | 24.50 | 3.63 |
| 26 | 24.80 | 3.59 |
| 27 | 25.08 | 3.55 |
| 28 | 25.63 | 3.47 |
| 29 | 26.31 | 3.38 |
| 30 | 26.50 | 3.36 |
| 31 | 27.05 | 3.29 |
| 32 | 28.02 | 3.18 |
| 33 | 28.36 | 3.14 |
| 34 | 29.23 | 3.05 |
| 35 | 29.60 | 3.02 |
| 36 | 29.79 | 3.00 |
| 37 | 30.51 | 2.93 |
| 38 | 30.76 | 2.90 |
| 39 | 31.62 | 2.83 |
| 40 | 31.89 | 2.80 |

TABLE 17-continued

| No. | 2-Theta (°) | d-spacing (Å) |
|---|---|---|
| 41 | 32.25 | 2.77 |
| 42 | 32.93 | 2.72 |
| 43 | 33.75 | 2.65 |
| 44 | 34.69 | 2.58 |
| 45 | 36.57 | 2.46 |
| 46 | 37.49 | 2.40 |
| 47 | 38.37 | 2.34 |
| 48 | 38.97 | 2.31 |

Figure 34:
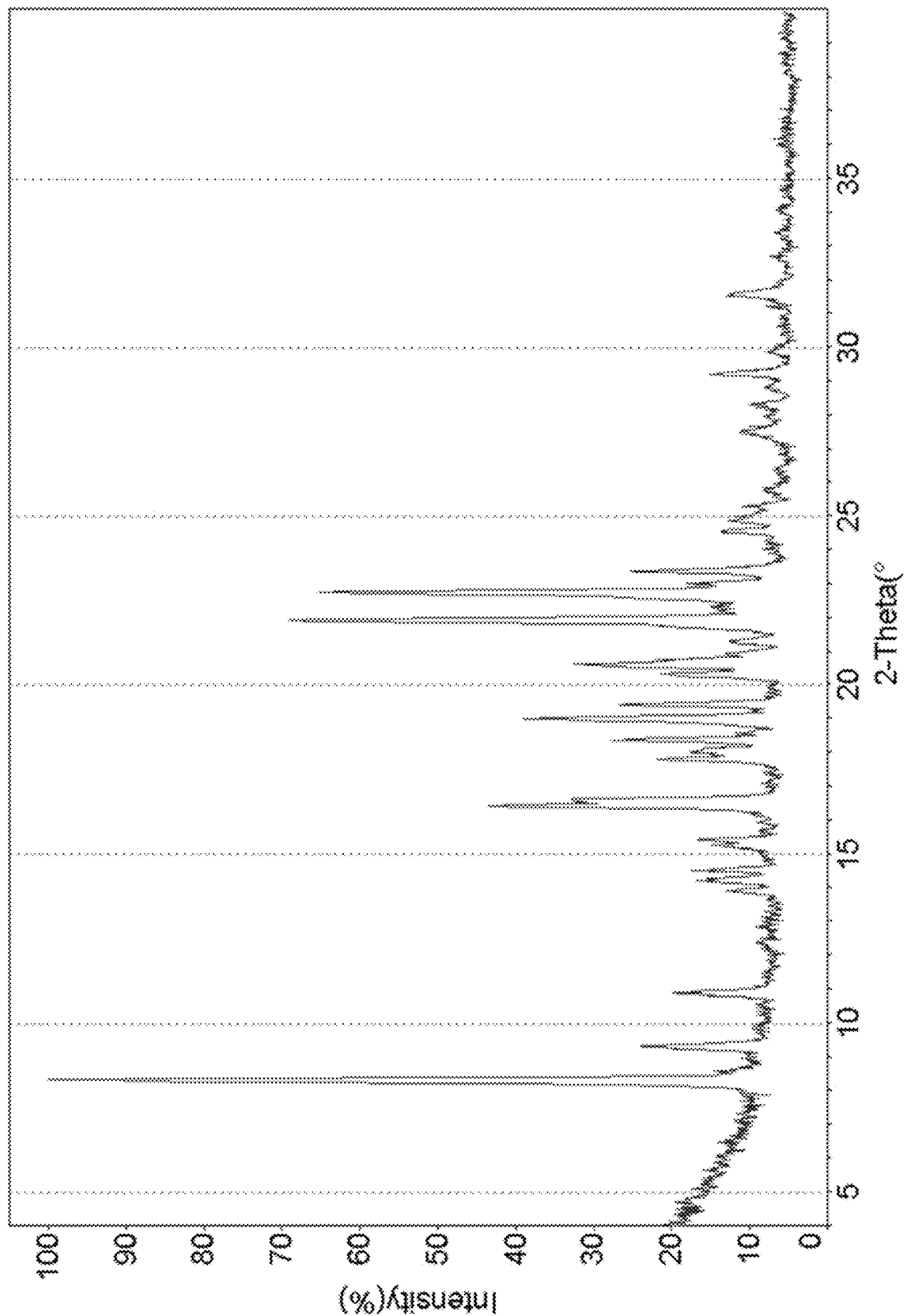
FIG. 34 depicts the characteristic X-ray diffraction pattern of the crystalline pyronaridine-Form IV.
Figure 35A:
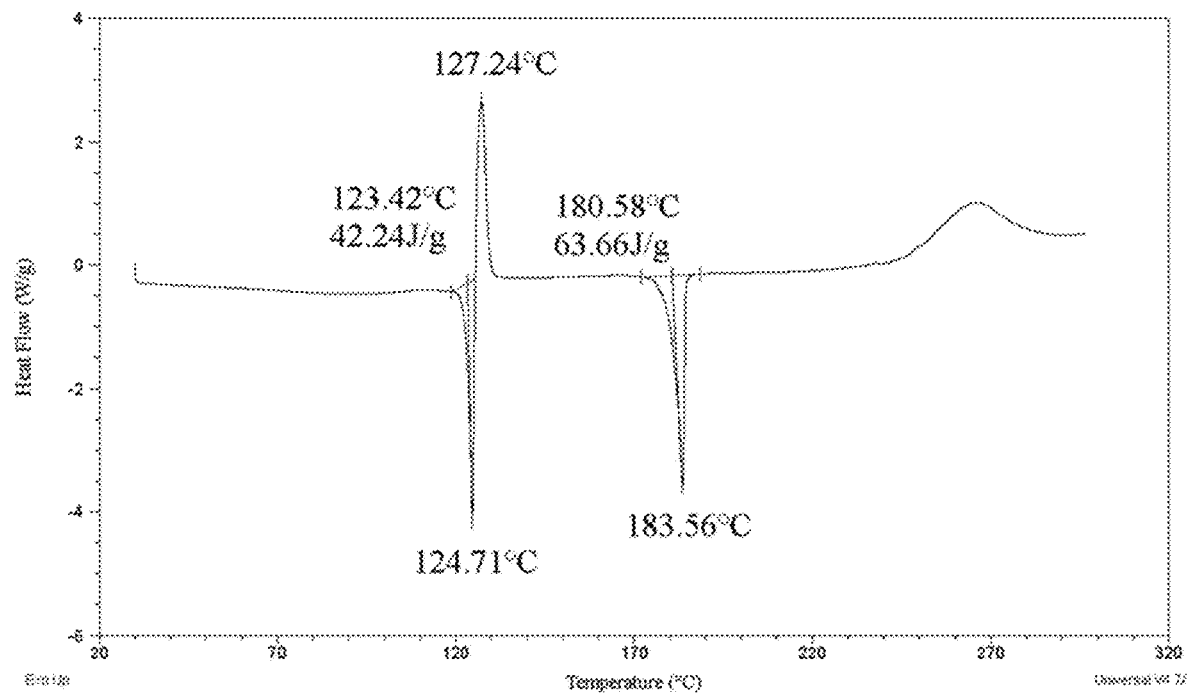
FIG. 35A depicts the DSC of crystalline pyronaridine-Form IV.
Figure 35B:
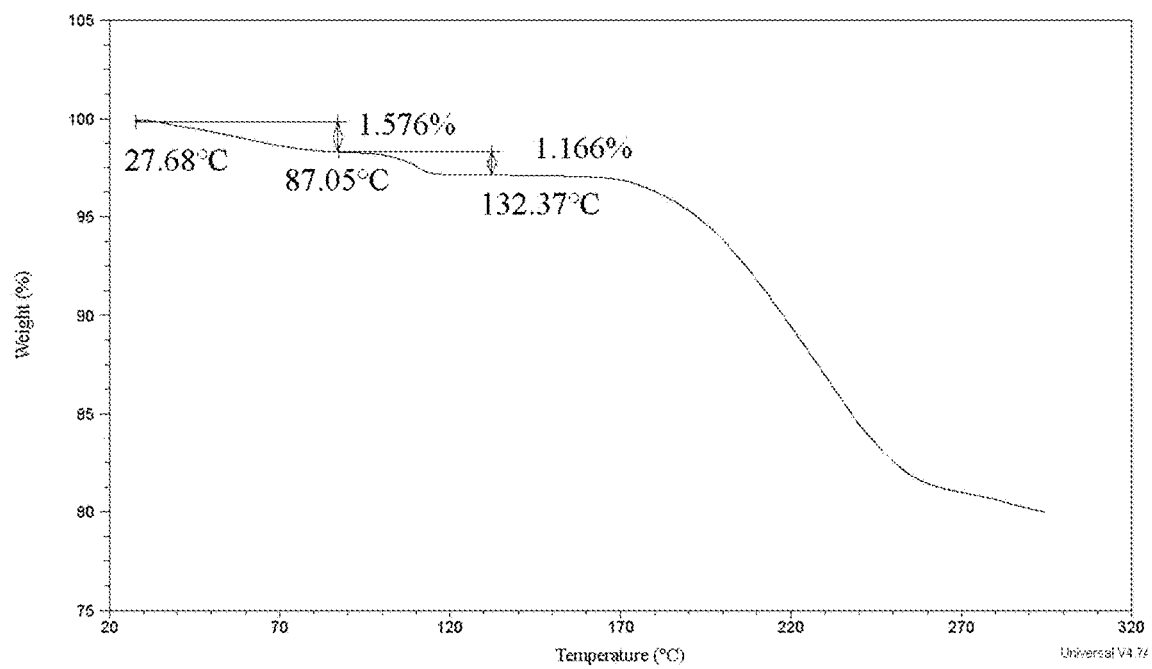
FIG. 35B depicts the TGA of crystalline pyronaridine-Form IV.

The dried crystals obtained after slurry in MeOH:$H_2O$ (v:v, 3:1), EtOH:$H_2O$ (v:v, 3:1), acetone:$H_2O$ (v:v, 1:2) and IPA:$H_2O$ (v:v, 1:1) showed a different crystalline form from Form I, II and III of pyronaridine and it was designated crystalline pyronaridine-Form IV. FIG. 34 shows the characteristic X-ray diffraction pattern of the crystalline pyronaridine-Form IV. Characteristic reflections and the corresponding d-spacings for crystalline Form IV are shown in Table 18. FIG. 35A shows the DSC of the crystalline pyronaridine-Form IV. FIG. 35B shows the TGA of the crystalline pyronaridine-Form IV.

TABLE 18

| No. | 2-Theta (°) | d-spacing (Å) |
|---|---|---|
| 1 | 8.36 | 10.57 |
| 2 | 9.35 | 9.45 |
| 3 | 10.93 | 8.09 |
| 4 | 14.27 | 6.20 |
| 5 | 14.55 | 6.08 |
| 6 | 15.46 | 5.73 |
| 7 | 16.48 | 5.38 |
| 8 | 17.84 | 4.97 |
| 9 | 18.04 | 4.91 |
| 10 | 18.40 | 4.82 |
| 11 | 19.03 | 4.66 |
| 12 | 19.45 | 4.56 |
| 13 | 20.37 | 4.36 |
| 14 | 20.65 | 4.30 |
| 15 | 21.32 | 4.16 |
| 16 | 21.97 | 4.04 |
| 17 | 22.80 | 3.90 |
| 18 | 23.41 | 3.80 |
| 19 | 24.58 | 3.62 |
| 20 | 24.91 | 3.57 |
| 21 | 25.33 | 3.51 |
| 22 | 25.88 | 3.44 |
| 23 | 27.54 | 3.24 |
| 24 | 28.01 | 3.18 |
| 25 | 28.35 | 3.15 |
| 26 | 28.86 | 3.09 |
| 27 | 29.26 | 3.05 |
| 28 | 29.93 | 2.98 |
| 29 | 31.57 | 2.83 |
| 30 | 32.73 | 2.73 |
| 31 | 33.43 | 2.68 |

Preparation of Crystalline Pyronaridine-Form V and Characterization Results

Figure 36:
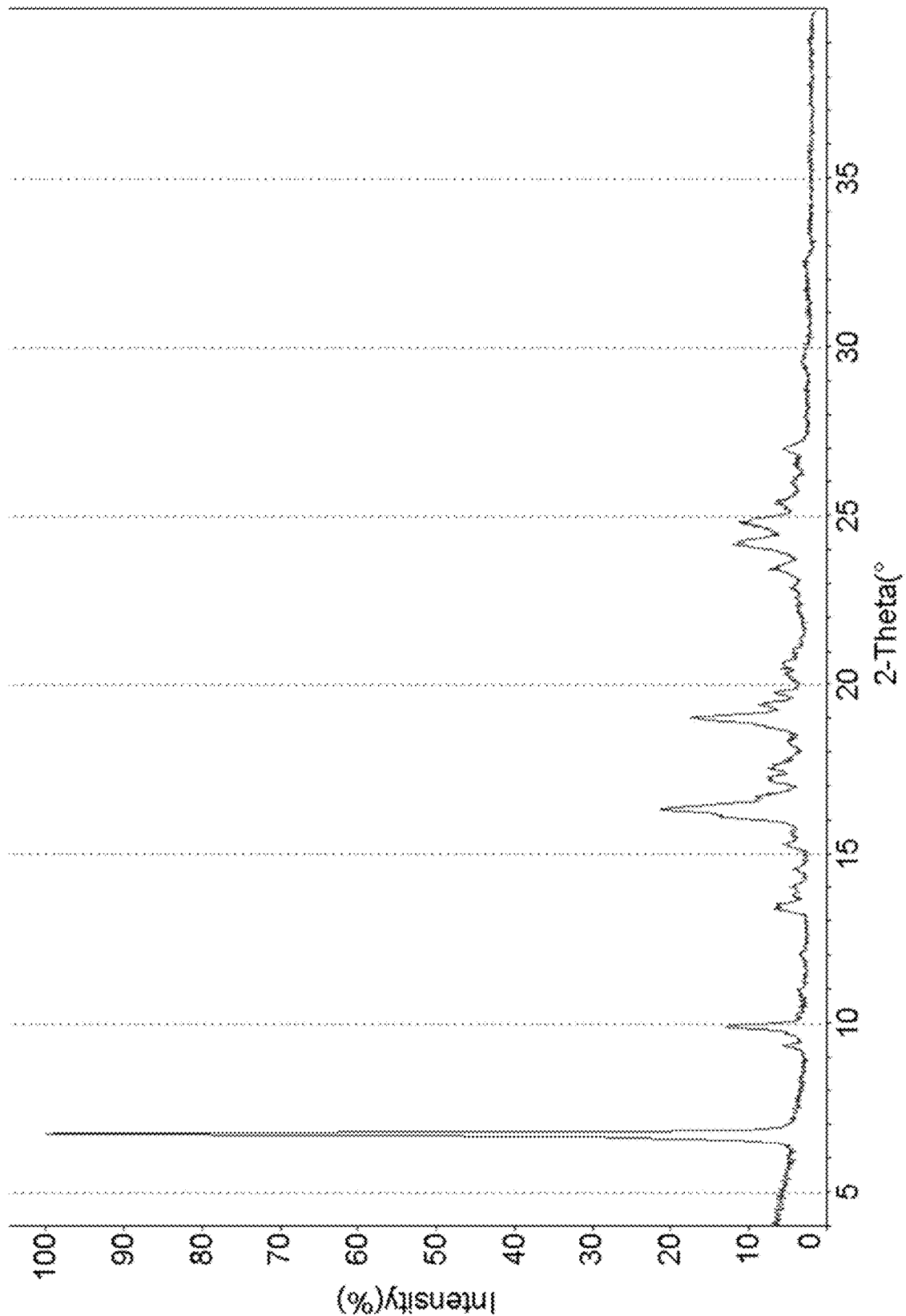
FIG. 36 depicts the characteristic X-ray diffraction pattern of the crystalline pyronaridine-Form V.
Figure 37:
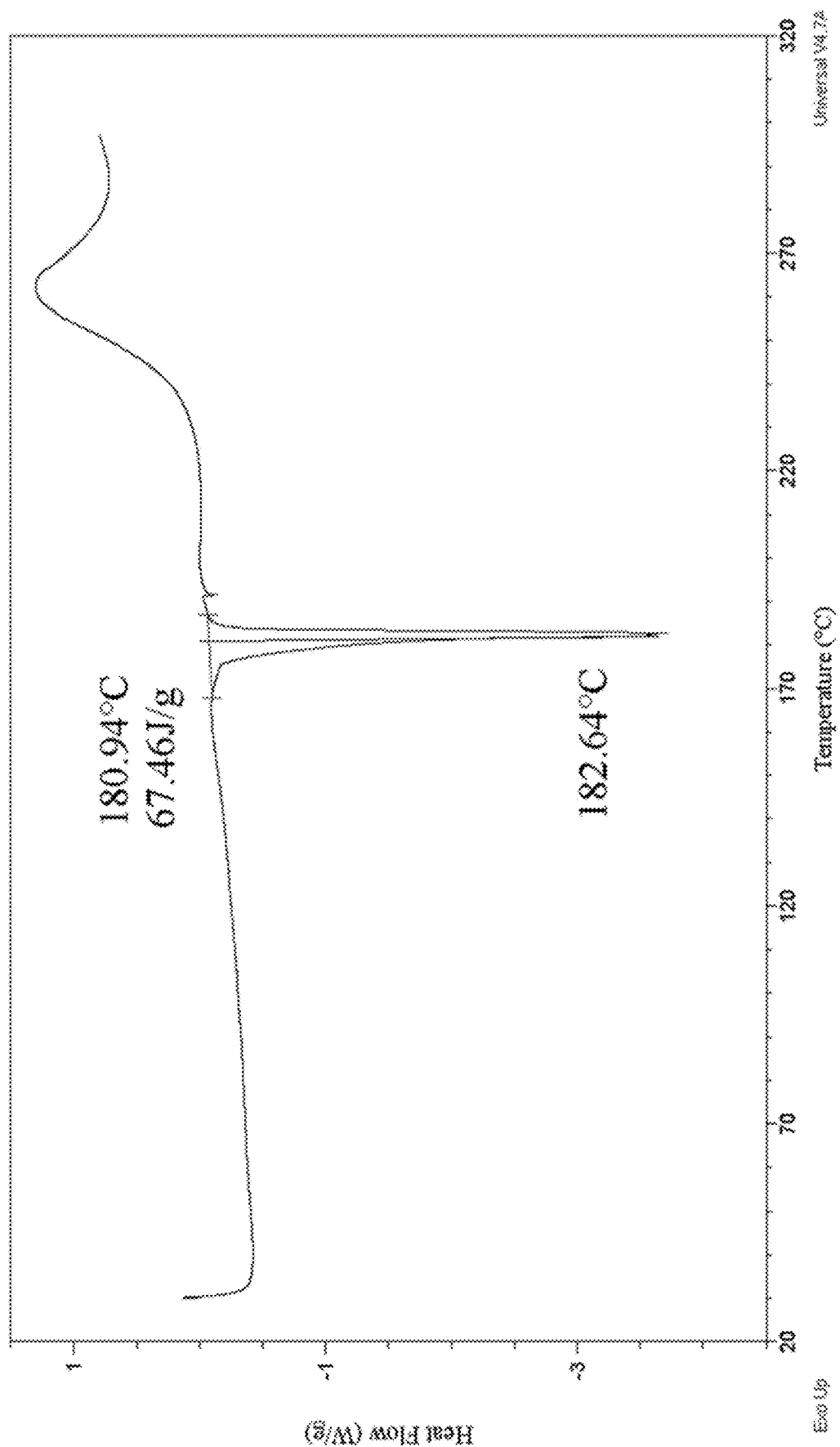
FIG. 37 depicts the DSC of crystalline pyronaridine-Form V.

Crystalline pyronaridine-Form V was prepared from crystalline pyronaridine-Form I by heating and cooling method. About 10 mg of crystalline pyronaridine-Form I was placed in an open platinum pan and heated by TA Q5000 TGA. The heating process was set to heat the sample from 25° C. to 120° C. at a rate of 10° C./min and maintained 120° C. for 5 min. After this, the powder was allowed to cool down to room temperature. The obtained solids were characterized by XRPD and DSC and showed to be a new crystalline form, which was designated crystalline pyronaridine-Form V. FIG. 36 shows the characteristic X-ray diffraction pattern of the crystalline pyronaridine-Form V. Characteristic reflections and the corresponding d-spacings for crystalline pyronaridine-Form V are shown in Table 19. FIG. 37 shows the DSC of the crystalline pyronaridine-Form V.

TABLE 19

| No. | 2-Theta (°) | d-spacing (Å) |
|---|---|---|
| 1 | 6.77 | 13.05 |
| 2 | 9.36 | 9.44 |
| 3 | 9.93 | 8.90 |
| 4 | 11.01 | 8.03 |
| 5 | 12.11 | 7.30 |
| 6 | 13.46 | 6.57 |
| 7 | 13.85 | 6.39 |
| 8 | 14.07 | 6.29 |
| 9 | 14.61 | 6.06 |
| 10 | 15.34 | 5.77 |
| 11 | 16.15 | 5.48 |
| 12 | 16.36 | 5.41 |
| 13 | 16.74 | 5.29 |
| 14 | 17.31 | 5.12 |
| 15 | 17.57 | 5.04 |
| 16 | 17.87 | 4.96 |
| 17 | 18.35 | 4.83 |
| 18 | 19.07 | 4.65 |
| 19 | 19.44 | 4.56 |
| 20 | 19.80 | 4.48 |
| 21 | 20.33 | 4.36 |
| 22 | 20.69 | 4.29 |
| 23 | 21.01 | 4.22 |
| 24 | 22.95 | 3.87 |
| 25 | 23.48 | 3.79 |
| 26 | 24.20 | 3.67 |
| 27 | 24.87 | 3.58 |
| 28 | 25.49 | 3.49 |
| 29 | 26.04 | 3.42 |
| 30 | 26.59 | 3.35 |
| 31 | 27.03 | 3.30 |
| 32 | 29.64 | 3.01 |
| 33 | 29.89 | 2.99 |
| 34 | 32.56 | 2.75 |
| 35 | 32.59 | 2.75 |

Example 12: Pharmacokinetic Studies

PO
1. Animals

Animals (Male CD-1 mice, 7-9 weeks) were obtained from an approved vendor (SLAC Laboratory Animal Co. Ltd., Shanghai, China; or SIPPR-B&K Laboratory Animal Co. Ltd., Shanghai, China).

Acclimation/Quarantine: Following arrival animals were assessed as to their general health by a member of the veterinary staff or other authorized personnel. Animals were acclimated for at least 3 days before being placed on study.

Animal Husbandry: Animals were group housed during acclimation and individually housed during the study. The animal room environment was controlled (target conditions: temperature 18 to 26° C., relative humidity 30 to 70%, 12 hours artificial light and 12 hours dark). Temperature and relative humidity was monitored daily.

Animals were fasted at least 12 hours prior to the administration. All animals had access to Certified Rodent Diet (Catalog #M01-F, SLAC Laboratory Animal Cl. Ltd., Shanghai, China) ad libitum 4 hours post dosing.

Water was autoclaved before provided to the animals ad libitum. Periodic analyses of the water was performed.
2. Formulation
PO Formulation Appropriate amount of test compound was accurately weighed and mixed with appropriate volume of vehicle to get a clear solution or a uniform suspension, vortexing or sonication in water bath was sometimes needed. The formulations were prepared on the day of dosing. Animals were dosed within four hours after the formulation was prepared. Two 20 µL aliquots of each formulation were removed from each of the formulation solutions, transferred into 1.5 mL of polypropylene microcentrifuge tubes and run dose validation by LC/UV or LC-MS/MS.

3. Dose Administration

The PO dose formulation was administered via oral gavage following facility SOPs.

4. Sample Collection

For PO group, Approximately 30 µL blood was collected from saphenous vein at each time point. All blood samples were transferred into microcentrifuge tubes containing 24 of $K_2EDTA$ (0.5M) as anti-coagulant and placed on wet ice until processed for plasma.

5. Blood/Plasma processing

Blood samples were processed for plasma by centrifugation at approximately 4° C., 3000 g 15 min within half an hour of collection. Plasma samples were stored in polypropylene tubes, quick frozen over dry ice and kept at −70±10° C. until LC/MS/MS analysis.

6. Sample Analysis

Dose Formulation Concentration Verification

Aliquots of the formulations were collected in the middle position of each dose formulation in duplicate.

The concentrations of the test compound in dose formulation samples were determined by the LC/UV or LC/MS/MS method.

Bioanalytical Method and Sample Analysis

LC-MS/MS methods for the quantitative determination of test compound in corresponding biological matrix was developed under non-GLP compliance.

A calibration curve with 8 non-zero calibration standards was applied for the method including LLOQ.

A set of QC samples consisting of low, middle, and high concentration was applied for the method.

The study sample analysis was performed concurrently with a set of calibration standards and two sets of QC samples using the LC-MS/MS method (If sample numbers are more than 48, then two calibration curves with 2 sets of QC samples will be applied).

Acceptance criteria:

Linearity: a minimum of 6 calibration standards was back calculated to within ±20% of their nominal values in plasma.

Accuracy: A minimum of 4 out of 6 QC samples was back calculated to within ±20% of their nominal values in plasma.

Specificity: The mean calculated concentration in the single blank matrix should be 0.5 times the LLOQ.

Sensitivity: LLOQ target: 1-3 ng/mL.

Carryover: the mean calculated carry-over concentration in the single blank matrix immediately after the highest standard injection should be <LLOQ. If the carryover couldn't meet the criteria, then the percent of carryover should be estimated following in-house bioanalytical SOP.

7. Data Analysis

Plasma concentration versus time data was analyzed by non-compartmental approaches using the Phoenix WinNonlin 6.3 software program. $C_{max}$, $T_{max}$, $T_{1/2}$, $AUC_{(0-t)}$, $AUC_{(0-inf)}$, $MRT_{(0-t)}$, $MRT_{(0-inf)}$, % F and graphs of plasma concentration versus time profile will be reported.

IM/SC

1. Animal

Rats (Sprague-Dawley, Male, 7-9 weeks) were obtained from an approved vendor (SLAC Laboratory Animal Co. Ltd., Shanghai, China or SIPPR/BK Laboratory Animal Co. Ltd., Shanghai, China.

Acclimation/Quarantine: Following arrival animals were assessed as to their general health by a member of the veterinary staff or other authorized personnel. Animals were acclimated for at least 3 days before being placed on study.

Animal Husbandry: Animals were group housed during acclimation and individually housed during the study. The animal room environment was controlled (target conditions: temperature 18 to 26° C., relative humidity 30 to 70%, 12 hours artificial light and 12 hours dark). Temperature and relative humidity was monitored daily.

Animals were fasted at least 12 hours prior to the administration. All animals had access to Certified Rodent Diet (Catalog #M01-F, SLAC Laboratory Animal Cl. Ltd., Shanghai, China) ad libitum 4 hours post dosing. Water was autoclaved before provided to the animals ad libitum. Periodic analyses of the water was performed.

2. Dose Formulation

Formulation will be picked up directly from PDS.

Two 20 µL aliquots of each formulation will be removed from each of the formulation solutions, transferred into 1.5 mL of polypropylene microcentrifuge tubes and run dose validation by LC/UV or LC-MS/MS.

3. Dose Administration

For IM/SC dosing, the dose formulation were administered via intramuscular/subcutaneous injection following facility SOPs.

4. Sample Collection

Approximately 200 µL blood were collected from saphenous vein at each time point. All blood samples were transferred into microcentrifuge tubes containing 40_, of $K_2EDTA$ (0.5M) as anti-coagulant and placed on wet ice until processed for plasma.

5. Blood/Plasma Processing

Blood samples were processed for plasma by centrifugation at approximately 4° C., 3000 g 15 min within half an hour of collection. Plasma samples will be stored in polypropylene tubes, quick frozen over dry ice and kept at −70±10° C. until LC/MS/MS analysis.

6. Sample Analysis

Dose formulation concentration verification

For the clear solution, 1 sample were collected in the middle of each dose formulation; for the suspension, 3 samples were collected from top, middle, button of each dose solution.

A LC/UV method was developed and 1 standard solution was prepared.

The peak area of test article in dose formulation solution and in standard solution samples was determined by the LC/UV method.

Acceptance criteria: the peak area of formulation solution sample was within 80%-120% of that in standard solution.

Bioanalytical Method and Sample Analysis

LC-MS/MS methods for the quantitative determination of test compound in corresponding biological matrix was developed under non-GLP compliance.

A calibration curve with 8 non-zero calibration standards was applied for the method including LLOQ.

A set of QC samples consisting of low, middle, and high concentration was applied for the method.

The study sample analysis was performed concurrently with a set of calibration standards and two sets of QC samples using the LC-MS/MS method (If sample numbers are more than 48, then two calibration curves with 2 sets of QC samples will be applied).

Acceptance criteria:

Linearity: a minimum of 6 calibration standards was back calculated to within ±20% of their nominal values in plasma.

Accuracy: A minimum of 4 out of 6 QC samples was back calculated to within ±20% of their nominal values in plasma.

Specificity: The mean calculated concentration in the single blank matrix should be 0.5 times the LLOQ.

Sensitivity: LLOQ target: 1-3 ng/mL.

Carryover: the mean calculated carry-over concentration in the single blank matrix immediately after the highest standard injection should be <LLOQ. If the carryover couldn't meet the criteria, then the percent of carryover should be estimated following in-house bioanalytical SOP.

7. Data Analysis

Plasma concentration versus time data will be analyzed by non-compartmental approaches using the Phoenix WinNonlin 6.3 software program. $C_{max}$, $T_{max}$, $T_{1/2}$, $AUC_{(0-t)}$, $AUC_{(0-inf)}$, $MRT_{(0-t)}$, $MRT_{(0-inf)}$, % F and graphs of plasma concentration versus time profile will be reported.

Table 20 shows the PK data for Compound 2 following PO and IM administration. Graph is shown in FIG. 1.

TABLE 20

|  | Compound 2 (PO) | | | Compound 2 (IM) | | |
|---|---|---|---|---|---|---|
| mpk | 0.03 | 0.1 | 0.3 | 0.03 | 0.1 | 0.3 |
| $C_{max}$ (nM) | 45.2 | 173.4 | 554.8 | ND | 5.6 | 18.7 |
| $T_{max}$ (h) | 3.67 | 3.0 | 4.67 | ND | 96 | 112 |
| $T_{1/2}$ (h) | 24.9 | 23.7 | 22.5 | ND | — | 418 |
| $AUC_{0-last}$ (nM · h) | 1450 | 4936 | 16524 | ND | 797 | 2801 |
| $AUC_{0-inf}$ (nM · h) | 1555 | 5044 | 16764 | ND | 2972 | 4823 |
| CL/F (mL/min/kg) | 0.576 | 0.599 | 0.520 | ND | 0.586 | 0.864 |

Figure 2A:
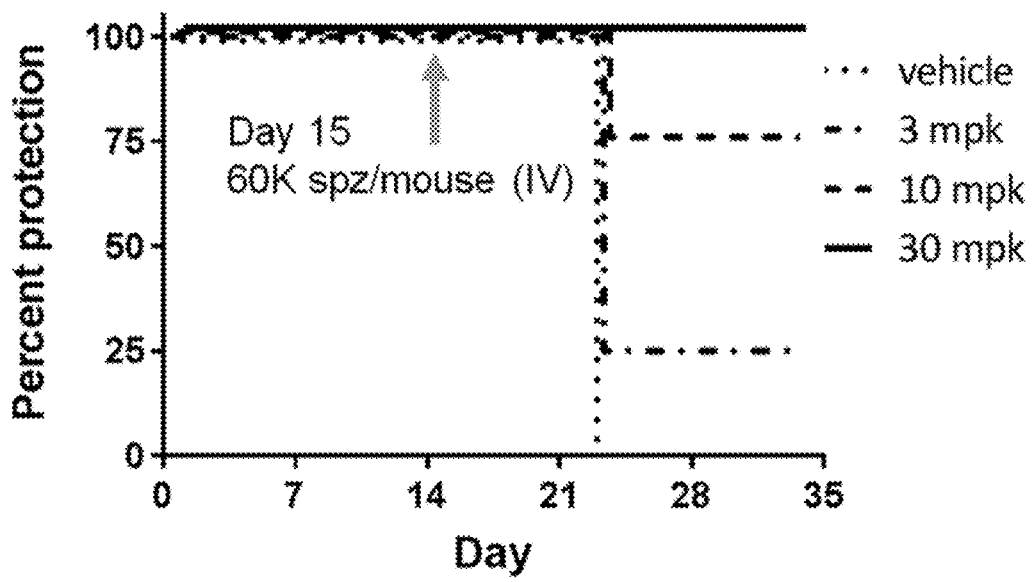
FIG. 2A depicts the percent protection following a sporozoite challenge at day 14 following IM administration of Compound 2 (3, 10, and 30 mg/kg).
Figure 2B:
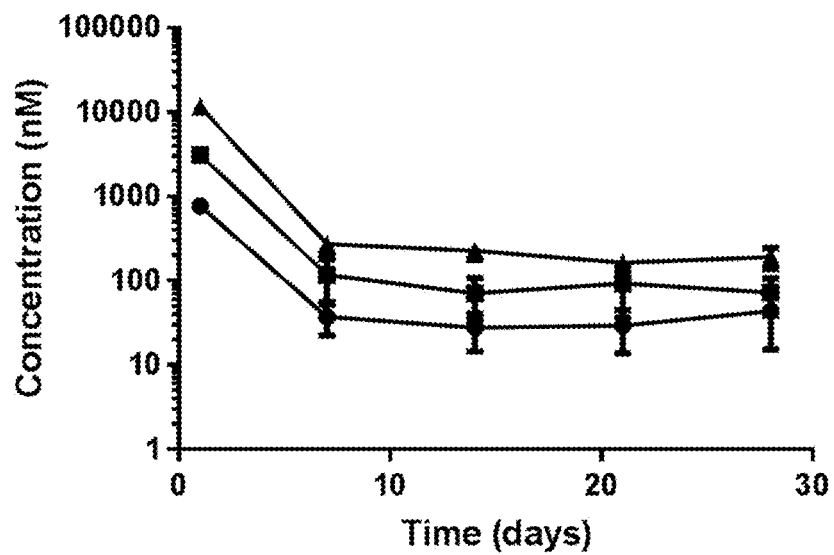
FIG. 2B depicts the exposure of ELQ-300 in mouse following IM administration of Compound 2 (3, 10, and 30 mg/kg).

Table 21 shows the average plasma concentration of ELQ-300 following IM administration of Compound 2 at 3 doses (3, 10, and 30 mg/kg). Table 22 shows the ELQ-300 plasma concentration in all animals at day 14 (prior to the sporozoites challenge). The exposure is not highly variable between animals in a given group. The $C_{trough}$ is about 83±32 nM for animals that are protected from infection. The graphs are shown in FIG. 2A and FIG. 2B.

TABLE 21

|  | ELQ-300 (nM) | | |
|---|---|---|---|
| Time | 3.33 mg/kg | 10 mg/kg | 30 mg/kg |
| 1 d | 723 ± 144 | 2942 ± 633 | 10959 ± 2029 |
| 7 d | 36 ± 16 | 112 ± 66 | 257 ± 70 |
| 14 d | 27 ± 14 | 68 ± 40 | 214 ± 54 |
| 21 d | 28 ± 17 | 88 ± 61 | 155 ± 38 |
| 28 d | 21 ± 32 | 69 ± 37 | 181 ± 59 |

TABLE 22

| 3 mg/kg | | 10 mg/kg | | 30 mg/kg | |
|---|---|---|---|---|---|
| 5 | 43 nM | 9 | 56 nM | 13 | 137 nM |
| 6 | 15 nM | 10 | 73 nM | 14 | 219 nM |
| 7 | 35 nM | 11 | 119 nM | 15 | 246 nM |
| 8 | 15 nM | 12 | 23 nM | 16 | 256 nM |

Figure 3A:
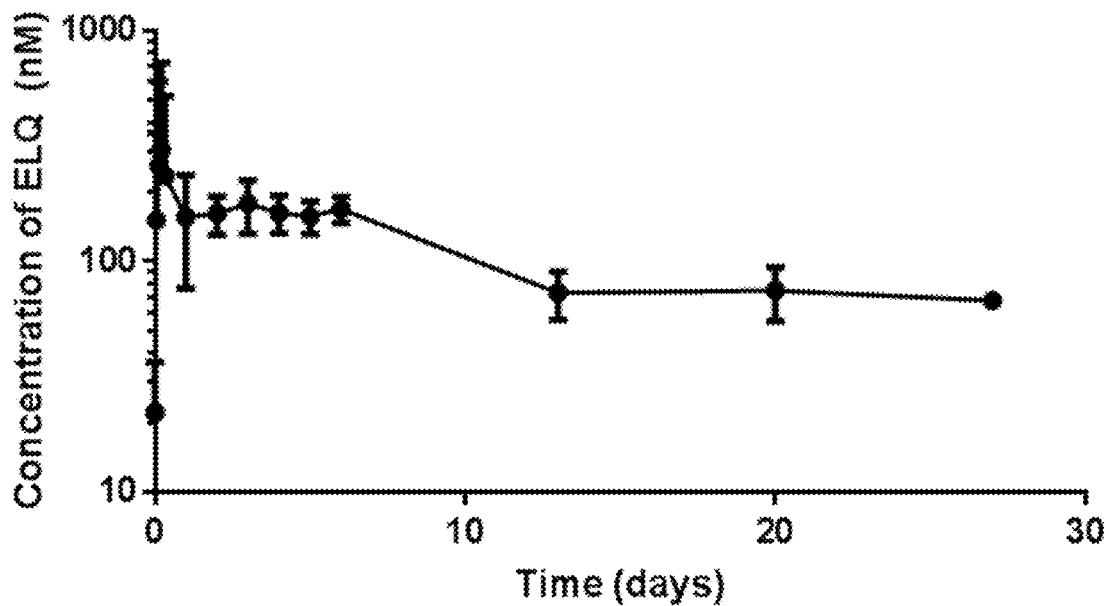
FIG. 3A depicts the exposure of ELQ-300 in rat following IM administration of Compound 2 (3.72 mg/kg in sesame oil).

Table 23 shows rat PK data for compound 2 (3.72 mg/kg in 100% sesame oil) injected intramuscularly. Table 24 shows the average plasma concentration of ELQ-300 following IM administration of Compound 2. Rat IM PK of Compound 2 demonstrated a slow release for the first month with ELQ-300 plasma level around 70 nM week two through four an significant burst in day 1 and significant drop in concentration between week one and two. The graph is shown in FIG. 3A.

TABLE 23

| mpk | 3.72 |
|---|---|
| $C_{max}$ (nM) | 399.3 ± 340 |
| $T_{max}$ (h) | 49.7 ± 38.7 |
| $T_{1/2}$ (h) | 359 ± 25.5 |
| $AUC_{0-last}$ (nM.h) | 68060 ± 3966 |
| $AUC_{0-inf}$ (nM.h) | 103311 ± 9144 |
| CL/F (mL/min/kg) | 1.05 ± 0.09 |

TABLE 24

| Time | ELQ-300 (nM) | Time | ELQ-300 (nM) |
|---|---|---|---|
| 1 h | 151 ± 209 | 6 d | 169 ± 22 |
| 8 h | 235 ± 281 | 13 d | 73 ± 17 |
| 1 d | 151 ± 209 | 20 d | 75 ± 19 |
| 3 d | 157 ± 80 | 27 d | 68 ± 5 |

Figure 3B:
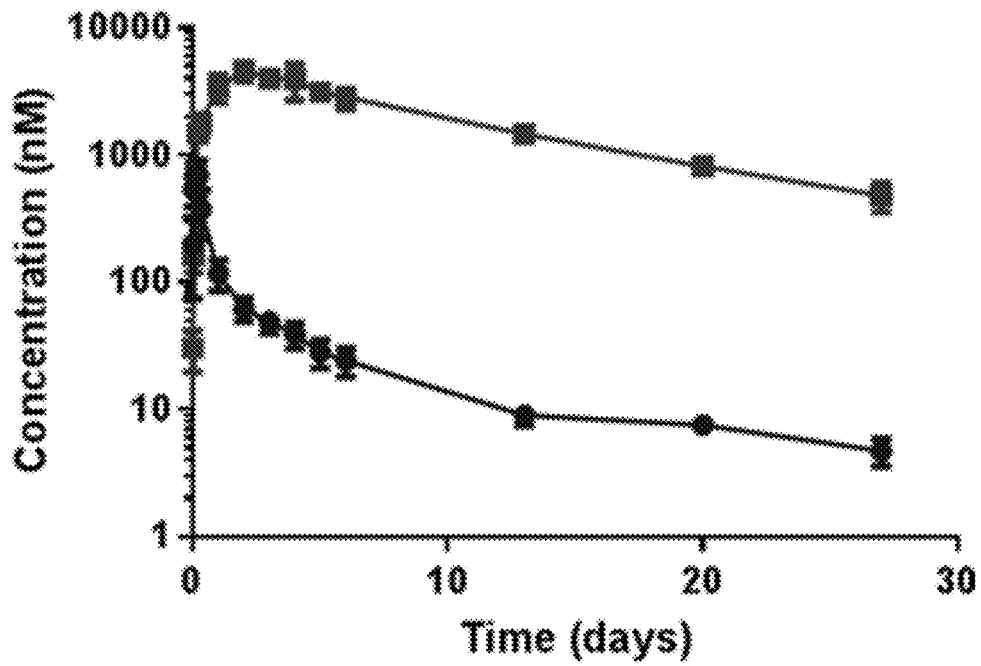
FIG. 3B depicts the plasma exposure of ELQ-300 and Compound 2 in dog following IM administration of Compound 2 (20 mg/mL, 3% TPGS, 1% HPMC E5 suspension).

Table 24A shows dog PK data for crystalline compound 2 (20 mg/mL, 3% TPGS, 1% HPMC E5 suspension) injected intramuscularly. Compound 2 was dosed in dog at 10 mg/kg (Injection volume: 0.5 mL/kg). The material was formulated as a 20 mg/mL suspension in 3% TPGS and 1% HPMC E5. Compound 2 plasma exposure was low but detectable throughout the duration of the study. Plasma concentrations of ELQ-300 remained several orders of magnitude higher than that of Compound 2. Half-life of ELQ-300 was about twice as long as that of compound 2 (205 and 124 respectively). Additionally, clearance of ELQ-300 remained very low (0.23 mL/min/kg). The graph is shown in FIG. 3B.

TABLE 24A

|  | Compound 2 | ELQ-300 |
|---|---|---|
| $T_{max}$ (h) | 3 (2) | 48 (0) |
| $T_{1/2}$ (h) | 124 (34) | 205 (39) |
| $C_{max}$ (nM) | 730 (149) | 4639 (832) |
| $C_{last}$ (mM) | 4.5 (4.7) | 482 (123) |
| $AUC_{0-last}$ (nM.h) | 16427 (3738) | 1140080 (100116) |
| $AUC_{0-inf}$ (nM.h) | 18054 (3387) | 1287335 (95176) |
| CL/F (mL/min/kg) | 14.4 (3.3) | 0.23 (0.02) |

Figure 4A:
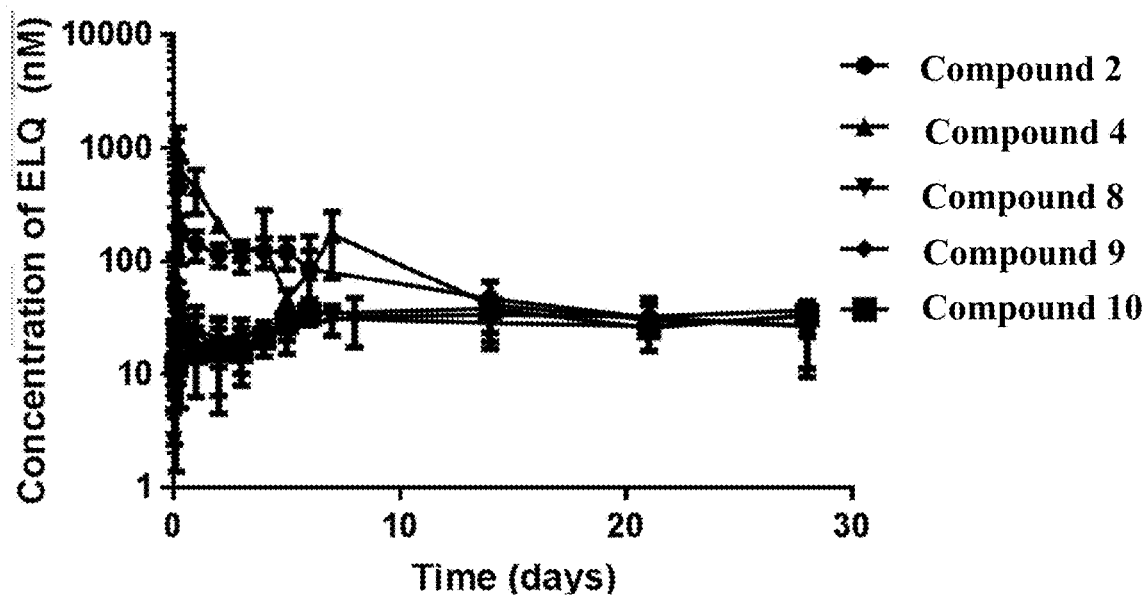
FIG. 4A depicts the exposure of ELQ-300 in mouse following IM administration of Compound 2, 4, 8, 9, and 10 (3 mg/kg, 1.5 mg/mL in sesame oil).
Figure 4B:
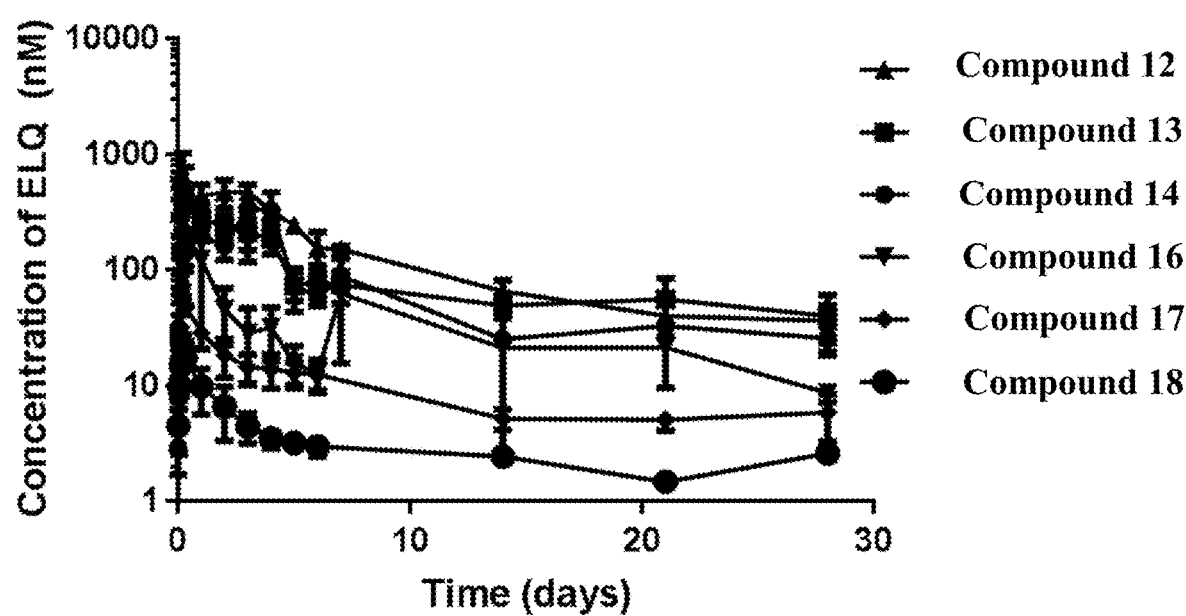
FIG. 4B depicts the exposure of ELQ-300 in mouse following IM administration of Compound 12, 13, 14, 16, 17, and 18 (3 mg/kg, 1.5 mg/mL in sesame oil).

Table 25 shows the ELQ-300 plasma concentration following administration of compounds 2, 8, 9, 10, 12, 16, 17, and 18 (3 mg/kg, 1.5 mg/mL in 100% sesame oil). Graphs are shown in FIG. 4A and FIG. 4B.

TABLE 25

| | ELQ-300 (nM) | | | | | | | |
|---|---|---|---|---|---|---|---|---|
| Time | 2 | 8 | 9 | 10 | 12 | 16 | 17 | 18 |
| 8 h | 175 ± 82 | 27 ± 22 | 38 ± 6 | 12 ± 11 | 948 ± 609 | 272 ± 393 | 50 ± 3 | 17 ± 7 |
| 1 d | 142 ± 42 | 23 ± 16 | 24 ± 4 | 15 ± 17 | 406 ± 165 | 137 ± 97 | 28 ± 5 | 10 ± 4 |
| 6 d | 85 ± 40 | 31 ± 9 | 32 ± 15 | 34 ± 7 | 156 ± 45 | 18 ± 5 | 12 ± 3 | 3.0 ± 5 |
| 13 d | 46 ± 8 | 28 ± 9 | 33 ± 10 | 38 ± 2 | 83 ± 30 | 20 ± 20 | 5 ± 1 | 1.6 ± 1.4 |
| 27 d | 27 ± 16 | 32 ± 11 | 36 ± 7 | 33 ± 5 | | | 6 ± 3 | 2.5 ± 0.4 |

Figure 18:
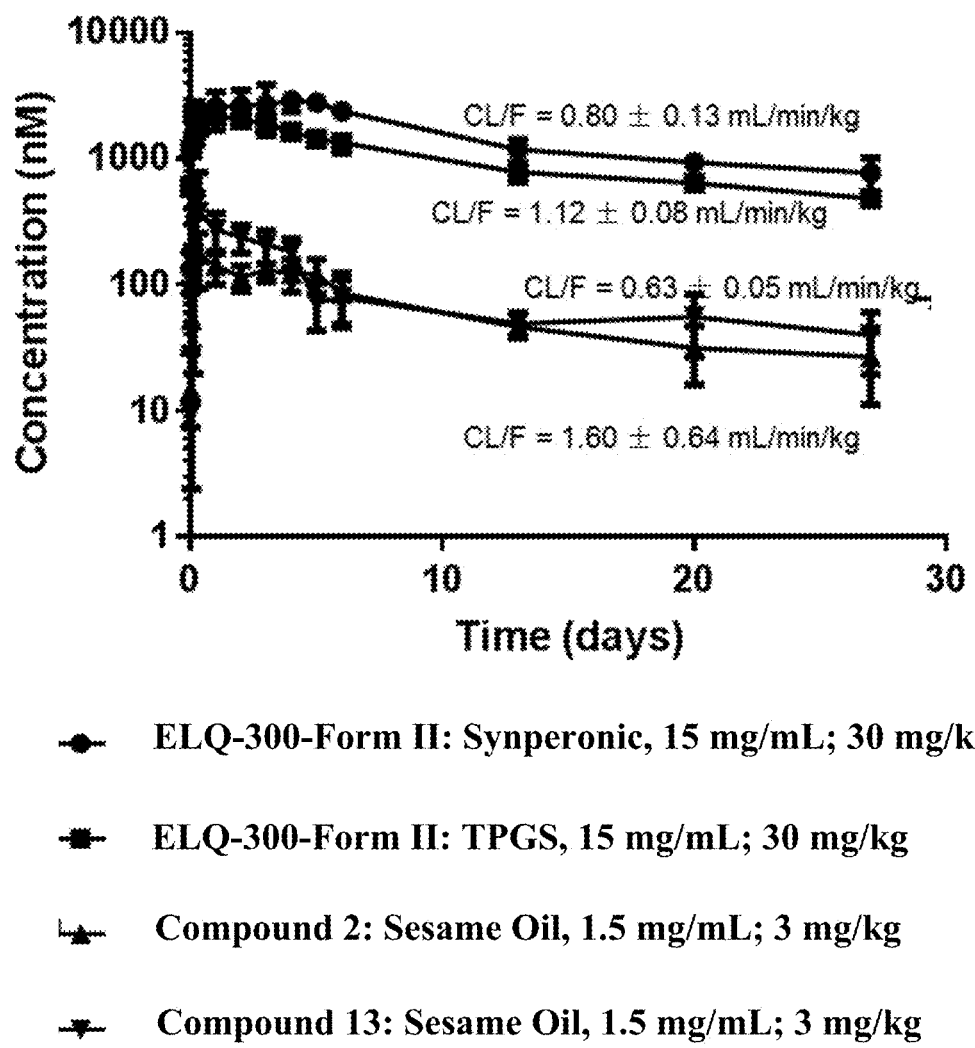
FIG. 18 depicts a comparison in exposure of ELQ-300 following IM administration of Compound 2 and 13 in sesame oil versus two ELQ-300-Form II suspensions.

Table 26 shows the average plasma concentration of ELQ-300 following IM administration of suspensions of ELQ-300-Form II in two different formulations (15 mg/mL, 30 mg/kg) as compared to the average plasma concentration of ELQ-300 following IM administration of Compound 2 and Compound 13 in 100% sesame oil (1.5 mg/mL, 3 mg/kg). The graph is shown in FIG. 18.

TABLE 26

| | ELQ-300 (µM) | | ELQ-300 (nM) | |
|---|---|---|---|---|
| | | 1% Synperonic ® F | | |
| Time | 3% TPGS | 108-0.2% SLS | Comp. 2 | Comp. 13 |
| 8 h | 1.7 ± 0.3 | 1.7 ± 0.1 | 175 ± 82 | 382 ± 48 |
| 1 d | 2.1 ± 0.4 | 2.5 ± 0.9 | 142 ± 42 | 410 ± 83 |
| 6 d | 1.3 ± 0.2 | 2.4 ± 0.3 | 123 ± 85 | 313 ± 89 |
| 13 d | 0.8 ± 0.1 | 1.1 ± 0.2 | 46 ± 8 | 110 ± 7 |
| 20 d | 0.64 ± 0.99 | 0.94 ± 0.03 | 32 ± 16 | 79 ± 6 |
| 27 d | 0.48 ± 0.04 | 0.78 ± 0.24 | 27 ± 16 | 80 ± 7 |

Figure 19A:
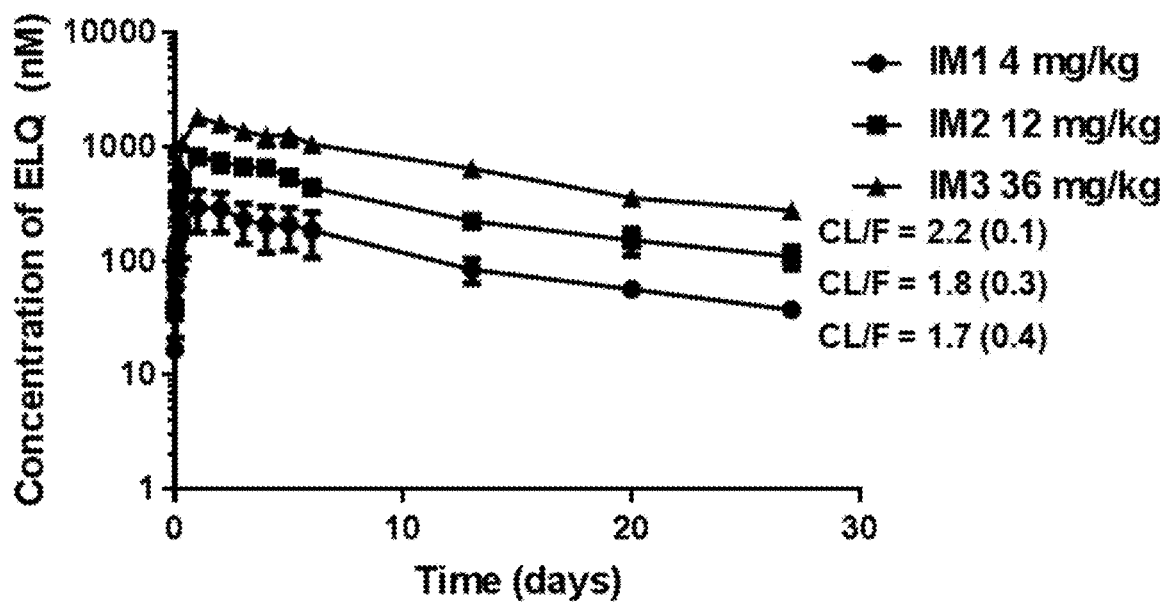
FIG. 19A depicts the exposure of ELQ-300 following IM injection of three ELQ-300-Form II suspensions (100 mg/mL Synperonic).
Figure 19B:
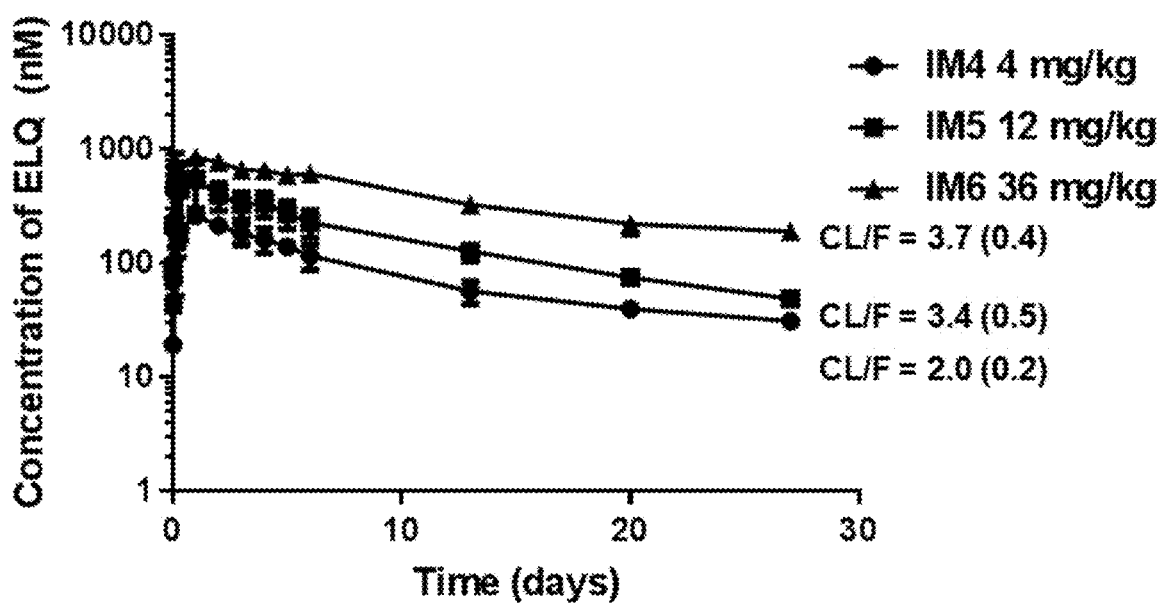
FIG. 19B depicts the exposure of ELQ-300 following IM injection of three ELQ-300-Form II suspensions (100 mg/mL 3% TPGS).

Table 27 shows the mouse PK data following IM administration of 6 different ELQ-300-Form II suspensions (100 mg/mL). IM1=Synperonic® 4 mg/kg, IM2=Synperonic® 12 mg/kg, IM3=Synperonic® 36 mg/kg. IM4=TPGS 4 mg/kg, IM5=TPGS 12 mg/kg, IM6=TPGS 36 mg/kg. Dose proportionality (up to 13 days) is observed in the 2 different vehicles. Graphs are shown in FIG. 19A and FIG. 19B.

TABLE 27

| | IM1 | IM2 | IM3 | IM4 | IM5 | IM6 |
|---|---|---|---|---|---|---|
| Nominal Dose (mg/kg) | 4 | 12 | 36 | 4 | 12 | 36 |
| Concentration (mg/mL) | 100 | 100 | 100 | 100 | 100 | 100 |
| Dose Volume (uL) | 10 | 30 | 90 | 10 | 30 | 90 |
| $t_{1/2}$ (h) | 242 (34) | 250 (36) | 250 (38) | 381 (182) | 227 (41) | 320 (83) |
| $C_{max}$ (nM) | 333 (118) | 820 (128) | 1813 (255) | 263 (17) | 605 (342) | 855 (33) |
| $C_{last}$ (nM) | 37 (2) | 109 (25) | 277 (13) | 31 (4) | 49 (4) | 190 (12) |
| AUC (0-∞) (nM · h/mL) | 87091 (22497) | 235908 (37505) | 566904 (27951) | 70864 (5521) | 123766 (16564) | 342465 (40399) |
| CL/F (mL/h/kg) | 1.7 (0.4) | 1.8 (0.3) | 2.2 (0.1) | 2.0 (0.2) | 3.4 (0.5) | 3.7 (0.4) |

Table 28 shows the mouse PK data following IM administration of 2 different ELQ-300-Form II suspensions (at 4 mg/kg) as compared with IM administration of Compound 2 (at 4 mg/kg) in sesame oil. The graph is shown in FIG. 20.

TABLE 28

| | ELQ-300-Form II (Synperonic ®) | ELQ-300-Form II (TPGS) | Compound 2 (sesame oil) |
|---|---|---|---|
| Nominal Dose (mg/kg) | 4 | 4 | 5 |
| Concentration (mg/mL) | 100 | 100 | 12.5 |
| Dose Volume (uL) | 10 | 10 | 100 |
| $t_{1/2}$ (h) | 242 (34) | 381 (182) | 359 (26) |
| $C_{max}$ (nM) | 333 (118) | 263 (17) | 399 (54) |
| $C_{last}$ (nM) | 37 (2) | 31 (4) | 68 (4) |
| $AUC_{0-\infty}$ (nM*h/mL) | 87091 (22497) | 70864 (5521) | 103321 (9160) |
| CL/F (mL/h/kg) | 1.7 (0.4) | 2.0 (0.2) | 1.0 (0.1) |

Figure 21:
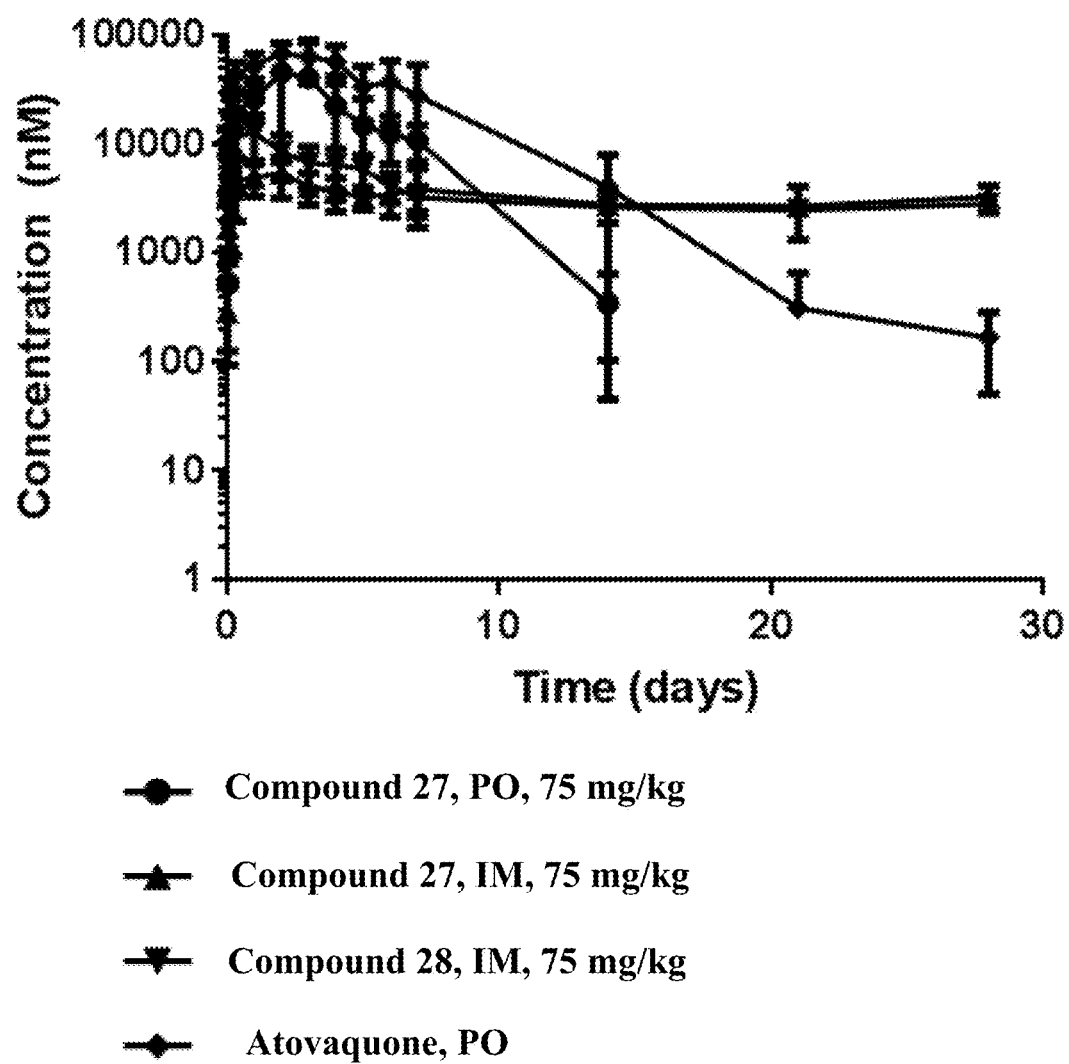
FIG. 21 depicts the exposure of atovaquone following PO or IM dosing with Compound 27, Compound 28, and atovaquone.

Table 29 shows the average atovaquone plasma concentration following IM and PO administration of Compound 27 (in sesame oil) as compared to PO administration of atovaquone. The graph is shown in FIG. 21.

TABLE 29

| | Atovaquone from Compound 27 (µM) | |
|---|---|---|
| Time | IM | PO |
| 8 h | 4.6 ± 2.7 | 19 ± 3 |
| 1 d | 4.9 ± 1.6 | 27 ± 9 |
| 7 d | 3.8 ± 2.1 | 15 ± 11 |
| 14 d | 2.8 ± 0.9 | 0.3 ± 0.3 |
| 28 d | 3.3 ± 0.9 | BQL |

Figure 22A:
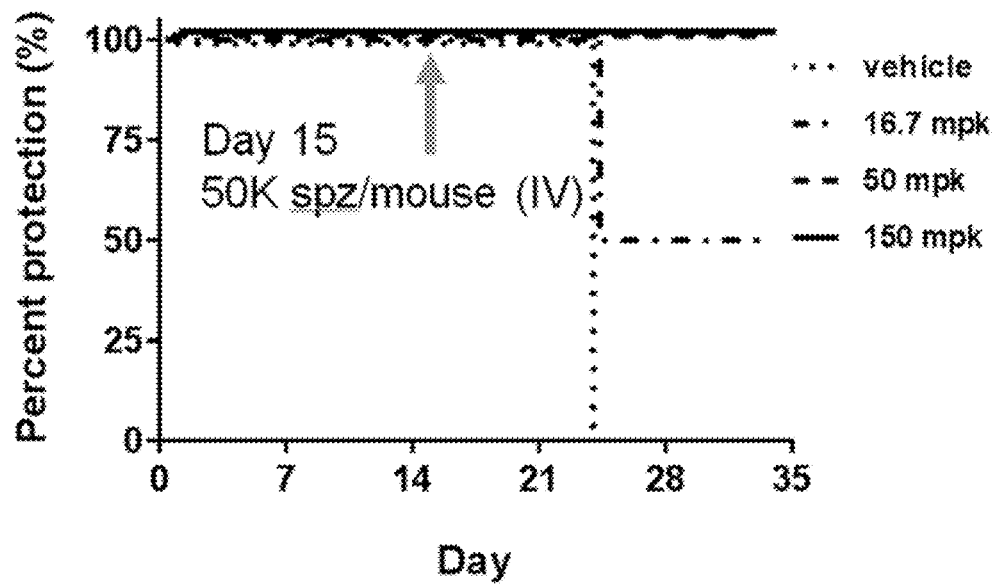
FIG. 22A depicts the percent protection following a sporozoite challenge at day 15 following IM administration of Compound 27 (16.6, 50, and 150 mg/kg).
Figure 22B:
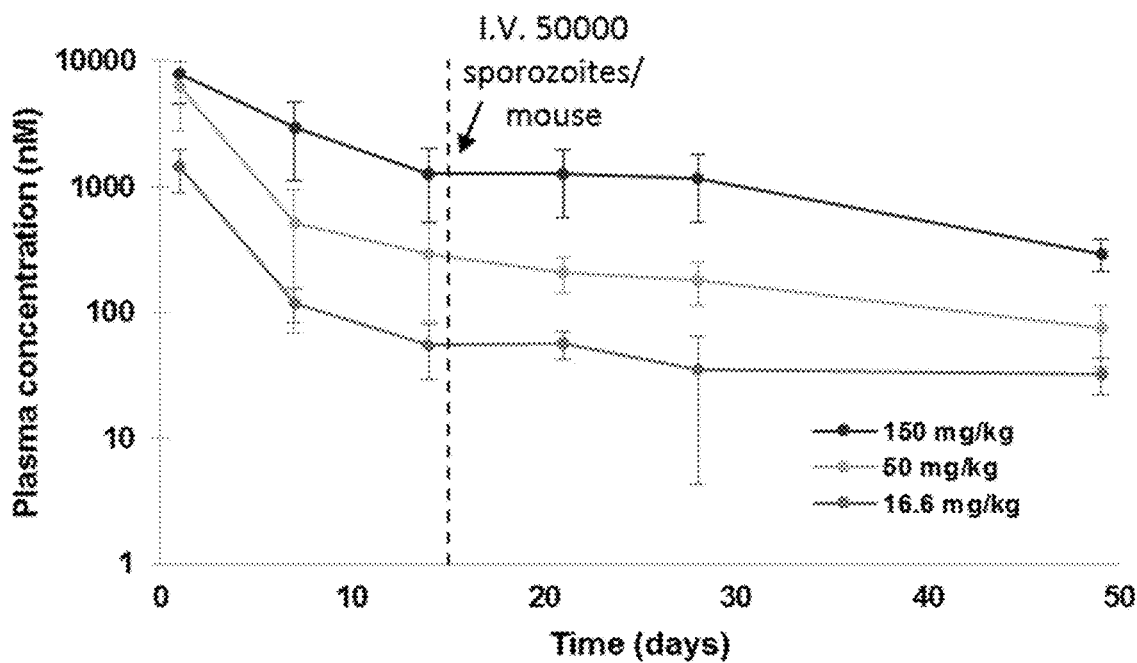
FIG. 22B depicts the exposure of atovaquone in mouse following IM administration of Compound 27 (16.6, 50, and 150 mg/kg).

Table 30 shows the average atovaquone plasma and liver concentration following IM administration of Compound 27 at three different doses (16.7, 50, and 150 mg/kg). Table 31 shows the plasma concentration by animal in the 16.7 mg/kg group. Graphs are shown in FIG. 22A and-FIG. 22B.

TABLE 30

| Time | Atovaquone (nM) | | |
| --- | --- | --- | --- |
| | 16.7 mg/kg | 50 mg/kg | 150 mg/kg |
| 1 d | 1445 ± 550 | 6371 ± 3619 | 8035 ± 3452 |
| 14 d | 55 ± 25 | 295 ± 280 | 1279 ± 752 |
| 28 d | 35 ± 31* | 180 ± 68 | 1170 ± 644 |
| 49 d | 33 ± 11* | 75 ± 38 | 294 ± 85 |
| 49 d (liver) | | 36.7 ± 0.2 | 138 ± 28 |

*For surviving animals

TABLE 31

| Time | Atovaquone (nM) | | | |
| --- | --- | --- | --- | --- |
| | Animal 5 | Animal 6 | Animal 7 | Animal 8 |
| 1 d | 1761 | 660 | 1477 | 1884 |
| 7 d | 78 | 148 | 152 | 102 |
| 14 d | 30 | 61 | 88 | 40 |
| 21 d | 47 | 49 | 78 | 55 |
| 28 d | — | 19 | 56 | 65 |
| 49 d | — | — | 40 | 25 |

Figure 38:
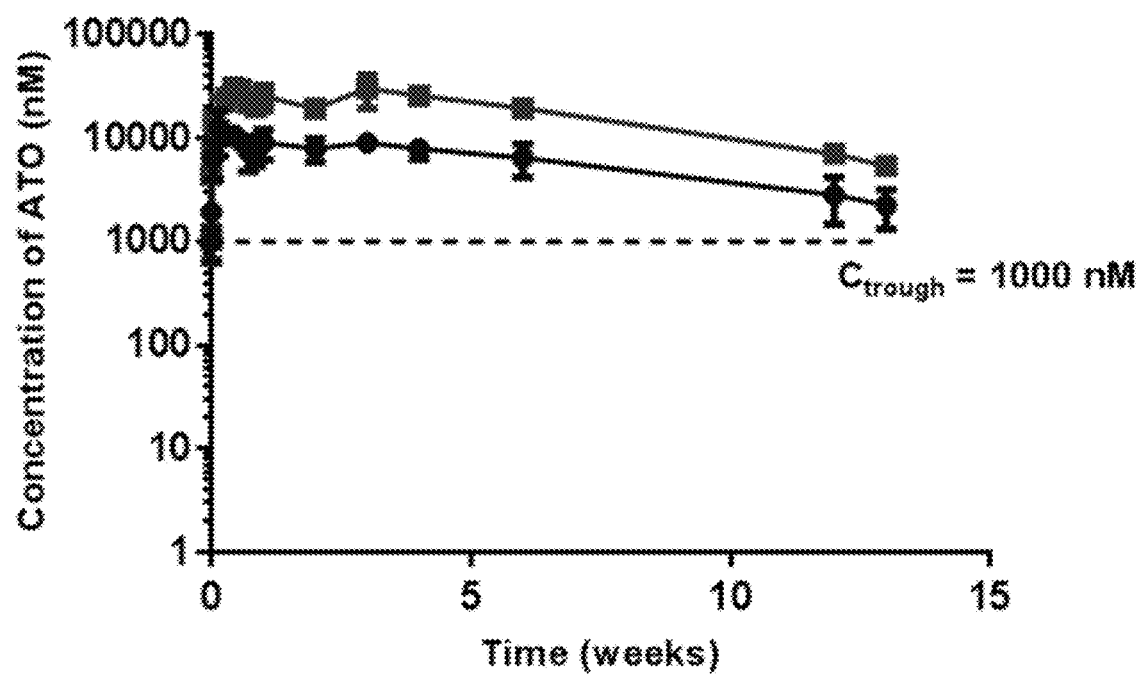
FIG. 38 depicts the rat exposure of Atovaquone following IM administration of Compound 33 in sesame oil.

Table 32 shows the average Atovaquone concentration following IM rat administration of Compound 33 at two different doses (20 and 60 mg/kg) formulated in sesame oil. Table 33 shows the liver and brain exposures at week 13. The Graph is shown in FIG. 38.

TABLE 32

| | Compound 33 | Compound 33 |
| --- | --- | --- |
| Dose of ATO (mg/kg) | 20 | 60 |
| Concentration of ATO (max concentration) | 295 mg/mL (650 mg/mL) | 295 mg/mL (650 mg/mL) |
| Injection Volume (uL) | 2x10 | 2x30 |
| Formulation | Sesame oil solution | Sesame oil solution |
| $C_{max}$ (nM) | 13813 (4909) | 35349 (5413) |
| $C_{last}$ (nM) | 2256 (935) | 5379 (886) |
| $AUC_{0-\infty}$ (nM*h/mL) | 8172753 (466892) | 23869258 (1387755) |
| CL/F (mL/min/kg) | 0.06 (0.02) | 0.06 (0.03) |

TABLE 33

| | Compound 33 | Compound 33 |
| --- | --- | --- |
| Dose of ATO (mg/kg) | 20 | 60 |
| Liver Exposure (nM) | 2793 (944) | 3717 (351) |
| Brain Exposure (nM) | 37.9 (13.8) | 64.0 (10.3) |

Figure 39:
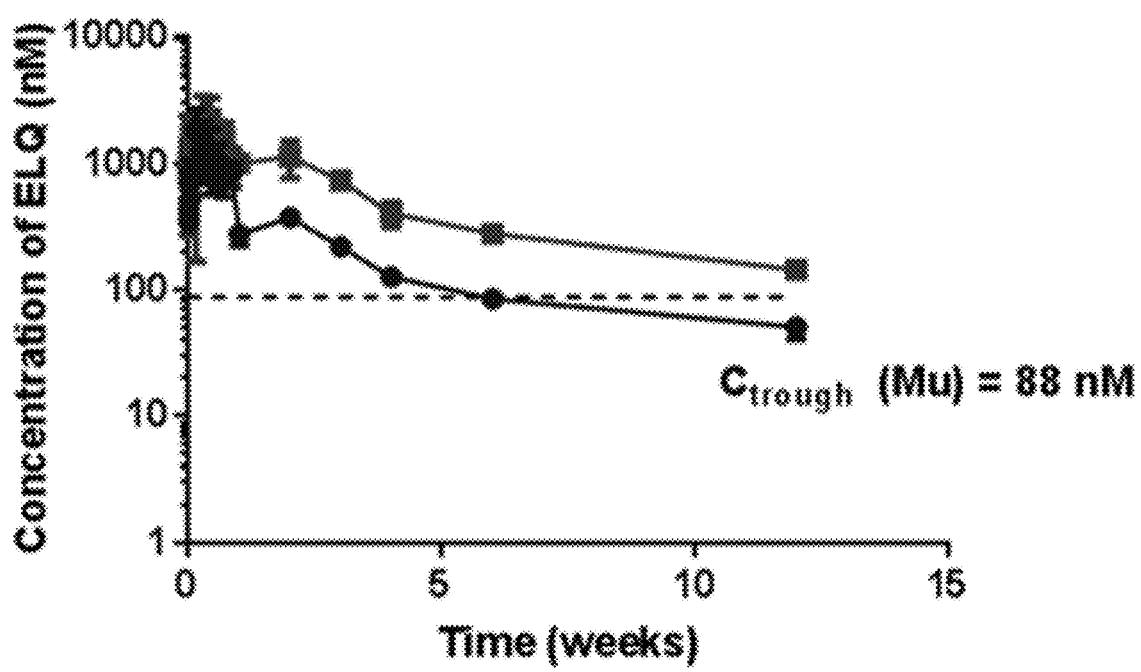
FIG. 39 depicts the rat exposure of ELQ-300 following IM administration of Compound 35.

Table 34 shows the average ELQ-300 concentration following IM rat administration of Compound 35 at two different doses (10.5 and 30 mg/kg) formulated in sesame oil. The Graph is shown in FIG. 39.

TABLE 34

| | Compound 35 | Compound 35 |
| --- | --- | --- |
| Dose of ELQ-300 (mg/kg) | 10.5 | 30 |
| Concentration of ELQ-300 (max concentration) | 291 mg/mL (580 mg/mL) | 291 mg/mL (580 mg/mL) |

TABLE 34-continued

| | Compound 35 | Compound 35 |
| --- | --- | --- |
| Injection Volume (uL) | 10 | 30 |
| $C_{max}$ (nM) | 2265 (512) | 2431 (1105) |
| $C_{last}$ (nM) | 51(10) | 145 (11) |
| $AUC_{0-\infty}$ (nM*h/mL) | 410174 (22195) | 1024416 (225651) |
| CL/F (mL/min/kg) | 0.8 (0.1) | 0.9 (0.2) |

Figure 40:
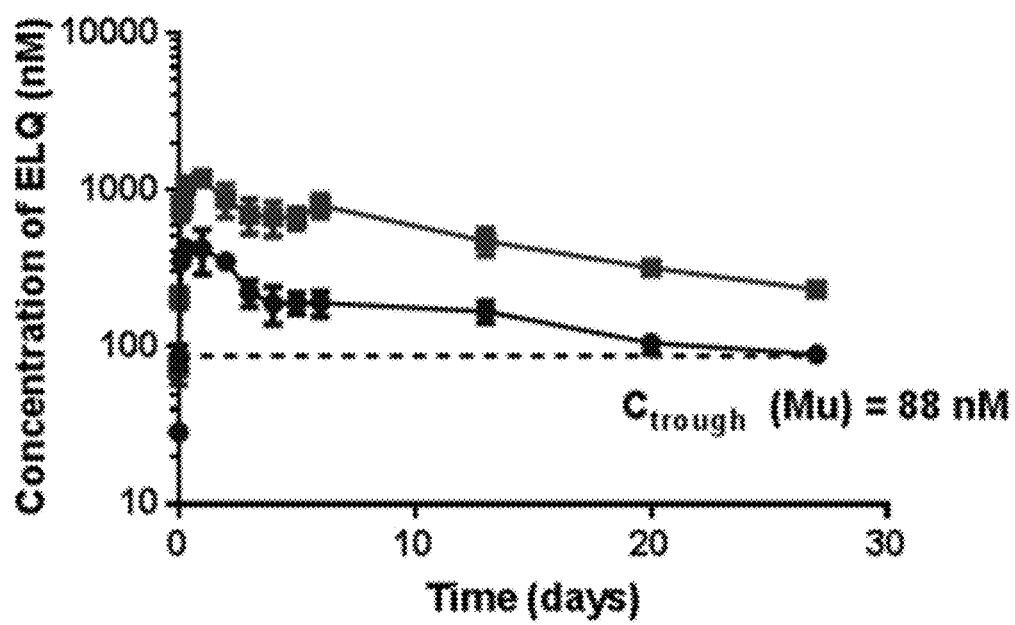
FIG. 40 depicts the exposure of ELQ-300 following IM administration of Compound 2 (8 and 24 mg/kg).

Table 35 shows the average ELQ-300 concentration following IM rat administration of crystalline Compound 2 at two different doses (8 and 24 mg/kg). Table 36 shows key in vitro ADME for Compound 2. The Graph is shown in FIG. 40.

TABLE 35

| | Compound 2 | Compound 2 |
| --- | --- | --- |
| Dose of ELQ-300 (mg/kg) | 8 | 24 |
| Formulation | 34 mg/mL in 3% TPGS and 1% HPMC E5 | |
| Injection Volume (uL) | 59 | 177 |
| Compound 2 | Compound | 2 |
| $C_{max}$ (nM) | 474 (70) | 1201 (114) |
| $C_{last}$ (nM) | 90 (10) | 232 (28) |
| $AUC_{0-\infty}$ (nM*h/mL) | 108338 (5183) | 332595 (47709) |
| CL/F (mL/min/kg) | 1.37 (0.22) | 1.57 (0.19) |

TABLE 36

| | Plasma | Liver S9 | Hepatocyte T1/2 |
| --- | --- | --- | --- |
| | % remaining after 2 hours | | |
| Mouse | 0% | | |
| Rat | 0% | | |
| Dog | 83% | 47% | 22 min |
| Monkey | 85% | | |
| Human | 82% | 35% | 77 min |

Example 13: Solid state characterization of (6-chloro-7-methoxy-2-methyl-3-(4-(4-(trifluoromethoxy)phenoxy)phenyl)quinolin-4-yloxy) methyl butyrate (Compound 2)

Figure 42B:
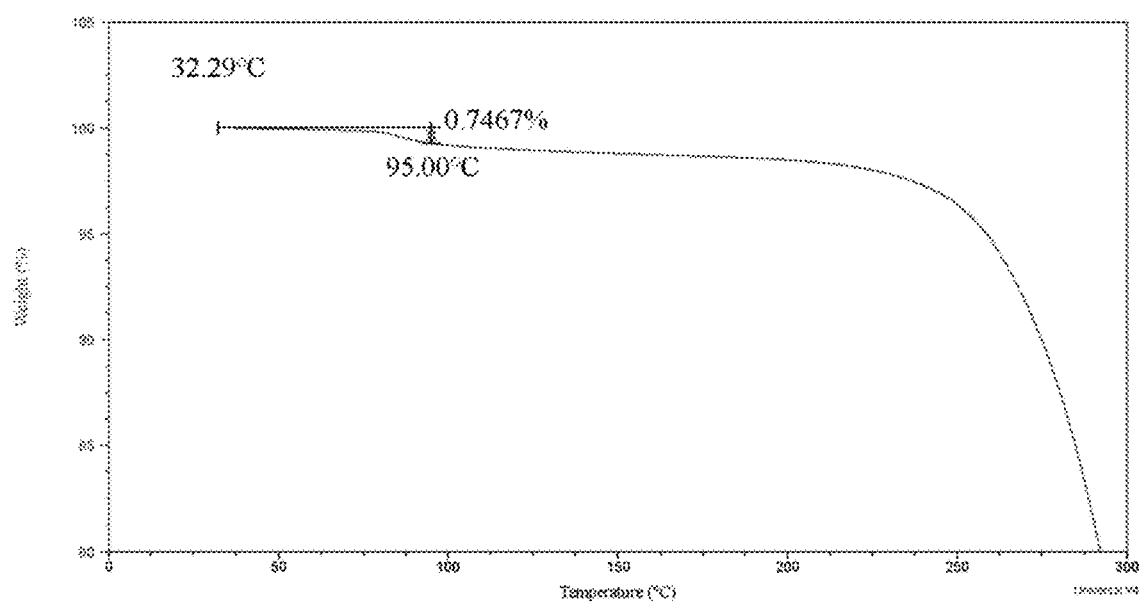
FIG. 42B depicts the TGA of crystalline Compound 2.

FIG. 41 shows the characteristic X-ray diffraction pattern of the Compound 2. Characteristic reflections and the corresponding d-spacings for crystalline Compound 2 are shown in Table 37. FIG. 42A shows the DSC of the crystalline compound 2 and FIG. 42B shows the TGA of the crystalline compound 2.

TABLE 37

| No. | 2-Theta (°) | d-spacing (Å) | Height | I% |
| --- | --- | --- | --- | --- |
| 1 | 8.90 | 9.93 | 503 | 6.3 |
| 2 | 12.31 | 7.19 | 474 | 5.9 |
| 3 | 13.04 | 6.78 | 337 | 4.2 |
| 4 | 13.93 | 6.35 | 749 | 9.4 |
| 5 | 14.44 | 6.13 | 6919 | 86.5 |
| 6 | 14.96 | 5.92 | 540 | 6.8 |
| 7 | 15.15 | 5.84 | 3178 | 39.7 |
| 8 | 16.30 | 5.44 | 251 | 3.1 |
| 9 | 16.50 | 5.37 | 745 | 9.3 |
| 10 | 16.89 | 5.25 | 317 | 4 |
| 11 | 17.03 | 5.20 | 224 | 2.8 |

TABLE 37-continued

| No. | 2-Theta (°) | d-spacing (Å) | Height | I% |
|---|---|---|---|---|
| 12 | 17.68 | 5.01 | 2694 | 33.7 |
| 13 | 18.11 | 4.89 | 2475 | 30.9 |
| 14 | 18.54 | 4.78 | 295 | 3.7 |
| 15 | 19.06 | 4.65 | 1048 | 13.1 |
| 16 | 20.30 | 4.37 | 973 | 12.2 |
| 17 | 20.52 | 4.33 | 383 | 4.8 |
| 18 | 20.80 | 4.27 | 721 | 9 |
| 19 | 21.21 | 4.19 | 1018 | 12.7 |
| 20 | 21.66 | 4.10 | 1910 | 23.9 |
| 21 | 21.94 | 4.05 | 946 | 11.8 |
| 22 | 22.32 | 3.98 | 2300 | 28.8 |
| 23 | 22.59 | 3.93 | 8000 | 100 |
| 24 | 22.99 | 3.87 | 566 | 7.1 |
| 25 | 23.44 | 3.79 | 332 | 4.2 |
| 26 | 23.62 | 3.76 | 646 | 8.1 |
| 27 | 24.09 | 3.69 | 783 | 9.8 |
| 28 | 24.62 | 3.61 | 430 | 5.4 |
| 29 | 25.75 | 3.46 | 1597 | 20 |
| 30 | 26.66 | 3.34 | 840 | 10.5 |
| 31 | 27.09 | 3.29 | 503 | 6.3 |
| 32 | 28.06 | 3.18 | 424 | 5.3 |
| 33 | 28.93 | 3.08 | 364 | 4.6 |
| 34 | 29.21 | 3.06 | 1023 | 12.8 |
| 35 | 29.93 | 2.98 | 486 | 6.1 |
| 36 | 31.36 | 2.85 | 614 | 7.7 |
| 37 | 31.85 | 2.81 | 220 | 2.8 |
| 38 | 31.99 | 2.80 | 177 | 2.2 |
| 39 | 32.80 | 2.73 | 277 | 3.5 |
| 40 | 33.19 | 2.70 | 162 | 2 |
| 41 | 33.41 | 2.68 | 345 | 4.3 |
| 42 | 33.65 | 2.66 | 244 | 3 |
| 43 | 35.64 | 2.52 | 178 | 2.2 |
| 44 | 35.90 | 2.50 | 416 | 5.2 |
| 45 | 36.23 | 2.48 | 63 | 0.8 |
| 46 | 37.02 | 2.43 | 96 | 1.2 |
| 47 | 37.32 | 2.41 | 110 | 1.4 |
| 48 | 37.75 | 2.38 | 130 | 1.6 |
| 49 | 39.03 | 2.31 | 195 | 2.4 |
| 50 | 39.39 | 2.29 | 183 | 2.3 |

Crystalline Compound 2 was also characterized by PLM which showed particle size range of 1-50 μm.

Example 14. Preparation and Characterization of Compound 2 Microsuspensions

Two Compound 2 microsuspensions were prepared.

1. Preparation and Characterization of 167.27 mg/mL Compound 2 Microsuspension

A Compound 2 microsuspension was prepared by wet-milling method. About 240 mg of Compound 2 was added to 1 mL of 3% (w/v) TPGS-1% (w/v) HPMC E5 in a milling jar. 2 mL of zirconium beads with a diameter of 0.8 mm (YTZ® Grinding Media, Nikkato Co., Japan) were added using a measuring cylinder. The milling jar was placed in a planetaty miller. The milling was conducted at a rotating speed of 800 rpm for 1 hour in each cycle and the suspension was collected after 3 milling cycles.

The collected suspension was about 0.1-0.2 mL. Large volume loss was due to sample residual on the milling beads. PLM showed most particles were below 5 μm in size. Concentration of Compound 2 in the suspension determined by HPLC was 167.27 mg/mL. The final product was stored in a 1.5 mL sealed glass vial at room temperature and protected from light before PK study. Visual inspection of the suspensions showed that the product was homogeneous, syringeable and easily resuspendable following short-time vortex or water-bath sonication, suitable for intramuscular injection.

2. Preparation and Characterization of 259.62 mg/mL Compound 2 Microsuspension

A Compound 2 microsuspension was prepared by wet-milling method. About 1.6 g of Compound 2 was added to 4 mL of 3% (w/v) TPGS-1% (w/v) HPMC E5 in a milling jar. 4 mL of zirconium beads with a diameter of 0.8 mm (YTZ® Grinding Media, Nikkato Co., Japan) were added using a measuring cylinder. The milling jar was placed in a planetaty miller. The milling was conducted at a rotating speed of 800 rpm for 1 hour in each cycle and the suspension was collected after 3 milling cycles.

The collected suspension was About 2.8 mL and most particles were between 1 μm and 5 μm in size. Concentration of Compound 2 in the suspension determined by HPLC was 259.62 mg/mL. The collected microsuspension was stored in a 1.5 mL sealed glass vial at room temperature and protected from light before PK study. Visual inspection of the suspension showed that the product was homogeneous, syringeable and easily resuspendable following short-time vortex or water-bath sonication, suitable for preclinical PK study via intramuscular injection.

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein may be employed in practicing the invention. It is intended that the following claims define the scope of the invention and that methods and structures within the scope of these claims and their equivalents be covered thereby.

Embodiments Directed to a Pharmaceutical Suspension Comprising Crystalline Formula (III)

Embodiment 1: A pharmaceutical suspension comprising nanoparticles or microparticles of a crystalline compound of Formula (III), or a pharmaceutically acceptable salt, solvate, or stereoisomer thereof:

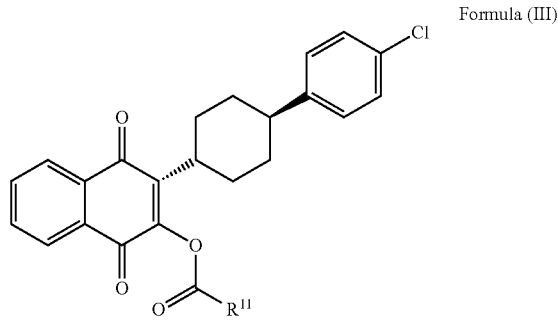

Formula (III)

wherein:
$R^{11}$ is a lipophilic moiety.

Embodiment 2: The pharmaceutical composition of Embodiment 1, wherein $R^{11}$ is optionally substituted $C_1$-$C_{30}$alkyl, optionally substituted $C_2$-$C_{30}$alkenyl, or optionally substituted $C_2$-$C_{30}$alkynyl.

Embodiment 3: The pharmaceutical composition of Embodiment 1 or 2, wherein $R^{11}$ is optionally substituted $C_1$-$C_{20}$alkyl, optionally substituted $C_2$-$C_{20}$alkenyl, or optionally substituted $C_2$-$C_{20}$alkynyl.

Embodiment 4: The pharmaceutical composition of Embodiment 1 or 2, wherein $R^{11}$ is $C_1$-$C_{20}$alkyl.

Embodiment 5: The pharmaceutical composition of Embodiment 1 or 2, wherein $R^{11}$ is $C_1$-$C_{30}$alkyl.

Embodiment 6: The pharmaceutical composition of Embodiment 1 or 2, wherein $R^{11}$ is $C_1$-$C_6$alkyl.

Embodiment 7: The pharmaceutical composition of Embodiment 1 or 2, wherein $R^{11}$ is $C_7$-$C_{30}$alkyl.

Embodiment 8: The pharmaceutical composition of Embodiment 1 or 2, wherein $R^{11}$ is $C_7$-$C_{20}$alkyl.

Embodiment 9: The pharmaceutical composition of any one Embodiments 1-8, wherein $R^{11}$ is

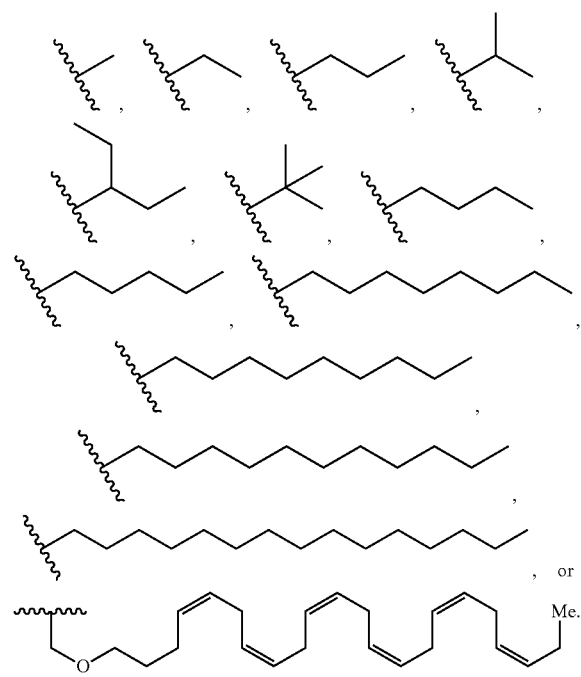

, or

Embodiment 10: The pharmaceutical composition of Embodiment 1 or 2, wherein $R^{11}$ is $C_2$-$C_{30}$alkenyl.

Embodiment 11: The pharmaceutical composition of Embodiment 10, wherein $R^{11}$ is

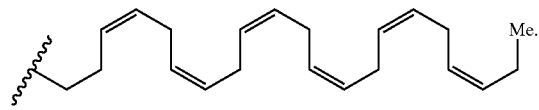 [SMILES: *CC/C=C\C/C=C\C/C=C\C/C=C\C/C=C\C/C=C\CC]

Embodiment 12: The pharmaceutical suspension of Embodiment 1, wherein the compound of formula (III) is:

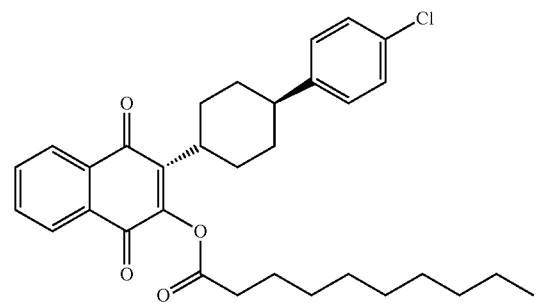

or a pharmaceutically acceptable salt, solvate, or stereoisomer thereof.

Embodiment 13: The pharmaceutical suspension of Embodiment 1, wherein the compound of formula (III) is:

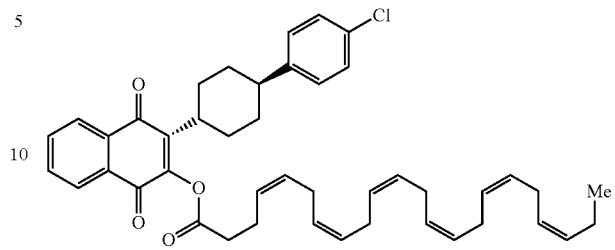

or a pharmaceutically acceptable salt, solvate, or stereoisomer thereof.

Embodiment 14: The pharmaceutical suspension of any one of Embodiments 1-13, wherein the size of the nanoparticles is between about 50 nm and about 1000 nm.

Embodiment 15: The pharmaceutical suspension of any one of Embodiments 1-14, wherein the size of the nanoparticles is about 100 nm.

Embodiment 16: The pharmaceutical suspension of any one of Embodiments 1-13, wherein the size of the microparticles is between about 1 μm and about 10 μm.

Embodiment 17: The pharmaceutical suspension of any one of Embodiments 1-13, wherein the size of the microparticles is between about 1 μm and about 5 μm.

Embodiment 18: The pharmaceutical suspension of any one of Embodiments 1-17, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

Embodiment 19: The pharmaceutical suspension of any one of Embodiments 1-18, further comprising a surfactant.

Embodiment 20: The pharmaceutical suspension of any one of Embodiments 1-19, further comprising a suspending agent.

Embodiment 21: The pharmaceutical suspension of any one of Embodiments 1-20, further comprising Synperonic® F108, dodecyl sodium sulfate (SLS), D-α-tocopheryl polyethylene glycol 1000 succinate (TPGS), hydroxypropyl methylcellulose (HPMC), and any combinations thereof.

Embodiment 22: The pharmaceutical suspension of any one of Embodiments 1-21, further comprising D-α-tocopheryl polyethylene glycol 1000 succinate (TPGS) and hydroxypropyl methylcellulose (HPMC).

Embodiment 23: The pharmaceutical composition of any one of Embodiments 1-22, wherein the concentration of the crystalline compound of Formula (III) or a pharmaceutically acceptable salt, solvate, or stereoisomer thereof is between about 10 mg/mL and about 50 mg/mL.

Embodiment 24: The pharmaceutical suspension of any one of Embodiments 1-23, wherein the concentration of the crystalline compound of Formula (III) is greater than about 50 mg/mL.

Embodiment 25: A method for the treatment or prevention of malaria in a subject comprising administering to the subject a pharmaceutical suspension of any one of Embodiments 1-24.

Embodiment 26: The method of Embodiment 25, wherein the pharmaceutical suspension is administered by subcutaneous or intramuscular injection.

Embodiment 27: The method of Embodiment 25, wherein the pharmaceutical suspension is effective for sustained or controlled release.

Embodiment 28: The method of any one of Embodiments 25-27, further comprising administering an additional antimalarial agent.

Embodiment 29: The method of Embodiment 28, wherein the additional antimalarial agent is selected from artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300

Embodiments Directed to a Pharmaceutical Suspension Comprising Crystalline Atovaquone Embodiment 1: A pharmaceutical suspension comprising nanoparticles or microparticles of a crystalline form of atovaquone, or a pharmaceutically acceptable salt, solvate, or stereoisomer thereof.

Embodiment 2: The pharmaceutical suspension of Embodiment 1, wherein the crystalline form of atovaquone, or a pharmaceutically acceptable salt, solvate, or stereoisomer thereof is atovaquone-Form I or atovaquone-Form II.

Embodiment 3: The pharmaceutical suspension of Embodiment 2, wherein the crystalline form of atovaquone, or a pharmaceutically acceptable salt, solvate, or stereoisomer thereof, is atovaquone-Form II wherein the crystalline form has at least one of the following properties:
 (a) an X-Ray powder diffraction (XRPD) pattern substantially the same as shown in FIG. 25; or
 (b) an X-ray powder diffraction (XRPD) pattern comprising characteristic peaks at about 7.0±0.1° 2θ, about 9.3±0.1° 2θ, about 14.3±0.1° 2θ, about 14.9±0.1° 2θ, about 18.6±0.1° 2θ, about 19.3±0.1° 2θ, about 20.1±0.1° 2θ, 22.8±0.1° 2θ, 23.4±0.1° 2θ, and 24.4±0.1° 2θ; or Embodiment 4: The pharmaceutical suspension of Embodiment 3, wherein the crystalline form of atovaquone-Form II has at least one of the following properties:
 (a) a DSC thermogram substantially the same to the one set forth in FIG. 26A; or
 (b) a DSC thermogram with an endotherm having a peak at about 219.9° C.

Embodiment 5: The pharmaceutical suspension of any one of Embodiments 1-4, wherein the size of the nanoparticles is between about 50 nm and about 1000 nm.

Embodiment 6: The pharmaceutical suspension of any one of Embodiments 1-5, wherein the size of the nanoparticles is about 100 nm.

Embodiment 7: The pharmaceutical suspension of any one of Embodiments 1-4, wherein the size of the microparticles is between about 1 µm and about 10 µm.

Embodiment 8: The pharmaceutical suspension of any one of Embodiments 1-4, wherein the size of the microparticles is between about 1 µm and about 5 µm.

Embodiment 9: The pharmaceutical suspension of any one of Embodiments 1-8, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

Embodiment 10: The pharmaceutical suspension of any one of Embodiments 1-9, further comprising a surfactant.

Embodiment 11: The pharmaceutical suspension of any one of Embodiments 1-10, further comprising a suspending agent.

Embodiment 12: The pharmaceutical suspension of any one of Embodiments 1-11, further comprising Synperonic® F108, dodecyl sodium sulfate (SLS), D-α-tocopheryl polyethylene glycol 1000 succinate (TPGS), hydroxypropyl methylcellulose (HPMC), and any combinations thereof.

Embodiment 13: The pharmaceutical suspension of any one of Embodiments 1-12, further comprising D-α-tocopheryl polyethylene glycol 1000 succinate (TPGS) and hydroxypropyl methylcellulose (HPMC).

Embodiment 14: The pharmaceutical composition of any one of Embodiments 1-13, wherein the concentration of the crystalline atovaquone or a pharmaceutically acceptable salt, solvate, or stereoisomer thereof is between about 10 mg/mL and about 50 mg/mL.

Embodiment 15: The pharmaceutical suspension of any one of Embodiments 1-13, wherein the concentration of the crystalline atovaquone is greater than about 50 mg/mL.

Embodiment 16: A method for the treatment or prevention of malaria in a subject comprising administering to the subject a pharmaceutical suspension of any one of Embodiments 1-15.

Embodiment 17: The method of Embodiment 16, wherein the pharmaceutical suspension is administered by subcutaneous or intramuscular injection.

Embodiment 18: The method of Embodiment 17, wherein the pharmaceutical suspension is effective for sustained or controlled release.

Embodiment 19: The method of any one of Embodiments 10-18, further comprising administering an additional antimalarial agent.

Embodiment 20: The method of Embodiment 19, wherein the additional antimalarial agent is selected from artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300.

Embodiments Directed to a Pharmaceutical Suspension Comprising Crystalline Pyronaridine Embodiment 1: A pharmaceutical suspension comprising nanoparticles or microparticles of a crystalline form of pyronaridine, or a pharmaceutically acceptable salt, solvate, or stereoisomer thereof.

Embodiment 2: The pharmaceutical suspension of Embodiment 1, wherein the pharmaceutical acceptable salt of pyronaridine is pyronaridine pamoate, pyronaridine benzenesulfonate, pyronaridine palmitate, or pyronaridine naphthalate.

Embodiment 3: The pharmaceutical suspension of Embodiment 1 or 2, wherein the crystalline form of pyronaridine, or a pharmaceutically acceptable salt, solvate, or stereoisomer thereof is pyronaridine-Form I, pyronaridine-Form II, pyronaridine-Form III, pyronaridine-Form IV, or pyronaridine-Form V.

Embodiment 4: The pharmaceutical suspension of any one of Embodiment 1-3, wherein the size of the nanoparticles is between about 50 nm and about 1000 nm.

Embodiment 5: The pharmaceutical suspension of any one of Embodiment 1-4, wherein the size of the nanoparticles is about 100 nm.

Embodiment 6: The pharmaceutical suspension of any one of Embodiment 1-3, wherein the size of the microparticles is between about 1 µm and about 10 µm.

Embodiment 7: The pharmaceutical suspension of any one of Embodiments 1-3, wherein the size of the microparticles is between about 1 µm and about 5 µm.

Embodiment 8: The pharmaceutical suspension of any one of Embodiments 1-7, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

Embodiment 9: The pharmaceutical suspension of any one of Embodiments 1-8, further comprising a surfactant.

Embodiment 10: The pharmaceutical suspension of any one of Embodiments 1-9, further comprising a suspending agent.

Embodiment 11: The pharmaceutical suspension of any one of Embodiments 1-10, further comprising Synperonic® F108, dodecyl sodium sulfate (SLS), D-α-tocopheryl polyethylene glycol 1000 succinate (TPGS), hydroxypropyl methylcellulose (HPMC), and any combinations thereof.

Embodiment 12: The pharmaceutical suspension of any one of Embodiments 1-11, further comprising D-α-tocopheryl polyethylene glycol 1000 succinate (TPGS) and hydroxypropyl methylcellulose (HPMC).

Embodiment 13: The pharmaceutical composition of any one of Embodiments 1-12, wherein the concentration of the crystalline pyronaridine or a pharmaceutically acceptable salt, solvate, or stereoisomer thereof is between about 10 mg/mL and about 50 mg/mL.

Embodiment 14: The pharmaceutical suspension of any one of Embodiments 1-13, wherein the concentration of the crystalline pyronaridine is greater than about 50 mg/mL.

Embodiment 15: A method for the treatment or prevention of malaria in a subject comprising administering to the subject a pharmaceutical suspension of any one of Embodiments 1-14.

Embodiment 16: The method of Embodiment 15, wherein the pharmaceutical suspension is administered by subcutaneous or intramuscular injection.

Embodiment 17: The method of Embodiment 15, wherein the pharmaceutical suspension is effective for sustained or controlled release.

Embodiment 18: The method of any one of Embodiments 15-17, further comprising administering an additional antimalarial agent.

Embodiment 19: The method of Embodiment 18, wherein the additional antimalarial agent is selected from artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300.

Embodiments Directed to a Pharmaceutical Composition Comprising a Crystalline ELQ-300

Embodiment 1: A pharmaceutical suspension comprising nanoparticles or microparticles of a crystalline form of ELQ-300, or a pharmaceutically acceptable salt, solvate, or stereoisomer thereof.

Embodiment 2: The pharmaceutical suspension of Embodiment 1, wherein the crystalline form of ELQ-300, or a pharmaceutically acceptable salt, solvate, or stereoisomer thereof is ELQ-300-Form IA, ELQ-300-Form IB, ELQ-300-Form II, ELQ-300-Form III, ELQ-300-Form IV, or ELQ-300-Form V.

Embodiment 3: The pharmaceutical suspension of Embodiment 2, wherein the crystalline form of ELQ-300, or a pharmaceutically acceptable salt, solvate, or stereoisomer thereof, is ELQ-300-Form II wherein the crystalline form has at least one of the following properties:
 (a) an X-Ray powder diffraction (XRPD) pattern substantially the same as shown in FIG. 9; or
 (b) an X-ray powder diffraction (XRPD) pattern comprising characteristic peaks at about 7.6±0.1° 2θ, about 12.7±0.1° 2θ, about 20.4±0.1° 2θ, about 23.0±0.1° 2θ, about 25.6±0.1° 2θ, about 28.2±0.1° 2θ, about 30.8±0.1° 2θ, about 33.5±0.1° 2θ, about 36.1° 2θ, and about 38.8±0.1° 2θ.

Embodiment 4: The pharmaceutical suspension of Embodiment 3, wherein the crystalline form of ELQ-300-Form II has at least one of the following properties:
 (a) a DSC thermogram substantially the same to the one set forth in FIG. 11; or
 (b) a DSC thermogram with an endotherm having a peak at about 297.5° C.

Embodiment 5: The pharmaceutical suspension of any one of Embodiments 1-4, wherein the size of the nanoparticles is between about 50 nm and about 1000 nm.

Embodiment 6: The pharmaceutical suspension of any one of Embodiments 1-5, wherein the size of the nanoparticles is about 100 nm.

Embodiment 7: The pharmaceutical suspension of any one of Embodiments 1-4, wherein the size of the microparticles is between about 1 μm and about 10 μm.

Embodiment 8: The pharmaceutical suspension of any one of Embodiments 1-4, wherein the size of the microparticles is between about 1 μm and about 5 μm.

Embodiment 9: The pharmaceutical suspension of any one of Embodiments 1-8, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

Embodiment 10: The pharmaceutical suspension of any one of Embodiments 1-9, further comprising a surfactant.

Embodiment 11: The pharmaceutical suspension of any one of Embodiments 1-10, further comprising a suspending agent.

Embodiment 12: The pharmaceutical suspension of any one of Embodiments 1-11, further comprising Synperonic® F108, dodecyl sodium sulfate (SLS), D-α-tocopheryl polyethylene glycol 1000 succinate (TPGS), hydroxypropyl methylcellulose (HPMC), and any combinations thereof.

Embodiment 13: The pharmaceutical suspension of any one of Embodiments 1-12, further comprising D-α-tocopheryl polyethylene glycol 1000 succinate (TPGS) and hydroxypropyl methylcellulose (HPMC).

Embodiment 14: The pharmaceutical suspension of any one of Embodiments 1-12, further comprising D-α-tocopheryl polyethylene glycol 1000 succinate (TPGS).

Embodiment 15: The pharmaceutical suspension of any one of Embodiments 1-12, further comprising Synperonic® F108.

Embodiment 16: The pharmaceutical composition of any one of Embodiments 1-15, wherein the concentration of the crystalline ELQ-300 or a pharmaceutically acceptable salt, solvate, or stereoisomer thereof is between about 10 mg/mL and about 50 mg/mL.

Embodiment 17: The pharmaceutical suspension of any one of Embodiments 1-15, wherein the concentration of the crystalline ELQ-300 is greater than about 50 mg/mL.

Embodiment 18: A method for the treatment or prevention of malaria in a subject comprising administering to the subject a pharmaceutical suspension of any one of Embodiments 1-17.

Embodiment 19: The method of Embodiment 18, wherein the pharmaceutical suspension is administered by subcutaneous or intramuscular injection.

Embodiment 20: The method of Embodiment 19, wherein the pharmaceutical suspension is effective for sustained or controlled release.

Embodiment 21: The method of any one of Embodiments 18-20, further comprising administering an additional antimalarial agent.

Embodiment 22: The method of Embodiment 21, wherein the additional antimalarial agent is selected from artemisinin, artemisinin derivatives, atovaquone, proguanil, quinine, chloroquine, amodiaquine, pyrimethamine, doxycycline, clindamycin, mefloquine, primaquine, pyronaridine, halofantrine, or ELQ-300.

Embodiments Directed to a Compound of Formula (I)

Embodiment 1: A compound of Formula (I) or a pharmaceutically acceptable salt, solvate, or stereoisomer thereof:

Formula (I)

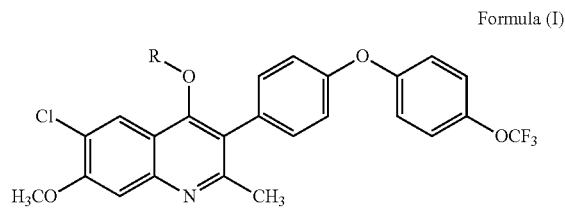

wherein:
R is —C(R$^{1a}$)$_2$OC(=O)R$^1$, —R$^2$, —C(=O)OR$^3$, or —C(=O)R$^4$;
R$^1$ is optionally substituted C$_1$-C$_{30}$alkyl, optionally substituted C$_2$-C$_{30}$alkenyl, optionally substituted C$_2$-C$_{30}$alkynyl, optionally substituted C$_3$-C$_8$cycloalkyl, or optionally substituted C$_2$-C$_8$heterocycloalkyl;
each R$^{1a}$ is independently hydrogen, halogen, or optionally substituted C$_1$-C$_6$alkyl;
or two R$^{1a}$ are taken together with the carbon atom to which they are attached to form an optionally substituted C$_3$-C$_8$cycloalkyl;
R$^2$ is optionally substituted (C$_1$-C$_6$alkylene)aryl, optionally substituted (C$_1$-C$_6$alkylene)heteroaryl, optionally substituted (C$_1$-C$_6$alkylene)C$_3$-C$_8$cycloalkyl, or optionally substituted (C$_1$-C$_6$alkylene)C$_2$-C$_8$heterocycloalkyl;
R$^3$ is optionally substituted C$_5$-C$_{30}$alkyl, optionally substituted C$_4$-C$_{30}$alkenyl, or optionally substituted C$_2$-C$_{30}$alkynyl; and
R$^4$ is optionally substituted C$_5$-C$_{30}$alkyl, optionally substituted C$_2$-C$_{30}$alkenyl, or optionally substituted C$_2$-C$_{30}$alkynyl.

Embodiment 2: The compound of Embodiment 1, wherein R is —C(R$^{1a}$)$_2$OC(=O)R$^1$.

Embodiment 3: The compound of Embodiment 1 or 2, wherein each R$^{1a}$ is hydrogen.

Embodiment 4: The compound of any one of Embodiments 1-3, wherein R$^1$ is optionally substituted C$_1$-C$_{20}$alkyl or optionally substituted C$_2$-C$_{30}$alkenyl.

Embodiment 5: The compound of any one of Embodiments 1-4, wherein R$^1$ is C$_1$-C$_6$alkyl.

Embodiment 6: The compound of any one of Embodiments 1-4, wherein R$^1$ is C$_7$-C$_{20}$alkyl.

Embodiment 7: The compound of any one of Embodiments 1-4, wherein R$^1$ is

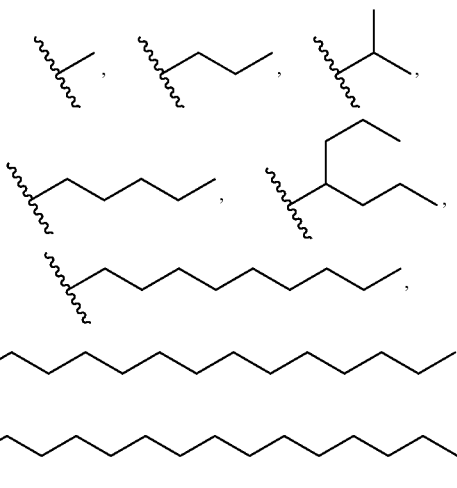

Embodiment 8: The compound of any one of Embodiments 1-4, wherein R$^1$

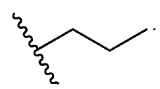 [SMILES: *CCC]

Embodiment 9: The compound of any one of Embodiments 1-3, wherein R$^1$ is C$_2$-C$_{30}$alkenyl.

Embodiment 10: The compound of Embodiment 9, wherein R$^1$ is C$_2$-C$_6$alkenyl.

Embodiment 11: The compound of Embodiment 9, wherein R$^1$ is C$_7$-C$_{30}$alkenyl.

Embodiment 12: The compound of Embodiment 9, wherein R$^1$ is

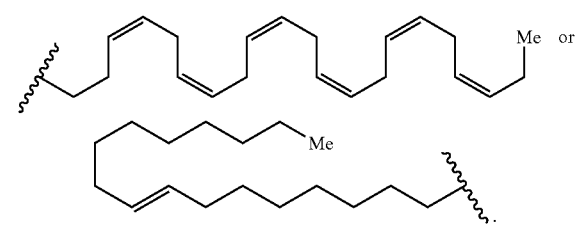

Embodiment 13: The compound of Embodiment 1, wherein R is —C(=O)OR$^3$.

Embodiment 14: The compound of Embodiment 13, wherein R$^3$ is C$_5$-C$_{20}$alkyl.

Embodiment 15: The compound of Embodiment 14, wherein R$^3$ is C$_5$-C$_{10}$alkyl.

Embodiment 16: The compound of Embodiment 14, wherein R$^3$ is C$_{11}$-C$_{20}$alkyl.

Embodiment 17: The compound of Embodiment 14, wherein R$^3$ is

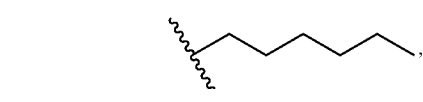

-continued

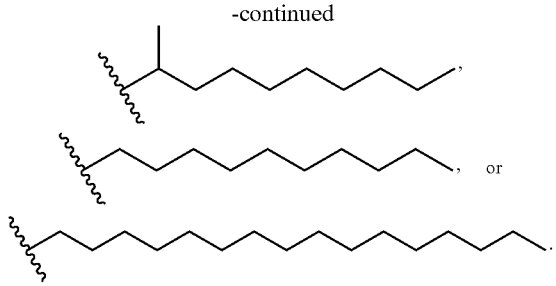

Embodiment 18: The compound of Embodiment 1, wherein R is —C(=O)R$^4$.

Embodiment 19: The compound of Embodiment 18, wherein R$^4$ is C$_5$-C$_{20}$alkyl.

Embodiment 20: The compound of Embodiment 18, wherein R$^4$ is C$_5$-C$_{10}$alkyl.

Embodiment 21: The compound of Embodiment 18, wherein R$^4$ is C$_{11}$-C$_{20}$alkyl.

Embodiments Directed to Crystalline Form of ((6-chloro-7-methoxy-2-methyl-3-(4-(4-(trifluoromethoxy)phenoxy)phenyl)quinolin-4-yl)oxy) methyl butyrate Embodiment 1: A crystalline form of ((6-chloro-7-methoxy-2-methyl-3-(4-(4-(trifluoromethoxy)phenoxy)phenyl)quinolin-4-yl)oxy)methyl butyrate:

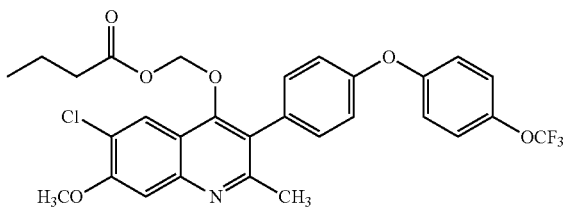 [SMILES: CCCC(=O)OCOc1c(-c2ccc(Oc3ccc(OC(F)(F)F)cc3)cc2)c(C)nc2cc(OC)c(Cl)cc12]

or a pharmaceutically acceptable salt, solvate, or stereoisomer thereof.

Embodiment 2: The crystalline form of Embodiment 1, wherein the crystalline form of ((6-chloro-7-methoxy-2-methyl-3-(4-(4-(trifluoromethoxy)phenoxy)phenyl)quinolin-4-yl)oxy)methyl butyrate has at least one of the following properties:

(a) an X-Ray powder diffraction (XRPD) pattern substantially the same as shown in FIG. 41; or (b) an X-ray powder diffraction (XRPD) pattern comprising characteristic peaks at about 14.4±0.1° 2θ, about 15.1±0.1° 2θ, about 17.7±0.1° 2θ, about 18.1±0.1° 2θ, about 22.3±0.1° 2θ, and about 22.6±0.1° 2θ; or (c) a DSC thermogram substantially the same to the one set forth in FIG. 42A; or (d) a DSC thermogram with an endotherm having a peak at about 99.5° C.

Embodiment 3: The crystalline form of Embodiment 2, wherein the X-ray powder diffraction (XRPD) pattern further comprises characteristic peaks at about 19.1°±0.1° 2θ, about 20.3°±0.1° 2θ, about 21.2°±0.1° 2θ, about 26.7°±0.1° 2θ, and about 29.21°±0.1° 2θ.

Embodiments Directed to a Pharmaceutical Composition Comprising a Compound of Formula (II)

Embodiment 1: A pharmaceutical composition comprising:
(i) an oil; and
(ii) a compound of Formula (II) or a pharmaceutically acceptable salt, solvate, or stereoisomer thereof:

Formula (II)

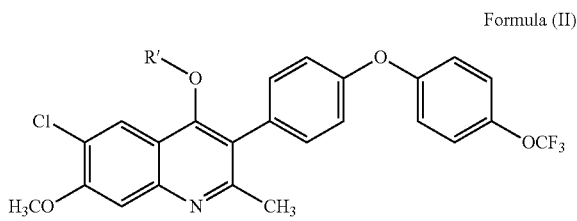

wherein:
R' is —C(R$^{7a}$)$_2$OC(=O)R$^7$, —R$^8$, —C(=O)OR$^9$, or —C(=O)R$^{10}$;

R$^7$ is optionally substituted C$_1$-C$_{30}$alkyl, optionally substituted C$_2$-C$_{30}$alkenyl, optionally substituted C$_2$-C$_{30}$alkynyl, optionally substituted C$_3$-C$_8$cycloalkyl, or optionally substituted C$_2$-C$_8$heterocycloalkyl;

each R$^{7a}$ is independently hydrogen, halogen, or optionally substituted C$_1$-C$_6$alkyl;

or two R$^{7a}$ are taken together with the carbon atom to which they are attached to form an optionally substituted C$_3$-C$_8$cycloalkyl;

R$^8$ is optionally substituted (C$_1$-C$_6$alkylene)aryl, optionally substituted (C$_1$-C$_6$alkylene)heteroaryl, optionally substituted (C$_1$-C$_6$alkylene)C$_3$-C$_8$cycloalkyl, or optionally substituted (C$_1$-C$_6$alkylene)C$_2$-C$_8$heterocycloalkyl;

R$^9$ is optionally substituted C$_1$-C$_{30}$alkyl, optionally substituted C$_2$-C$_{30}$alkenyl, or optionally substituted C$_2$-C$_{30}$alkynyl; and R$^{10}$ is optionally substituted C$_1$-C$_{30}$alkyl, optionally substituted C$_2$-C$_{30}$alkenyl, or optionally substituted C$_2$-C$_{30}$alkynyl.

Embodiment 2: The pharmaceutical composition of Embodiment 1, wherein R' is —C(R$^{7a}$)$_2$OC(=O)R$^7$.

Embodiment 3: The pharmaceutical composition of Embodiment 1 or 2, wherein each R$^{7a}$ is hydrogen.

Embodiment 4: The pharmaceutical composition of any one of Embodiment 1-3, wherein R$^7$ is optionally substituted C$_1$-C$_{20}$alkyl or optionally substituted C$_2$-C$_{30}$alkenyl.

Embodiment 5: The pharmaceutical composition of any one of Embodiments 1-4, wherein R$^7$ is C$_1$-C$_6$alkyl.

Embodiment 6: The pharmaceutical composition of any one of Embodiments 1-4, wherein R$^7$ is C$_7$-C$_{20}$alkyl.

Embodiment 7: The pharmaceutical composition of any one of Embodiments 1-4, wherein R$^7$ is

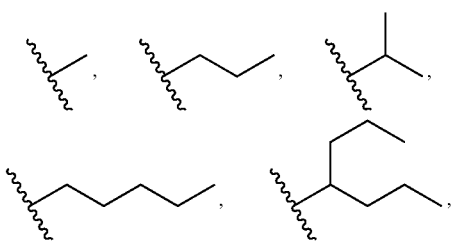

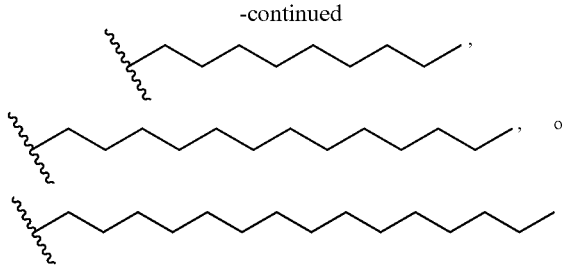

Embodiment 8: The pharmaceutical composition of any one of Embodiments 1-4, wherein $R^7$ is

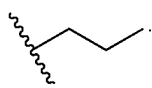

Embodiment 9: The pharmaceutical composition of any one of Embodiment 1-4, wherein $R^7$ is $C_2$-$C_{30}$alkenyl.

Embodiment 10: The pharmaceutical composition of Embodiment 9, wherein $R^7$ is $C_2$-$C_6$alkenyl.

Embodiment 11: The pharmaceutical composition of Embodiment 9, wherein $R^7$ is $C_7$-$C_{30}$alkenyl.

Embodiment 12: The pharmaceutical composition of Embodiment 9 or 11, wherein $R^7$ is

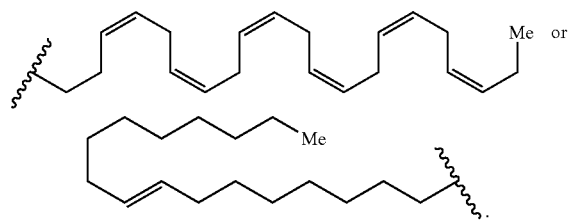

Embodiment 13: The pharmaceutical composition of Embodiment 1, wherein R' is —C(=O)OR$^9$.

Embodiment 14: The pharmaceutical composition of Embodiment 13, wherein $R^9$ is optionally substituted $C_5$-$C_{30}$alkyl, optionally substituted $C_4$-$C_{30}$alkenyl, or optionally substituted $C_2$-$C_{30}$alkynyl.

Embodiment 15: The pharmaceutical composition of Embodiment 13, wherein $R^9$ is $C_1$-$C_6$alkyl.

Embodiment 16: The pharmaceutical composition of Embodiment 13, wherein $R^9$ is $C_7$-$C_{20}$alkyl.

Embodiment 17: The pharmaceutical composition of Embodiment 13, wherein $R^9$ is $C_5$-$C_{20}$alkyl.

Embodiment 18: The pharmaceutical composition of Embodiment 13, wherein $R^9$ is $C_5$-$C_{10}$alkyl.

Embodiment 19: The pharmaceutical composition of Embodiment 13, wherein $R^9$ is $C_{11}$-$C_{20}$alkyl.

Embodiment 20: The pharmaceutical composition of Embodiment 13, wherein $R^9$ is

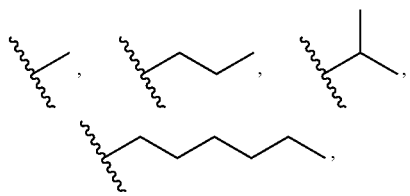

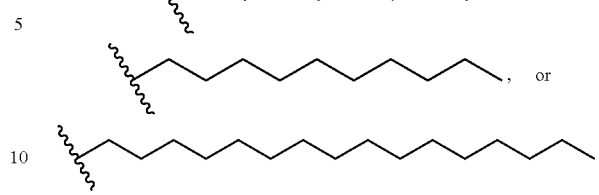

Embodiment 21: The pharmaceutical composition of Embodiment 1, wherein R' is —C(=O)R$^{10}$.

Embodiment 22: The pharmaceutical composition of Embodiment 21, wherein $R^{10}$ is optionally substituted $C_5$-$C_{30}$alkyl, optionally substituted $C_2$-$C_{30}$alkenyl, or optionally substituted $C_2$-$C_{30}$alkynyl.

Embodiment 23: The pharmaceutical composition of Embodiment 21, wherein $R^{10}$ is $C_1$-$C_6$alkyl.

Embodiment 24: The pharmaceutical composition of Embodiment 21, wherein $R^{10}$ is $C_7$-$C_{20}$alkyl.

Embodiment 25: The pharmaceutical composition of Embodiment 21, wherein $R^{10}$ is $C_5$-$C_{20}$alkyl.

Embodiment 26: The pharmaceutical composition of Embodiment 21, wherein $R^{10}$ is $C_5$-$C_{10}$alkyl.

Embodiment 27: The pharmaceutical composition of Embodiment 21, wherein $R^{10}$ is $C_{11}$-$C_{20}$alkyl.

Embodiment 28: The pharmaceutical composition of any one of Embodiments 1-27, wherein the oil is a vegetable oil.

Embodiment 29: The pharmaceutical composition of any one of Embodiments 1-28, wherein the oil is selected from corn oil, peanut oil, sesame oil, olive oil, palm oil, safflower oil, soybean oil, cottonseed oil, rapeseed oil, sunflower oil and mixtures thereof.

Embodiment 30: The pharmaceutical composition of Embodiments 1-29, wherein the oil is sesame oil.

Embodiment 31: The pharmaceutical composition of any one of Embodiments 1-30, wherein the concentration of the compound of Formula (II) or a pharmaceutically acceptable salt, solvate, or stereoisomer thereof is greater than about 50 mg/mL.

Embodiments Directed to a Pharmaceutical Suspension Comprising Crystalline Formula (II)

Embodiment 1: A pharmaceutical suspension comprising nanoparticles or microparticles of a crystalline compound of Formula (II), or a pharmaceutically acceptable salt, solvate, or stereoisomer thereof:

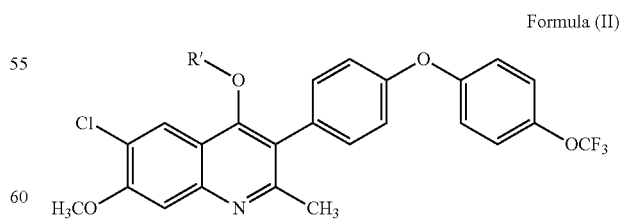

Formula (II)

wherein:
R' is —C(R$^{7a}$)$_2$OC(=O)R$^7$, —R$^8$, —C(=O)OR$^9$, or —C(=O)R$^{10}$;
$R^7$ is optionally substituted $C_1$-$C_{30}$alkyl, optionally substituted $C_2$-$C_{30}$alkenyl, optionally substituted $C_2$-$C_{30}$alkynyl, optionally substituted $C_3$-$C_8$cycloalkyl, or optionally substituted $C_2$-$C_8$heterocycloalkyl;

each $R^{7a}$ is independently hydrogen, halogen, or optionally substituted $C_1$-$C_6$alkyl;

or two $R^{7a}$ are taken together with the carbon atom to which they are attached to form an optionally substituted $C_3$-$C_8$cycloalkyl;

$R^8$ is optionally substituted ($C_1$-$C_6$alkylene)aryl, optionally substituted ($C_1$-$C_6$alkylene)heteroaryl, optionally substituted ($C_1$-$C_6$alkylene)$C_3$-$C_8$cycloalkyl, or optionally substituted ($C_1$-$C_6$alkylene)$C_2$-$C_8$heterocycloalkyl;

$R^9$ is optionally substituted $C_1$-$C_{20}$alkyl, optionally substituted $C_2$-$C_{20}$alkenyl, or optionally substituted $C_2$-$C_{20}$alkynyl; and $R^{10}$ is optionally substituted $C_1$-$C_{20}$alkyl, optionally substituted $C_2$-$C_{20}$alkenyl, or optionally substituted $C_2$-$C_{20}$alkynyl.

Embodiment 2: The pharmaceutical suspension of Embodiment 1, wherein R' is —C($R^{7a}$)$_2$OC(=O)$R^7$.

Embodiment 3: The pharmaceutical suspension of Embodiment 1 or 2, wherein each $R^{7a}$ is hydrogen.

Embodiment 4: The pharmaceutical suspension of any one of Embodiment 1-3, wherein $R^7$ is optionally substituted $C_1$-$C_{20}$alkyl or optionally substituted $C_2$-$C_{30}$alkenyl.

Embodiment 5: The pharmaceutical suspension of any one of Embodiments 1-3, wherein $R^7$ is $C_1$-$C_6$alkyl.

Embodiment 6: The pharmaceutical suspension of any one of Embodiments 1-3, wherein $R^7$ is $C_7$-$C_{20}$alkyl.

Embodiment 7: The pharmaceutical suspension of any one of Embodiments 1-3, wherein $R^7$ is

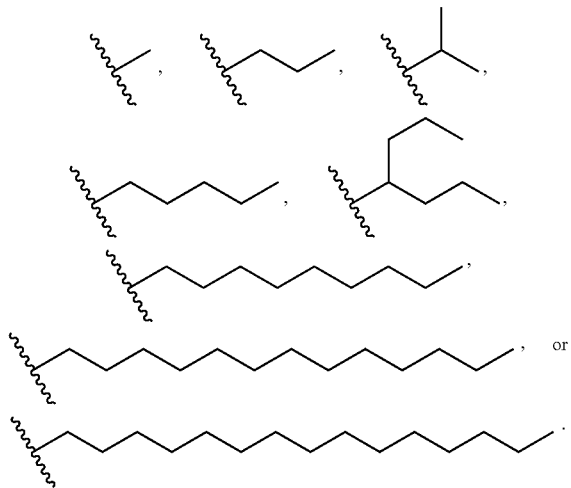

Embodiment 8: The pharmaceutical suspension of any one of Embodiments 1-3, wherein $R^7$ is

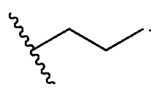

Embodiment 9: The pharmaceutical suspension of any one of Embodiment 1-3, wherein $R^7$ is $C_2$-$C_{20}$alkenyl.

Embodiment 10: The pharmaceutical suspension of Embodiment 9, wherein $R^7$ is $C_2$-$C_6$alkenyl.

Embodiment 11: The pharmaceutical suspension of Embodiment 9, wherein $R^7$ is $C_7$-$C_{30}$alkenyl.

Embodiment 12: The pharmaceutical suspension of any one of Embodiments 9, wherein $R^7$ is

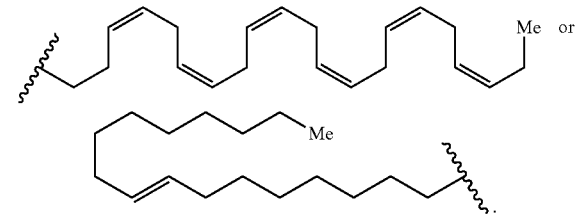

Embodiment 13: The pharmaceutical suspension of Embodiment 1, wherein R' is —C(=O)O$R^9$.

Embodiment 14: The pharmaceutical suspension of Embodiment 13, wherein $R^9$ is optionally substituted $C_5$-$C_{30}$alkyl, optionally substituted $C_4$-$C_{30}$alkenyl, or optionally substituted $C_2$-$C_{30}$alkynyl.

Embodiment 15: The pharmaceutical suspension of Embodiment 13, wherein $R^9$ is $C_1$-$C_6$alkyl.

Embodiment 16: The pharmaceutical suspension of Embodiment 13, wherein $R^9$ is $C_7$-$C_{20}$alkyl.

Embodiment 17: The pharmaceutical suspension of Embodiment 13, wherein $R^9$ is $C_5$-$C_{20}$alkyl.

Embodiment 18: The pharmaceutical suspension of Embodiment 13, wherein $R^9$ is $C_5$-$C_{10}$alkyl.

Embodiment 19: The pharmaceutical suspension of Embodiment 13, wherein $R^9$ is $C_{11}$-$C_{20}$alkyl.

Embodiment 20: The pharmaceutical suspension of Embodiment 13, wherein $R^9$ is

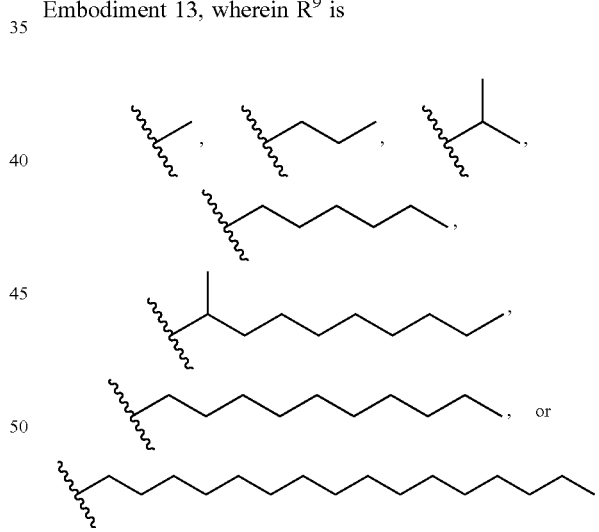

Embodiment 21: The pharmaceutical suspension of Embodiment 1, wherein R' is —C(=O)$R^{10}$.

Embodiment 22: The pharmaceutical suspension of Embodiment 21, wherein $R^{10}$ is optionally substituted $C_5$-$C_{30}$alkyl, optionally substituted $C_2$-$C_{30}$alkenyl, or optionally substituted $C_2$-$C_{30}$alkynyl.

Embodiment 23: The pharmaceutical suspension of Embodiment 21, wherein $R^{10}$ is $C_1$-$C_6$alkyl.

Embodiment 24: The pharmaceutical suspension of Embodiment 21, wherein $R^{10}$ is $C_7$-$C_{20}$alkyl.

Embodiment 25: The pharmaceutical suspension of Embodiment 21, wherein $R^{10}$ is $C_5$-$C_{20}$alkyl.

Embodiment 26: The pharmaceutical suspension of Embodiment 21, wherein $R^{10}$ is $C_5$-$C_{10}$alkyl.

Embodiment 27: The pharmaceutical suspension of Embodiment 21, wherein $R^{10}$ is $C_{11}$-$C_{20}$alkyl.

Embodiment 28: The pharmaceutical suspension of Embodiment 21, wherein the compound of formula (II) is ((6-chloro-7-methoxy-2-methyl-3-(4-(4-(trifluoromethoxy)phenoxy)phenyl)quinolin-4-yl)oxy)methyl butyrate or a pharmaceutically acceptable salt, solvate, or stereoisomer thereof.

Embodiment 29: The pharmaceutical suspension of Embodiment 28, wherein the crystalline ((6-chloro-7-methoxy-2-methyl-3-(4-(4-(trifluoromethoxy)phenoxy)phenyl)quinolin-4-yl)oxy)methyl butyrate has at least one of the following properties:
 (a) an X-Ray powder diffraction (XRPD) pattern substantially the same as shown in FIG. 41; or
 (b) an X-ray powder diffraction (XRPD) pattern comprising characteristic peaks at about 14.4±0.1° 2θ, about 15.1±0.1° 2θ, about 17.7±0.1° 2θ, about 18.1±0.1° 2θ, about 22.3±0.1° 2θ, and about 22.6±0.1° 2θ; or
 (c) a DSC thermogram substantially the same to the one set forth in FIG. 42A; or
 (d) a DSC thermogram with an endotherm having a peak at about 99.5° C.

Embodiment 30: The pharmaceutical suspension of Embodiment 29, wherein the X-ray powder diffraction (XRPD) pattern further comprises characteristic peaks at about 19.1°±0.1° 2θ, about 20.3°±0.1° 2θ, about 21.2°±0.1° 2θ, about 26.7°±0.1° 2θ, and about 29.2°±0.1° 2θ.

Embodiment 31: The pharmaceutical suspension of any one of Embodiments 1-30, wherein the size of the microparticles is between about 1 μm and about 10 μm.

Embodiment 32: The pharmaceutical suspension of any one of Embodiments 1-31, wherein the size of the microparticles is between about 1 μm and about 5 μm.

Embodiment 33: The pharmaceutical suspension of any one of Embodiments 1-32, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

Embodiment 34: The pharmaceutical suspension of any one of Embodiments 1-33, further comprising a surfactant.

Embodiment 35: The pharmaceutical suspension of any one of Embodiments 1-34, further comprising a suspending agent.

Embodiment 36: The pharmaceutical suspension of any one of Embodiments 1-35, further comprising Synperonic® F108, dodecyl sodium sulfate (SLS), D-α-tocopheryl polyethylene glycol 1000 succinate (TPGS), hydroxypropyl methylcellulose (HPMC), and any combinations thereof.

Embodiment 37: The pharmaceutical suspension of any one of Embodiments 1-36, further comprising D-α-tocopheryl polyethylene glycol 1000 succinate (TPGS) and hydroxypropyl methylcellulose (HPMC).

Embodiment 38: The pharmaceutical composition of any one of Embodiments 1-37, wherein the concentration of the crystalline compound of Formula (II) or a pharmaceutically acceptable salt, solvate, or stereoisomer thereof is between about 10 mg/mL and about 50 mg/mL.

Embodiment 39: The pharmaceutical suspension of any one of Embodiments 1-38, wherein the concentration of the crystalline compound of Formula (II) is greater than about 50 mg/mL.

We claim:

1. A pharmaceutical suspension comprising nanoparticles or microparticles of a crystalline compound of Formula (III) or a pharmaceutically acceptable salt, solvate, or stereoisomer thereof:

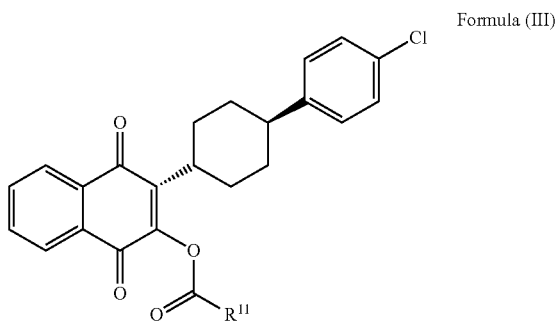

Formula (III)

wherein: $R^{11}$ is $C_1$-$C_6$ alkyl.

2. The pharmaceutical suspension according to claim 1, wherein $R^{11}$ is $C_6$ alkyl.

3. The pharmaceutical suspension according to claim 1, wherein the compound of Formula (III) is

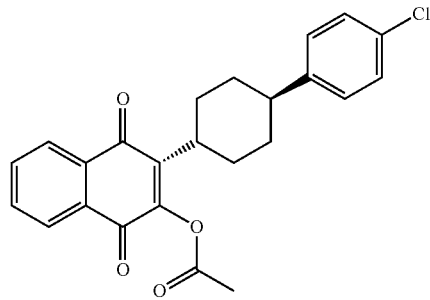

or a pharmaceutically acceptable salt, solvate, or stereoisomer thereof.

4. The pharmaceutical suspension according to claim 1, wherein the suspension comprises microparticles of a crystalline compound of Formula (III) with average particle size in the range of about 1 μm to about 50 μm.

5. The pharmaceutical suspension according to claim 4, wherein the suspension comprises microparticles of a crystalline compound of Formula (III) with average particle size in the range of about 5 μm to about 20 μm.

6. The pharmaceutical suspension according to claim 5, wherein the suspension comprises microparticles of a crystalline compound of Formula (III) with average particle size in the range of about 10 μm to about 20 μm.

7. The pharmaceutical suspension according to claim 1, further comprising a pharmaceutically acceptable excipient selected from surfactants, solubilizers, emulsifiers, preservatives, isotonicity agents, dispersing agents, wetting agents, fillers, solvents, buffers, stabilizers, lubricants, thickening agents, suspending agents, and any combinations thereof.

8. The pharmaceutical suspension according to claim 1, further comprising Synperonic® F108, dodecyl sodium sulfate (SLS), D-a-tocopheryl polyethylene glycol 1000 succinate (TPGS), hydroxypropyl methylcellulose (HPMC), and any combinations thereof.

9. The pharmaceutical suspension according to claim 1, wherein the concentration of the crystalline compound of Formula (III) or a pharmaceutically acceptable salt, solvate, or stereoisomer thereof is between about 20 mg/mL and about 300 mg/mL.

10. The pharmaceutical suspension according to claim 9, wherein the concentration of the crystalline compound of Formula (III) or a pharmaceutically acceptable salt, solvate, or stereoisomer thereof is at least about 100 mg/mL.

11. The pharmaceutical suspension according to claim 1, wherein $R^{11}$ is methyl.

* * * * *